United States Patent
Hertz et al.

(10) Patent No.: US 11,202,731 B2
(45) Date of Patent: Dec. 21, 2021

(54) SURGICAL PATIENT SUPPORT AND METHODS THEREOF

(71) Applicant: ALLEN MEDICAL SYSTEMS, INC., Batesville, IN (US)

(72) Inventors: Ben Hertz, Acton, MA (US); Joshua C. Hight, Sommerville, MA (US); Jason S. Bernotsky, Dunmore, PA (US); Christopher B. Dubois, Marlborough, MA (US); Andrew L. Thompson, Townsend, MA (US); Zachary B. Konsin, Brighton, MA (US); David C. Newkirk, Lawrenceburg, IN (US); Andrew D. Clark, Allston, MA (US); Kyle S. McKenney, Maynard, MA (US)

(73) Assignee: Allen Medical Systems, Inc., Batesville, IN (US)

( * ) Notice: Subject to any disclaimer, the term of this patent is extended or adjusted under 35 U.S.C. 154(b) by 399 days.

(21) Appl. No.: 16/275,728

(22) Filed: Feb. 14, 2019

(65) Prior Publication Data
US 2019/0262204 A1 Aug. 29, 2019

Related U.S. Application Data

(60) Provisional application No. 62/636,563, filed on Feb. 28, 2018.

(51) Int. Cl.
*A61G 13/10* (2006.01)
*A61G 13/04* (2006.01)
(Continued)

(52) U.S. Cl.
CPC ......... *A61G 13/101* (2013.01); *A61G 7/0528* (2016.11); *A61G 13/04* (2013.01);
(Continued)

(58) Field of Classification Search
CPC ........ A61G 13/02; A61G 13/04; A61G 13/06; A61G 13/101; A61G 13/12;
(Continued)

(56) References Cited

U.S. PATENT DOCUMENTS

| 1,021,335 A | 3/1912 | Robinson et al. |
| 1,098,477 A | 6/1914 | Cashman |

(Continued)

FOREIGN PATENT DOCUMENTS

| DE | 1162508 B | 2/1964 |
| DE | 3438956 A1 | 5/1985 |

(Continued)

OTHER PUBLICATIONS

Examination report No. 1 for standard patent application for Australian Patent Application No. 2019201321 dated Feb. 20, 2020 (4 pages).

(Continued)

*Primary Examiner* — Nicholas F Polito
(74) *Attorney, Agent, or Firm* — Barnes & Thornburg LLP

(57) ABSTRACT

Devices, systems, and methods for patient support include arrangements of patient support tops, that are selectively connectible with a connection assembly, through a slide assembly allowing particular arrangement of the patient support tops. The patient support tops can be arranged for flip rotation to assist in positioning a patient's body.

30 Claims, 82 Drawing Sheets

(51) Int. Cl.
    *A61G 13/06*     (2006.01)
    *A61B 5/00*     (2006.01)
    *A61G 13/12*     (2006.01)
    *A61G 7/05*     (2006.01)

(52) U.S. Cl.
    CPC .......... *A61G 13/06* (2013.01); *A61G 13/104* (2013.01); *A61G 13/1295* (2013.01); *A61B 5/704* (2013.01)

(58) Field of Classification Search
    CPC .... A61G 13/1285; A61G 1/06; A61G 3/0891; A61G 7/0528; A61G 13/104; A61G 13/1295; A61B 5/704; E05B 57/00
    See application file for complete search history.

(56) References Cited

U.S. PATENT DOCUMENTS

| | | | |
|---|---|---|---|
| 1,160,451 | A | 11/1915 | Sanford |
| 1,171,713 | A | 2/1916 | Gilkerson |
| 1,372,565 | A | 3/1921 | Skelly |
| 1,528,835 | A | 3/1925 | McCollough |
| 1,662,464 | A | 3/1928 | McCutchen |
| 1,799,692 | A | 4/1931 | Knott |
| 1,938,006 | A | 12/1933 | Blanchard |
| 2,103,693 | A | 12/1937 | Ernst |
| 2,188,592 | A | 1/1940 | Hosken |
| 2,261,297 | A | 11/1941 | Anthony |
| 2,337,505 | A | 12/1942 | Swift |
| 2,452,816 | A | 11/1948 | Wagner |
| 2,509,086 | A | 5/1950 | Eaton |
| 2,613,371 | A | 10/1952 | Keyes |
| 2,636,793 | A | 4/1953 | Mayer |
| 2,667,169 | A | 1/1954 | Kambourakis |
| 2,688,410 | A | 9/1954 | Nelson |
| 2,691,979 | A | 10/1954 | Watson |
| 2,764,150 | A | 9/1956 | Ettinger |
| 2,792,945 | A | 5/1957 | Brenny |
| 2,803,022 | A | 8/1957 | Wyhnkoop |
| 2,880,720 | A | 4/1959 | Houghtaling |
| 2,935,286 | A | 5/1960 | Skelt |
| 3,046,071 | A | 7/1962 | Shampaine et al. |
| 3,046,072 | A | 7/1962 | Douglass, Jr. et al. |
| 3,049,726 | A | 8/1962 | Getz |
| 3,090,381 | A | 5/1963 | Watson |
| 3,099,441 | A | 7/1963 | Frederuck |
| 3,188,079 | A | 6/1965 | Boetcker et al. |
| 3,226,734 | A | 3/1966 | Coventon |
| 3,238,539 | A | 3/1966 | Koch |
| 3,281,141 | A | 10/1966 | Smiley et al. |
| 3,286,707 | A | 11/1966 | Shafer |
| 3,302,218 | A | 2/1967 | Stryker |
| 3,388,700 | A | 6/1968 | Kindle |
| 3,428,307 | A | 2/1969 | Hunter et al. |
| 3,434,165 | A | 3/1969 | Keane |
| 3,584,321 | A | 6/1971 | Buchanan |
| 3,599,964 | A | 8/1971 | Magni |
| 3,640,416 | A | 2/1972 | Temple |
| 3,652,851 | A | 3/1972 | Zaalberg |
| 3,739,406 | A | 6/1973 | Koetter |
| 3,745,996 | A | 7/1973 | Rush, Sr. |
| 3,751,028 | A | 8/1973 | Scheininger et al. |
| 3,766,384 | A | 10/1973 | Anderson |
| 3,795,018 | A | 3/1974 | Breaded |
| 3,814,414 | A | 6/1974 | Chapa |
| 3,827,089 | A | 8/1974 | Grow |
| 3,828,377 | A | 8/1974 | Fary, Sr. |
| 3,832,742 | A | 9/1974 | Stryker |
| 3,859,982 | A | 1/1975 | Dove |
| 3,873,061 | A | 3/1975 | Smith |
| 3,890,668 | A | 6/1975 | Stosberg et al. |
| 3,895,403 | A | 7/1975 | Davis |
| 3,930,548 | A | 1/1976 | Wallraff |
| 3,946,452 | A | 3/1976 | Eery, Sr. |
| 3,947,686 | A | 3/1976 | Cooper et al. |
| 3,949,983 | A | 4/1976 | Tommasino |
| 3,988,790 | A | 11/1976 | Mracek et al. |
| 4,018,412 | A | 4/1977 | Kees, Jr. et al. |
| 4,054,282 | A | 10/1977 | Hamer |
| 4,071,916 | A | 2/1978 | Nelson |
| 4,101,120 | A | 7/1978 | Seshima |
| 4,108,426 | A | 8/1978 | Lindstroem et al. |
| 4,131,802 | A | 12/1978 | Braden et al. |
| 4,139,917 | A | 2/1979 | Fenwick |
| 4,143,652 | A | 3/1979 | Meier et al. |
| 4,144,880 | A | 3/1979 | Daniels |
| 4,175,550 | A | 11/1979 | Leininger et al. |
| 4,186,917 | A | 2/1980 | Rais et al. |
| 4,205,413 | A | 6/1980 | Collignon et al. |
| 4,225,125 | A | 9/1980 | Lee |
| 4,227,269 | A | 10/1980 | Johnston |
| 4,239,039 | A | 12/1980 | Thompson |
| 4,244,358 | A | 1/1981 | Pyers |
| 4,248,445 | A | 2/1981 | Vassar |
| 4,257,407 | A | 3/1981 | Macchi |
| 4,355,631 | A | 10/1982 | LeVahn |
| 4,356,577 | A | 11/1982 | Taylor et al. |
| 4,383,351 | A | 5/1983 | Fenwick |
| 4,384,378 | A | 5/1983 | Getz et al. |
| 4,398,707 | A | 8/1983 | Cloward |
| 4,459,712 | A | 7/1984 | Pathan |
| 4,474,364 | A | 10/1984 | Brendgord |
| 4,484,911 | A | 11/1984 | Berlin et al. |
| 4,487,523 | A | 12/1984 | Monroe |
| 4,503,844 | A | 3/1985 | Siczek |
| 4,506,872 | A | 3/1985 | Westerberg et al. |
| 4,526,355 | A | 7/1985 | Moore et al. |
| 4,545,571 | A | 10/1985 | Chambron |
| 4,552,346 | A | 11/1985 | Schnelle et al. |
| 4,579,111 | A | 4/1986 | Ledesma |
| 4,583,725 | A | 4/1986 | Arnold |
| 4,658,450 | A | 4/1987 | Thompson |
| 4,667,365 | A | 5/1987 | Martinek |
| 4,671,728 | A | 6/1987 | Clark et al. |
| 4,712,781 | A | 12/1987 | Watanabe |
| 4,729,535 | A | 3/1988 | Frazier et al. |
| 4,730,606 | A | 3/1988 | Leininger |
| 4,763,643 | A | 8/1988 | Vrzalik |
| 4,771,785 | A | 9/1988 | Duer |
| 4,827,541 | A | 5/1989 | Vollman et al. |
| 4,840,362 | A | 6/1989 | Bremer et al. |
| 4,840,363 | A | 6/1989 | McConnell |
| 4,850,775 | A | 7/1989 | Lee et al. |
| 4,852,840 | A | 8/1989 | Marks |
| 4,856,128 | A | 8/1989 | Alsip et al. |
| 4,866,796 | A | 9/1989 | Robinson et al. |
| 4,868,937 | A | 9/1989 | Connolly |
| 4,872,657 | A | 10/1989 | Lüssi |
| 4,887,325 | A | 12/1989 | Tesch |
| 4,901,963 | A | 2/1990 | Yoder |
| 4,901,964 | A | 2/1990 | McConnell |
| 4,923,187 | A | 5/1990 | Mombrinie |
| 4,924,537 | A | 5/1990 | Alsip et al. |
| 4,937,901 | A | 7/1990 | Brennan |
| 4,939,801 | A | 7/1990 | Schaael et al. |
| 4,944,054 | A | 7/1990 | Bossert |
| 4,944,500 | A | 7/1990 | Mueller et al. |
| 4,947,496 | A | 8/1990 | Connolly |
| 4,953,245 | A | 9/1990 | Jung |
| 4,970,737 | A | 11/1990 | Sagel |
| 4,971,037 | A | 11/1990 | Pelta |
| 4,989,848 | A | 2/1991 | Monroe |
| 4,998,320 | A | 3/1991 | Lange |
| 5,020,170 | A | 6/1991 | Ruf |
| 5,088,706 | A | 2/1992 | Jackson |
| 5,108,213 | A | 4/1992 | Shields |
| 5,121,892 | A | 6/1992 | Herzog |
| 5,131,106 | A | 7/1992 | Jackson |
| 5,135,210 | A | 8/1992 | Michaelson |
| 5,152,024 | A | 10/1992 | Chrones et al. |
| 5,161,267 | A | 11/1992 | Smith |
| 5,181,289 | A | 1/1993 | Kassai |
| 5,205,601 | A * | 4/1993 | Ferris ...................... A61G 1/06 296/20 |

(56) References Cited

U.S. PATENT DOCUMENTS

| | | |
|---|---|---|
| 5,210,887 A | 5/1993 | Kershaw |
| 5,210,888 A | 5/1993 | Canfield |
| 5,231,741 A | 8/1993 | Maguire |
| 5,239,716 A | 8/1993 | Fisk |
| 5,274,862 A | 1/1994 | Palmer, Jr. et al. |
| 5,276,927 A | 1/1994 | Day |
| 5,287,575 A | 2/1994 | Allen et al. |
| 5,320,444 A | 6/1994 | Bookwaiter et al. |
| 5,333,334 A | 8/1994 | Kassai |
| 5,393,018 A | 2/1995 | Roth et al. |
| 5,400,772 A | 3/1995 | LeVahn et al. |
| 5,404,603 A | 4/1995 | Fukai et al. |
| 5,444,882 A | 8/1995 | Andrews et al. |
| 5,461,740 A | 10/1995 | Pearson |
| 5,483,323 A | 1/1996 | Matsuda et al. |
| 5,487,195 A | 1/1996 | Ray |
| 5,494,386 A * | 2/1996 | Paull ............ A61G 1/06 296/20 |
| 5,499,408 A | 3/1996 | Nix |
| 5,502,853 A | 4/1996 | Singleton et al. |
| 5,503,416 A | 4/1996 | Aoki et al. |
| 5,524,304 A | 6/1996 | Shutes |
| 5,538,215 A | 7/1996 | Hosey |
| 5,544,371 A | 8/1996 | Fuller |
| 5,579,550 A | 12/1996 | Bathrick et al. |
| 5,588,215 A | 12/1996 | Chang |
| 5,613,254 A | 3/1997 | Clayman et al. |
| 5,626,362 A | 5/1997 | Mottola |
| 5,658,315 A | 8/1997 | Lamb et al. |
| 5,673,443 A | 10/1997 | Marmor |
| 5,701,991 A | 12/1997 | Helmetsie |
| 5,737,781 A | 4/1998 | Votel |
| 5,741,210 A | 4/1998 | Dobrovoiny |
| 5,758,374 A | 6/1998 | Ronci |
| 5,778,467 A | 7/1998 | Scott et al. |
| 5,794,286 A | 8/1998 | Scott |
| 5,836,026 A | 11/1998 | Reed |
| 5,836,559 A | 11/1998 | Ronci |
| 5,889,469 A | 3/1999 | Mykytiuk et al. |
| 5,890,238 A | 4/1999 | Votel |
| 5,901,388 A | 5/1999 | Cowan |
| 5,926,871 A | 7/1999 | Howard |
| 5,928,101 A | 7/1999 | Hancock et al. |
| 5,937,456 A | 8/1999 | Norris |
| 5,950,259 A | 9/1999 | Boggs |
| 6,003,174 A | 12/1999 | Kantrowitz et al. |
| 6,035,465 A | 3/2000 | Rogozinski |
| 6,049,923 A | 4/2000 | Ochiai |
| 6,076,525 A | 6/2000 | Hoffman |
| 6,094,760 A | 8/2000 | Nonaka et al. |
| 6,108,838 A | 8/2000 | Comnolly et al. |
| 6,112,349 A | 9/2000 | Connolly |
| 6,120,397 A | 9/2000 | Julian |
| 6,154,901 A | 12/2000 | Carr |
| 6,161,849 A | 12/2000 | Schweninger |
| 6,230,342 B1 | 5/2001 | Haugs |
| 6,260,220 B1 | 7/2001 | Lamb et al. |
| 6,282,736 B1 | 9/2001 | Hand et al. |
| 6,286,164 B1 | 9/2001 | Lamb et al. |
| 6,286,183 B1 | 9/2001 | Stickel et al. |
| 6,295,671 B1 | 10/2001 | Reesby et al. |
| 6,311,349 B1 | 11/2001 | Kazakia et al. |
| 6,315,564 B1 | 11/2001 | Levisman |
| 6,320,510 B2 | 11/2001 | Menkedick et al. |
| 6,324,710 B1 | 12/2001 | Hernandez et al. |
| 6,382,576 B1 | 5/2002 | Heimbrock |
| 6,385,801 B1 | 5/2002 | Watanabe et al. |
| 6,421,854 B1 | 7/2002 | Heimbrock |
| 6,438,777 B1 | 8/2002 | Bender |
| 6,490,737 B1 | 12/2002 | Mazzei et al. |
| 6,496,991 B1 | 12/2002 | Votel |
| 6,499,158 B1 | 12/2002 | Easterling |
| 6,499,160 B2 | 12/2002 | Hand et al. |
| 6,502,669 B1 | 1/2003 | Harris |
| 6,505,365 B1 | 1/2003 | Hanson et al. |
| 6,523,197 B2 | 2/2003 | Zitzmann |
| 6,526,610 B1 | 3/2003 | Hand et al. |
| 6,584,630 B1 | 7/2003 | Dinkier |
| 6,609,260 B2 | 8/2003 | Hand et al. |
| 6,615,430 B2 | 9/2003 | Heimbrock |
| 6,622,324 B2 | 9/2003 | VanSteenburg et al. |
| 6,622,980 B2 | 9/2003 | Boucher et al. |
| 6,634,043 B2 | 10/2003 | Lamb et al. |
| 6,638,299 B2 | 10/2003 | Cox |
| 6,662,388 B2 | 12/2003 | Friel et al. |
| 6,662,391 B2 | 12/2003 | Wilson et al. |
| 6,663,055 B2 | 12/2003 | Boucher et al. |
| 6,668,396 B2 | 12/2003 | Wei |
| 6,668,965 B2 | 12/2003 | Strong |
| 6,671,904 B2 | 1/2004 | Easterling |
| 6,681,423 B2 | 1/2004 | Zachrisson |
| 6,691,347 B2 | 2/2004 | Hand et al. |
| 6,691,350 B2 | 2/2004 | Weismiller |
| 6,701,553 B1 | 3/2004 | Hand et al. |
| 6,701,554 B2 | 3/2004 | Heimbrock |
| 6,721,976 B2 | 4/2004 | Schwaeerle |
| 6,735,794 B1 | 5/2004 | Way et al. |
| 6,754,923 B2 | 6/2004 | Borders et al. |
| 6,813,788 B2 | 11/2004 | Dinkier et al. |
| 6,817,363 B2 | 11/2004 | Biondo et al. |
| 6,854,137 B2 | 2/2005 | Johnson |
| 6,857,144 B1 | 2/2005 | Huang |
| 6,859,967 B2 | 3/2005 | Harrison et al. |
| 6,862,759 B2 | 3/2005 | Hand et al. |
| 6,862,761 B2 | 3/2005 | Hand et al. |
| 6,865,775 B2 | 3/2005 | Ganace |
| 6,874,181 B1 | 4/2005 | Connolly et al. |
| 6,886,199 B1 | 5/2005 | Schwaegerle |
| 6,898,811 B2 | 5/2005 | Zucker et al. |
| 6,912,959 B2 | 7/2005 | Kolody et al. |
| 6,928,676 B1 | 8/2005 | Schwaegerle |
| 6,941,951 B2 | 9/2005 | Hubert et al. |
| 6,951,034 B2 | 10/2005 | Shiery et al. |
| 6,966,081 B1 | 11/2005 | Sharps et al. |
| 6,971,997 B1 | 12/2005 | Ryan et al. |
| 6,986,179 B2 | 1/2006 | Varadharajulu et al. |
| 7,017,228 B2 | 3/2006 | Silverstein et al. |
| 7,020,917 B1 | 4/2006 | Kolody et al. |
| 7,086,103 B2 | 8/2006 | Barthelt |
| 7,089,612 B2 | 8/2006 | Rocher et al. |
| 7,089,884 B2 | 8/2006 | Wang et al. |
| 7,103,932 B1 | 9/2006 | Kandora |
| 7,137,160 B2 | 11/2006 | Hand et al. |
| 7,152,261 B2 | 12/2006 | Jackson |
| 7,159,695 B2 | 1/2007 | Strong |
| 7,171,709 B2 | 2/2007 | Weismiller |
| 7,197,778 B2 | 4/2007 | Sharps |
| 7,200,892 B2 | 4/2007 | Block et al. |
| 7,216,385 B2 | 5/2007 | Hill |
| 7,234,180 B2 | 6/2007 | Horton et al. |
| 7,290,302 B2 | 11/2007 | Sharps |
| 7,343,635 B2 | 3/2008 | Jackson |
| 7,343,916 B2 | 3/2008 | Biondo et al. |
| 7,496,980 B2 | 3/2009 | Sharps |
| 7,520,007 B2 | 4/2009 | Skripps |
| 7,520,008 B2 | 4/2009 | Wong et al. |
| 7,565,708 B2 | 7/2009 | Jackson |
| 7,600,281 B2 | 10/2009 | Skripps |
| 7,603,731 B2 | 10/2009 | Bradcovich |
| D603,967 S | 11/2009 | Berry et al. |
| 7,653,953 B2 | 2/2010 | Lopez-Sansalvador |
| 7,669,262 B2 | 3/2010 | Skripps et al. |
| 7,681,269 B2 | 3/2010 | Biggie et al. |
| 7,690,059 B2 | 4/2010 | Lemire et al. |
| 7,694,369 B2 | 4/2010 | Hinders et al. |
| 7,739,762 B2 | 6/2010 | Lamb et al. |
| 7,810,185 B2 | 10/2010 | Bürstner et al. |
| 7,882,583 B2 | 2/2011 | Skripps |
| 7,931,607 B2 | 4/2011 | Biondo et al. |
| 7,954,996 B2 | 6/2011 | Boomgaarden et al. |
| 8,006,332 B2 | 8/2011 | Lemire et al. |
| D645,967 S | 9/2011 | Sharps |
| 8,020,227 B2 | 9/2011 | Dimmer et al. |
| 8,042,208 B2 | 10/2011 | Gilbert et al. |

(56) References Cited

U.S. PATENT DOCUMENTS

| | | | |
|---|---|---|---|
| 8,056,163 B2 | 11/2011 | Lemire et al. | |
| 8,060,960 B2 | 11/2011 | Jackson | |
| 8,118,029 B2 | 2/2012 | Gneiting et al. | |
| 8,196,237 B2 | 6/2012 | Herbst et al. | |
| 8,205,297 B2 | 6/2012 | Fallshaw et al. | |
| D663,427 S | 7/2012 | Sharps | |
| D665,912 S | 8/2012 | Skripps | |
| 8,234,730 B2 | 8/2012 | Skripps | |
| 8,234,731 B2 | 8/2012 | Skripps | |
| 8,256,050 B2 | 9/2012 | Wong et al. | |
| 8,286,283 B2 | 10/2012 | Copeland et al. | |
| D676,971 S | 2/2013 | Sharps | |
| 8,381,331 B2 | 2/2013 | Sharps et al. | |
| 8,397,323 B2 | 3/2013 | Skripps et al. | |
| D683,032 S | 5/2013 | Sharps | |
| 8,486,068 B2 | 7/2013 | Starr | |
| 8,555,439 B2 | 10/2013 | Soto et al. | |
| 8,584,281 B2 | 11/2013 | Diel et al. | |
| 8,590,074 B2 | 11/2013 | Hornbach et al. | |
| 8,635,725 B2 | 1/2014 | Tannoury et al. | |
| 8,676,293 B2 | 3/2014 | Breen et al. | |
| 8,677,529 B2 | 3/2014 | Jackson | |
| 8,707,476 B2 | 4/2014 | Sharps | |
| 8,707,484 B2 | 4/2014 | Jackson et al. | |
| 8,719,979 B2 | 5/2014 | Jackson | |
| 8,732,876 B2 | 5/2014 | Lachenbrch et al. | |
| 8,763,178 B1 | 7/2014 | Martin et al. | |
| 8,777,878 B2 | 7/2014 | Deitz | |
| 8,782,832 B2 | 7/2014 | Blyakher et al. | |
| 8,806,679 B2 | 8/2014 | Soto et al. | |
| 8,826,474 B2 | 9/2014 | Jackson | |
| 8,826,475 B2 | 9/2014 | Jackson | |
| 8,833,707 B2 | 9/2014 | Steinberg et al. | |
| 8,839,471 B2 | 9/2014 | Jackson | |
| 8,844,077 B2 | 9/2014 | Jackson et al. | |
| 8,845,264 B2 | 9/2014 | Kubiak et al. | |
| 8,856,986 B2 | 10/2014 | Jackson | |
| 8,864,205 B2 | 10/2014 | Lemire et al. | |
| 8,893,333 B2 | 11/2014 | Soto et al. | |
| D720,076 S | 12/2014 | Sharps et al. | |
| 8,938,826 B2 | 1/2015 | Jackson | |
| 8,978,180 B2 | 3/2015 | Jackson | |
| 8,997,286 B2 | 4/2015 | Wyslucha et al. | |
| 9,072,646 B2 * | 7/2015 | Skripps | A61G 13/1245 |
| 9,180,062 B2 | 11/2015 | Jackson | |
| 9,205,013 B2 | 12/2015 | Jackson | |
| 9,211,223 B2 | 12/2015 | Jackson | |
| 9,233,037 B2 | 1/2016 | Sharps et al. | |
| 9,289,342 B2 | 3/2016 | Jackson | |
| 9,295,433 B2 | 3/2016 | Jackson et al. | |
| 9,308,145 B2 | 4/2016 | Jackson | |
| 9,339,430 B2 | 5/2016 | Jackson et al. | |
| 9,364,380 B2 | 6/2016 | Jackson | |
| 9,498,397 B2 | 11/2016 | Hight et al. | |
| 9,561,145 B2 | 2/2017 | Jackson et al. | |
| 9,572,734 B2 | 2/2017 | Jackson et al. | |
| 9,687,399 B2 | 6/2017 | Jackson et al. | |
| 9,700,476 B2 * | 7/2017 | Hoel | A61G 13/104 |
| 9,757,299 B2 | 9/2017 | Hight et al. | |
| 9,877,883 B2 | 1/2018 | Jackson et al. | |
| 9,968,503 B2 | 5/2018 | Hight et al. | |
| 2002/0138906 A1 | 10/2002 | Bartlett et al. | |
| 2004/0123389 A1 | 7/2004 | Boucher et al. | |
| 2004/0133983 A1 | 7/2004 | Newkirk et al. | |
| 2006/0010643 A1 | 1/2006 | Hombach et al. | |
| 2006/0185091 A1 | 8/2006 | Jackson | |
| 2007/0174965 A1 | 8/2007 | Lemire et al. | |
| 2010/0293713 A1 * | 11/2010 | Sharps | A61G 13/04 5/86.1 |
| 2011/0247903 A1 | 10/2011 | Boukhny et al. | |
| 2012/0198625 A1 | 8/2012 | Jackson | |
| 2013/0096701 A1 | 4/2013 | Suorajaervi et al. | |
| 2013/0111666 A1 | 5/2013 | Jackson | |
| 2013/0205500 A1 | 8/2013 | Jackson | |
| 2013/0219623 A1 | 8/2013 | Jackson | |
| 2013/0254995 A1 | 10/2013 | Jackson | |
| 2013/0254996 A1 | 10/2013 | Jackson | |
| 2013/0254997 A1 | 10/2013 | Jackson | |
| 2013/0269710 A1 | 10/2013 | Hight et al. | |
| 2013/0312181 A1 | 11/2013 | Jackson et al. | |
| 2013/0312187 A1 | 11/2013 | Jackson | |
| 2013/0312188 A1 | 11/2013 | Jackson | |
| 2013/0326813 A1 | 12/2013 | Jackson | |
| 2014/0007349 A1 | 1/2014 | Jackson | |
| 2014/0020181 A1 | 1/2014 | Jackson | |
| 2014/0033436 A1 | 2/2014 | Jackson | |
| 2014/0068861 A1 | 3/2014 | Jackson et al. | |
| 2014/0082842 A1 | 3/2014 | Jackson | |
| 2014/0109316 A1 | 4/2014 | Jackson et al. | |
| 2014/0173826 A1 | 6/2014 | Jackson | |
| 2014/0196212 A1 | 7/2014 | Jackson | |
| 2014/0201913 A1 | 7/2014 | Jackson | |
| 2014/0201914 A1 | 7/2014 | Jackson | |
| 2014/0208512 A1 | 7/2014 | Jackson | |
| 2014/0317847 A1 | 10/2014 | Jackson | |
| 2015/0059094 A1 | 3/2015 | Jackson | |
| 2015/0150743 A1 | 6/2015 | Jackson | |
| 2015/0245969 A1 | 9/2015 | Hight | |
| 2017/0112698 A1 | 4/2017 | Hight et al. | |
| 2017/0112699 A1 | 4/2017 | Hight et al. | |
| 2017/0202523 A1 | 7/2017 | Jackson | |
| 2017/0209325 A1 | 7/2017 | Jackson et al. | |
| 2017/0348171 A1 | 12/2017 | Jackson | |
| 2017/0354563 A1 | 12/2017 | McKenney et al. | |
| 2018/0147106 A1 * | 5/2018 | Soundararajan | A61G 13/04 |
| 2018/0235823 A1 | 8/2018 | Hight et al. | |
| 2019/0029906 A1 | 1/2019 | Konsin et al. | |

FOREIGN PATENT DOCUMENTS

| | | |
|---|---|---|
| DE | 3438956 C2 | 11/1989 |
| DE | 4039907 A1 | 7/1991 |
| DE | 4429062 C2 | 8/2000 |
| DE | 19723927 C2 | 5/2003 |
| DE | 10158470 A1 | 6/2003 |
| DE | 202008001952 U1 | 5/2008 |
| EP | 617947 B1 | 1/1995 |
| EP | 1210049 A1 | 6/2002 |
| EP | 1686944 A1 | 8/2006 |
| EP | 1159947 B1 | 9/2006 |
| EP | 1982680 B1 | 7/2011 |
| FR | 2247194 B1 | 5/1975 |
| GB | 2210554 B | 6/1989 |
| JP | 2001112582 A | 4/2001 |
| WO | WO 85/00967 A1 | 3/1985 |
| WO | WO 86/00221 A1 | 1/1986 |
| WO | WO 99/53997 A1 | 10/1999 |
| WO | WO 00/62731 A1 | 10/2000 |
| WO | WO 02/05740 A2 | 7/2002 |
| WO | WO 03/096958 A1 | 11/2003 |
| WO | WO2004026212 A1 | 4/2004 |
| WO | WO2006006106 A1 | 1/2006 |
| WO | WO2006061606 A1 | 6/2006 |

OTHER PUBLICATIONS

Extended European Search Report for European Patent Application No. 19159469.6 dated Jun. 28, 2019 (8 pages).

* cited by examiner

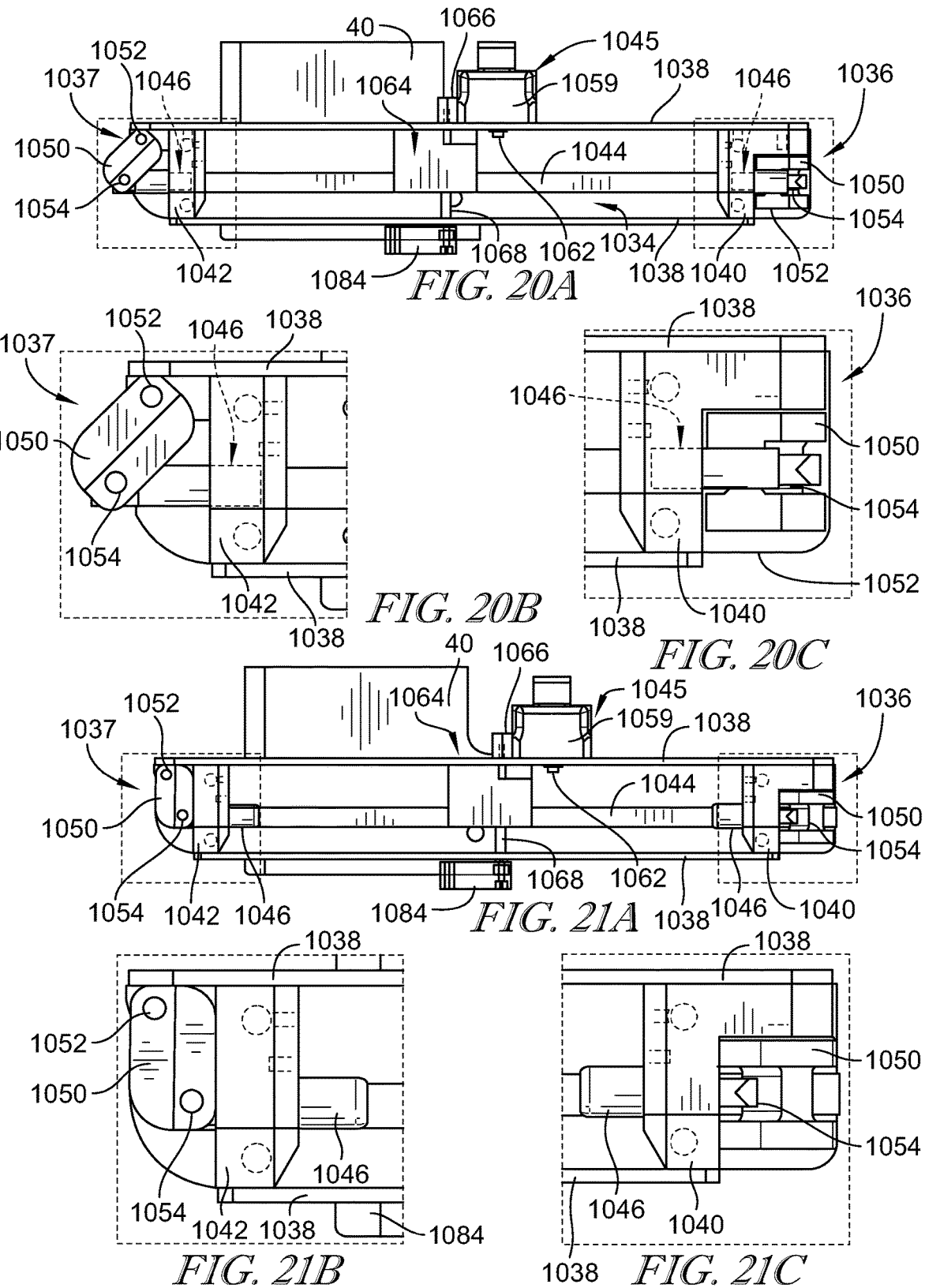

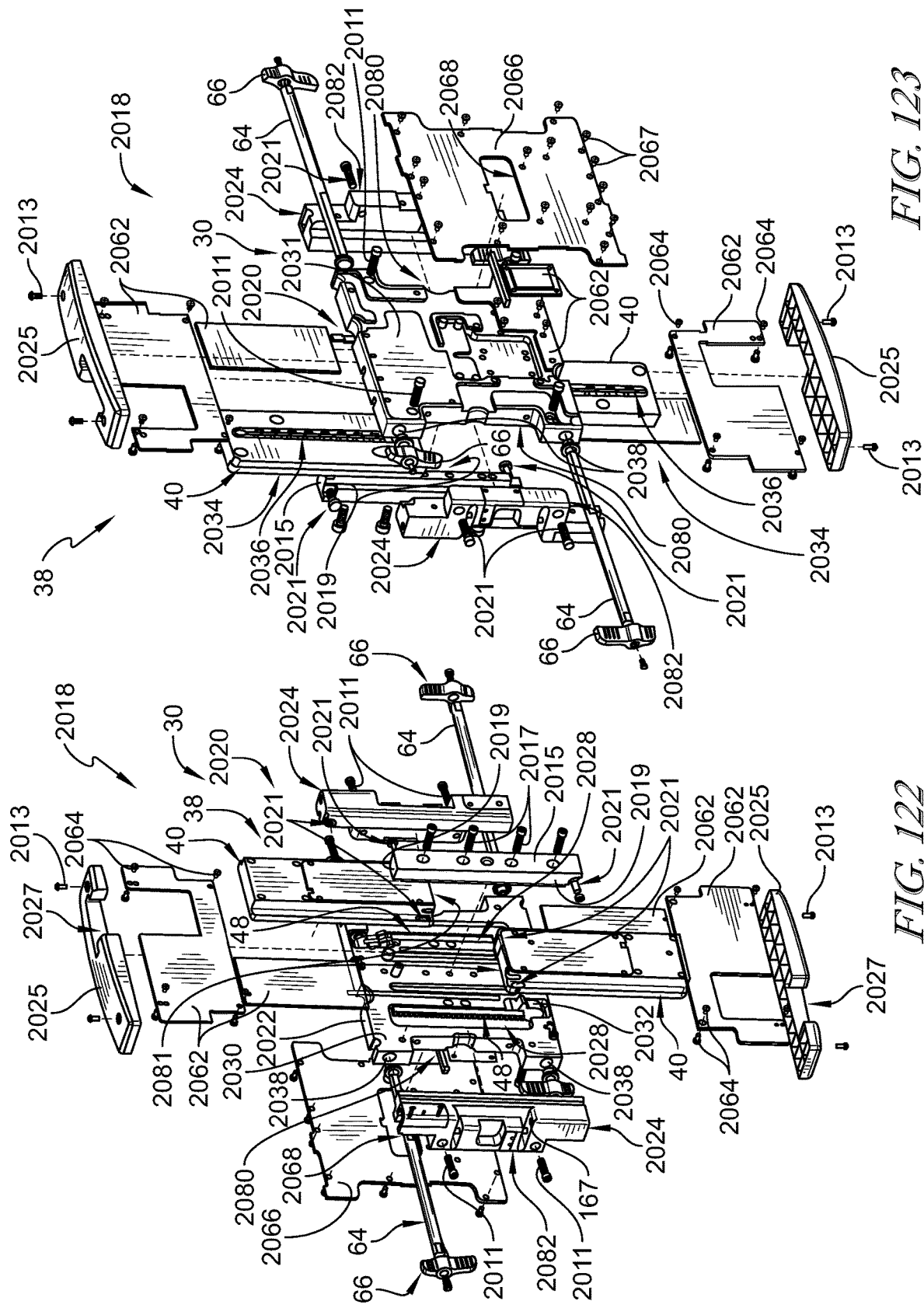

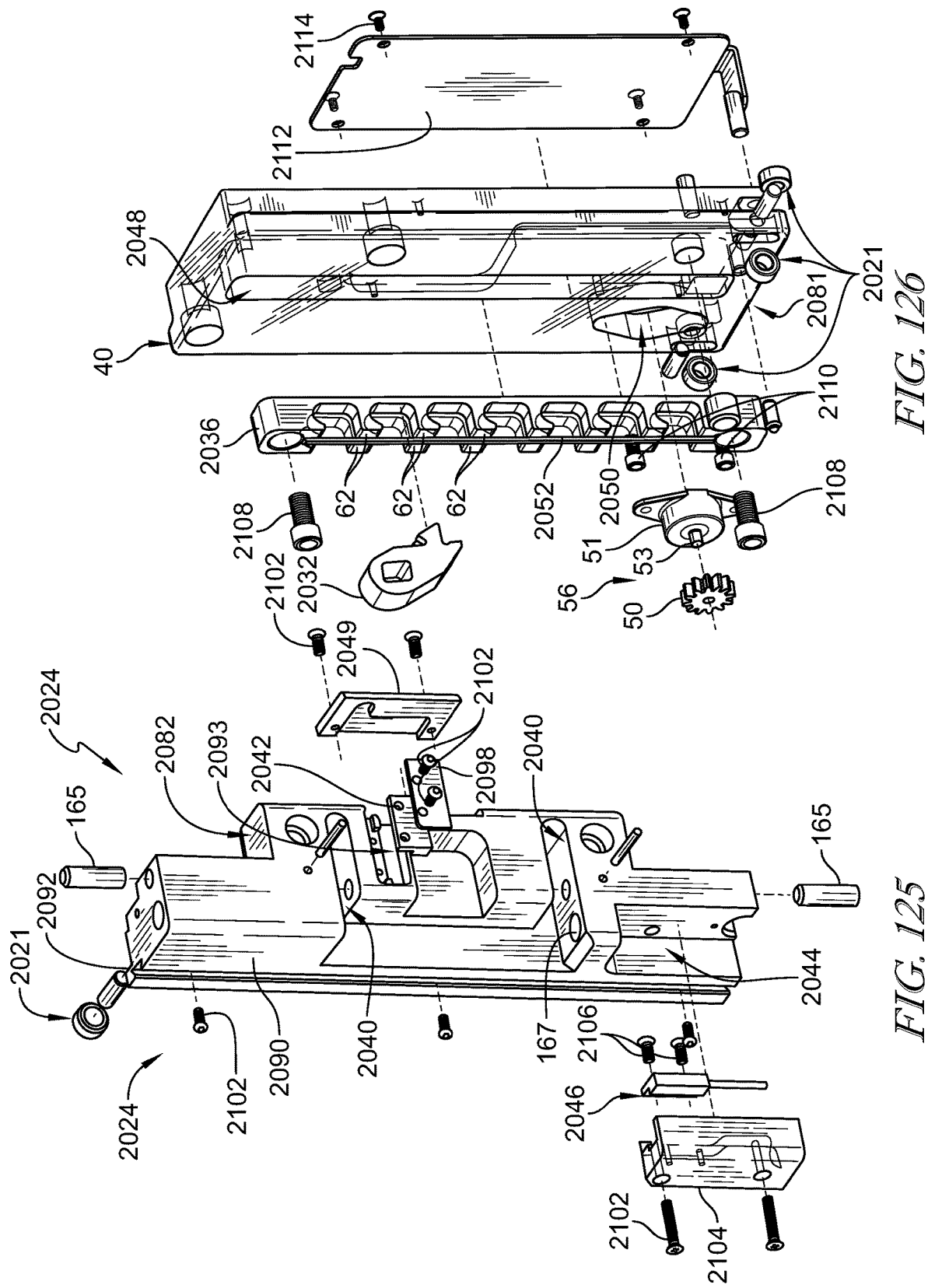

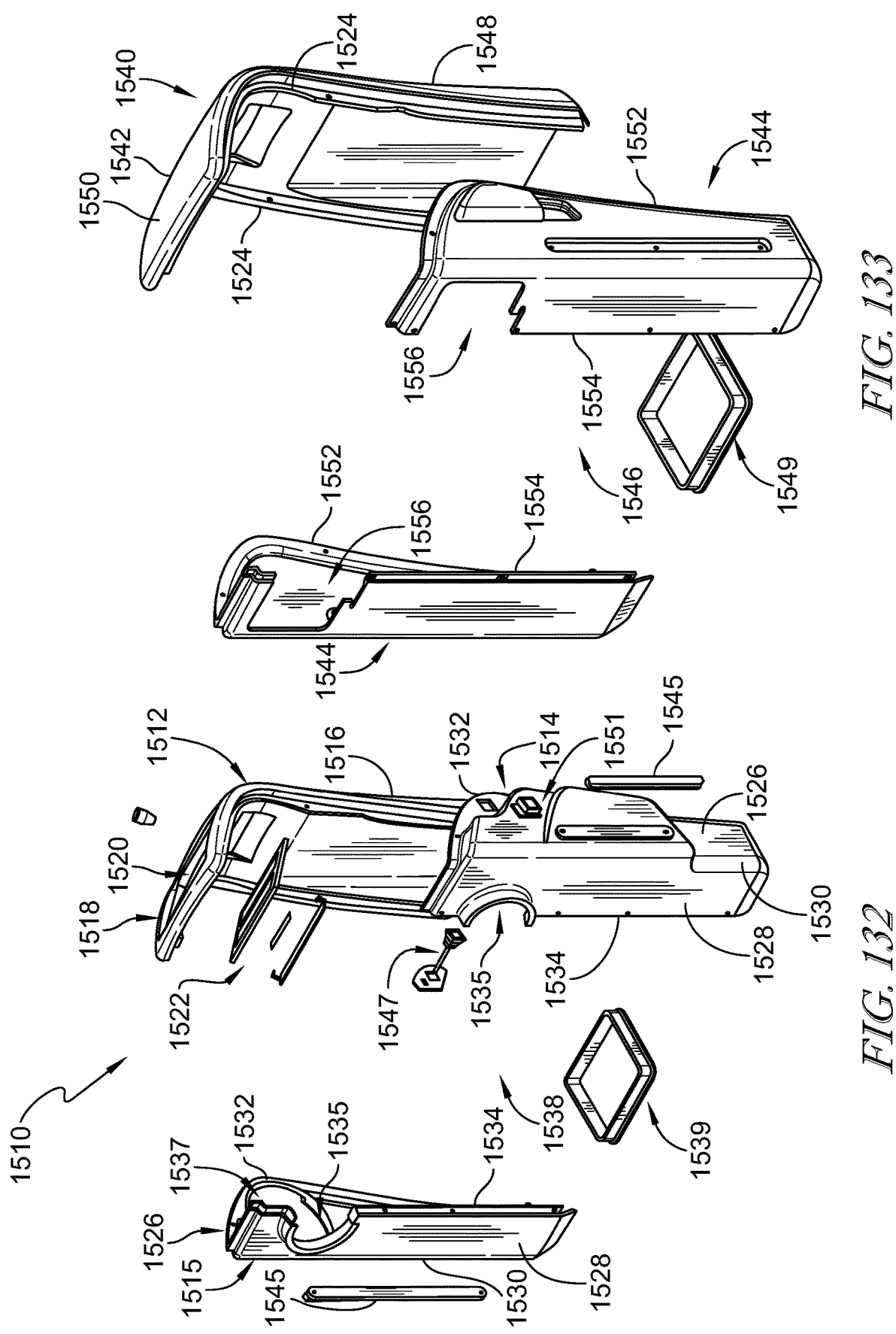

SURGICAL PATIENT SUPPORT AND METHODS THEREOF

CROSS-REFERENCE TO RELATED APPLICATION

This application claims the benefit of priority under 35 U.S.C. § 119(e) to U.S. Provisional Application No. 62/636,563, filed Feb. 28, 2018, which is hereby incorporated by reference in its entirety, including at least those portions related to devices, systems, and methods of patient support.

BACKGROUND

The present disclosure relates to devices, systems, and methods for patient support. More specifically, the present disclosure relates to devices, systems, and methods for surgical patient support.

Patient supports, such as surgical support tables, provide support to various portions of a patient's body. Versatile positioning of table tops of the patient supports provides access to various parts of a patient's body to assist in patient treatment and/or diagnosis. Positioning patient supports should be performed with consideration for the safety and security of the patient while promoting ease of operation to the user.

SUMMARY

The present application discloses one or more of the features recited in the appended claims and/or the following features which, alone or in any combination, may comprise patentable subject matter:

According to an aspect of the present disclosure a patient support device may include at least one patient top for supporting a patient's body above the floor, the at least one patient top including at least one tube connector for receiving support connection, at least one end support for connection with the patient top to support the patient top for selective rotation about a rotation axis, and a connection assembly for selectively connecting the at least one patient support top with the at least one end support. The connection assembly may include at least one docking receiver defining a tube slot for receiving the at least one tube connector. The docking receiver may include a docking gate for selectively blocking against disconnection of the patient top with the at least one end support, the docking gate movable between an unlocked position clear from an entrance of the tube slot and a locked position extending across at least a portion of the entrance to block removal of the at least one tube connector. The entrance of the tube slot may open outwardly from the rotation axis.

In some embodiments, the at least one docking receiver may include at least one end stop defining a receiver slot as at least a portion of the tube slot. The receiver slot may have an opening facing radially outward relative to the rotation axis as part of the entrance of tube slot. The at least one docking receiver may be arranged as a bottom docking receiver and the receiver slot may face downward when the connection assembly is arranged in a level position.

In some embodiments, the docking gate may include at least one gate latch including a body and an arm extending from the body for selective interaction with the tube slot. The arm may extend across the entrance in the locked position to block removal of the tube connector from the tube slot and clear from the entrance in the unlocked position.

In some embodiments, the connection assembly may include a lock pin moveable between a disengaged position permitting movement of the docking gate out from the locked position and an engaged position blocking the docking gate from movement out from the locked position. In the engaged position the lock pin may be inserted into a pin slot of the gate body. In the locked position of the docking gate, the pin slot may be positioned in correspondence with the lock pin. The pin slot may be out of correspondence with the lock pin in positions of the docking gate other than the locked position. In some embodiments, the body may include a wing extending from an interior surface of the pin slot preventing removal of the pin without unloading.

In some embodiments, the lock pin may be concentrically mounted on an actuation rod that is translatable to achieve the engaged and disengaged positions of the lock pin. The actuation rod may include a second lock pin for engagement with a second gate latch of the docking gate. Each of the first and second lock pins may be moveable between engaged and disengaged positions under the movement of the actuation rod.

In some embodiments, the at least one docking receiver may be mounted to a slide assembly for positioning the docking receiver relative to the end support. The slide assembly may include a ratchet assembly for controlled positioning of the docking receiver. The slide assembly may include a slide plate having the docking receiver mounted thereon. The slide plate may be translatably connected with a frame of the connection assembly.

In some embodiments, the ratchet assembly may include a first portion mounted on the frame and a second portion mounted on the slide plate. The first and second portions may be arranged for selective engagement with each other to define the position of the slide plate relative to the frame. The first portion of the ratchet assembly may be one of a pawl and a ratchet track and the second portion of the ratchet assembly may be the other of the pawl and the ratchet track. In some embodiments, the first portion may be connected with a handle extending from the frame for engagement by a user's hand. The handle may be operable between a latched position arranging the first portion in engagement with the second portion, and an unlatched position removing the first portion from engagement with the second portion.

In some embodiments, the patient support device may include a position sensor arranged to determine a position of the slide plate relative to the frame. The slide assembly may include another slide plate having another docking receiver to receive connection of another patient top. The another slide plate may be arranged opposite the slide plate for rotating a patient into another position.

In some embodiments, the slide assembly may include a slide plate having the docking receiver mounted thereon, the slide plate translatably connected with a frame of the connection assembly. The slide assembly may include a damper assembly coupled with the slide plate to dampen the movement of the slide plate relative to the frame. In some embodiments, the damper assembly may include a rack portion and a pinion portion engaged with each other to provide a dampening force by their interaction. One of the rack and pinion portions may be secured with the slide plate and the other of the rack and pinion portions may be secured with the frame. The pinion portion may be formed as a gear arranged to provide a dampening rotational force by translation of the slide plate.

In some embodiments, the connection assembly may include a base frame, and the patient support device includes a lateral extension selectively connectible with the base frame to extend laterally from the frame. The lateral extension may include a docking receiver mounted thereon. The docking receiver mounted on the lateral extension may be arranged orthogonal to the at least one docking receiver when the lateral extension is connected with the base frame.

According to another aspect of the present disclosure, a patient support device may include at least one patient top for supporting a patient's body above the floor, the at least one patient top including at least one tube connector for receiving support connection, at least one end support for connection with the patient top to support the patient top for selective rotation about a rotation axis, and a connection assembly for selectively connecting the at least one patient support top with the at least one end support. The connection assembly may include at least one docking receiver defining a tube slot for receiving the at least one tube connector. The docking receiver may include at least one latch pin assembly having a latch pin operable between an unlocked position retracted from the tube slot and a locked position extended into the tube slot for engagement with the at least one tube connector to secure the patient support top with the connection assembly.

In some embodiments, the latch pin may be arranged for insertion into a longitudinal end of the at least one tube connector in the locked position. The at least one latch pin assembly may include a pair of latch pin assemblies, the latch pin of each latch pin assembly arranged for insertion into opposite longitudinal end of the at least one tube connector in their locked positions.

In some embodiments, the pair of latch pin assemblies may be coupled together by a linkage. The linkage may arranged to provide a corresponding configuration of each the latch pins between their locked and unlocked positions. The latch pin assembly may be coupled with a handle for operation between the unlocked and locked positions. The handle may be operable between a disengaged position and an engaged position corresponding respectively with the unlocked and locked positions of the latch pin assembly.

In some embodiments, the latch pin assembly may be coupled with the handle via a linkage comprising a drive shaft that is rotatably and translatably fixed with a strut, and a key shaft coupled with the strut and spaced apart from the drive shaft. The key shaft may be coupled with the handle to transfer movement of the handle to the latch pin assembly.

In some embodiments, the latch pin may be arranged through a key track for guiding movement of the key shaft. The key track may include a travel section for translation of the key shaft to transfer movement of the handle between the disengaged and engaged positions to the latch pin assembly, and a lock section extending at an angle from connection with the travel section. The key shaft may be operable to enter the lock section by pivoting the strut about the drive shaft to block against translation of the strut when the handle is in the engaged position.

According to another aspect of the present disclosure, a connection assembly of a patient support device for receiving a tube connector of a patient top for selective connection of the patient top with an end support of the patient support device for supporting the patient body above the floor for selective rotation about a rotation axis may include a frame adapted for connection with the end support of the patient support device, a slide assembly coupled with the frame and operable for translatable movement relative to the rotation axis, and a docking system including a docking receiver coupled with the slide assembly for selectively translatable positioning relative to the rotational axis. The docking receiver may define a tube slot for receiving the at least one tube connector of the patient top. The docking receiver may include a docking gate for selectively blocking against disconnection of the patient top with the at least one end support. The docking gate may be movable between an unlocked position clear from an entrance of the tube slot and a locked position extending across at least a portion of the entrance to block removal of the at least one tube connector.

In some embodiments, the at least one docking receiver may include at least one end stop defining a receiver slot as at least a portion of the tube slot. The receiver slot may have an opening facing radially outward relative to the rotation axis. In some embodiments, the at least one docking receiver may be arranged as a bottom docking receiver and the receiver slot may face downward when the connection assembly is arranged in a level position.

In some embodiments, the docking gate may include at least one gate latch including a body and an arm extending from the body for selective interaction with the tube slot. The arm may extend across the entrance in the locked position to block removal of the tube connector from the tube slot and may extend clear from the entrance in the unlocked position.

In some embodiments, the connection assembly may include a lock pin moveable between a disengaged position permitting movement of the docking gate out from the locked position and an engaged position blocking the docking gate from movement out from the locked position. In the engaged position the lock pin may be inserted into a pin slot of the gate body. In the locked position of the docking gate, the pin slot may be positioned in correspondence with the lock pin. The pin slot may be out of correspondence with the lock pin in positions of the docking gate other than the locked position.

In some embodiments, the body may include a wing extending from an interior surface of the pin slot preventing removal of the pin without unloading. The lock pin may be concentrically mounted on an actuation rod that is translatable to achieve the engaged and disengaged positions of the lock pin. The actuation rod may include a second lock pin for engagement with a second gate latch of the docking gate. Each of the first and second lock pins may be moveable between engaged and disengaged positions under the movement of the actuation rod.

In some embodiments, the at least one docking receiver may be mounted to a slide assembly for positioning the docking receiver relative to the end support. The slide assembly may include a ratchet assembly for controlled positioning of the docking receiver. In some embodiments, the slide assembly may include a slide plate having the docking receiver mounted thereon. The slide plate may be translatably connected with a frame of the connection assembly. The ratchet assembly may include a first portion mounted on the frame and a second portion mounted on the slide plate. The first and second portions may be arranged for selective engagement with each other to define the position of the slide plate relative to the frame.

In some embodiments, the first portion of the ratchet assembly may be one of a pawl and a ratchet track and the second portion of the ratchet assembly may be the other of the pawl and the ratchet track. The first portion may be connected with a handle extending from the frame for engagement by a user's hand. The handle may be operable between a latched position arranging the first portion in engagement with the second portion, and an unlatched position removing the first portion from engagement with the second portion.

In some embodiments, the patient support device may include a position sensor arranged to determine a position of the slide plate relative to the frame. The slide assembly may include another slide plate having another docking receiver to receive connection of another patient top. The another slide plate may be arranged opposite the slide plate for rotating a patient into another position.

In some embodiments, the slide assembly may include a slide plate having the docking receiver mounted thereon. The slide plate may be translatably connected with a frame of the connection assembly. The slide assembly may include a damper assembly coupled with the slide plate to dampen the movement of the slide plate relative to the frame.

In some embodiments, the damper assembly may include a rack portion and a pinion portion engaged with each other to provide a dampening force by their interaction. One of the rack and pinion portions may be secured with the slide plate and the other of the rack and pinion portions may be secured with the frame. The pinion portion may be formed as a gear arranged to provide a dampening rotational force by translation of the slide plate.

In some embodiments, the connection assembly may include a base frame. The patient support device may include a lateral extension selectively connectible with the base frame to extend laterally from the frame. The lateral extension may include a docking receiver mounted thereon. The docking receiver mounted on the lateral extension may be arranged orthogonal to the at least one docking receiver when the lateral extension is connected with the base frame.

According to another aspect of the present disclosure, a patient support assembly for connection with a tube connector of at least one patient top for supporting a patient's body above the floor may include at least one support tower for supporting the at least one patient top above the floor for selective rotation about a rotation axis, a connection assembly secured with the at least one support tower for selectively connecting with the tube connector of the at least one patient top, and a user interface adapted to display a 3-dimensional depiction of the patient support assembly.

In some embodiments, the user interface may be operable to indicate that an acceptable clearance height of the at least one patient top above the floor has been reached to permit selective rotation of the at least one patient top about the rotation axis. In some embodiments, the patient support assembly may include a controller adapted to detect the type of the at least one patient support top connected with the connection assembly. In some embodiments, the user interface may be configured to display the type of the at least one patient support top connected with the connection assembly. The type of the at least one patient support top connected with the connection assembly may be selected from a group comprising: a supine top, a lateral top, and a prone top. In some embodiments, the 3-dimensional depiction may include representation of the user interface.

In some embodiments, the 3-dimensional depiction of the patient support assembly may include representation of the arrangement of the patient support assembly corresponding with an actual arrangement of the patient support assembly. In some embodiments, the 3-dimensional depiction of the patient support assembly may include representation of the arrangement of the patient support assembly to have an angle of Trendelenburg inclination corresponding with an actual angle of Trendelenburg inclination of the patient support assembly. In some embodiments, the 3-dimensional depiction of the patient support assembly may include representation of the arrangement of the patient support assembly to have an angle of tilt corresponding with an actual angle of tilt of the patient support assembly. In some embodiments, the 3-dimensional depiction of the patient support assembly may include representation of the arrangement of the patient support assembly to have a height of the at least one end support corresponding with an actual height of the at least one end support of the patient support assembly. In some embodiments, the 3-dimensional depiction of the patient support assembly may include representation of the arrangement of the patient support assembly to have an amount of extension of a slide plate of the connection assembly corresponding with an actual amount of extension of the slide plate of the connection assembly of the patient support assembly. In some embodiments, the 3-dimensional depiction of the patient support assembly may include representation of the arrangement of the patient support assembly to have an amount of leg drop of the at least one patient support top corresponding with an actual amount of the at least one patient support top of the patient support assembly.

In some embodiments, the user interface may be adapted to display an indication of a desired angle of Trendelenburg inclination together with the depiction of 3-dimensional depiction of the patient support assembly. In some embodiments, the user interface may be adapted to display an indication of a desired angle of tilt together with the depiction of 3-dimensional depiction of the patient support assembly. In some embodiments, the user interface may be adapted to display an indication of a desired height of the at least one end support together with the depiction of 3-dimensional depiction of the patient support assembly. In some embodiments, the user interface may adapted to display an indication of a desired amount of extension of a slide plate of the connection assembly together with the depiction of 3-dimensional depiction of the patient support assembly.

In some embodiments, the 3-dimensional depiction of the patient support assembly may include at least one of: an angle of Trendelenburg inclination corresponding with an actual angle of Trendelenburg inclination, an angle of tilt corresponding with an actual angle of tilt, a height of the at least one end support corresponding with an actual height, and an amount of extension of a slide plate of the connection assembly corresponding with an actual amount of extension of the slide plate of the connection assembly of the patient support assembly.

In some embodiments, the user interface may be configured to display a warning indicating that the arrangement of the patient support assembly is incompatible with particular operations. The particular operations may include rotation of the at least one patient support top about the rotation axis. The user interface may configured to display the warning responsive to the arrangement of the patient support assembly including at least of one of: an angle of Trendelenburg inclination other than zero, a height of the at least one end support below a threshold height, an angle of tilt other than zero, a disengagement of a lock mechanism of the connection assembly to permit flip rotation the at least one patient support top about the rotation axis. In some embodiments, the particular operations may include lateral leg drop of a leg section of the at least one patient support top and the user interface is configured to display the warning responsive to the arrangement of the patient support assembly including at least of one of: an angle of Trendelenburg inclination other than zero, a height of the at least one end support below a threshold height, an angle of tilt other than zero, disengagement of a lock mechanism of the connection assembly to permit flip rotation about the rotation axis.

In some embodiments, the patient support assembly may include a detector adapted to detect as an input an indication of a type of support top of the at least one support top. The detector includes at least one reed switch.

In some embodiments, the patient support assembly may include at least one detector adapted to detect as an input an indication of at least one of: an angle of Trendelenburg inclination, a height of the at least one end support, an amount of extension of a slide plate of the docking assembly, an angle of tilt, a disengagement of a lock mechanism of the connection assembly to permit flip rotation the at least one patient support top about the rotation axis, a type of support top of the at least one support top, a presence of the tube connector in a receiver of the docking assembly, a presence of a lateral extension connected with the connection assembly, and a correct securement of the lateral extension with the connection assembly.

In some embodiments, the user interface may be configured to display a menu of preset positions for selection by the user to adjust the patient support assembly to corresponding predetermined configurations responsive to the execution by the user of the selected one of the preset positions. The menu of preset positions for selection by the user may include at least one of a preset operating position, a preset imaging position, and another preset imaging position.

In some embodiments, the user interface may be adapted to display an indication of the configuration of the patient support assembly corresponding to an active one of the number of preset positions together with the depiction of 3-dimensional depiction of the patient support assembly. The indication of the configuration of the patient support assembly corresponding to the active one of the preset positions may be a transparent overlay of at least a portion of the patient support assembly in the active one of the preset positions together with the depiction of 3-dimensional depiction of the patient support assembly. In some embodiments, the patient support assembly may include a control system in communication with at least one sensor for communicating the actual arrangement of the patient support assembly.

According to another aspect of the present disclosure, a connection assembly of a patient support device for receiving a tube connector of a patient top for selective connection of the patient top with an end support of the patient support device for supporting the patient body above the floor for selective rotation about a rotation axis may include a frame adapted for connection with the end support of the patient support device, a slide assembly coupled with the frame and operable for translatable movement relative to the rotation axis, and a docking system including docking receiver coupled with the slide assembly for selective translatable positioning relative to the rotational axis. The docking receiver may define a tube slot for receiving the at least one tube connector of the patient top, and a latch pin system for selectively blocking against disconnection of the patient top with the frame. The latch pin system may include at least one latch pin movable between an engaged position extending into the tube slot and a disengaged position clear from the tube slot.

In some embodiments, in the engaged position the at least one latch pin may extend into the docking slot for insertion within an end of the tube connector to block against removal of the tube connector from the docking slot. The docking assembly may include an operational handle adapted for engagement with a user's hand and operable between engaged and disengaged positions corresponding to the positions of the latch pin assembly. The operational handle may be coupled with the latch pin assembly to allow positioning of the latch pin assembly. In some embodiments, the operational handle may include a trigger operable between a locked position restricting movement of the operational handle and an unlocked position allowing movement of the operational handle between the engaged and disengaged position to allow positioning of the latch pin assembly.

In some embodiments, the trigger may be engaged with an L-shaped track. The L-shaped track may have a first section extending in a first direction for allowing selective movement of the trigger between the locked and unlocked positions, and a second section extending in a second direction for allowing translation of the operational handle while the trigger is in the unlocked position.

According to another aspect of the present disclosure, a patient support device may include at least one patient top for supporting a patient's body above the floor, at least one end support for connection with the patient top to support the patient top for selective rotation about a rotation axis, and a caster system coupled with the at least one end support. The caster system may include at least one rolling wheel for rolling the patient support device across the floor. The caster system may include an actuator coupled with a braking assembly to selectively operate the braking assembly between a brake mode blocking against rolling of the at least one wheel and a release mode permitting rolling of the at least one wheel. The caster system may include an actuation handle coupled with the braking assembly and operable between a rest position and a release position to provide manual operation of the braking assembly into the release mode. The actuation handle may be out of communication with the braking assembly in the brake mode.

In some embodiments, the actuation handle may be coupled with the braking assembly by a rotation shaft rotatable between a locked position to operate the braking assembly into the brake mode and an unlocked position to operate the braking assembly into the release mode. The actuation handle may include at least one tooth arranged for selective engagement with at least one tooth of the rotation shaft to rotate the shaft between the locked position and the unlocked position. The at least one tooth of the actuation handle and the shaft may be arranged spaced apart from each other to permit engagement only to rotate the shaft in one direction towards the unlocked position. In some embodiments, the at least one tooth of the actuation handle may include a pair of teeth arranged 180 degrees from each other. In some embodiments, the at least one tooth of the rotation shaft may include a pair of teeth arranged 180 degrees from each other. In some embodiments, the actuator may be an electrical actuator.

According to another aspect of the present disclosure, a caster system for coupling with the at least one end support of a patient support may include at least one rolling wheel for rolling the patient support across the floor, a braking assembly including a brake element that selectively positionable between a brake position engaging a braking element of at least one rolling wheel to block against rolling of the at least one wheel and a release position disengaged from the braking element to permit rolling of the at least one wheel, an actuator coupled with the braking assembly to selectively operate the brake element between the brake and release positions, and an actuation handle coupled with the braking assembly. The actuation handle may be operable between a rest position and a release position to provide manual operation of the braking element into the release position. The actuation handle may be out of communication with the braking assembly in the brake position.

In some embodiments, the actuation handle may be coupled with the braking assembly by a rotation shaft rotatable between a locked position to operate the braking assembly into the brake position and an unlocked position to operate the braking assembly into the release position. The actuation handle may include at least one tooth arranged for selective engagement with at least one tooth of the rotation shaft to rotate the shaft between the locked position and the unlocked position. The at least one tooth of the actuation handle and the shaft may be arranged spaced apart from each other to permit engagement only to rotate the shaft in one direction towards the unlocked position. In some embodiments, the at least one tooth of the actuation handle may include a pair of teeth arranged 180 degrees from each other. In some embodiments, the at least one tooth of the rotation shaft may include a pair of teeth arranged 180 degrees from each other. In some embodiments, the actuator may be an electrical actuator.

According to another aspect of the present disclosure, a patient support device may include at least one patient top for supporting a patient's body above the floor, the at least one patient top including at least one tube connector for receiving support connection, at least one end support for connection with the patient top to support the patient top for selective rotation about a rotation axis, and a connection assembly for selectively connecting the at least one patient support top with the at least one end support. The connection assembly may include at least one docking receiver defining a tube slot for receiving the at least one tube connector.

In some embodiments, the at least one docking receiver may be mounted to a slide assembly for positioning the docking receiver relative to the end support. The slide assembly may include a ratchet assembly for controlled positioning of the docking receiver. In some embodiments, the slide assembly may include a slide plate having the docking receiver mounted thereon. The slide plate may be translatably connected with a frame of the connection assembly. The ratchet assembly may include a first portion mounted on the frame and a second portion mounted on the slide plate. The first and second portions may be arranged for selective engagement with each other to define the position of the slide plate relative to the frame.

In some embodiments, the first portion of the ratchet assembly may be one of a pawl and a ratchet track and the second portion of the ratchet assembly is the other of the pawl and the ratchet track. The pawl may be formed as a split pawl having a base and at least two pawl arms, each pawl arm including a pawl head secured to a distal end spaced apart from the base. A gap may be defined between the at least two pawl arms. The ratchet track may be formed as a split track having pairs of ratchet teeth spaced apart from each other by a separation plate.

In some embodiments, the pawl is formed as a split pawl having a base and at least two pawl arms, each pawl arm including a pawl head secured to a distal end spaced apart from the base. The pawl head of each pawl arm may be arranged complimentary with one of the ratchet teeth of each pair. A gap may be defined between the at least two pawl arms to receive the separation plate when the at least two pawl heads are engaged with the pairs of ratchet teeth.

Additional features, which alone or in combination with any other feature(s), including those listed above and those listed in the claims, may comprise patentable subject matter and will become apparent to those skilled in the art upon consideration of the following detailed description of illustrative embodiments exemplifying the best mode of carrying out the invention as presently perceived.

BRIEF DESCRIPTION OF THE DRAWINGS

The detailed description particularly refers to the accompanying figures in which:

FIG. 20A is a bottom plan view of the docking assembly of FIGS. 18 and 19 showing that the latch assembly is in the unlatched position such that the pins are in the unlatched position retracted from the tube slot;

FIG. 20B is an enlarged view of the left hand portion of FIG. 20A showing that a left hand pin is retracted into the unlatched position under the actuation of the latch assembly;

FIG. 20C is an enlarged view of the right hand portion of FIG. 20A showing that a right hand pin is retracted into the unlatched position under the actuation of the latch assembly;

FIG. 21A is a bottom plan view of the docking assembly of FIGS. 18 and 19 showing that the latch assembly is in the latched position such that the pins are in the latched position inserted into the tube slot for engagement with the gimbal tube;

FIG. 21B is an enlarged view of the left hand portion of FIG. 20A showing that a left hand pin is inserted into the latched position under the actuation of the latch assembly to engage the gimbal tube;

FIG. 21C is an enlarged view of the right hand portion of FIG. 20A showing that a right hand pin is inserted into the latched position under the actuation of the latch assembly to engage the gimbal tube;

FIG. 25A is perspective view of a top side of the docking assembly of FIGS. 18 and 19, similar to FIG. 24A, having the handle removed to show a two-step assembly including a pair of pins each inserted within corresponding tracks of the docking assembly, a first pin (left hand pin) extending through a first slot and arranged for pivoting movement, and a second pin (right hand pin, connected with the handle of FIGS. 24A-C) extending through a second slot and arranged for pivoting movement about the first pin by connection with a linkage to the first pin, and showing that the second track includes a translate section in which the second pin is currently arranged to place the latch assembly in the unlatch position, and showing that the second track includes a pivot section extending transverse to the translate section to permit the pin to be rotated in correspondence with the pivot of the first pin;

FIG. 25B is the perspective view of the top side of the docking assembly of FIG. 25A showing that the pins have been slid to the right to an intermediate position to arrange the latch assembly into the latched position but having the second pin remaining in the translation section of the second track permitting movement of the latch assembly out from the locked position;

FIG. 25C is the perspective view of the top side of the docking assembly of FIGS. 25A and 25B showing that the first pin has been rotated and the second pin has been pivoted into the rotation section of the second track, blocking translation of the latch assembly out from the locked position;

FIGS. 122 and 123 are front and rear exploded perspective views, respectively, of a connection assembly similar to the connection assembly of FIG. 3 having certain external portions of the frame removed to reveal the slide assemblies;

FIG. 125 is an exploded perspective view of a side mount for receiving connection by the lateral extension for supporting a prone support top to enable a lateral-to-prone transfer of the patient;

FIG. 126 is an exploded perspective view of a portion of the slide assembly of FIG. 122 showing that a ratchet track is formed as a split track for selective engagement with the pawl to determine the position of the slide assembly;

FIGS. 132 and 133 are exploded perspective view of skins of the head end and foot end tower bases, respectively, showing that the skins form exterior coverings of the tower bases, and showing that the user interface of the head end tower is mounted in the skin for access by the user;

DETAILED DESCRIPTION

Figure 1:
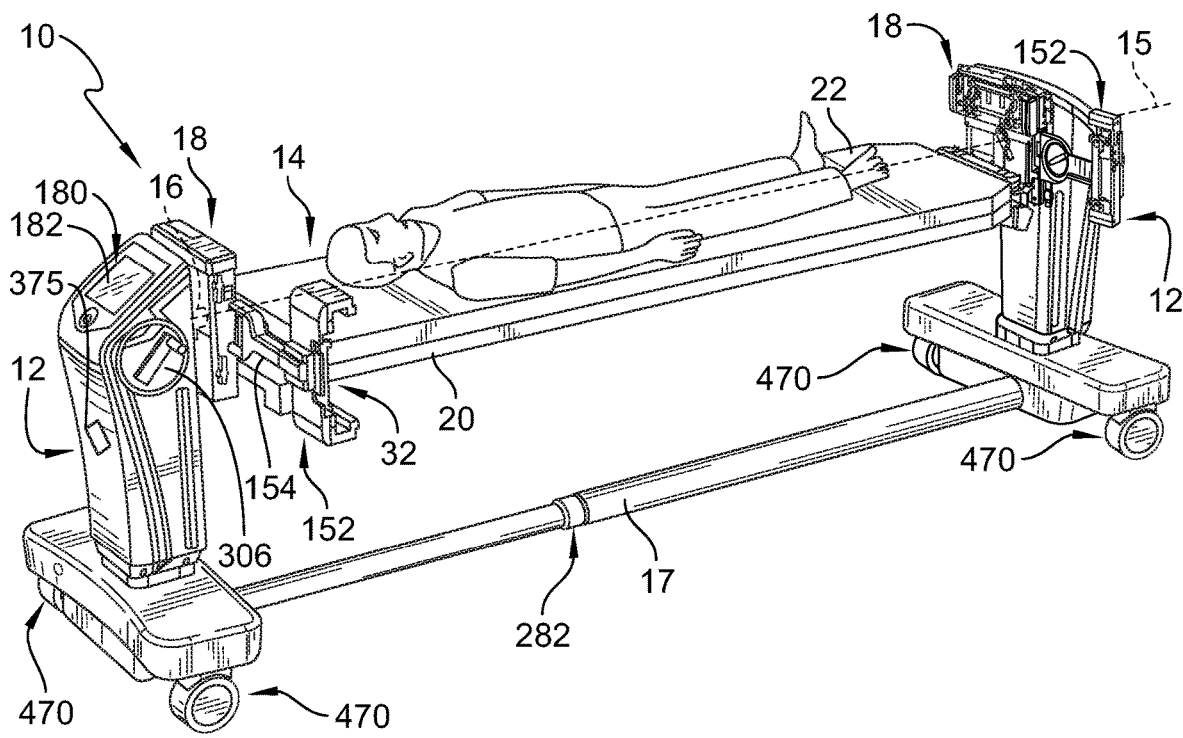
FIG. 1 is a perspective view of a patient support including a pair of end supports formed as tower bases supporting a patient support top above the floor, on which the patient is positioned, for selective rotation about the longitudinal axis of the patient support top, showing that the patient support includes connection assemblies secured to each end support for selective connection with the patient support top, and showing that the head end tower base includes a user interface including a display.

For the purposes of promoting an understanding of the principles of the disclosure, reference will now be made to a number of illustrative embodiments illustrated in the drawings and specific language will be used to describe the same.

In performance of various producers, whether treatment, diagnosis, or otherwise, providing access to patient body areas can be beneficial. For example, in performing surgical procedures, providing surgical access to surgical sites on a patient's body can promote favorable surgical conditions and can increase the opportunity for successful results. Patient support devices can assist in suitably positioning the patient's body in various manners to provide a surgical team with preferred and/or appropriate access to particular surgical sites. Patient supports devices can include patient support tops which are supported above the floor by support structures. Such support structures can provide enhanced maneuverability to assist in positioning the patient's body by permitting selective movement of the patient support top. The safety concerns related to positioning a patient's body can impose complex and/or multi-step processes onto the positioning devices. Ease of operating the positioning devices can reduce user strain, reduce time in positioning, and reduce impact to the patient in obtaining various patient body positions.

In the illustrative embodiment as shown in FIG. 1, a patient support 10 includes a pair of tower bases, such as illustrative elevator tower bases 12, and a patient support top 14 connected at each longitudinal end with one of the tower bases 12. The tower bases 12 illustratively support the patient support top 14 above the floor and are embodied as elevator towers permitting selective vertical extension to adjust the height of the patient support top 14 above the floor. The tower bases 12 are connected with each other via a collapsible cross tube 17. As discussed in additional detail herein, the tower bases 12 illustratively support the patient support top 14 for selective rotation about an axis 15. Rotation of the patient support top 14 about axis 15 can assist in positioning the body of a patient supported on the top 14.

The tower bases 12 each illustratively include a connection rod 16 connected with the support top 14 by a connection assembly 18. Non-limiting examples of acceptable connection bars and connection (coupler) assemblies are disclosed in U.S. Patent Application Publication No. 2013/0269710 to Hight et al., (for example, shaft 112 may form the connection rod 16), the contents of which are hereby incorporated by reference in their entirety, and at least including the descriptions and figures related to yoke brackets and motion couplers and related features disclosed therein. In some embodiments, the patient support top 14 may be connected with the connection rod 16 in any suitable manner. In the illustrative embodiment, the connection rods 16 are illustratively arranged for controlled rotation about the axis 15 to provide rotation to the support top 14. Although generally shown as horizontal, the axis 15 may be selectively inclined by operation of the elevator towers to adjust the height of their respective connection with the patient support top 14.

The patient support top 14 is illustratively embodied as a flat platform including a rail frame 20 having support padding 22 secured thereto. The support top 14 is embodied as adapted for support of a patient in the supine position, including padding 22 arranged accordingly, but in some embodiments, may be adapted for support of a patient in any suitable position. In the illustrative embodiment, the patient support top 14 selectively connects with the connection rod 16 of each tower base 12 via the respective connection assembly 18 for selective rotation about axis 15.

Figure 2:
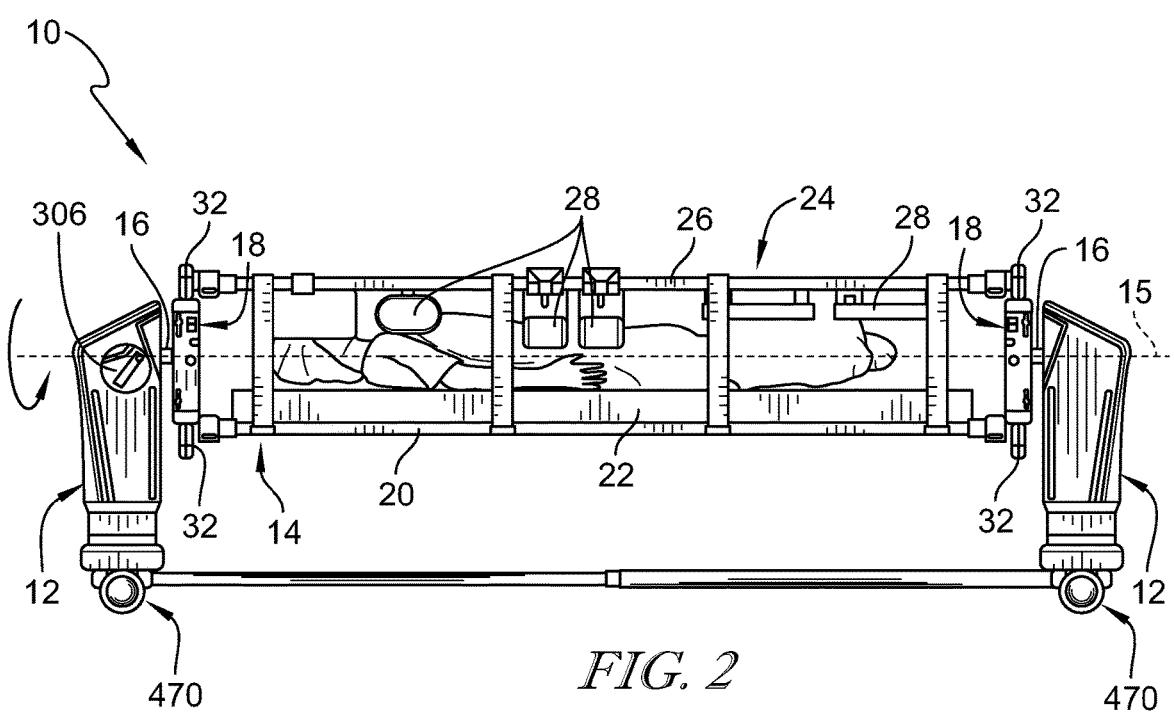
FIG. 2 is a side elevation view of the patient support of FIG. 1 showing that the connection assemblies are each selectively connected with the patient support top (lower) supporting the patient from underneath and another patient support top (upper) that is engaging the patient's front side in preparation for a rotation of the patient about the longitudinal axis from supine to prone position.

As shown in FIG. 2, the patient is supported in a supine position on the support top 14 and another patient support top, embodied as a prone support top 24, is mounted to engage the patient's front. The prone support top 24 is illustratively embodied as an adaptable platform including a rail frame 26 having various support pads 28 secured with the rail frame 26. The prone support top 24 is adapted for engagement with the patient's front to support the patient in the prone position, including pads 28 adapted and arranged accordingly, but in some embodiments, may be adapted for support of a patient in any suitable position. The prone support top 24 is connected with the connection assembly 18 of each tower base 12.

As discussed in additional detail below, each of the patient support tops 14, 24 can be rotated about the axis 15 to transfer the patient into the prone position. The patient support top 14 and the prone support top 24 are each shown simultaneously connected with the connection assemblies 18 to enable a flip rotation of the patient. The patient support tops 14, 24 are illustratively arranged such that the support top 14 contacts one side of the patient's body (backside) and the prone support top 24 contacts another side of the patient's body (frontside). In the illustratively embodiment, the patient support tops 14, 24 are arranged about 180 degrees from each other about axis 15, but may be arranged in any suitable position according to the positioning required for the patient's body. By releasing the connection assemblies 18 for rotation (by unlocking the connection rods 16 as discussed in additional detail herein), the user can rotated the support tops 14, 24 about the axis 15 to transfer the patient into the prone position. The support top 14 can subsequently be removed to provide suitable access to the patient's posterior in the prone position. Although the examples discussed above have illustrated a supine-to-prone transfer, any suitable combination of support tops may be applied to transfer the patient's body between positions.

Figure 3:
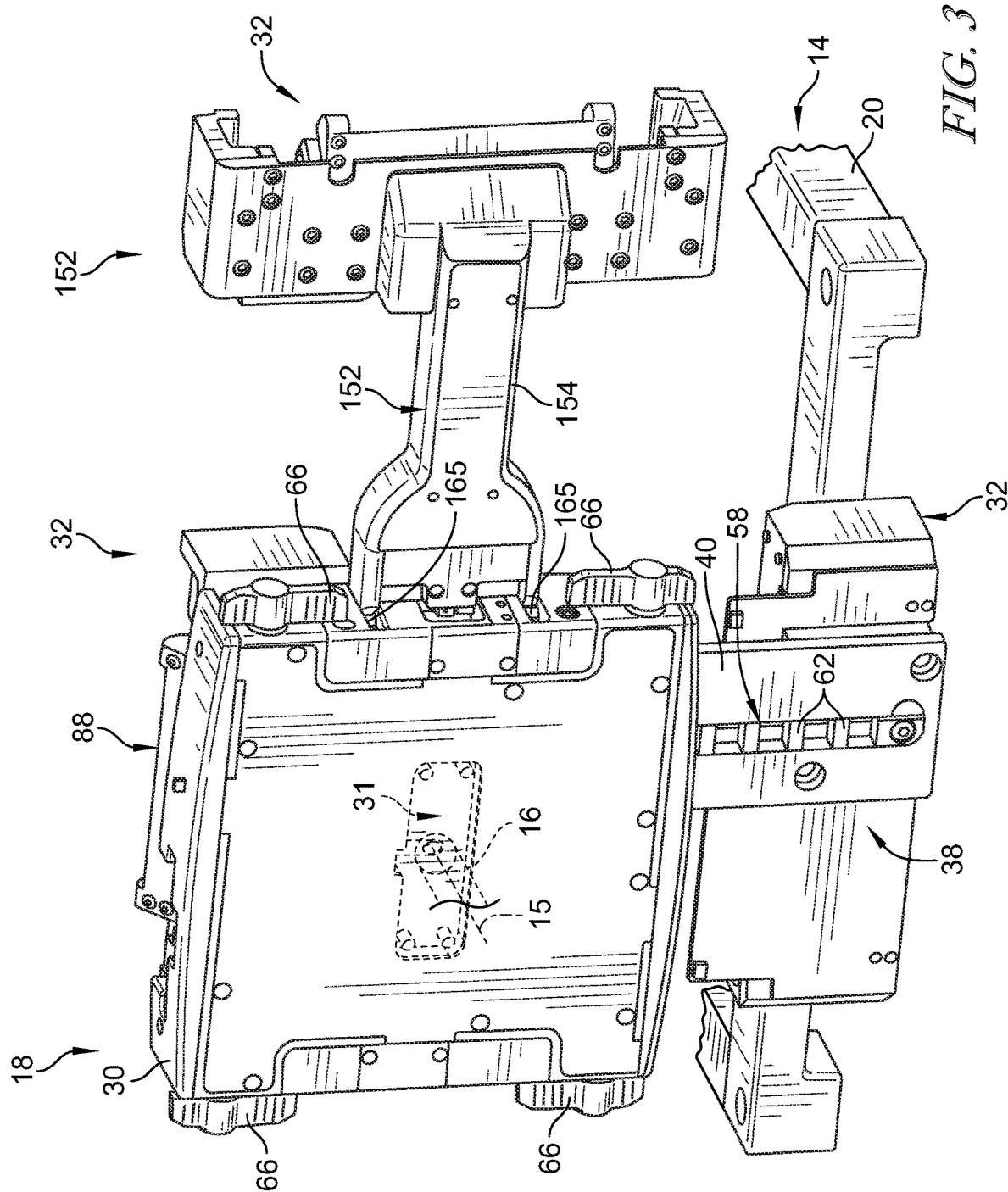
FIG. 3 is a rear perspective view of one connection assembly of the patient support of FIGS. 1 and 2 showing that the connection assembly includes a frame for connection with the tower bases and a pair of slide assemblies (upper and lower) translatably mounted on the frame and each having a docking system mounted thereon for translatable positioning.

In the illustrative embodiment as shown in FIG. 3, the connection assembly 18 is shown from the rear perspective having certain outer portions removed for descriptive purposes. The connection assembly 18 includes a frame 30 having a connector for connection with an adapter 31 (indicated in broken line) of the connection rod 16 of the tower base 12 for fixing the connection assembly 18 for rotation with the connection rod 16. The connection assembly 18 illustratively includes docking receivers 32 adapted for selective connection with the patient support tops 14, 24 to connect the support tops 14, 24 with the tower bases 12.

Figure 4:
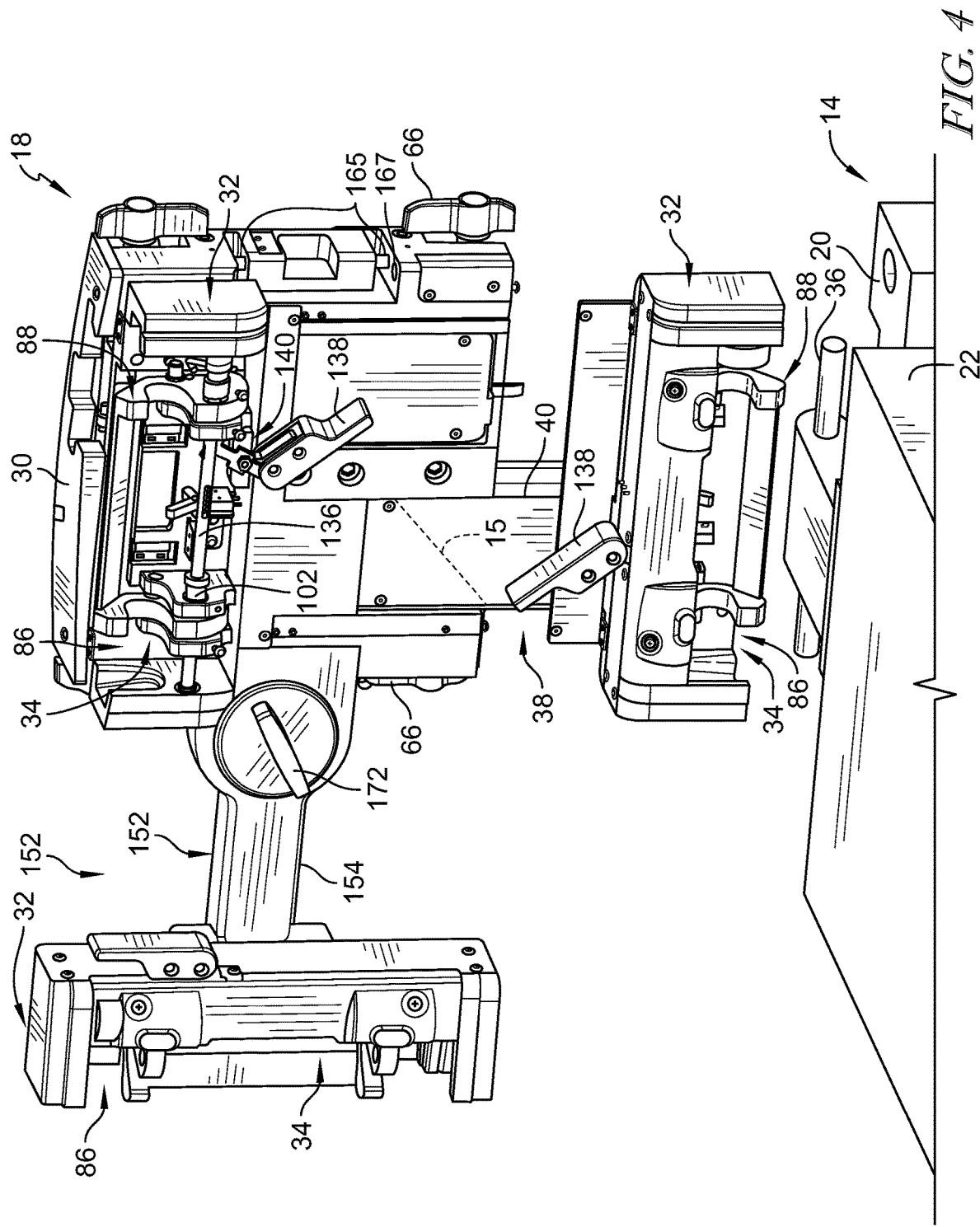
FIG. 4 is a front perspective view of the connection assembly of FIG. 3 having certain external portions of the frame removed to reveal the slide assemblies and showing that the docking systems each include a docking receiver, the upper docking system having an external cover of the docking receiver removed to show a tube slot and showing the patient support top includes a gimbal tube for insertion into the tube slot of the lower docking receiver to secure the patient support top with the connection assembly.

In the illustrative embodiment as shown in FIG. 4, the front of the connection assembly 18 is shown having certain outer portions of the frame 30 removed for descriptive purposes. Upper and lower docking receivers 32 are illustratively positioned opposite each other, for connection with the upper and lower support tops 14, 24. Each docking receiver 32 illustratively defines a docking slot 34 formed to receive a connection tube 36 of the respective patient support top 14, 24. The connection tubes 36 are illustratively embodied as gimbal tubes having limited play to accommodate the movements of the support top. An example of a suitable connection tube includes the gimbal tube disclosed in U.S. Patent Application Publication No. 2013/0269710 to Hight et al., the contents of which are hereby incorporated by reference in their entirety, and at least including the descriptions and figures related to gimbal tubes and related features disclosed therein.

As shown in the illustrative embodiment FIG. 4, the upper and lower docking receivers 32 are illustratively mounted to the frame 30 by a slide assembly 38 for selective translational positioning of the docking receiver 32 relative to the frame 30. The lower docking receiver 32 (in the orientation of FIG. 4) is arranged in an extended position radially outward from the axis 15, while the upper docking receiver 32 (in the orientation of FIG. 4) is arranged in a retracted position relative to the axis 15. The slide assemblies 38 permit selective positioning of their respective docking receivers 32 between retracted and extended positions relative to the axis 15 to provide additional degrees of adjustment to the positioning of attached patient support tops 14, 24.

Figure 5:
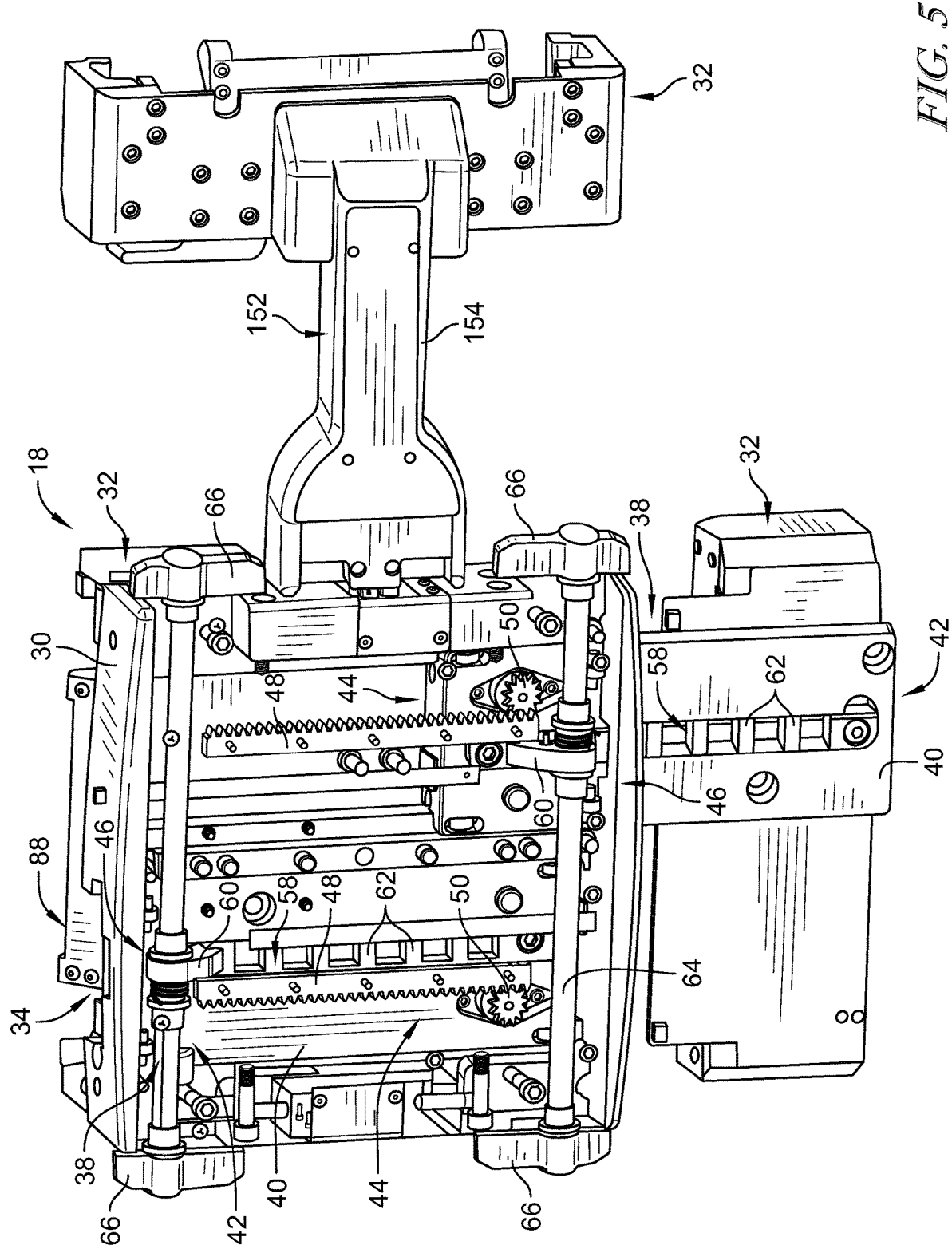
FIG. 5 is a rear perspective view of the connection assembly of FIG. 3 having an outer portion of the frame removed to show that the slide assemblies (upper and lower) each include a slide plate on which their docking system is mounted, the slide plates being selectively translatable between retracted and extended positions by a ratchet system and being dampened for translational movement by a dampening system for comfortable movement.

As shown in FIG. 5, an additional rear portion of the frame 30 is omitted from the connection assembly 18 to reveal the slide assemblies 38. The slide assemblies each include a slide plate 40 that is translatably connected with the frame 30. Each respective docking receiver 32 is secured to its respective slide plate 40 near an end 42 thereof. A dampening assembly 44 softens the movement of the slide plate 40 while the translational position of each slide plate 40 is controlled by a respective ratchet assembly 46.

Figure 6:
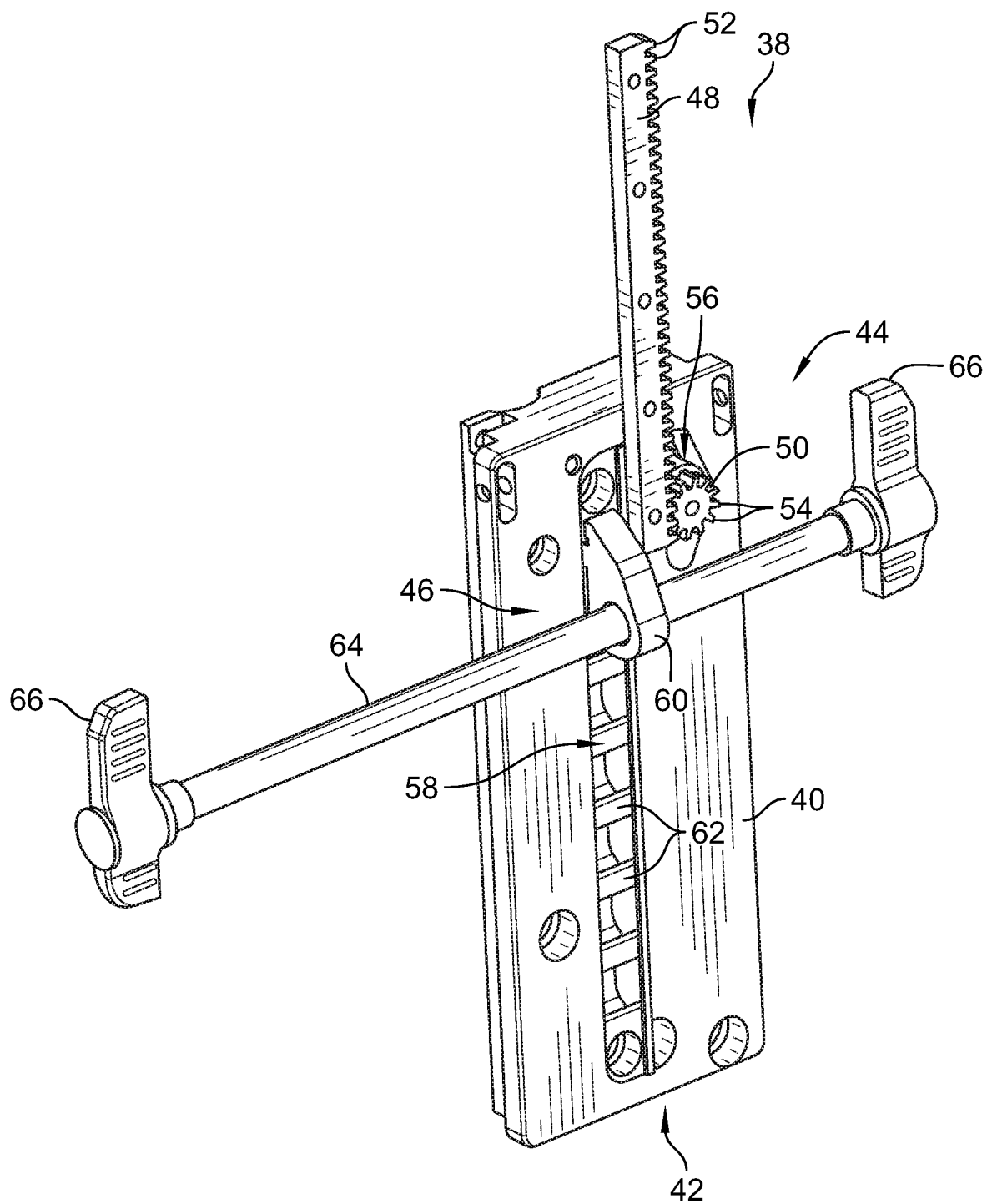
FIG. 6 is perspective view of portions of the (lower) slide assembly of FIG. 5 shown in isolation and showing that the ratchet system includes a pair of handles for disengaging a ratchet mechanism to allow translation of the slide plate, and showing that the dampening system includes a rack and pinion providing dampened rotation of the pinion for comfortable movement of the slide plate.

In the illustrative embodiment as shown in FIG. 6, the slide plate 40 is isolated from the frame 30. The dampening assembly 44 illustratively includes a rack 48 secured with the frame 30 and a pinion 50 mounted to the slide plate 40 and engaged with the rack 48 to provide dampening effect under movement of the slide plate 40. The rack 48 remains fixed relative to the frame 30 and includes teeth 52 engaged with the pinion 50.

The pinion 50 is illustratively embodied as a gear including teeth 54 disposed radially outward for engagement with the teeth 52 of the rack 48. The pinion 50 is rotatably mounted on the slide plate 40 having an internal damper 56 fixed with the slide plate 40 to (at least partially) resist rotation of the pinion 50. One example of a suitable damper 56 is a viscous fluid damper including an outer housing 51, an inner inertia ring having a shaft 53 extending from the housing to connect with the pinion 50 and disposed within the outer housing spaced from the inside surface of the outer housing to define a shear gap therebetween, and viscous fluid disposed within the shear gap to provide damping as the inertia ring rotates. In some embodiments, the slide assembly 38 may include any suitable damper style and/or arrangement. On translational movement of the slide plate 40, the teeth 52 of the rack 48 engage the teeth 54 of the pinion 50 causing rotation of the pinion 50. The damper 56 (partially) resists rotation and imposes a dampening on the rotation of the pinion 50 and thus on the translational movement of the slide plate 40 and its respective docking receiver 32. In some embodiments, the pinion 50 may be mounted on the frame 30 and the rack 48 may be mounted on the slide plate 40.

Referring to FIG. 6, as previously mentioned, the ratchet assembly 46 controls the movement of the slide plate 40 relative to the frame 30. The ratchet assembly 46 illustratively includes a ratchet track 58 and a pawl 60 selectively engaged with the ratchet track 58 to define the position of the slide plate 40 relative to the frame 30. The ratchet track 58 is illustratively fixed to the slide plate 40 having teeth 62 exposed for selective engagement with the pawl 60.

The pawl 60 is movable to selectively engage the teeth 62 of the ratchet track 58. The pawl 60 is illustratively secured with a shaft 64 having handles 66 secured on opposite ends thereof for engagement with a user's hand to rotate the shaft 64 about its longitudinal axis to move (pivot) the pawl 60 between engaged and disengaged positions.

Figure 7:
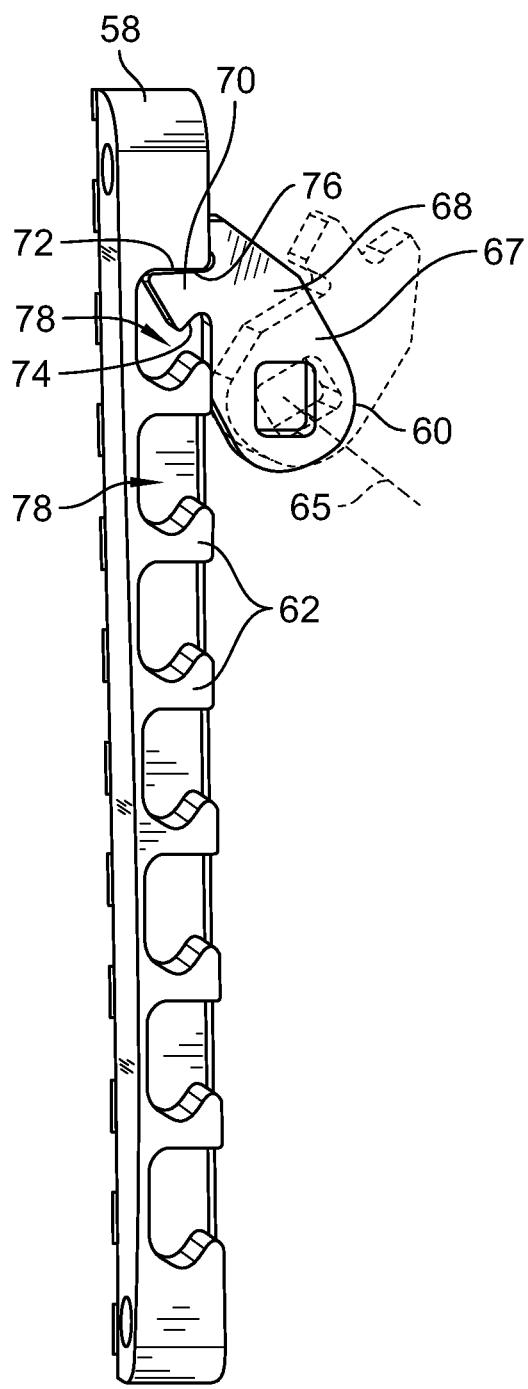
FIG. 7 is a closer view of the ratchet system of the (lower) slide assembly of FIG. 6 showing that the ratchet system includes a ratchet track including teeth and a pawl that is rotated into engagement with the ratchet track, and showing that under loading of the docking system, such as when a patient support top is connected with the connection assembly, the top of the pawl is engaged with a lower surface of one of the teeth to block disengagement of the pawl from between the teeth of the ratchet track.

As shown in FIG. 7, the pawl 60 is in the engaged position relative to the track 58 to arrest the movement of the slide plate 40. The pawl 60 illustratively includes a body 67 secured with the shaft 64 to define a rotation axis 65, a stem 68 extending from the body, and a head 70 extending from the stem 68 for engagement with the track 58. The head 70 is illustratively formed to have a triangular shape, including engagement surfaces 72, 74 for contact with the track 58 to prevent relative motion in the engaged position.

In FIG. 7, the track 58 is illustratively bearing load from the slide plate 40 such that the surface 72 of the pawl 60 is engaged with a surface 76 of the track 58 to block the pawl 60 from rotation out of the engaged position. The pawl head 70 is positioned within a gap 78 defined between the teeth 62 of the track 58. When the pawl 60 is in the engaged position and the track 58 is loaded to prevent the pawl 60 from rotation out from the gap 78 (into the disengaged position as indicated in dashed line in FIG. 7), the track 58 is blocked against (downward) translation relative to the pawl 60. Accordingly, the position of the track 58 relative to the pawl 60 is fixed.

Figure 8:
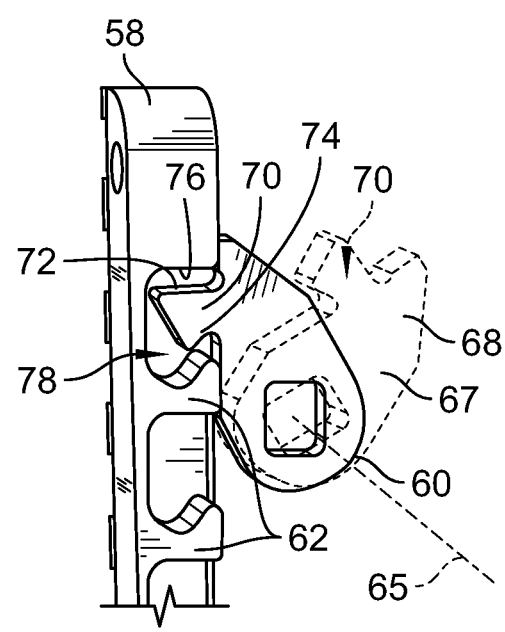
FIG. 8 is the closer view of the ratchet system of the (lower) slide assembly of FIG. 7 showing that the ratchet track has been shifted slightly upward (in the orientation of FIG. 8), for example, by unloading the weight of the patient support top connected with docking system, to permit the pawl to be rotated out from between the teeth without being blocked by contact with the lower surface of the tooth.

As shown in FIG. 8, the track 58 has been translated slightly upward relative to the pawl head 70 such that the head 70 is within the gap 78 but out of correspondence and contact with the surface 76. More specifically, the head 70 is arranged with the gap 78 with enough clearance such that rotation of the pawl 60 about the shaft rotation axis 65 will allow the pawl head 70 to clear the surface 76 and freely assume the disengaged position (as shown in dashed line in FIG. 8). A user can unburden load from the slide plate 40 to appropriately position the pawl head 70 within the gap 78 with clearance to avoid the surface 76, and then rotate the handle 66 to drive the pawl 60 into the disengaged position to permit translation of the slide plate 40 relative to the pawl 60. By requiring the slide plate 40 to be unloaded before the pawl 60 can be rotated out from engagement with the track 58, a two-step securement system provides a practical safety element to reduce the risk of inadvertent movement of the docking receiver 32 and a connected support top.

Figure 9:
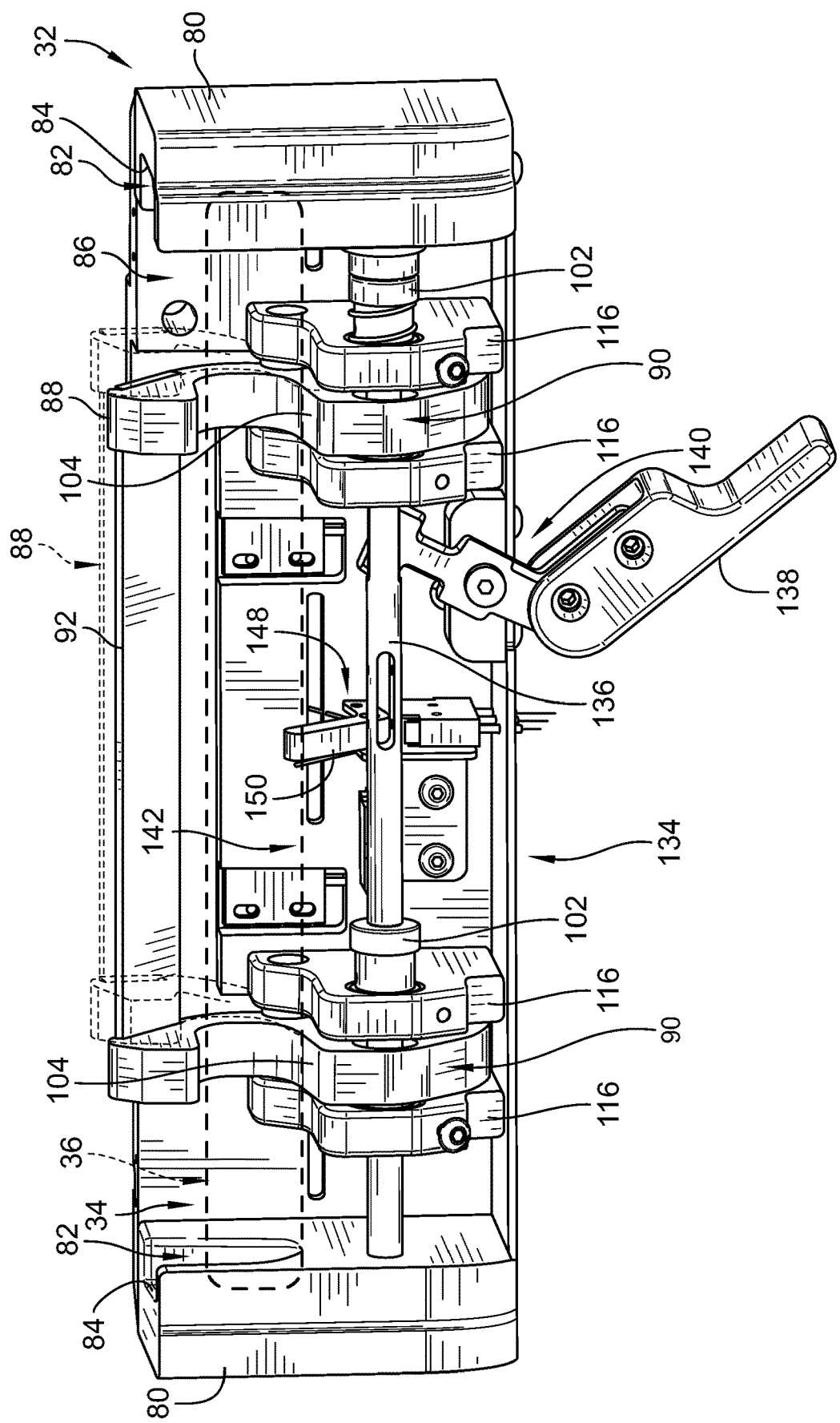
FIG. 9 is a front perspective view of the docking system of the patient support of FIGS. 1-4 having an outer cover removed to show that the docking receiver defines the tube slot including a receiver slot defined by end portions of the docking receiver, and showing that the tube slot opens in the upward direction to receive the gimbal tube (shown in dashed line) of the patient support top, and showing that the docking system includes a docking gate positionable between a locked position to block removal of the gimbal tube and unlocked position to permit removal of the gimbal tube from the tube slot, and showing a pair of pins arranged on a translatable shaft for selective engagement of the pins with the docking gate to selectively block against movement of the docking gate out from the locked position.

In the illustrative embodiment as shown in FIG. 9, the (upper) docking receiver 32 is shown having an outer front wall portion removed to show the docking slot 34 for descriptive purposes. The docking receiver 32 illustratively includes a pair of end stops 80 arranged on longitudinal ends of the docking slot 34. Each end stop 80 illustratively defines an end portion 82 of the docking slot 34 for receiving the ends of the connection tube 36 (shown in dashed line in FIG. 9). Opposing end walls 84 defining the respective end portion 82 can engage the connection tube 36 to assist in positioning the connection tube 36 when received within the docking slot 34. The docking slot 34 is embodied as an outward facing slot having a radially outward opening 86 defined between the end stops 80 for receiving the connection tube 36 passed through to enter and exit reception by the docking slot 34. In the orientation as shown in FIG. 9, the opening 86 faces upward.

Referring briefly to FIG. 4, each of the docking slots 34 are embodied as radially outward facing relative to the axis 15 permitting the connection tubes 36 of the patient supports to be loaded from a radially outward location. For example, in the orientation shown in FIG. 4, the lower docking receiver 32 can receive the connection tube 36 of the support top 14 into its docking slot 34 from below, while the upper docking receiver 32 can receive a connection tube 36 from above. As discussed in additional detail below, another docking receiver 32 is mounted orthogonal to the upper and lower docking receivers 32 having a radially outward facing docking slot 34 to receive a (vertical) connection tube 36 laterally inserted through its opening 86.

Returning to FIG. 9, the docking receiver 32 illustratively includes a docking gate 88 for selectively blocking against removal of the connection tube 36 from the docking slot 34. The docking gate 88 is positionable in a locked position (as shown in solid line in FIG. 9) extending at least partially across the opening 86 to prevent removal of the connection tube 36 from the docking slot 34 and an unlocked position (as shown in dashing line in FIG. 9) clear from the opening 86 to permit passing of the connection tube 36 into and out from the docking slot 34. A locking assembly 134 is positionable between engaged and disengaged positions to selectively restrict the docking gate 88 from moving out of the locked position. The docking gate 88 illustratively includes a pair of latches 90 and a gate bar 92 extending between the latches 90 for selectively locking the connection tube 36.

Figure 10:
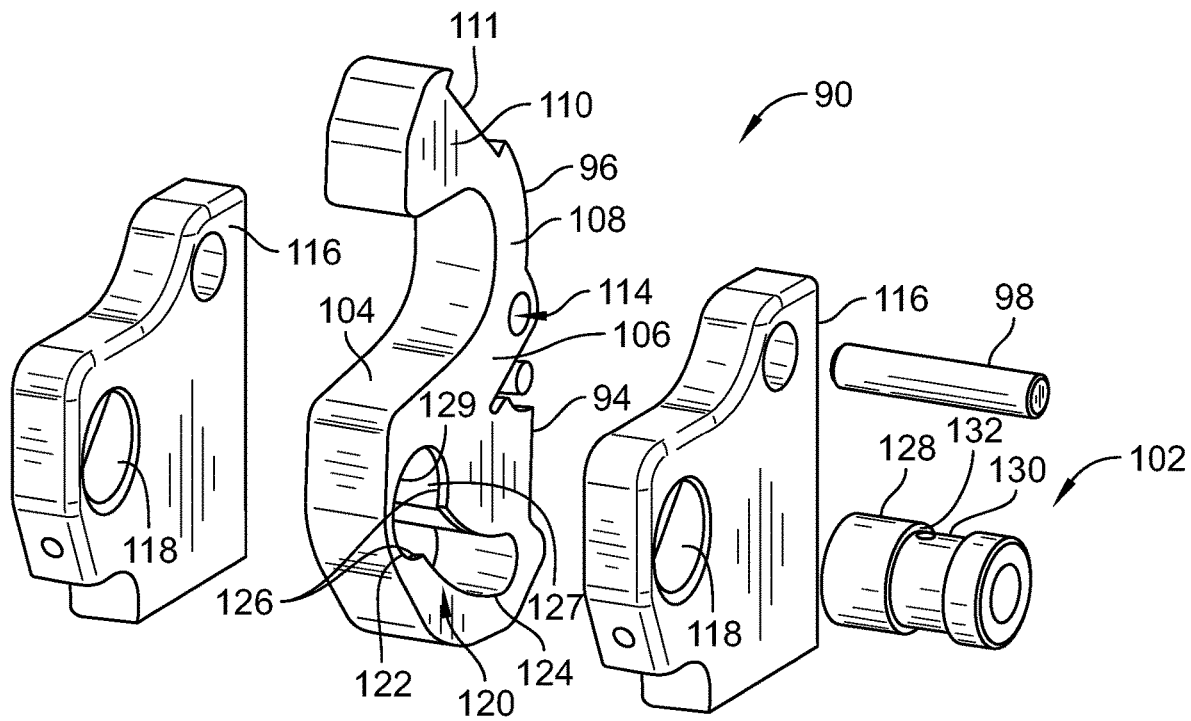
FIG. 10 is an exploded perspective view of a portion of a gate latch of the docking gate of FIG. 9 showing that the gate latch includes a pin slot arranged with correspondence to holes of a pair of gate stops that are fixed in position for receiving selective insertion of the pin through each of the pin slot and holes to block against movement of the gate latch from the locked position to retain connection of the patient support top.

As shown in FIG. 10, each gate latch 90 illustratively includes a gate body 94 and an arm 96 extending from the body 94 to selectively extend across the opening 86. Each gate latch 90 forms a slot surface 104 for complimentary engagement with the connection tube 36. The slot surface 104 is formed complimentary with the shape of the connection tube 36 and defines an inner curvature of the arm 96. The arm 96 illustratively extends from the body 94 in a U-shape defining a space for receiving the connection tube 36. The arm 96 illustratively includes a proximal section 106 formed in connection with the body 94, a mid-section 108 extending generally orthogonal from the proximal section 106, and another distal section 110 extending generally orthogonally from the mid-section 108 for selective arrangement across the opening 86 of the docking slot 34. A receptacle 111 is illustratively defined in the distal section 110 for receiving the gate bar 92.

The gate latch 90 is illustratively pinned by a pin 98 for pivotable movement between the engaged and disengaged positions. The pin 98 extends through a pin hole 114 formed in the arm 96 and is illustratively supported on walls 116 arranged on opposite sides of the gate latch 90. The walls 116 are illustratively mounted with fixed position within the docking receiver 32. The walls 116 each illustratively include a pin hole 118 define therethrough for receiving a locking pin 102 of the locking assembly 134 as discussed in additional detail below.

The gate body 94 illustratively includes a pin slot 120 defined therethrough for selectively receiving the locking pin 102. The pin slot 120 illustratively includes a home hole 122 and a track hole 124 extending from the home hole 122. The track hole 124 is formed with curvature corresponding to the pivoting movement of the gate latch 90 about the pin 98 to accommodate a shaft 136 on which the locking pin 102 is mounted during movement of the gate latch 90. When the gate latch 90 is arranged in the locked position, the home hole 122 is arranged in correspondence with the pin holes 118 of the support walls 116 to receive the locking pin 102 through each to restrict pivoting movement of the gate latch 90.

Figure 11:
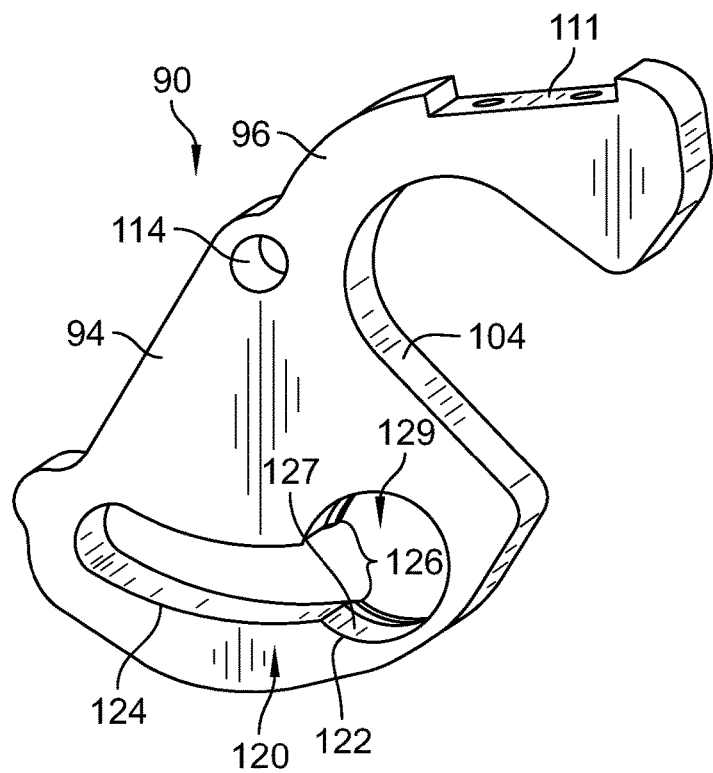
FIG. 11 is side elevation view of the gate latch of FIG. 10 showing that the pin slot includes wings extending partially across the pin slot to prevent removal of the pin from the pin slot when the tube slot is under load, for example, when the gimbal tube is received within the tube slot and its weight remains loaded on the docking system.

As shown in FIG. 11, the home hole 122 illustratively includes wings 126 for imposing a two-step operation for disengagement of the locking pin 102 from the pin slot 120. The wings 126 are illustratively formed as a flanged extension of the boundary wall 127 of the home hole 122 to require unloading of the gate latch 90 (when the position of the docking receiver 32 applies load to the arm 96 such as when the particular docking receiver 32 is the lower docking receiver, e.g., the opening 86 faces downward) before the locking pin 102 can clear the wings 126 to permit removal of the locking pin 102 from the home hole 122. Thus, for docking receivers 32 in an orientation with the opening 86 facing downward, gravity loading to the gate latch 90, including loading from a connection tube 36, prevents the locking pin 102 from being removed from the home hole 122 because the wings 126 cannot be cleared by the larger diameter section 128 without (partial) unloading. Accordingly, inadvertent unlocking of the gate latch 90 can be avoided when the orientation of the docking receiver 32 might permit the connection tube 36 to fall under force of gravity from the docking slot 34. The wings 126 are illustratively arranged on one axial end (retraction end) of the home hole 122 only on one circumferential side near the connection with the track hole 124. Wings are illustratively excluded from the other circumferential sides of the home hole 122 as gravity would not ordinarily cause "falling" in other positions of the docking receiver 32, however, in some embodiments, the wings may extend along any suitable circumferential portion of the home hole 122.

Returning briefly to FIG. 10, the locking pin 102 is embodied to have a cylindrical shape illustratively including a larger diameter section 128 and a smaller diameter section 130 defining a step 132 therebetween. The curvature of the wall 127, excluding the wings 126, is larger than the larger diameter section 128 to permit minor relative movement between the locking pin 102 and the home hole 122 when the locking pin 102 is arranged within the home hole 122. By way of example, for the lower docking receiver 32 (in FIG. 4, having the gate latch 90 arranged upside down relative to FIGS. 10 and 11), when a connection tube 36 being received in the docking slot 34 and the gate latch 90 in the locked position with the locking assembly 134 engaged such that the locking pin 102 is received in the home hole 122, the load of the connection tube 36 (from the associated patient support top) would be directed downward onto the arm 96, slightly rotating the gate latch 90 such that larger diameter section 128 of the locking pin 102 engages with the wall 127 near the connection of the home hole 122 with the track hole 124 and aligning the step 132 with the wings 126 such that they would engage each other if withdrawal of the locking pin 102 from the pin slot 120 were attempted without unloading of the gate latch 90. In this example, relative to FIG. 10, the gate latch 90 would endure a load applied upward against the arm 96 (downward relative to the lower docking receiver 32 in FIG. 4), while the locking pin 102 remains within the home hole 112 but slightly shifted to interfere the step 132 with the wings 126 to block removal of the locking pin 102 from the home hole 112. Upon at least partial unloading of the gate latch 90, the gate latch 90 pivots slightly to align an opening 129 of the home hole 122 with the locking pin 102 to allow removal of the locking pin 102 through the opening 129 without engagement of the step 132 with the wings 126. The opening 129 is defined by the wall 127 including the wings 126 to permit passage of the locking pin 102 upon proper unloading of the gate latch 90. In the illustrative embodiment, the wings 126 are arranged to require unloading of the gate latch 90 only when the docking receiver 32 is oriented to apply some gravitational load of the connection tube 36 that would rotate the gate latch 90 to the unlocked position (e.g., to prevent automatic release of the connection tube 36 upon disengaging the locking pin 102), for example, for the docking receiver 32 in the lower position in FIG. 4 having a connection tube 36 applying a gravitational load to the arm 96 and tending to pivot the gate latch 90 counterclockwise in the orientation of FIG. 11 about the pin hole 114. By contrast, for the upper docking receiver 32 of FIG. 4, the gravitational load of the connection tube 36 would be directed downward onto the body 94 of the gate latch 90, tending to pivot the gate latch 90 clockwise about the pin hole 114 in the orientation of FIG. 11. The position of the upper docking receiver thus does not coincidentally allow the docking gate 88 to move to the unlatched position under the gravitational load of the connection tube 36, and thus does not require unloading of the gate latch 90 to disengage the locking pin 102 of the upper docking receiver 32. In some embodiments, the wings 126 may be provided about any amount and/or position of the circumferential extent of the opening 129 to require unloading of gravitational loading on the gate latch 90 in one or more orientations of the docking receiver 32.

Figure 12:
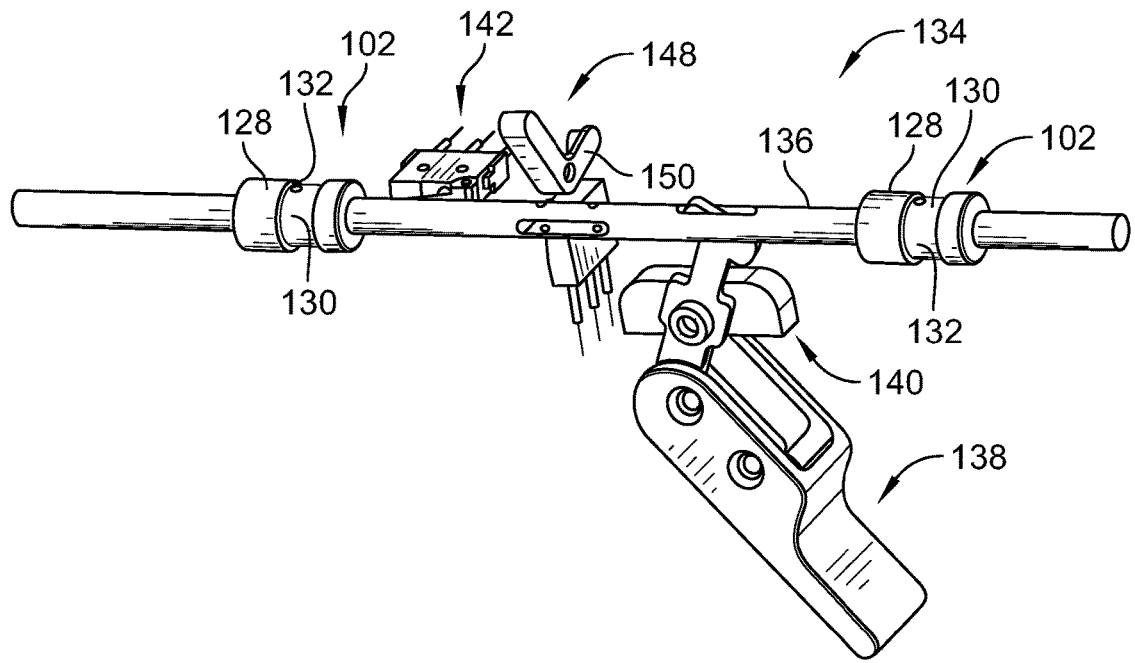
FIG. 12 is a perspective view of portions of the connection assembly of FIG. 9 showing that the translatable shaft is engaged with a lever having a handle for engagement with a user's hand to drive the shaft for translation to disengage the pins from the gate latches, and showing that a shaft sensor is arranged to determine the position of the shaft and a tube sensor is arranged to determine whether a gimbal tube is within the tube slot.

As shown in FIG. 12, the locking assembly 134 illustratively includes a translatable shaft 136 having the locking pins 102 mounting coaxially thereon. The locking pins 102 are arranged on the shaft 136 for selective insertion into the home hole 122 of the respective gate latch 90 under translation of the shaft 136. When the locking pins 102 are disengaged from the pin slot 120, the track hole 124 of the gate latch 90 accommodates the shaft 136 under relative movement of the gate latch 90 (i.e., when the pin 102 is not within the hole 122). A handle 138 is adapted for engagement with a user's hand and is coupled with the shaft 136 via a lever assembly 140 to transfer manual operation of the handle 138 into lateral translation of the shaft 136 to engage or disengage the locking pin 102 with the gate latches 90.

Figure 13:
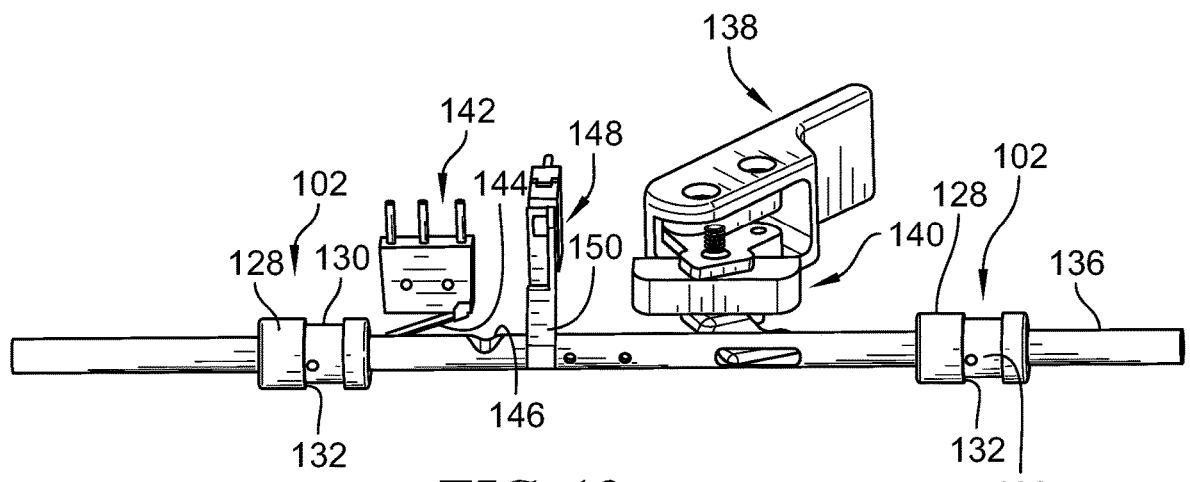
FIG. 13 is a top plan view of the portions of the connection assembly of FIG. 12 showing that the translatable shaft includes a indent for releasing a trigger of the shaft sensor for extension to indicate that the pins are in the locked position.

As shown in FIG. 13, a sensor 142 is arranged in communication with shaft 136 to determine the shaft position. The sensor 142 is embodied as a contact switch including an outrigger 144. The outrigger 144 is illustratively engaged with the shaft 136 and maintains a first position when out of contact with a detent 146 of the shaft 136, and assumes a second position when the shaft 136 is translated to insert the locking pins 102 into their respective home holes 122 placing the outrigger 144 in contact with the detent 146. The second position of the outrigger 144 triggers the sensor 142 to provide a signal indicating that the locking assembly 134 is in the engaged position to block movement of the locking gate out from the locked position. In some embodiments, the sensor 142 may provide a signal when the outrigger 144 is in the first position to indicate the disengagement of the locking pin 102.

A tube sensor 148 is illustratively arranged within the docking slot 34 to detect when a connection tube 36 is received therein. The tube sensor 148 illustratively includes a trigger arm 150 arranged to engage the connection tube 36 to be driven into a triggered position (as shown in FIG. 9) when the connection tube 36 is received within the docking slot 34, and an untriggered position (as shown in FIGS. 12 and 13) when the connection tube is not received within the docking slot 34. In the illustrative embodiments, the sensors 142, 148 are contact type sensors, but in some embodiments, the sensors 142, 148 may be any suitable type, arrangement, and/or manner of sensor, for example, non-contact sensors.

Figure 14:
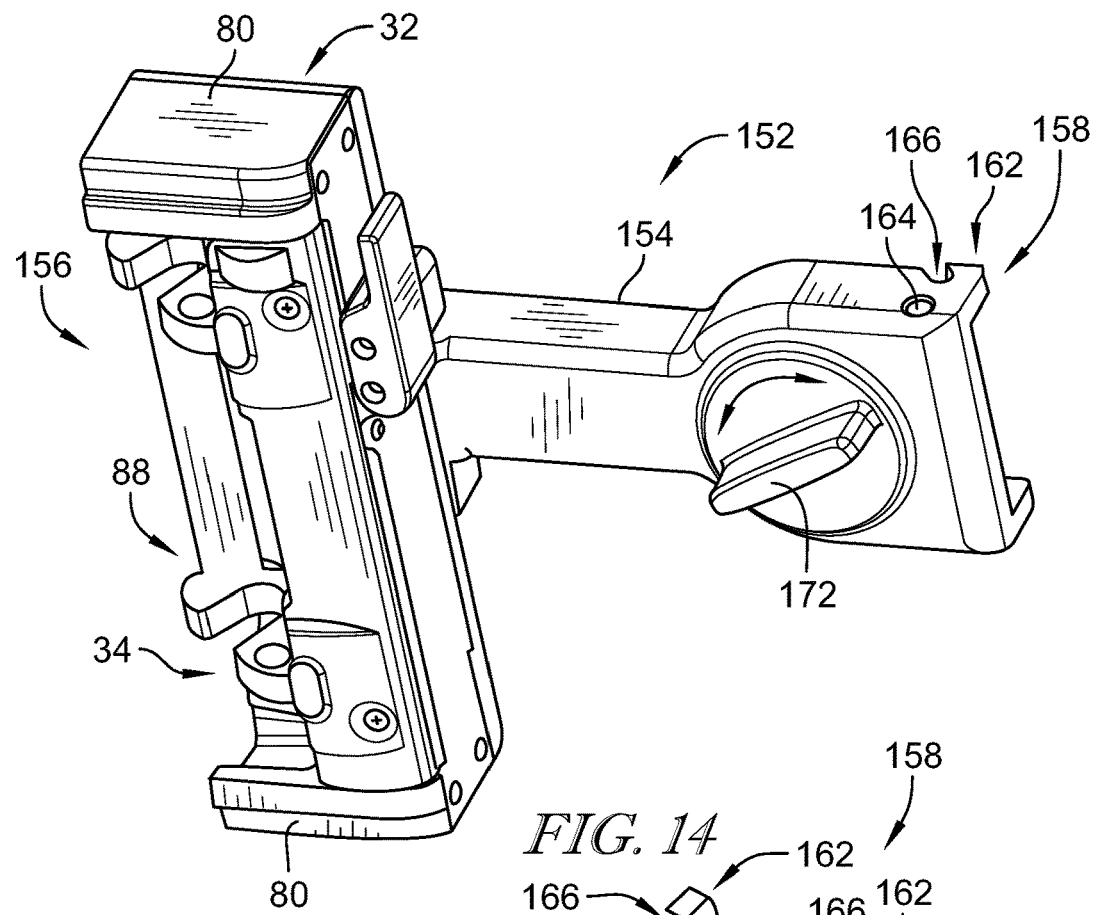
FIG. 14 is perspective view of a side arm assembly of the connection assembly of FIGS. 2 and 3 for extending laterally to support a prone support top to enable a lateral-to-prone transfer of the patient, showing that the side arm assembly includes an extension arm including an attachment assembly for securing with the frame of the connection assembly, and showing that the side arm assembly includes another docking assembly arranged sideways (vertically) for selective connection with one of the patient support tops to support lateral-to-prone transfer of the patient.

Referring to the illustrative embodiment as shown in FIG. 14, a lateral extension 152 of the connection assembly 18 is shown including an additional docking receiver 32. The lateral extension 152 can be secured to extend laterally from the frame 30 to provide its docking receiver 32 for connection with a support top positioned orthogonally to those support tops connected with the other docking receivers 32 (upper and lower docking receivers 32 in FIG. 4). For example, referring briefly to FIG. 4, the lower docking receiver 32 may be connected with a lateral support top adapted for supporting the patient in a lateral position (e.g., lateral recumbent), while the lateral extension 152 may be connected with the prone support top 24 arranged orthogonally relative to the lateral support top to contact the patient's front for rotation about the axis 15 to transfer the patient from the lateral position to the prone position.

As shown in FIG. 14, the lateral extension 152 illustratively includes an extension arm 154 having the docking receiver 32 secured at one end 156 and configured at a connection end 158 for connection with the frame 30 of the connection assembly 18. At the connection end 158 the lateral extension 152 includes hooks 162 and movable pins 164 for securing the lateral extension 152 with the frame 30.

Figure 15:
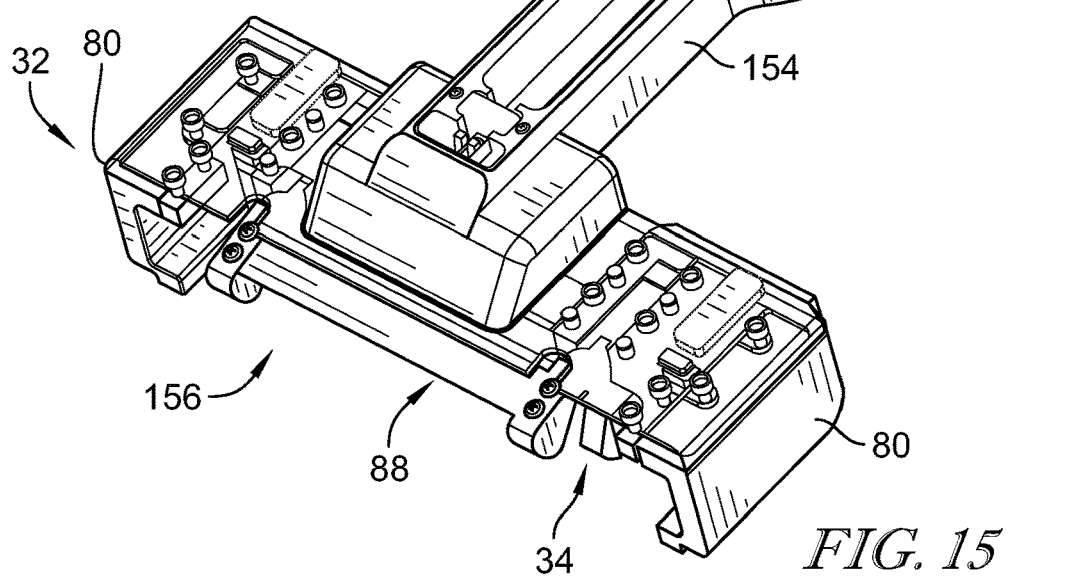
FIG. 15 is a perspective rear view of the side arm assembly of FIG. 14 showing that the attachment assembly includes hooks and pins for selective connection with the frame of the connection assembly.

As shown in FIG. 15, the extension arm 154 includes the hooks 162 formed to include slanted slots 166 defined in the extension arm 154. The hooks 162 are arranged to receive a shaft 165 (as indicated in FIG. 4) of the frame 30. Upon seating of the shaft 165 within the slots 166, the extension arm 154 can be pivoted to align the pins 164 with complimentary holes 167 in the frame 30 (as indicated in FIG. 4) for insertion therein to secure the position of the lateral extension 152 relative to the frame 30. A corresponding shaft 165 and holes 167 are illustratively provided on each lateral side of the frame 30 (in the orientation of FIG. 4) for selective connection of the lateral extension 152 on either lateral side of the frame 30.

Figure 16:
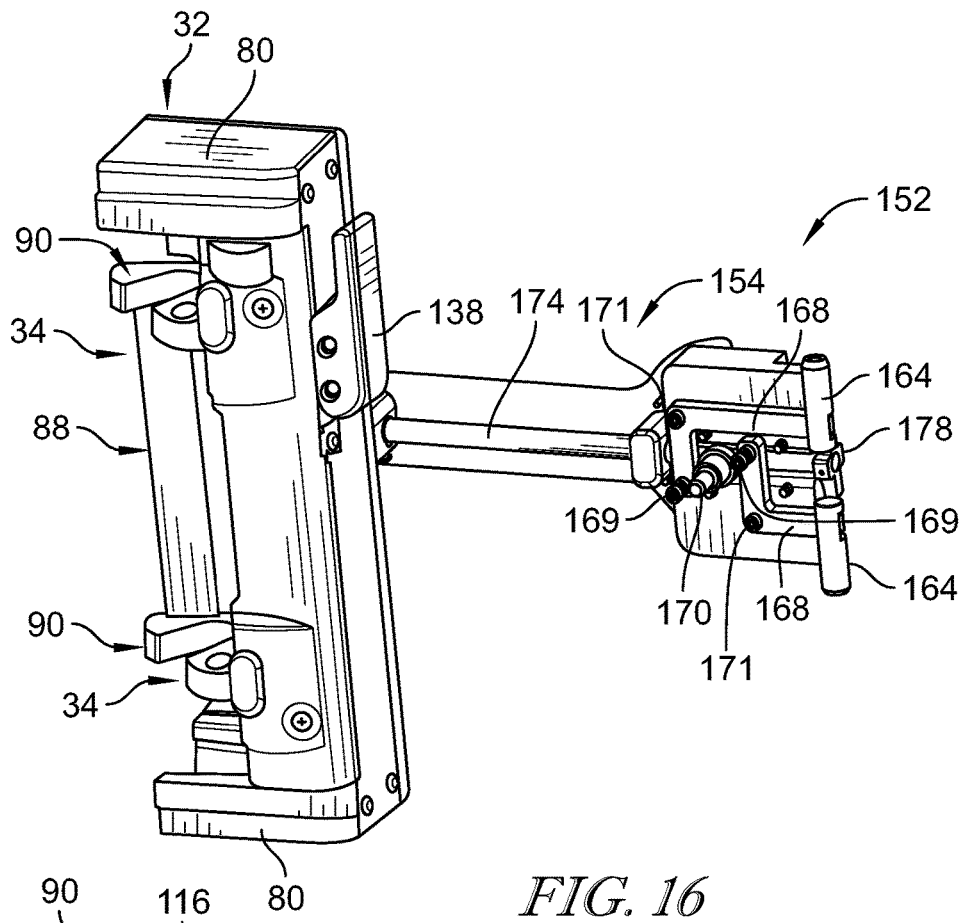
FIG. 16 is the perspective view of the side arm assembly of FIG. 13 having portions of the extension arm assembly removed to show a release mechanism of the attachment assembly includes pivotable armatures attached with the pins to move the pins between (vertically) extended and retracted positions for selective engagement with the frame of the connection assembly.

Referring to FIG. 16, an outer portion of the extension arm 154 including the hooks 162 has been removed to reveal the internals. The movable pins 164 are arranged coaxially with each other and are each movable between an extended position (outward from each other) for insertion into the holes 167 to prevent pivoting of the hooks 162 about the shaft 165 of the frame 30 to secure the lateral extension 152 with the frame 30, and a retracted position (towards each other, as shown in FIG. 16) to remove the pins 164 from the holes 167 to allow pivoting and removal of the hooks 162 from the shaft 165 of the frame 30.

Each of the pins 164 is illustratively connected with a pivot arm 168 arranged for manual operation to move the pins 164. The pivot arm 168 is illustratively formed as an L-shaped arm including an engagement end 169 coupled with a handle 172 and a pivot point 171 about which motion of the handle 172 is transferred through the pivot arm 168 to the pins 164. The handle 172 is mounted on the drive shaft 170 and is operable between a first rotational position corresponding with the retracted position of the pins 164 and a second rotational position corresponding with the extended position of the pins 164. The handle 172 adapted for engagement with a user's hand to allow the user to operate the pins 164 between their engaged and disengaged positions for selectively attaching the lateral extension 152 with the frame 30 of the connection assembly 18.

Figure 17:
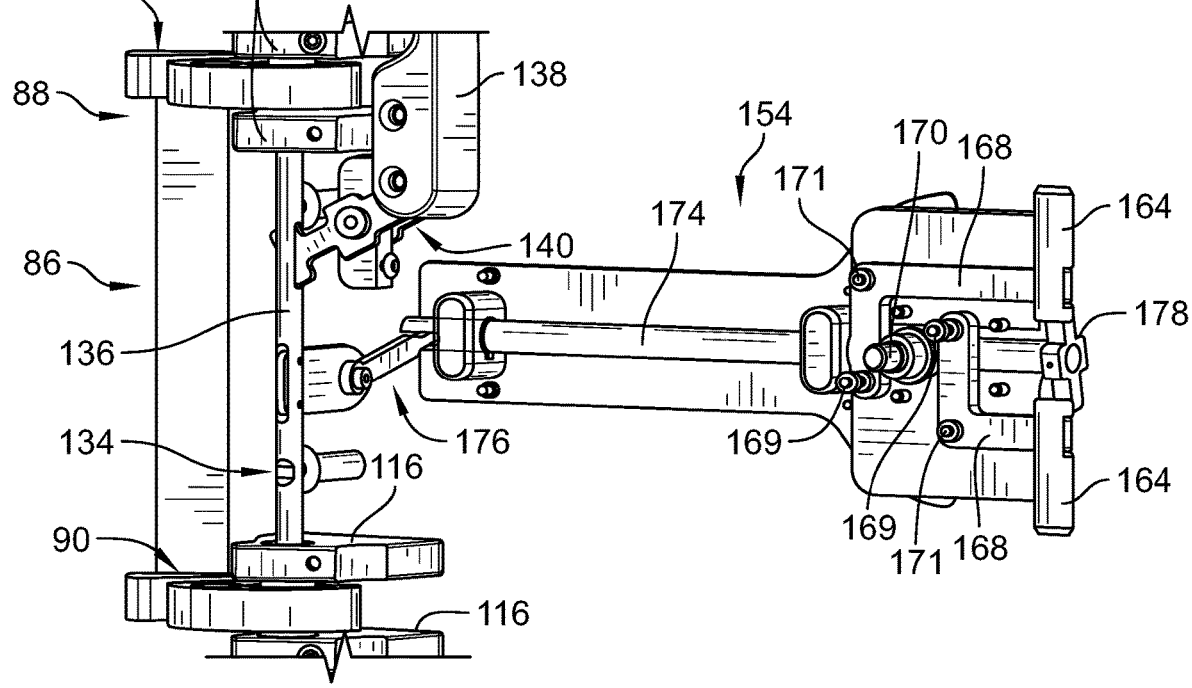
FIG. 17 is another perspective view of the side arm assembly of FIGS. 14-16 having outer portions removed to show that a trigger assembly is movably connected with the translatable shaft of the docking assembly to rotate a trigger to activate a position switch of the connection assembly to indicate the position of the translatable shaft.

As shown in FIG. 17, the docking receiver 32 of the lateral extension 152 illustratively includes a docking slot 34 and docking gate 88 for receiving and securing the connection tube 36 with the connection assembly 18. A rotation shaft 174 extends through the extension arm 154 and is connected with the shaft 136 by a linkage 176 to rotate the shaft 174 according to the translation of the shaft 136. On an opposite end from the linkage 176, the rotation shaft 174 includes a connector 178, embodied to have a t-shape, being secured to rotate with the rotation shaft 174 for triggering a sensor on board the frame 30 to relay the position of the shaft 136 to the connection assembly 18.

Figure 18:
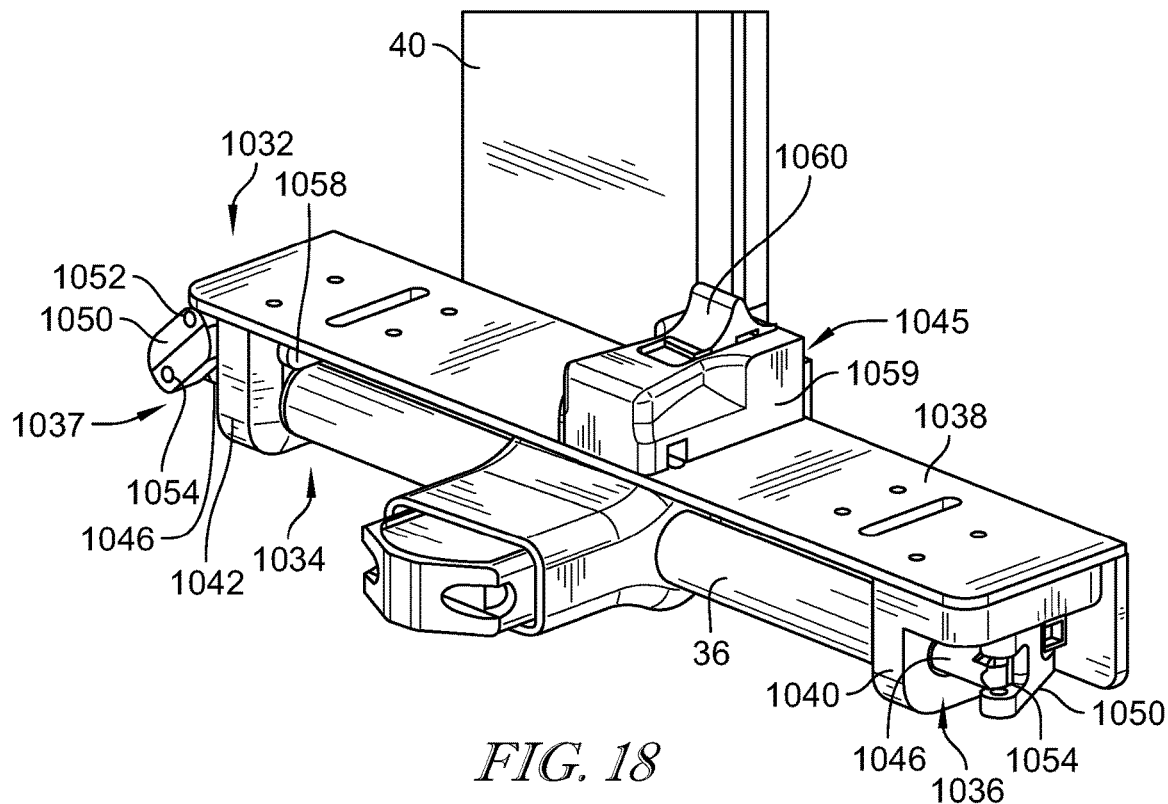
FIG. 18 is a perspective view another embodiment of a docking assembly of the connection assembly of FIGS. 3-5, showing that the docking assembly includes a docking receiver defining a tube slot in which is received the gimbal tube of a patient support top, and showing that a latch assembly provides selective latching of the gimbal tube in the tube slot by selectively inserting latch pins into the ends of the gimbal tube by two-step operation.

As shown in FIG. 18, another illustrative embodiment of a docking receiver 1032 is shown for connection of the patient support tops 14, 24. The docking receiver 1032 is similar to the docking receiver 32, and the description and drawings of the docking receiver 32 apply equally to the docking receiver 1032, except in instances of conflict with the specific disclosure of docking receiver 1032.

A connection tube 36 is shown received within a docking slot 1034 of the docking receiver 1032 as shown in FIG. 18. A housing 1038 of the docking receiver 1032 is secured with the slide plate 40 for adjustable positioning of the docking receiver 1032. Latch pin assemblies 1036, 1037 are illustratively shown arranged in an disengaged position allowing the connection tube 36 to be inserted into and removed from the docking slot 1034.

Figure 19:
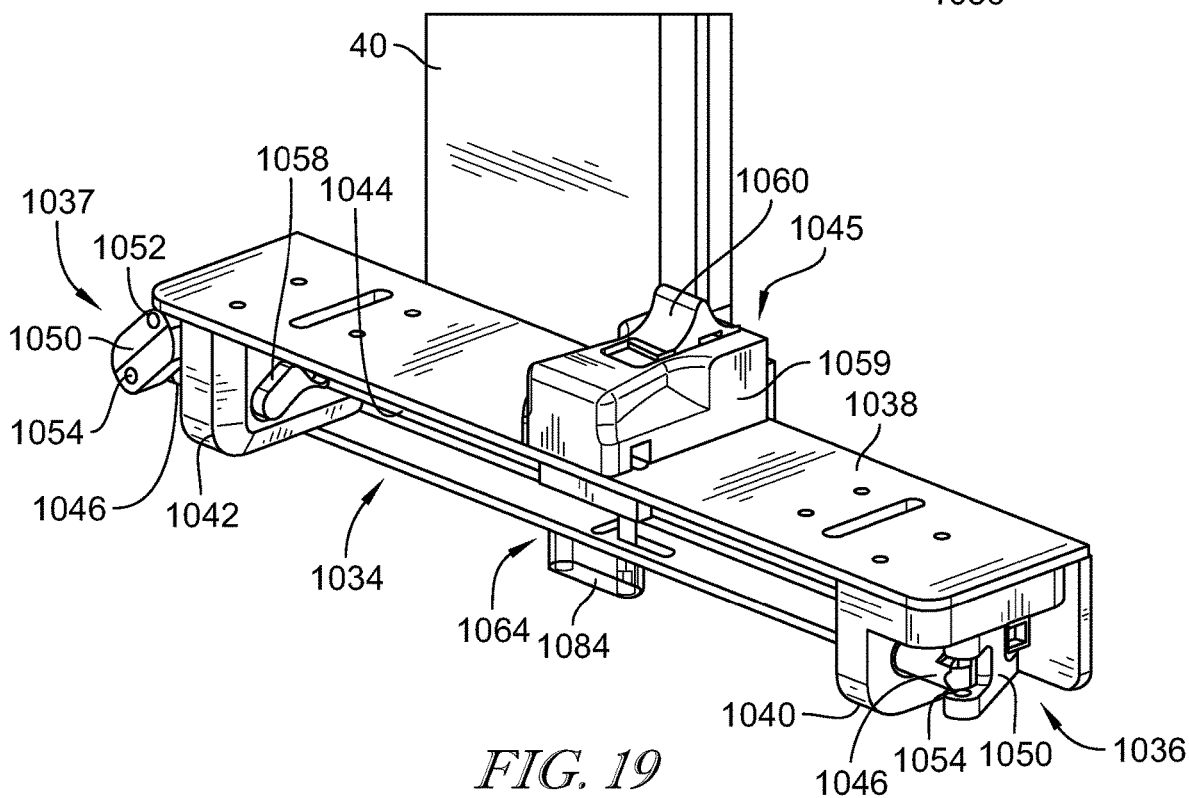
FIG. 19 is the perspective view of the docking assembly of FIG. 18 showing that the gimbal tube has been removed from the tube slot to show that a hatch mechanism is in a closed position to prevent movement of the pins into a latched position, and showing that a handle includes a switch for two-step operation to move the latch assembly between latched and unlatched positions.

As shown in FIG. 19, the connection tube 36 has been removed from the docking slot 1034. The docking receiver 1032 illustratively includes a pair of end walls 1040, 1042 defining the longitudinal ends of the docking slot 1034. Latch pins 1046 of the latch pin assemblies 1036, 1037 can be selectively extended through the walls 1040, 1042 for connection with the connection tube 36. A translatable connection bar 1044 extends between the latch pin assemblies 1036, 1037 to move the latch pin assemblies 1036,1037 between the engaged and disengaged positions. An operation handle 1045 is mounted on the housing 1038 for translation to drive the connection bar 1044 and the latch pin assemblies 1036, 1037.

As shown in FIG. 20A-C, the latch pin assemblies 1036, 1037 are arranged in the retracted position such that latch pins 1046 are retracted from the docking slot 1034. Each latch pin assembly 1036, 1037 illustratively includes a lever 1050 that is pinned for pivoting about a fulcrum 1052 and at a pin joint 1054 with its latch pin 1046. Each lever 1050 is coupled with the connection bar 1044 at opposite ends, and to its respective latch pin 1046. Translatable motion of the connection bar 1044 pivots each lever 1050 about its fulcrum 1052 to move the latch pins 1046 between the engaged and disengaged positions. The lever 1050 of the latch pin assembly 1036 is illustratively positioned orthogonally along the lateral axis in FIG. 20A with respect to the lever 1050 of the latch pin assembly 1037 (as discussed in additional detail below regarding FIG. 22).

A shown in FIG. 20B, the latch pin assembly 1037 is arranged in the retracted position. The latch pin 1046 is retracted from the docking slot 1034, partially within the wall 1042. Accordingly, the connection tube 36 can be arranged within the docking slot 1034 because the latch pin 1046 is retracted. Once the connection tube 36 is received within the docking slot 1034, coaxially with the latch pin 1046, the latch pin 1046 can be moved into the extended position for insertion within the longitudinal end of the connection tube 36 to secure the connection tube 36 in the docking slot 1034.

As shown in FIG. 20C, the latch pin assembly 1036 is arranged in the retracted position. The latch pin 1046 is retracted from the docking slot 1034, partially within the wall 1040. Accordingly, the connection tube 36 can be arranged within the docking slot 1034 because the latch pin 1046 is retracted. Once the connection tube 36 is received within the docking slot 1034, coaxially with the latch pin 1046, the latch pin 1046 can be moved into the extended position for insertion within the connection tube 36 to secure the connection tube 36 in the docking slot 1034.

As shown in FIGS. 21A-C, the latch pin assemblies 1036, 1037 are arranged in the extended position such that latch pins 1046 are extended into the docking slot 1034. Each latch pin 1046 extends through its respective wall 1040,1042 into the docking slot 1034 for insertion into the longitudinal ends of connection tube 36 when located in the docking slot 1034.

As shown in FIG. 21B, the lever 1050 of the latch pin assembly 1037 has been pivoted about its fulcrum 1052 under the force of the connection bar 1044. The fulcrum 1052 of the latch pin assembly 1037 is illustratively arranged at an opposite end of the lever 1050 from the pin joint 1054. The lever 1050 of the of the latch pin assembly 1037 extends parallel to the wall 1042 in the extended position to drive the latch pin 1046 into the docking slot 1034.

As shown in FIG. 21C, the lever 1050 of the latch pin assembly 1036 has been pivoted about its fulcrum 1052 under the force of the connection bar 1044. The fulcrum 1052 of the latch pin assembly 1036 is illustratively arranged between the coupling with the connection bar 1044 and the pin joint 1054 to "seesaw" the pin joint 1054 under force from the connection bar 1044 (as illustrated in additional detail below regarding FIG. 22). The pin joint 1054 of the latch pin assembly 1036 extends towards the wall 1042 in the extended position to drive the latch pin 1046 into the docking slot 1034.

Figure 22:
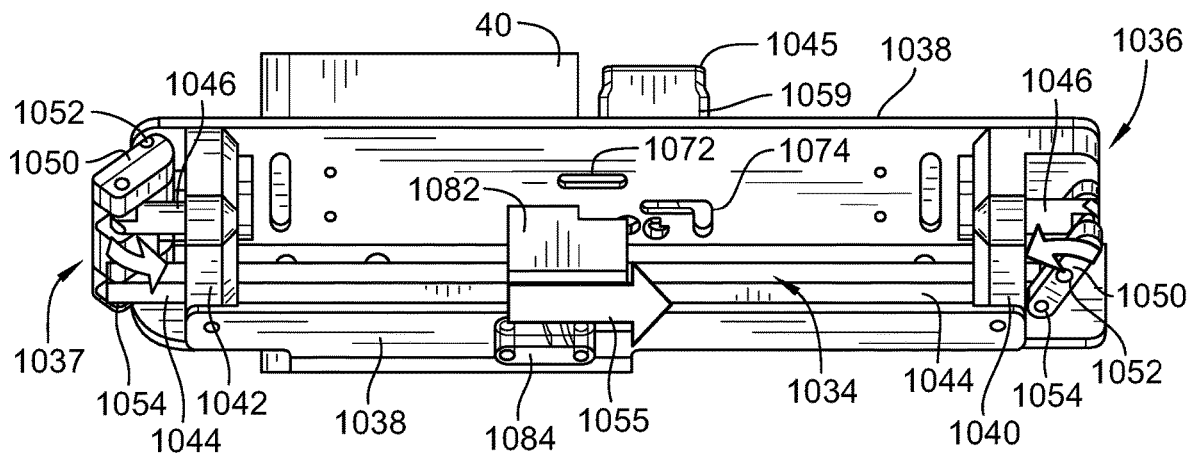
FIG. 22 is a bottom view of the docking assembly of FIG. 20A illustrating a movement of the latch assembly from the unlatched position into the latched position by sliding movement of the handle to the right to drive translation of a connection bar to drive the pins into the latched positions through linkages.

As shown in FIG. 22, the latch pin assemblies 1036, 1037 are arranged in the retracted positions having the latch pins 1046 retracted from the docking slot 1034. The connection bar 1044 is illustratively positioned to the left towards the latch pin assembly 1037. Translation of the connection bar 1044 to the right (as indicated by arrow 1055) pivots the levers 1050 about their fulcrums 1052 to drive the latch pins 1046 through their walls 1040, 1042 into the docking slot 1034. Accordingly, the levers 1050 each pivot towards their respective walls 1040, 1042 under the rightward movement of the connection bar 1044. As previously mentioned, the lever 1050 of the latch pin assembly 1036 is arranged orthogonally relative to the lever 1050 of the latch pin assembly 1037. In the illustrative embodiment, the fulcrums 1052 of the different latch pin assemblies 1036, 1037 are each orthogonal to each other and to the translation direction of the connection bar 1044. Translation of the connection bar 1044 is provided by connection with the operation handle 1045.

Figures 23A, 23B, 23C:
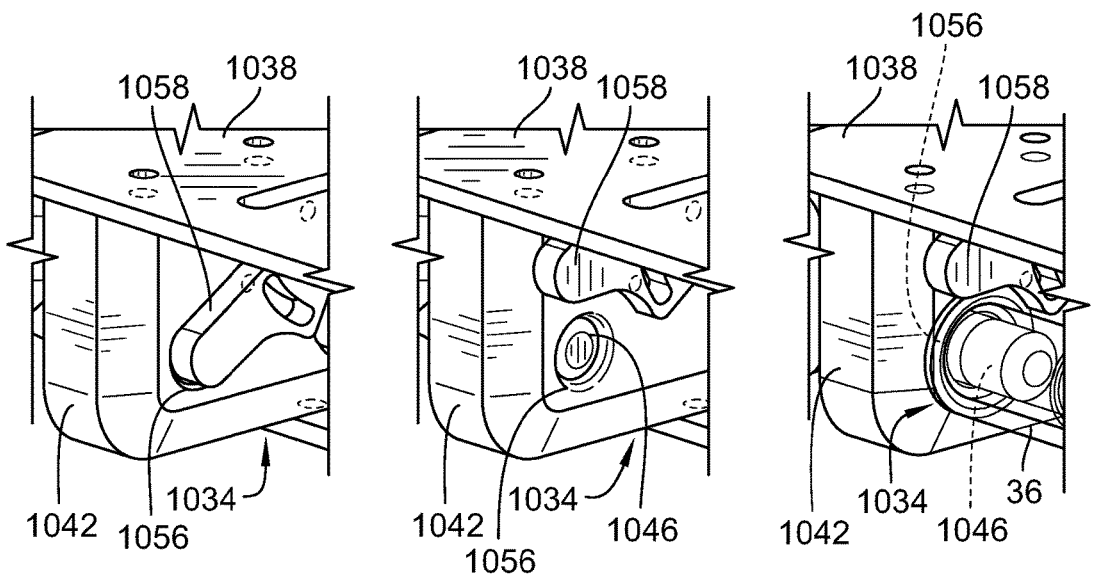

As shown in FIGS. 23A-C, a pair of pin stoppers 1058 is arranged, one to each hole 1056. The pin stopper 1056 are illustratively operable to cover each hole 1056 of the walls 1040,1042 when the connection tube 36 is not fully seated in the docking slot 1034. Each pin stopper 1058 is pivotable between a closed position (as shown in FIG. 23A) to cover the hole 1056 to prevent extension of the latch pin 1046 into the docking slot 1034, and an open position (as shown in FIGS. 23B and C) free from the hole 1056 to allow extension of the latch pins 1046 into the docking slot 1034. The stoppers 1058 are illustratively biased into the closed position and can be displaced into the open position. As shown in FIG. 23C, when the connection tube 36 is received within the docking slot 1034, the connection tube 36 engages and moves the pin stoppers 1058 into the open position to permit the latch pins 1046 to extend into the docking slot 1034 and into the connection tube 36 to secure the connection tube 36 in place. The arrangement of the pin stoppers 1058 can assist in prevent insertion of less than both latch pins 1046 into the connection tube 36 by requiring proper arrangement of the connection tube 36 for any single latch pin 1046 to enter the docking slot 1034.

Figure 24A:
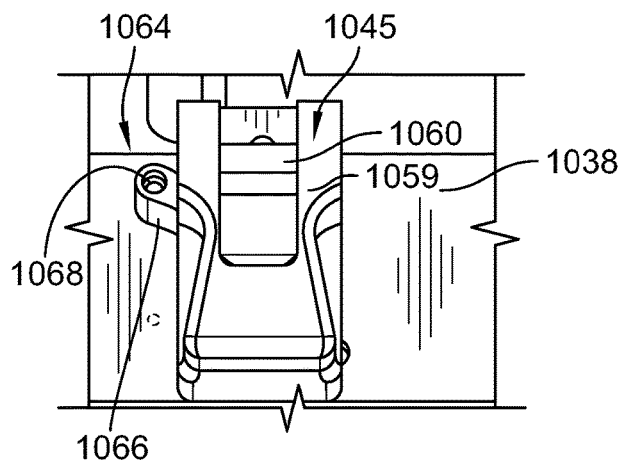
FIGS. 24A-C are perspective views of a top side of the docking assembly of FIGS. 18 and 19 showing a handle in place to show that a trigger is moveable between a locked position (FIGS. 24A and 24B) and an unlocked position (FIG. 24C)
Figure 24B:
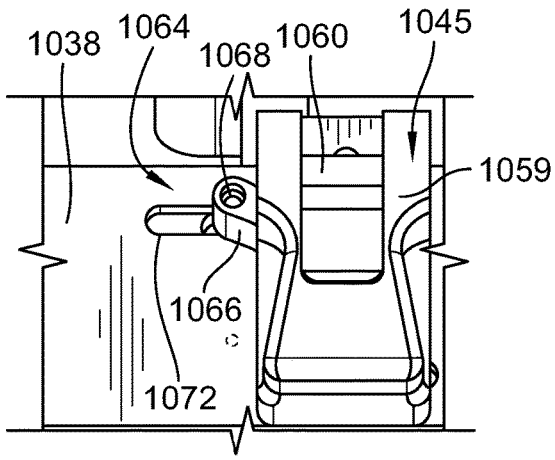
Figure 24C:
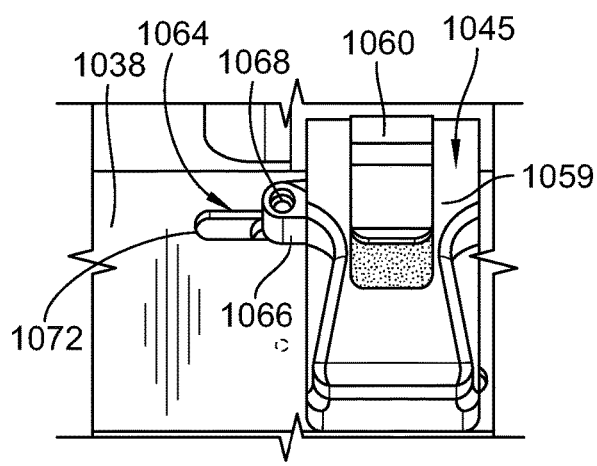

Referring to FIGS. 24A-C, a sequence of operating the operational handle 1045 to lock and unlock the connection tube 36 from the docking receiver 1032 is shown. The lateral position of the operational handle 1045 in the orientation of the FIGS. 24A-C corresponds to the lateral position of the connection bar 1044 in the orientation of FIG. 23. As shown in FIG. 24A, the operational handle 1045 illustratively includes a handle body 1059 and a trigger 1060 mounted on the handle body 1059 for selective movement. The trigger 1060 is illustratively arranged in a disengaged position (downward as shown in FIGS. 24A,B) and is moveable to a engaged position (upward as shown in FIG. 24C, revealing a color indication shown as fill), when the operational handle 1045 is shifted to the right, to lock the position of the operational handle 1045 and thus lock the latch pins 1046 in the engaged position. The operational handle 1045 is coupled with the latch pin assemblies 1036,1037 to transfer operable motion.

Figure 25A:
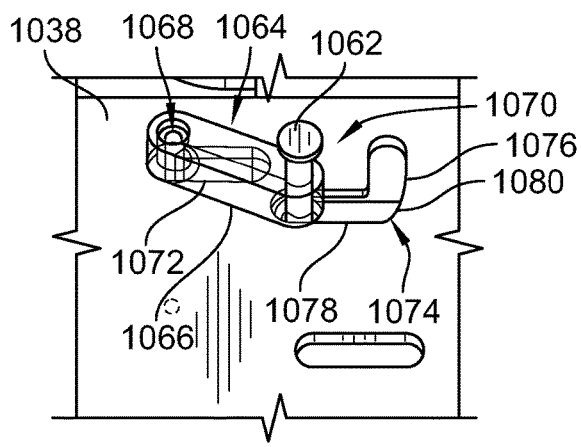
FIG. 25A-C are perspective views of a left hand portion of the docking assembly of FIGS. 18 and 19, showing the latch mechanism in a blocking position in FIG. 23A, in a free position in FIG. 23B, and in a free position having the gimbal tube received in the tube slot in FIG. 23C.
Figure 25B:
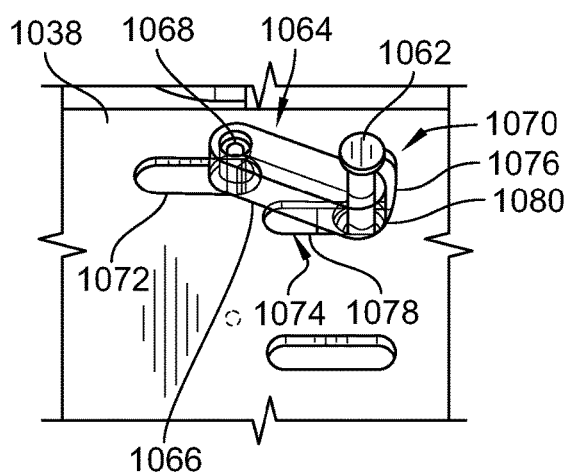
Figure 25C:
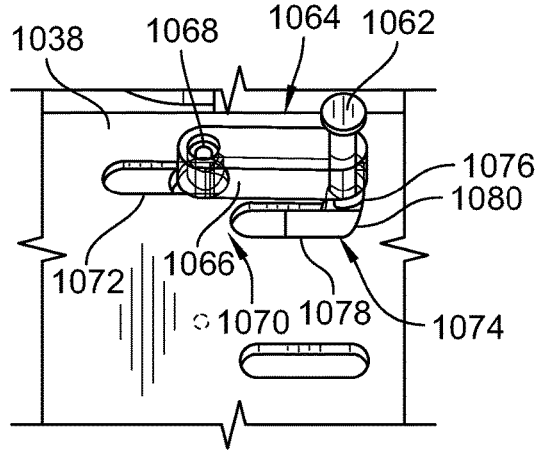

Referring to FIG. 25A-C, the operational handle 1045 has been omitted to show that a key shaft 1062 is coupled with the operational handle 1045 for movement. The key shaft 1062 is illustratively connected with the trigger 1060 and via the trigger 1060 is connected with the handle body 1059. The key shaft 1062 forms a portion of a linkage assembly 1064 coupling the operational handle 1045 with the latch pin assemblies 1036, 1037 to allow the user to move the latch pins 1046 between the engaged and disengaged positions via the handle 1045.

The linkage assembly 1064 illustratively includes a strut 1066 connecting the key shaft 1062 with other portions of the linkage assembly 1064. The strut 1066 at one end is illustratively connected with the key shaft 1062 to allow rotation of the key shaft 1062 about its extension from the housing 1038 (rotation about the vertical extension of the key shaft 1062 in the orientation of FIGS. 25A-C). The strut 1066 is connected with a drive shaft 1068 at another end to provide translational movement to the connection bar 1044. The key shaft 1062 and drive shaft 1068 are illustratively arranged parallel to each other, spaced apart by the strut 1066. The strut 1066 is illustratively fixed for rotation with the drive shaft 1068 to transfer rotational force.

The linkage assembly 1064 illustratively includes a track system 1070 for guiding movement of the shafts 1062, 1068. The track system 1070 includes a drive track 1072 and a key track 1074 defined through the housing 1038 and having corresponding shapes to support coordinate movement of the shafts 1062, 1068. In the illustrative embodiment, the drive track 1072 receives the drive shaft 1068 and the key track 1074 receives the key shaft 1062 for guiding movement of the operational handle 1045. The drive track 1072 is illustratively a linear track shaped to closely support the drive shaft 1068 for translation and having a (lateral) extension length corresponding with the lateral movement of the connection bar 1044 as indicated in FIGS. 20A-22. The drive shaft 1068 is operable under the user's control between a left hand position (as indicated in FIG. 25A) corresponding with the disengaged position of the latch pin assemblies 1036, 1037, and a right hand position (as indicated in FIGS. 25B and C) corresponding to the engaged position of the latch pin assemblies 1036, 1037.

The key track 1074 illustratively includes a lock section 1076 and a travel section 1078 connected with a joint 1080 of the lock section 1076. The lock section 1076 illustratively extends from the joint 1080 out of correspondence with the drive track 1072 to enable a two-step operation. The lock section 1076 illustratively extends from the joint 1080 in a direction orthogonal to the drive track 1072 such that when the key shaft 1062 is within the lock section 1076 (as indicated in FIG. 25B), translation of the shafts 1062,1068 along their respective track 1072 or section 1078 is blocked to prevent translation of the operational handle 1045 and disengagement of the latch pin assemblies 1036, 1037. The lock section 1076 is illustratively formed to extend with curvature to accommodate the arc of the key shaft 1062 to traverse the lock section 1076 to drive pivoting of the strut 1066 about the drive shaft 1068. The travel section 1078 illustratively extends parallel with the drive track 1072 to permit the lateral motion of the operation handle 1045 when the key shaft 1062 is arranged in the travel section 1078.

In the locked position of key shaft 1062 (as indicated in FIGS. 24C and 25C) the key shaft 1062 is within the lock section 1076 blocking the operational handle 1045 from movement (to the left) to disengage the latch pin assemblies 1036,1037. From the locked position of the key shaft 1062, the trigger 1060 can be moved (downward) into the disengaged position (as indicated in FIGS. 24B and 25B) to place the key shaft 1062 in the travel section 1078. The operational handle 1045 is now free to traverse its lateral movement because the key shaft 1062 is within the travel section 1078. The operational handle 1045 can be moved to the left position (as indicated in FIGS. 24A and 25A) to position the drive pin in the left hand position corresponding to the disengaged position of the latch pin assemblies 1036,1037. Accordingly, when the trigger 1060 is in the disengaged position, the operational handle 1045 can be moved laterally to drive the latch pin assemblies 1036,1037 between the engaged and disengaged positions.

Figure 26:
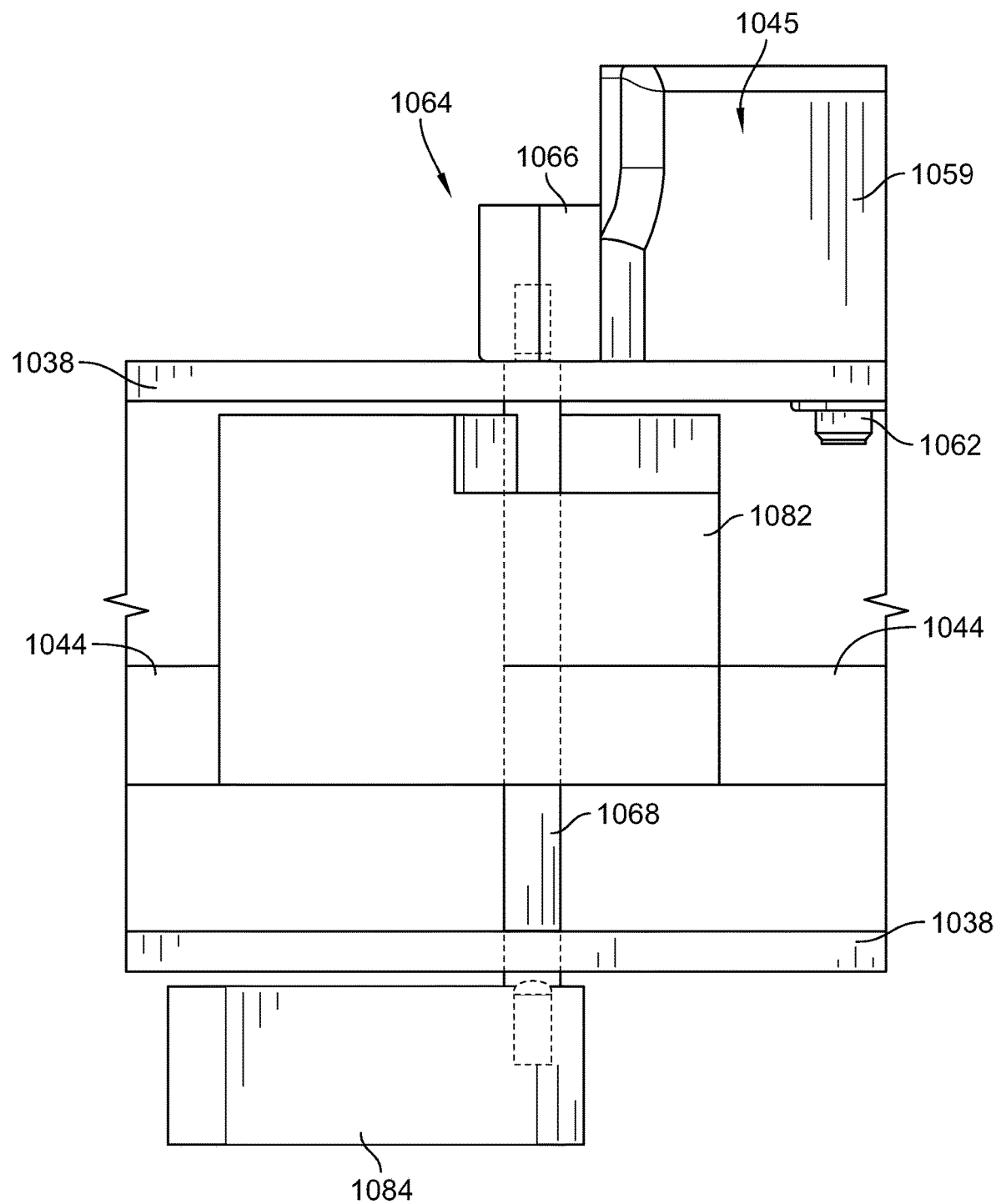
FIG. 26 is a bottom plan view of the docking assembly of FIGS. 18 and 19 having portions removed or rendered transparent to show that the first pin extends through the docking receiver and connects with a second handle for engagement with a user's hand to pivot the second handle to rotate the first pin and pivot the second pin out from the rotation track to enable translation of the latch assembly out of the locked position, and showing that a carriage is connected between the first pin and the connection bar to transfer translation to the latch pins.

As shown in FIG. 26, the linkage assembly 1064 illustratively includes a carriage 1082 connected with each of the connection bar 1044 and the drive shaft 1068 to transmit translational force. The drive shaft 1068 extends through the drive track 1072 in the housing 1038 (upper portion), through the carriage 1082, through a slot in the housing 1038 (lower portion), and connects with a handle 1084. The drive shaft 1068 illustratively extends through the carriage 1082 free for rotation relative to the carriage 1082. The handle 1084 is adapted for engagement with a user's hand and is fixed with the drive shaft 1068 for rotation such that a user can rotate the handle 1084 to rotate the drive shaft 1068 to selectively move the key shaft 1062 along the lock section 1076 of the key track 1074. The user can, thus, operate the trigger 1060 between engaged and disengaged positions from the opposite side of the docking receiver 1032 from the operational handle 1045.

Returning briefly to FIG. 1, the tower base 12 on a head end of the patient support 10 illustratively includes a graphical user interface (GUI) 180 for operation of the patient support 10. The GUI 180 is illustratively arranged on an upper end of the tower base 12 facing slightly upward and away from the connection assembly 18 for ease in viewing and access by the user. In the illustrative embodiment, only the head end tower base 12 includes a GUI 180 but in some embodiments, either or both of the head end and foot end tower bases 12 may include the GUI 180.

The GUI 180 is illustratively embodied to include a screen 182 for display of graphical images and text. The screen 182 is embodied as a touch screen display allowing interactive user-input directly (or hovering in close proximity) on the screen by hand or instrument. In some embodiments, the GUI 180 may include any suitable type of input devices, for example but without limitation, a touch pad, voice recognition systems, physical buttons/switches, and/or gesture based systems.

Figure 120:
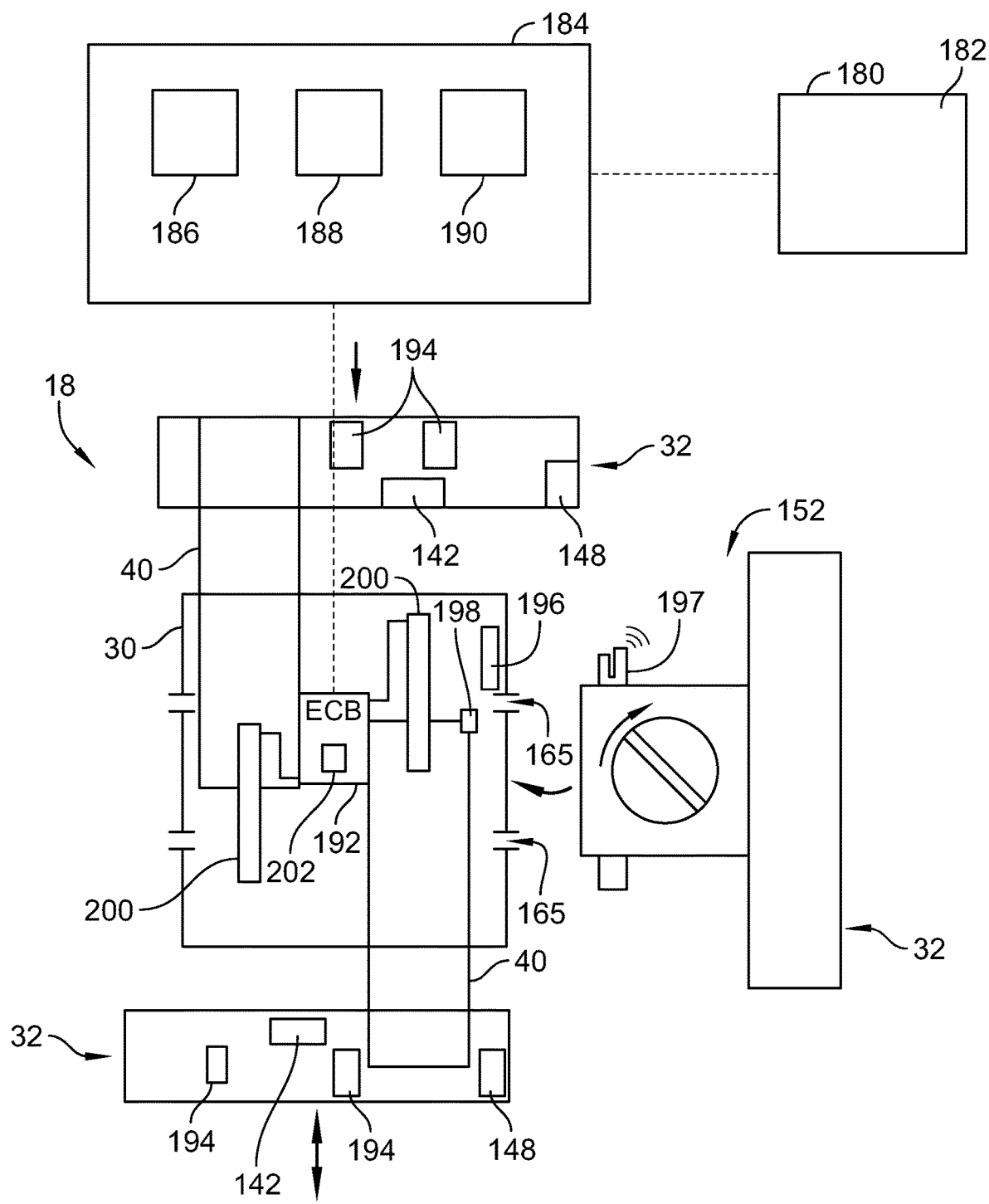
FIG. 120 is a diagrammatic view of a control system of the patient support arranged in communication with various features of the display and the connection assemblies to facilitate patient support operations.

As shown in FIG. 120, the GUI 180 is illustratively coupled for operation with a control system 184 of the patient support 10. The control system 184 illustratively includes processor 186, memory device 188, and communications and graphical circuitry 190 arranged for conducting GUI and/or patient support operations. Communications and graphical circuitry 190 may include wireless communications circuitry for wirelessly communicating with various devices. The control system 184 is illustratively arranged within the head end tower base 12, but in some embodiments, may be arranged in any suitable location. Various operations of the patient support 10 can be controlled and/or monitored via the GUI 180.

In the illustrative embodiment as shown in FIG. 120, each connection assembly 18 includes an electronic control board (ECB) 192 in communication with the control system 184. The ECB 192 is arranged in communication with various sensors to enable operations of the patient support 10. In some embodiments, components and/or functionality of the ECB 192 and control system 184 may be partly or fully shared. On each docking receiver 32, the sensors 142, 148 are in communication with the ECB 192 to communicate the position of the locking assembly 134 and whether a connection tube 36 is received within the docking slot 34. Each of the sensors 142, 148 are illustratively formed as a limit switch, but in some embodiments, may include proximity switches and/or any other suitable type or arrangement of sensors.

Each docking receiver 32 illustratively includes a pair of sensors 194 arranged in communication with the ECB 192 to determine the type of support top connected with the docking receiver 32. The pair of sensors 194 are illustratively embodied as reed switches arranged to detect signals from the support tops indicating their type, for example, as a flat support top 14, prone support top 24, or lateral support top. The support tops may include embedded magnetic code identifiers (e.g., code or tags) which can be sensed by the sensors 194 and communicated to the control system 184 to determine the type of support top for operation of the patient support 10.

A sensor 196 is illustratively arranged on the frame 30 in communication with the ECB 192 for determining the attachment of the lateral extension 152 with the frame 30. The sensor 196 can detect the proximity of a magnetic element 197 embedded in the pins 164 of the lateral extension 152 and is arranged to generate a signal when the pins 164 are properly seated in the holes 167 of the frame 30. Another sensor 198 is illustratively arranged near each of the shafts 165 which support the lateral extension 152. When the lateral extension 152 is attached with the frame 30, the corresponding sensor 198 is arranged for communication with the connector 178 to communicate the position of the locking assembly 134 of the lateral extension 152 with the ECB 192.

The connection assembly 18 illustratively includes a position sensor 200 for each slide plate 40 arranged to determine the position of the corresponding slide plate 40 relative to the frame 30. The position sensors 200 are illustratively embodied as soft potentiometers for detecting the position of the corresponding slide plate 40 to determine the amount of extension of the slide plate 40 out from the axis 15 (axis 15 extending into the page in FIG. 115). The position sensors 200 are in communication with the ECB 192 to communicate the detected position of their corresponding slide plates 40.

The ECB 192 itself includes a sensor 202 for determining the rotational position of the connection assembly 18 about the axis 15. The sensor 202 is embodied as an accelerometer arranged to detect the amount of tilt of the frame 30. The sensor 202 is arranged in communication with the ECB 192 to communicate the detected tilt position for determination of the angular position of the connection assembly 18, and thus the angular position of any connected support top.

The control system 184 can provide coordinated operation of the patient support 10. The control system 184 together with the ECBs 192 of the connection assemblies 18 accesses actively updated configuration information for use in configuration of the patient support 10 and operation of the GUI 180 as discussed in additional detail below.

Figure 27:
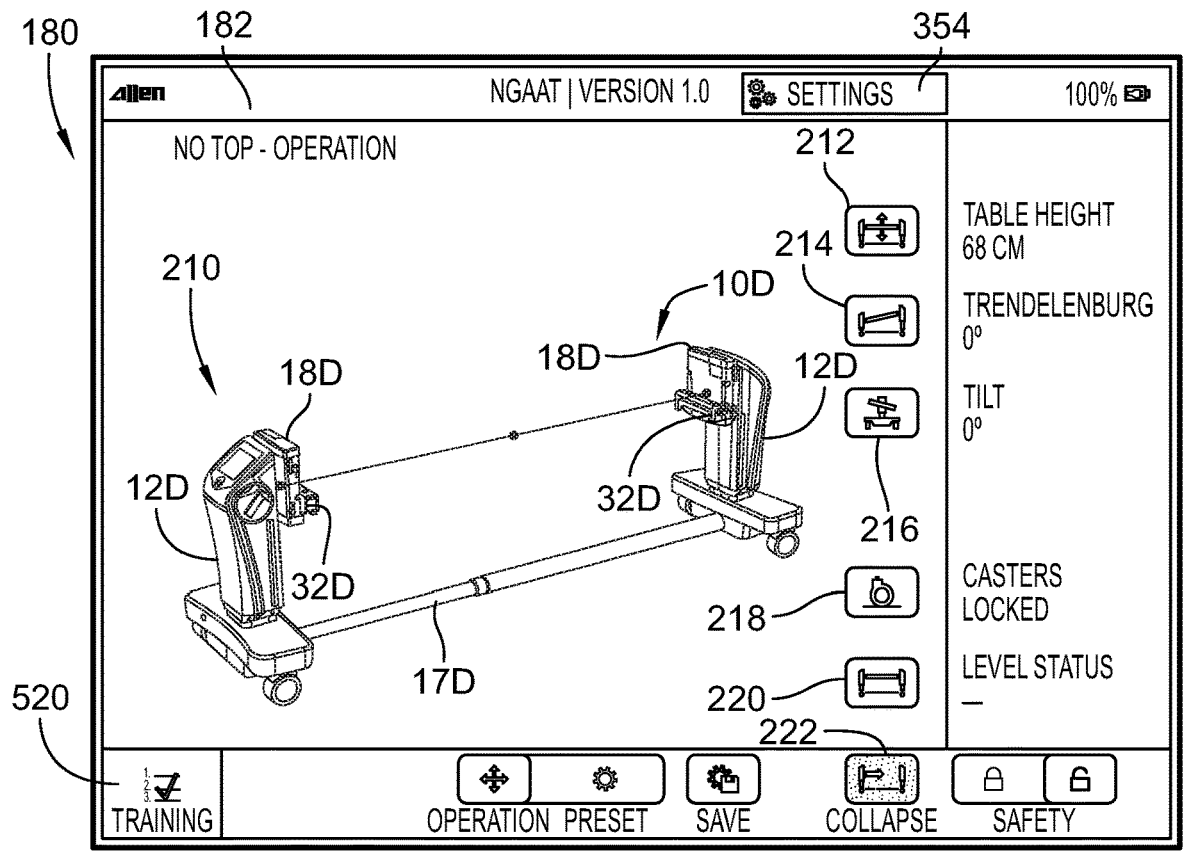
FIG. 27 is a screen shot of the display of the patient support of FIGS. 1-4 showing that a depiction of the patient support is presented on the display including the end supports with the connection assemblies and without a patient support top connected.
Figure 116:
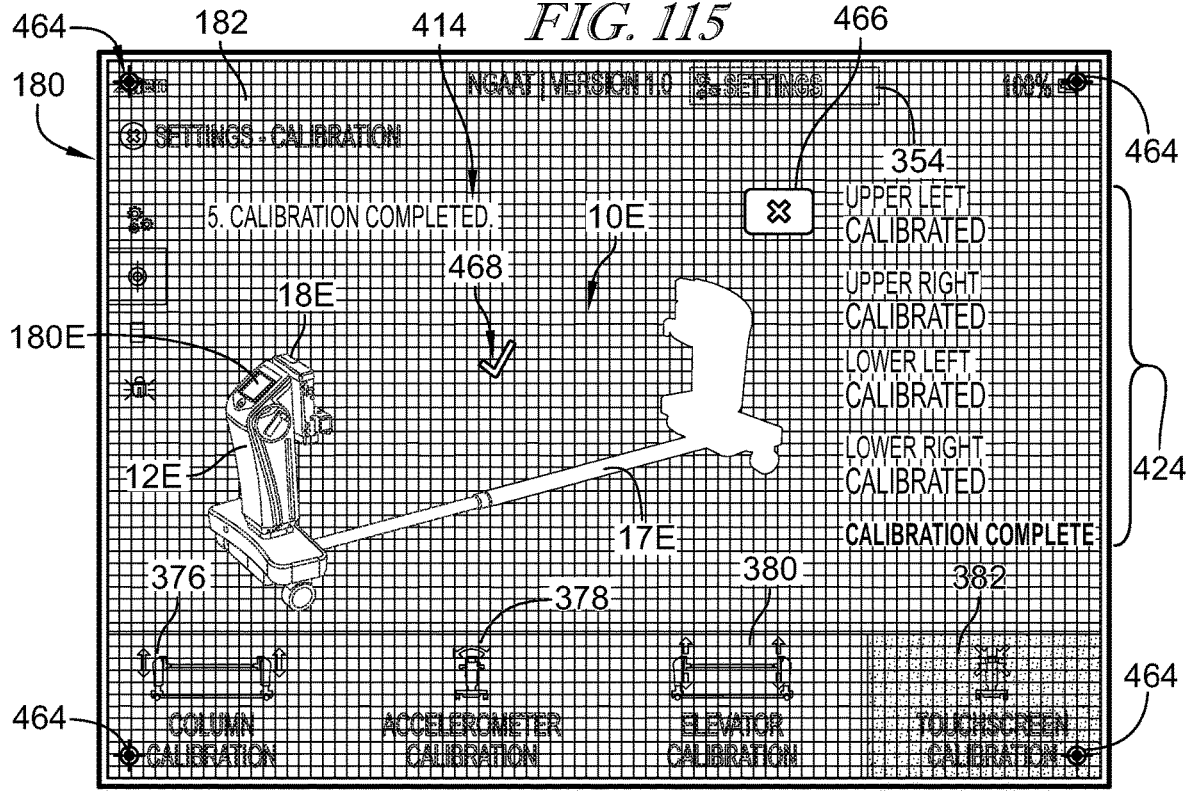

As shown in FIGS. 27-116, screen shots of the graphical user interface 180 are presented. Referring to FIG. 27, the screen 182 illustratively displays a 3-dimensional (3D) depiction 210 of the patient support 10. The 3D depiction 210 is embodied as a perspective image of the patient support 10 arranged as currently positioned. For example, the positions of the tower bases 12 and connection assemblies 18 are depicted according to the actual current positions of the patient support 10 as indicated by the appropriate sensors in communication with the control system 184, as discussed above. For descriptive purposes, reference to features of the 3D depiction 210 which correspond with features of the patient support 10 include an "D" designation, for example, the tower bases 12 are depicted as part of the 3D depiction 210 as indicated by numeral "12D" as shown in FIG. 27.

As shown in FIG. 27, the screen 182 displays a number of icons for review and/or control of various parameters of the patient support 10. A number of status icons include a table height icon 212, a Trendelenburg icon 214, a tilt icon 216, a caster icon 218, and a leveling icon 220, each available for user selection to adjust the associated parameter of the patient support 10. A training button 520 is presented for user selection to enter a training mode as discussed in additional detail relative to FIGS. 137-140, below.

Referring to FIG. 27, the height icon 212 is available for user selection to adjust the overall height of an attached support top above the floor. Associated status information is illustratively displayed near the appropriate status icon. For example, the "Table Height 68 cm" is displayed to the right of the height icon 212 to indicate that the connection assembly 18 is currently arranged to position an attached support top at a height of 68 cm above the floor. The Trendelenburg icon 214 is available for user selection to adjust the angle of an attached support top along the direction of the axis 15 (head to foot end), otherwise known as the Trendelenburg angle. As indicated to the right of the Trendelenburg icon 214, the current Trendelenburg angle as communicated by the control system 184 is 0 degrees. The tilt icon 216 is available for user selection to adjust the angle of tilt of an attached support top about the axis 15. As indicated to the right of the tilt icon 216, the current tilt angle as communicated by the control system 184 is 0 degrees. The caster icon 218 is available for user selection to adjust between locked, unlocked, and steering modes as discussed in additional detail herein. As indicated to the right of the caster icon 218, the current caster mode is locked as communicated by the control system 184. The level icon 220 is available for user selection to adjust a current position of the patient support to a level positon having 0 degrees of tilt and 0 degrees of Trendelenburg angle. In arrangements having an attached lateral top with leg break action, the leg break may also be leveled to a 0 degree position by operation of the level icon 220. Accordingly, the level icon 220 can provide a single operation to level out multiple variables of the patient support 10.

In the illustrative embodiment as shown in FIG. 27, the 3D depiction 210 displays no support top connected with the connection assemblies 18D. The sensors 142 indicate to the control system 184 that no connection tube 36 is received within the docking slot 34 and the sensors 148 indicate to the control system 184 that no type of support top is detected. In the illustrative embodiment, the indication from the sensors 142, 148 of no support top is embodied as no signal, but in some embodiments, a signal indicating no support top may be provided. The control system 184 has determined that no support tops are connected with the connection assemblies 18 and communicates with the GUI 180 to display the 3D depiction 210 to include no support tops on the screen 182 as the current status of the patient support 10.

Notably, when no support tops are secured with the connection assemblies 18, a user can collapse the patient support 10 along the longitudinal direction to reduce the distance between the tower bases 12 for ease of transport and/or storage. Responsive to the determination of no support tops, the control system 184 communicates with GUI 180 to display a collapse icon 222. The collapse icon 222 is selectable by the user to prompt collapse of the cross tube 17 as discussed in additional detail herein.

Figure 28:
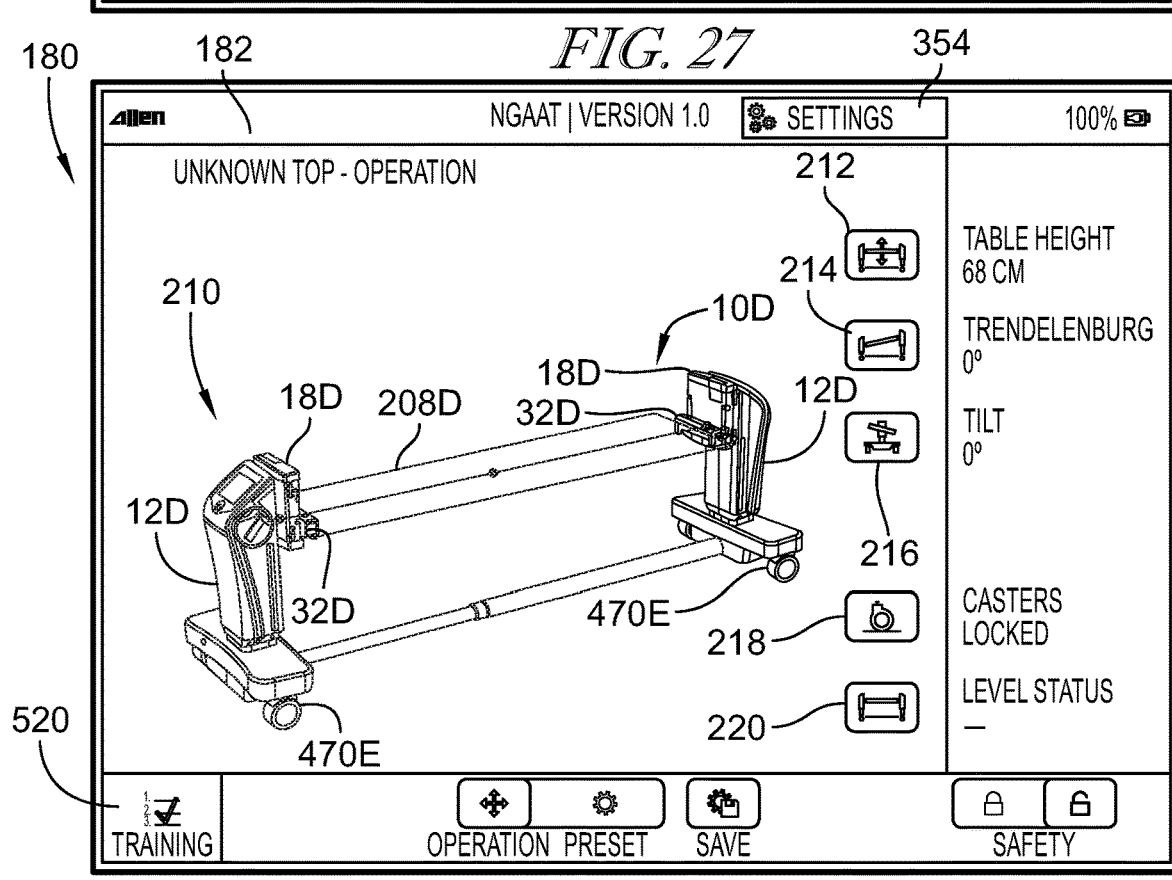
FIG. 28 is a screen shot of the display of the patient support of FIGS. 1-4 showing that a depiction of the patient support is presented on the display including the end supports with the connection assemblies connected with a generic patient support top and showing that the type of patient support top is unknown.

As shown in FIG. 28, the control system 184 has communicated to the GUI 180 that a generic support top is connected with the connection assemblies 18. The control system 184 illustratively receives communication from the sensors that a connection tube 36 is received within the docking slots 34 but no (discernible) communication of support top type, and thus determines that a generic support top is connected. The GUI 180 illustratively indicates the generic support top as 208D in the 3D depiction 210. The indication of the generic support top 208D is merely a non-specific outline of a table top because the illustrative generic support top has not communicated its type (as either supine, prone, lateral, etc.) to the control system 184.

Figure 29:
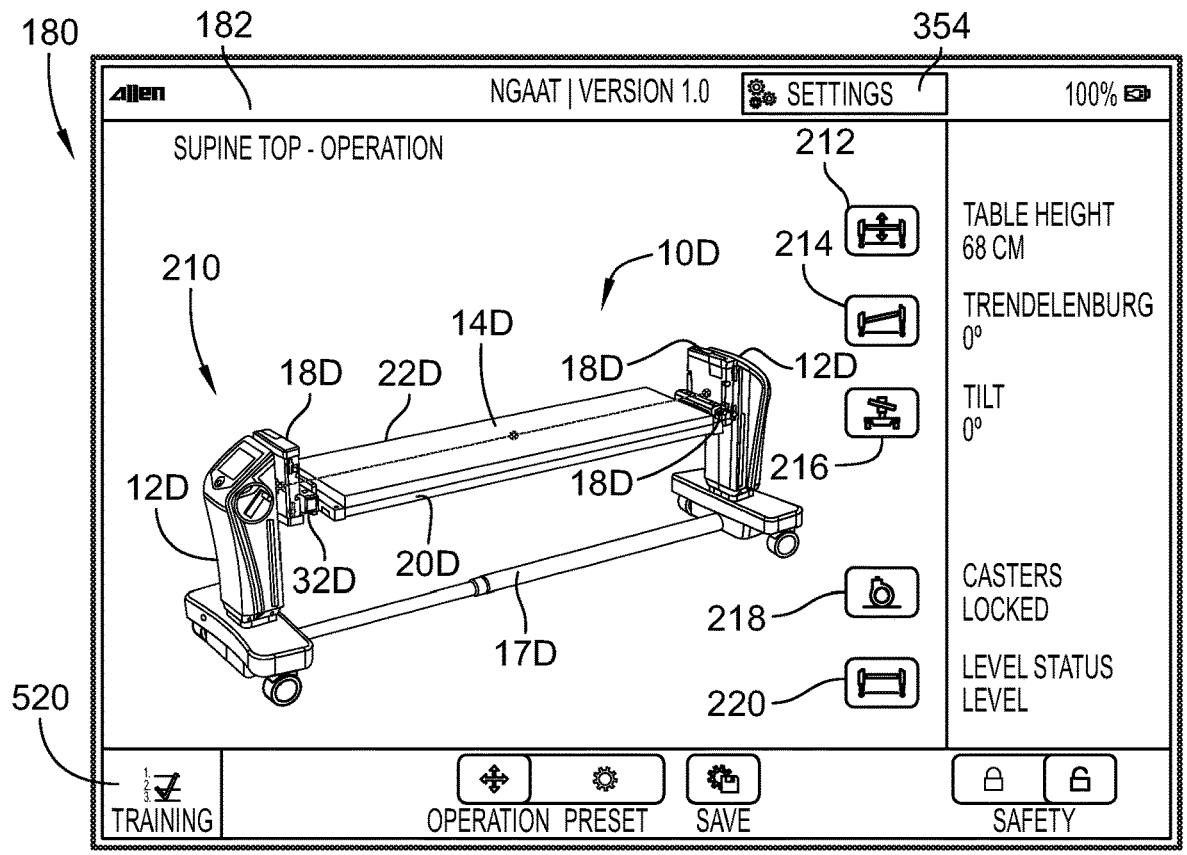
FIG. 29 is a screen shot of the display of the patient support of FIGS. 1-4 showing that a depiction of the patient support is presented on the display including the tower bases with the connection assemblies connected with a patient support top and showing that the patient support has determined that the patient support top is a supine support top.

As shown in FIG. 29, the control system 184 has communicated to the GUI 180 that the supine top 14 is connected with the connection assemblies 18. The control system 184 receives communication from the sensors that a connection tube 36 is received within the docking slots 34 and communication from the sensors of the supine type of support top. The GUI 180 illustratively indicates the supine top as 14D in the 3D depiction 210. The indication of the supine support top 14D includes indication of the shape and features of the supine support top 14 including the frame 20D and padding 22D.

Figure 30:
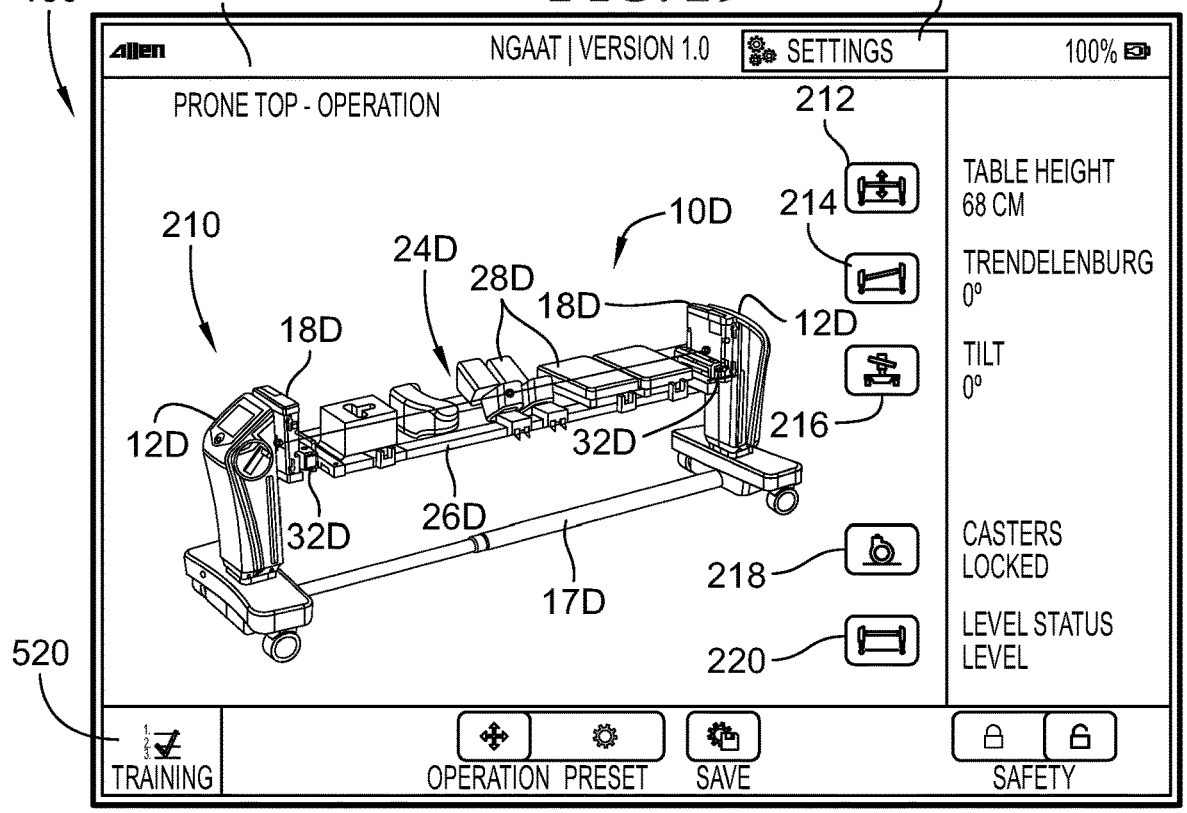
FIG. 30 is a screen shot of the display of the patient support of FIGS. 1-4 showing that a depiction of the patient support is presented on the display including the tower bases with the connection assemblies connected with a patient support top and showing that the patient support has determined that the patient support top is a prone support top.

As shown in FIG. 30, the control system 184 has communicated to the GUI 180 that the prone top 24 is connected with the connection assemblies 18. The control system 184 receives communication from the sensors that a connection tube 36 is received within the docking slots 34 and communication from the sensors of the prone type of support top. The GUI 180 illustratively indicates the prone top as 24D in the 3D depiction 210. The indication 24D includes indication of the shape and features of the prone top 24 including the frame 26D and padding 28D.

Figure 31:
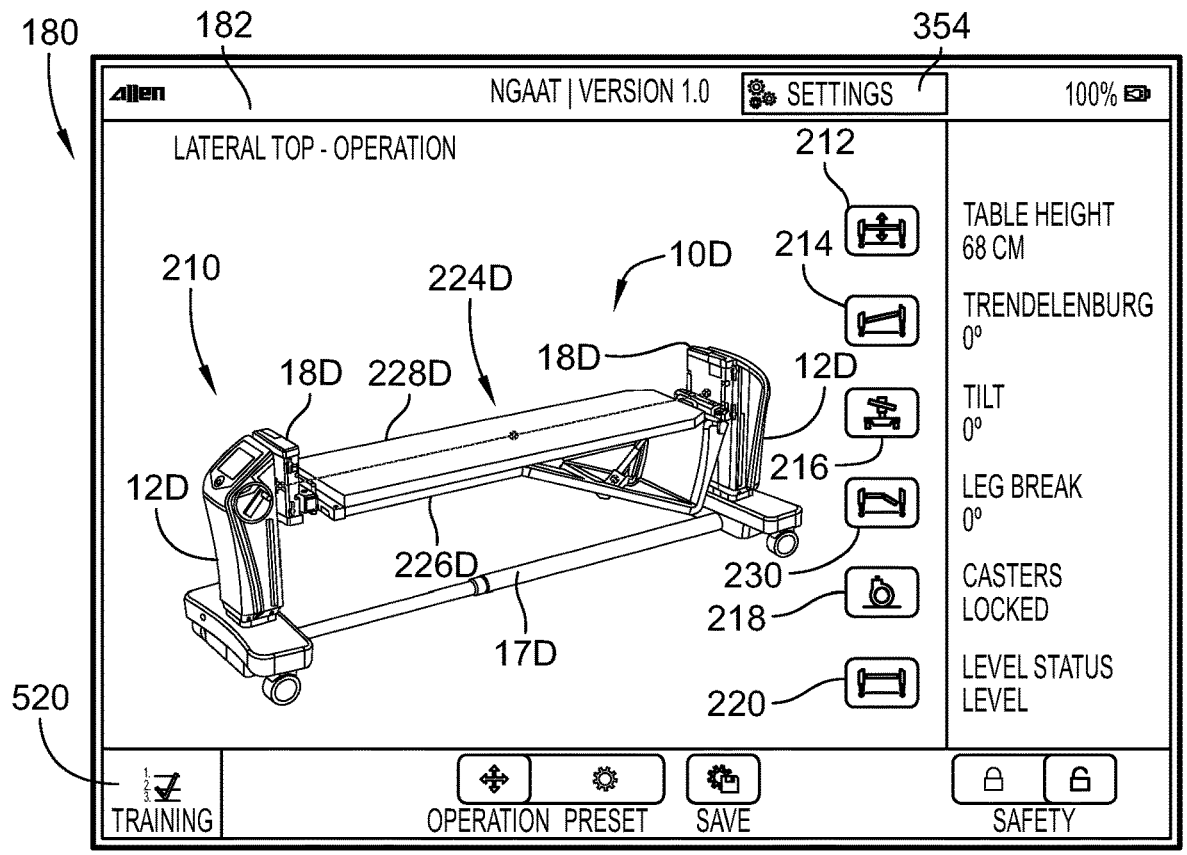
FIG. 31 is a screen shot of the display of the patient support of FIGS. 1-4 showing that a depiction of the patient support is presented on the display including the tower bases with the connection assemblies connected with a patient support top and showing that the patient support has determined that the patient support top is a lateral support top having a leg break (lowering) feature.

As shown in FIG. 31, the control system 184 has communicated to the GUI 180 that a lateral support top 224 is connected with the connection assemblies 18. The lateral support top 224 is illustratively embodied to allow leg drop arrangements in which a leg portion of the support top is tilted downward from a hinge near the center of the support top (e.g., near the patient's hip) to lower the patient's legs relative to her torso, providing particular access to a patient's spine. An example of a suitable lateral support top includes those lateral support tops as disclosed with U.S. Patent Application Publication Nos. 2017/0112699 and 2017/0112698, the contents of which are incorporated by reference herein, including at least those portions pertaining to patient support systems and lateral patient support tops. The control system 184 receives communication from the sensors that a connection tube 36 is received within the docking slots 34 and communication from the sensors of the lateral type of support top. The GUI 180 illustratively indicates the lateral top as 224D in the 3D depiction 210. The indication of the lateral support top 224D includes indication of the shape and features of the lateral top including a lateral frame 226D and padding 228D.

As mentioned above, the lateral support top 224 is adapted to provide a leg break action in which a patient's legs are lowered relative to her torso to provide particular skeletal and/or muscle arrangement. Responsive to determination of the connection of the lateral support top 224, the control system 184 communicates with the GUI 180 to present a leg break icon 230. The leg break icon 230 is user selectable to adjust the angle of leg break applied to the support top 224, and ultimately to the patient. As indicated to the right of the leg break icon 230, the current leg break angle as communicated by the control system 184 is 0 degrees.

Figure 32:
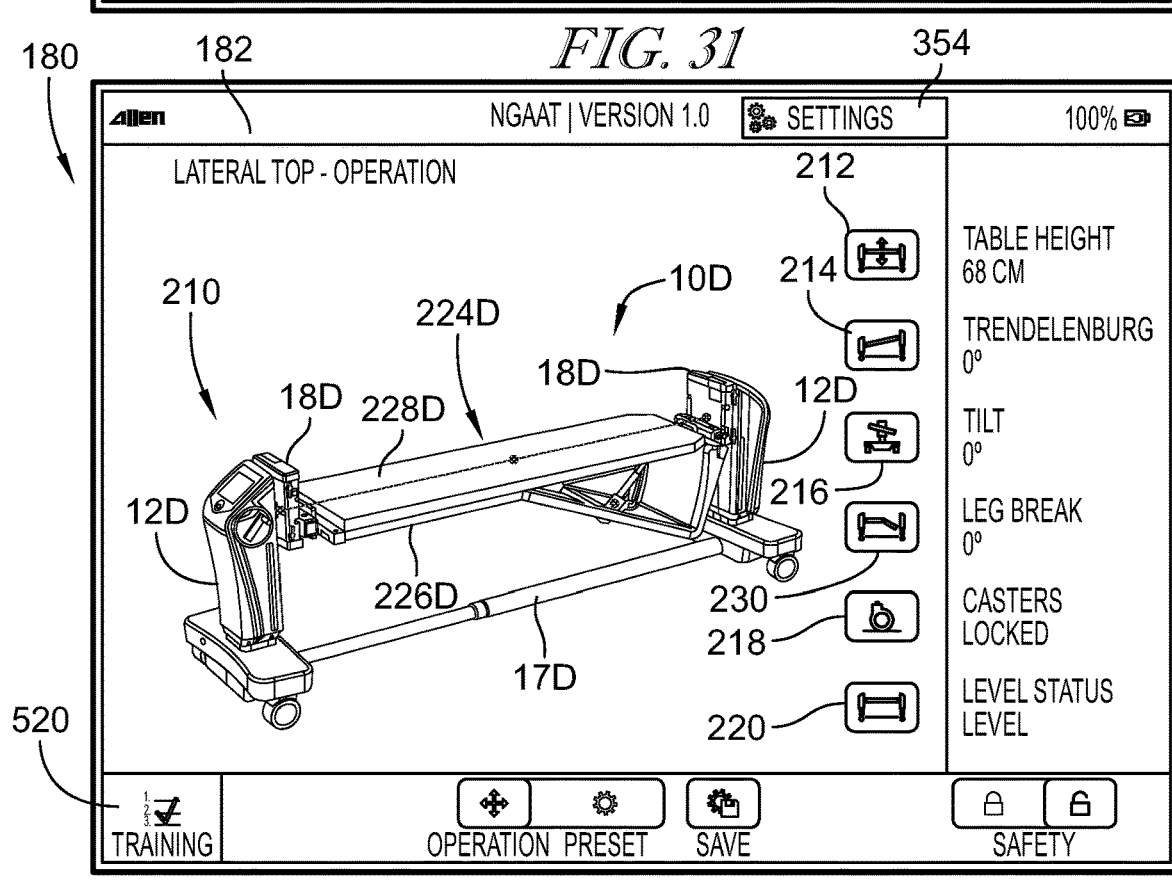
FIG. 32 is a screen shot of the display of the patient support of FIGS. 1-4 similar to FIG. 31 showing that the patient support has determined that the patient support top is a lateral support top, and showing an initial operation screen for the lateral support top.

As shown in FIG. 32, an initial state of the lateral support top 224D is presented as a main screen. In the present example, the lateral support top 224 has been connected and is arranged with a table height of 68 cm, level, with no leg break, and with casters 470 locked. From this exemplary initial position, adjustment of the patient support 10 using the GUI 180 is described.

Figure 33:
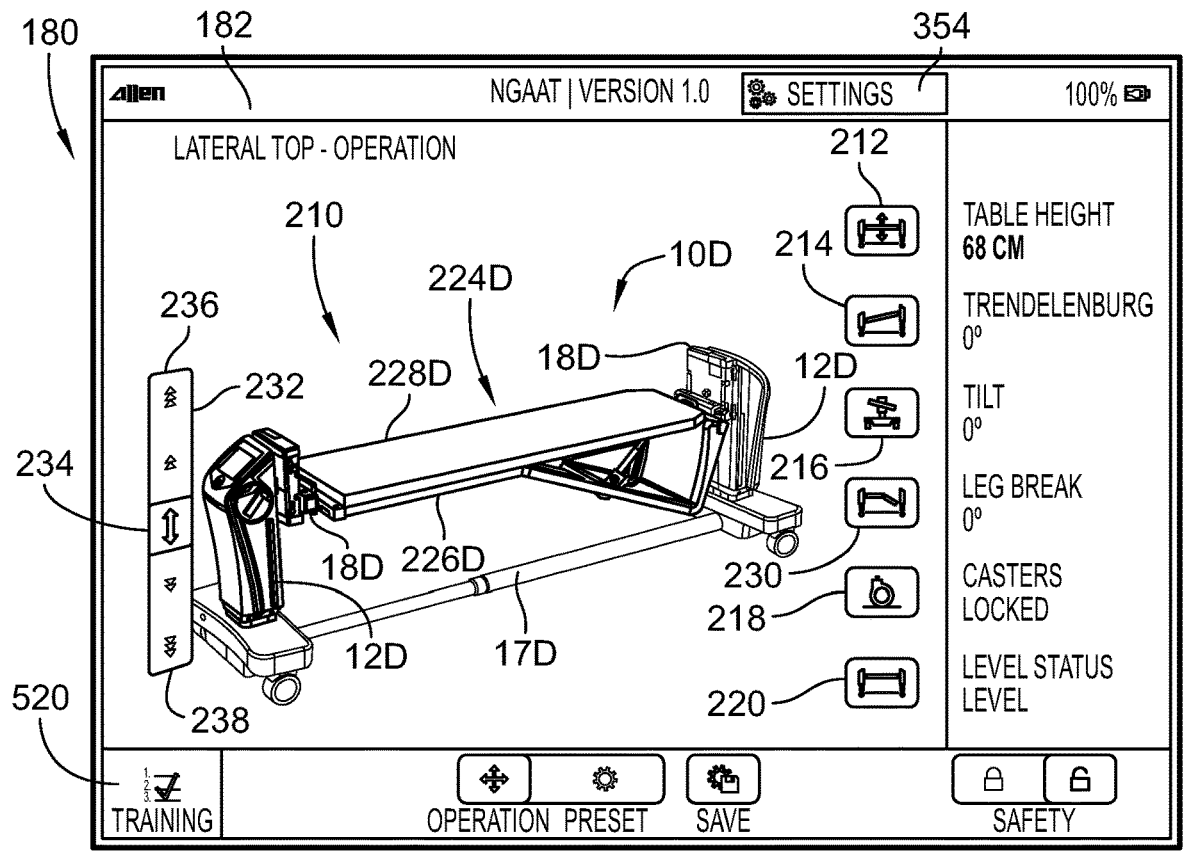
FIG. 33 is a screen shot of the display of the patient support of FIGS. 1-4 similar to FIG. 32 showing that the patient support has determined that the patient support top is a lateral support top, and showing that a head side (left) tower base has been selected for height adjustment and indicating the selection of the head side tower base by highlighting the head side tower base, the lateral support top, and a table height indication icon, and by displaying an adjustment bar for user interface near the head side tower base (left)

In the illustrative embodiment as shown in FIG. 33, the user has selected the tower base 12 at the head end for adjustment. The user has selected the head end tower base 12 by directly touching on (or hovering near for a minimum time) the indication of the head end tower base 12D on the screen 182. Selection of the head end tower base 12D is indicated by highlighting the head end tower base 12D and support top 224D (represented by bolding in FIG. 33).

As shown in FIG. 33, responsive to the user's selection of the head end tower base 12D, a height adjustment bar 232 is displayed near the head end. The height adjustment bar 232 is embodied as a slide bar including slider 234. The user can drag the slider 234 between ends 236, 238 of the bar 232 to adjust the height of the head end tower base 12 (independently from the height of the foot end tower base 12).

In the illustrative embodiment, the bar 232 is illustratively arranged vertically to correspond with the directions of adjustment of the height of the tower base 12. The slider 234 has a default position in the center of the bar 232 and the direction of dragging of the slider 234 corresponds with the desired movement of the tower base 12 height—i.e., user dragging of the slider 234 towards the upper end 236 initiates raising of the head end tower base 12, and dragging towards the lower end 238 initiates lowering of the head end tower base 12. Dragging the slider 234 towards the upper end 236 or lower end 238 communicates with the control system 184 to raise or lower the height of the head end tower base 12, respectively. The slider 234 is illustratively dragged by user touching of the slider 234 and dragging the slider 234 towards the respective end 236, 238 and holding until the desired height position of the tower base 12 is achieved. In some embodiments, touching (or hovering over for a minimal time) the slider bar 232 at the desired drag location for the slider 234 automatically moves the slider 234 to that location. Orienting the slider bar 232 to correspond with the movements of the adjustment can provide an intuitive interface for the user, reducing acclimation time and/or confusion.

In the illustrative embodiment, the height adjustment bar 232 is illustratively an incremental variable control having a first >> and second speed >>> designation such that dragging the slider 234 closer towards an end 236, 238 of the bar 232 provides faster adjustment operation. In some embodiments, a single speed of adjustment may be provided, and the initiation and continuation of adjustment may require the user to drag and hold the slider 234 fully to the selected end 236, 238. The slider 234 illustratively springs back to the center of the bar 232 upon release of the slider 234 by the user. The GUI 180 depicts the transitioning height of the head end tower base 12D (tracks) as the height adjustment is performed by the patient support 10.

Figure 34:
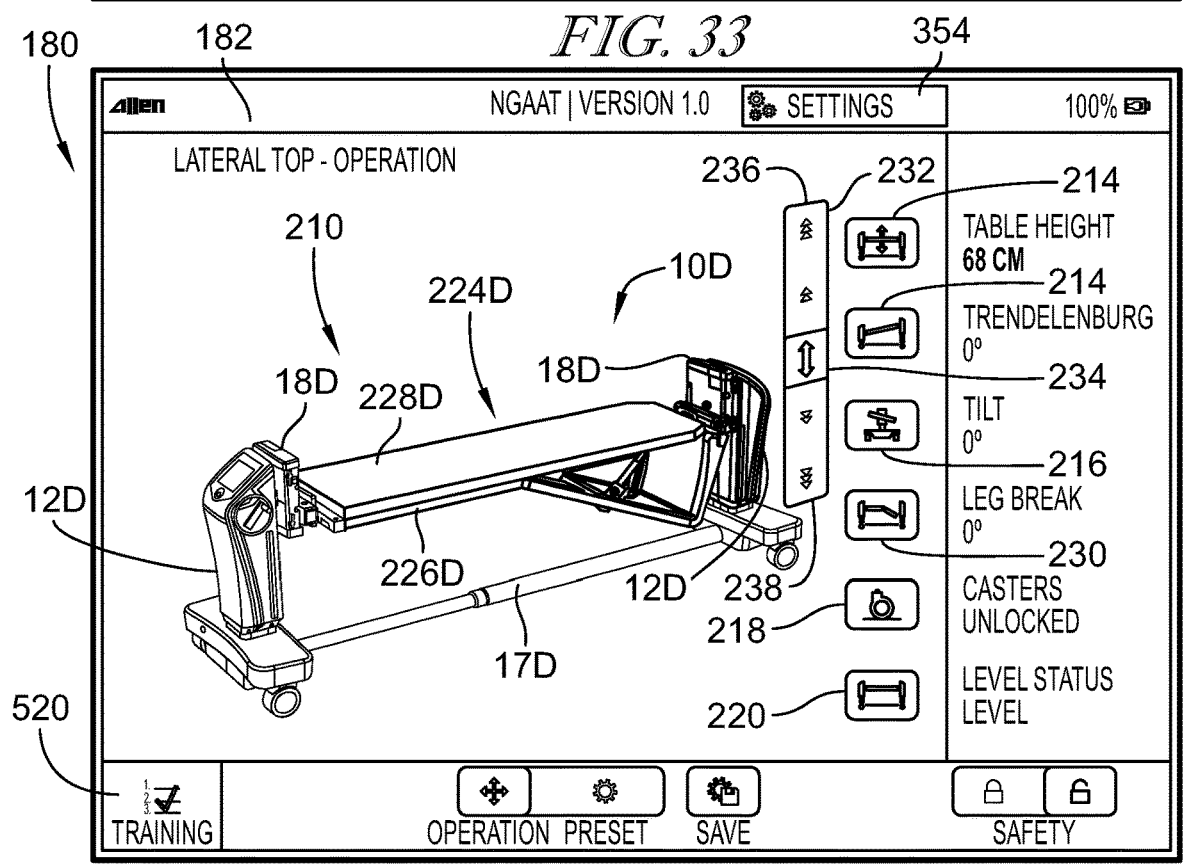
FIG. 34 is a screen shot of the display of the patient support of FIGS. 1-4 similar to FIG. 32 showing that the patient support has determined that the patient support top is a lateral support top, and showing that a foot side (right) tower base has been selected for height adjustment and indicating the selection of the foot side tower base by highlighting the head side tower base, the lateral support top, and the table height indication icon, and by displaying an adjustment bar for user interface near the foot side tower base (right)

As shown in FIG. 34, an adjustment operation of the foot end tower base 12 is shown. Responsive to the user's selection of the foot end tower base 12D, the foot end tower base 12D and the lateral support top 224D are highlighted (represented as bolding), and a height adjustment bar 232 is displayed near the foot end. Notably, previously selected features (e.g., head end tower base 12D) are illustratively deselected (no longer bolded) and the associated head end adjustment bars 232 has been removed. The height adjustment bar 232 for the foot end tower base 12 is adjustable to raise and lower the height of the foot end base tower 12 in the same manner as described above for the bar 232 for the head end tower base 12. The GUI 180 depicts the transitioning height of the foot end tower base 12D as the height adjustment is performed.

Figure 35:
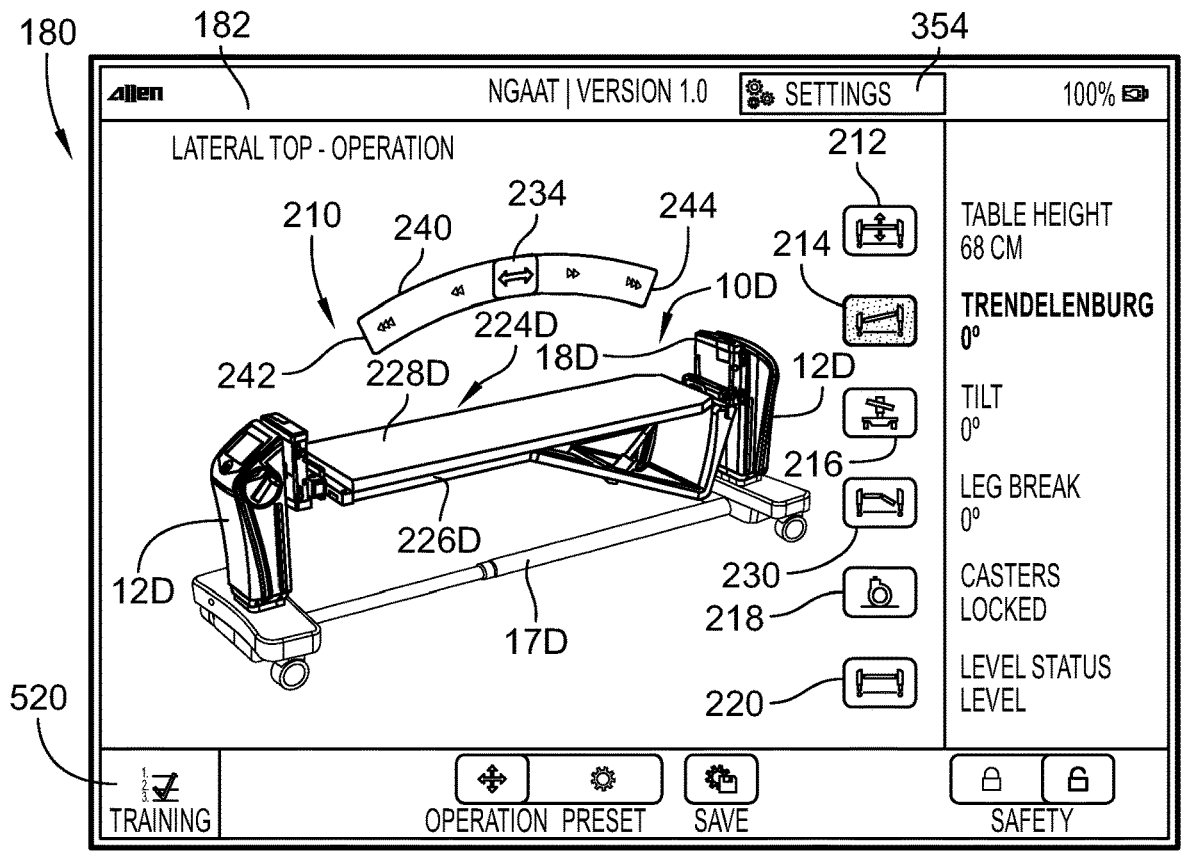
FIG. 35 is a screen shot of the display of the patient support of FIGS. 1-4 similar to FIG. 32 showing that the patient support has determined that the patient support top is a lateral support top, and showing that a Trendelenburg (and/or reverse Trendelenburg) adjustment has been selected and indicating the selection of the Trendelenburg adjustment by highlighting the tower bases, the lateral support top, and a Trendelenburg indication icon, and by displaying an adjustment bar for user interface over the lateral support top (center)

As shown in FIG. 35, the Trendelenburg icon 214 has been selected by the user to adjust the Trendelenburg angle of the support top 224. The selection of the Trendelenburg icon 214 is illustratively indicated on the GUI 180 by highlighting the icon 214 (represented by fill of icon 214) and highlighting the attached support top 224D and tower bases 12D (represented by bolding). Responsive to user selection of the Trendelenburg icon 214, a Trendelenburg adjustment bar 240 is displayed above the support top 224D. The adjustment bar 240 includes head end 242 and foot end 244 and a slider 234 operable between the ends 242, 244 similar to the previous adjustment bars 232. The adjustment bar 240 is arranged with curvature, and having ends 242,244 arranged along the horizontal corresponding with the motion of the Trendelenburg angle adjustment. A user can drag the slider 234 of the adjustment bar 240 towards the head end 242 to adjust the Trendelenburg angle of the support top 224 counter-clockwise or towards the towards the foot end 244 to adjust the Trendelenburg angle of the support top 224 clockwise, in the orientations of FIG. 36. The adjustment bar 240 illustratively supports variable control adjustment speed approaching the ends 242,244, but in some embodiments supports only one speed of adjustment. The GUI 180 depicts the transitioning Trendelenburg angle of the support top 224D and presents the current Trendelenburg angle information (right of icon 214) as the angle adjustment is performed.

Figure 36:
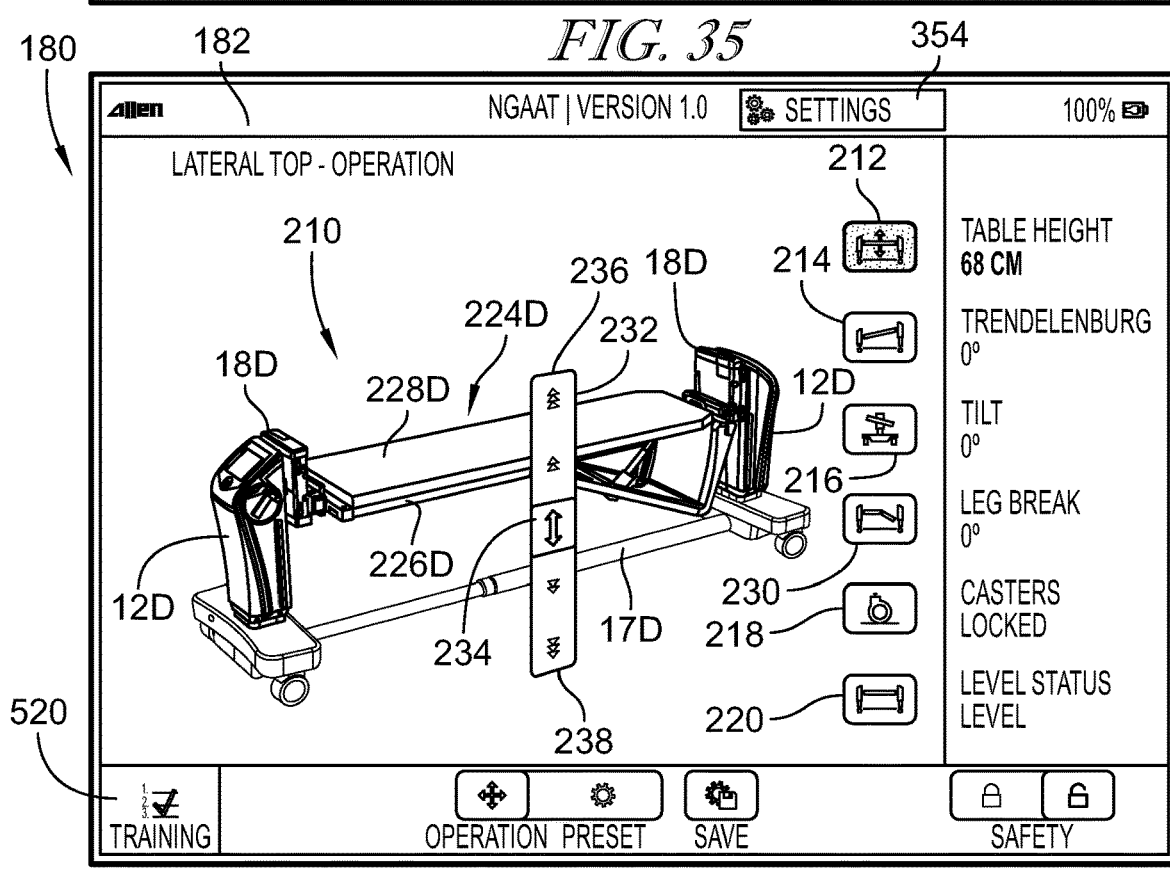
FIG. 36 is a screen shot of the display of the patient support of FIGS. 1-4 similar to FIG. 32 showing that the patient support has determined that the patient support top is a lateral support top, and showing that an overall table height adjustment has been selected and indicating the selection of the table height adjustment by highlighting the tower bases, the lateral support top, and the table height indication icon, and by displaying an adjustment bar for user interface near the center in front of the lateral support top.

As shown in FIG. 36, the table height icon 212 has been selected by the user. The selection is indicated by highlighting of the icon 212 (represented by fill of icon 212) and highlighting the tower bases 12D and support top 224D (represented by bolding). A table height adjustment bar 232 is presented in front of the patient support 10D near the middle of the patient support 10D. The adjustment bar 232 for the table height is illustratively operated similar to the other adjustment bars 232, 240. Adjustment of the table height using the adjustment bar 232 provides simplified adjustment of the height of both of the tower bases 12 simultaneously. The GUI 180 depicts the transitioning height of the support top 224D and presents the current table height information (right of icon 212) as the height adjustment is performed.

Figure 37:
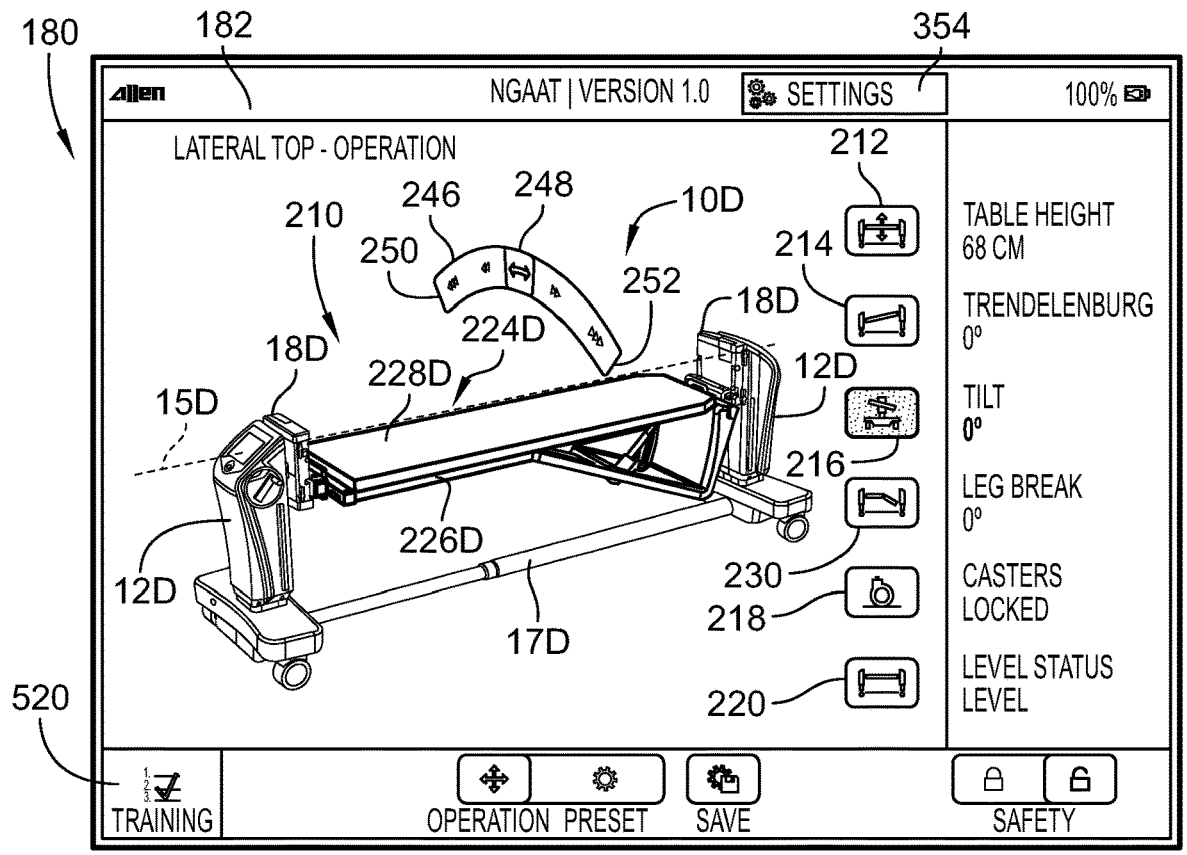
FIG. 37 is a screen shot of the display of the patient support of FIGS. 1-4 similar to FIG. 32 showing that the patient support has determined that the patient support top is a lateral support top, and showing that a table tilt adjustment has been selected and indicating the selection of the table tilt adjustment by highlighting the tower bases, the lateral support top, and the table tilt indication icon, and by displaying a lateral tilt adjustment bar for user interface over the center of the lateral support top.

As shown in FIG. 37, the tilt icon 216 has been selected by the user. The selection is indicated by highlighting the icon 216 (represented by fill of icon 216) and highlighting the support top 224D (represented by bolding). A tilt adjustment bar 246 is presented above the support top 224D. The tilt adjustment bar 246 illustratively extends with curvature between its ends 250,252 arranged near respective lateral sides of the support top 224D complimentary to the movement of the support top 224 under tilt adjustment (about the axis 15D). The adjustment bar 246 for the tilt angle is illustratively operated similar to the other adjustment bars 232, 240 by dragging the slider 248 between the ends 250,252 according to desired direction of tilt adjustment about axis 15 (clockwise or counterclockwise). The GUI 180 depicts the transitioning tilt angle of the support top 224D and presents the current tilt angle information (right of icon 216) as the tilt adjustment is performed.

Figure 38:
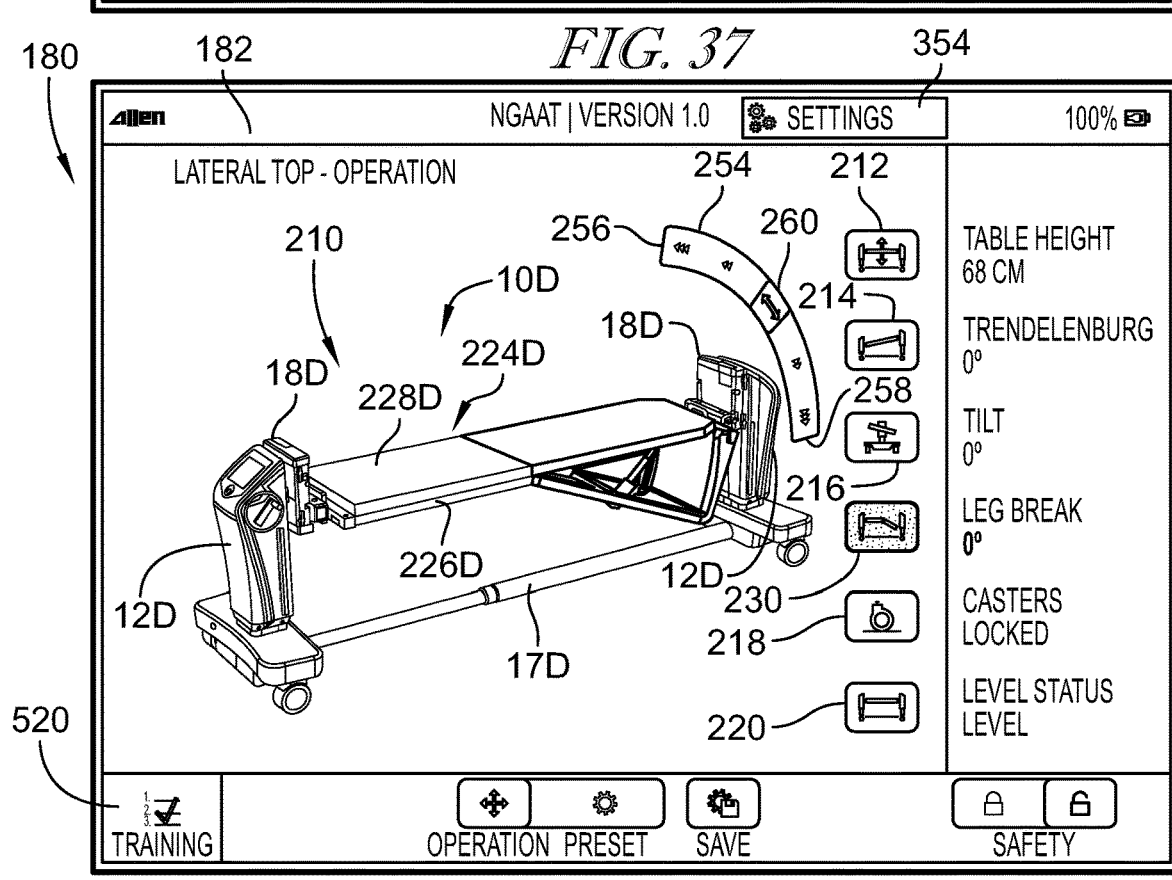
FIG. 38 is a screen shot of the display of the patient support of FIGS. 1-4 similar to FIG. 32 showing that the patient support has determined that the patient support top is a lateral support top, and showing that a leg break adjustment has been selected and indicating the selection of the leg break adjustment by highlighting a leg section of the lateral support top, and the leg break indication icon, and by displaying a leg break adjustment bar for user interface near the foot end of the lateral support top.

As shown in FIG. 38, the leg break function has been selected by the user by either selecting the icon 230 or the leg break portion of the depiction 210. The selection is indicated by highlighting the icon 230 (represented by fill of icon 230) and highlighting the leg portion of the support top 224D (represented by bolding). A leg break adjustment bar 254 is illustratively presented near the foot end of the patient support 10D extending with curvature between ends 256, 258 corresponding to the movement of the leg portion of the support top 224D under leg break adjustment (pivoting of the leg portion about the mid-section of the support top 224D corresponding with the patient's hip in the lateral position). The adjustment bar 254 for the leg break angle is illustratively operated similar to the other adjustment bars 232, 240, 246 by sliding the slider 248 between the ends 250,252 according to desired direction of tilt adjustment about axis 15 (clockwise or counterclockwise). The GUI 180 depicts the transitioning leg break angle of the support top 224D and presents the current leg break angle information (right of icon 230) as the leg break adjustment is performed.

Figure 39:
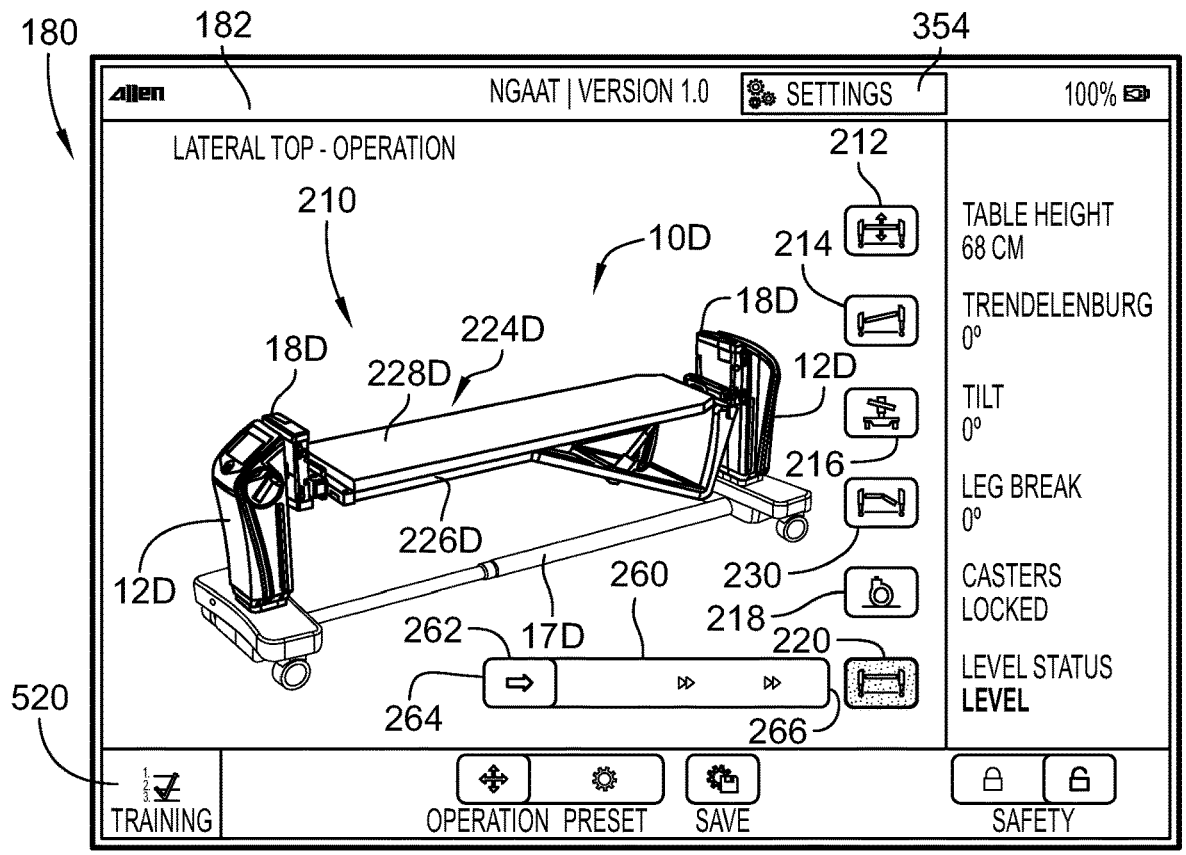
FIG. 39 is a screen shot of the display of the patient support of FIGS. 1-4 similar to FIG. 32 showing that the patient support has determined that the patient support top is a lateral support top, and showing that a leveling adjustment has been selected and indicating the selection of the leveling adjustment by highlighting the tower bases, the lateral support top, and the level status indication icon, and by displaying a leveling adjustment bar for user interface near the level status indication icon.

As shown in FIG. 39, the user has selected the level icon 220 to configure the support top 224 in the level position. The selection is indicated by highlighting the icon 220 (represented by fill of icon 220) and highlighting the support top 224D and the tower bases 12D (represented by bolding). A level adjustment bar 260 illustratively presented near the icon 220 and extends laterally between ends 264,266. The adjustment bar 260 for the leveling of the patient support 10 is illustratively operated similar to the other adjustment bars 232, 240, 246 by dragging the slider 262, however, the slider 262 is defaulted to the left end 264 and is triggered by sliding to the right end 266. The GUI 180 depicts the transitioning level positions of the support top 224D and presents the current level positions information (right of icons 214, 216, 230) as the leveling adjustment is performed. In some embodiments, the table height may be adjusted by operation of the level adjustment bar 260 to have a default position.

Figure 40:
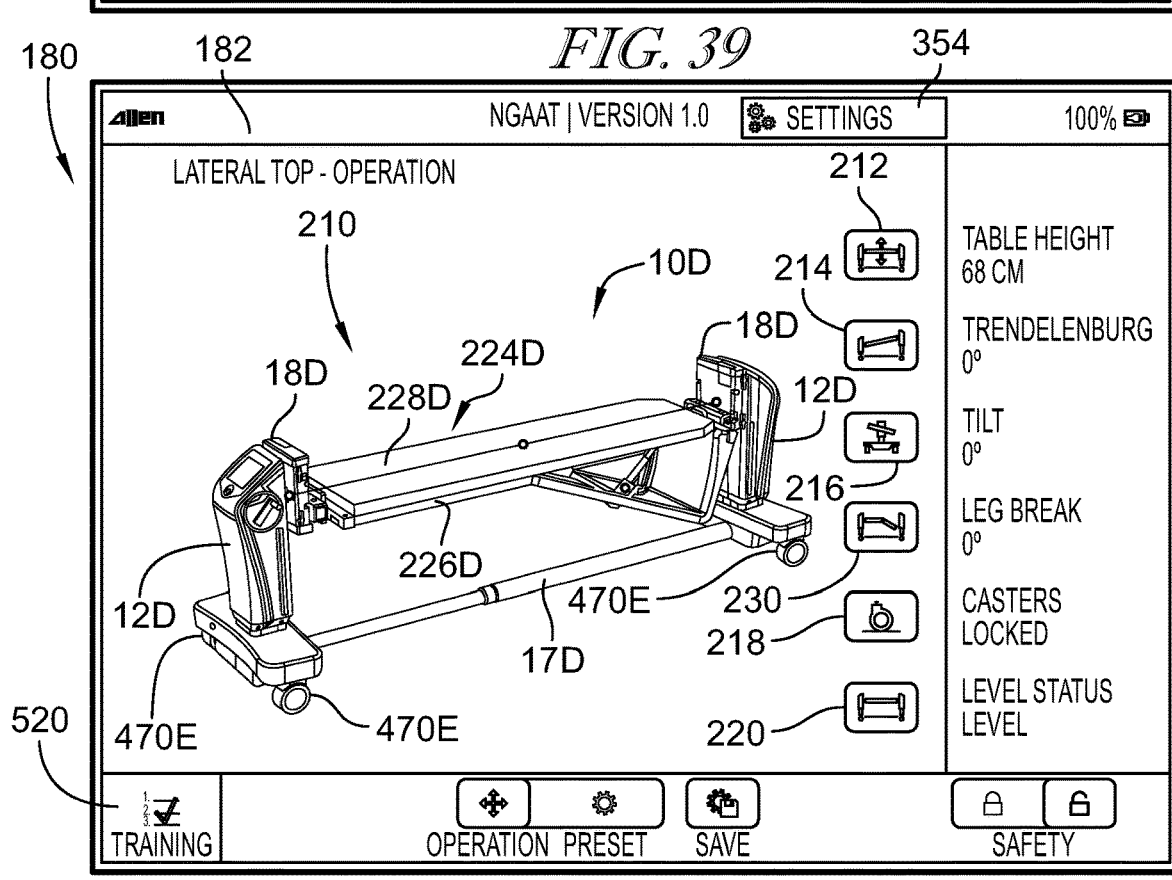
FIG. 40 is a screen shot of the display of the patient support of FIGS. 1-4 similar to FIG. 32 showing that the patient support has determined that the patient support top is a lateral support top, and showing that an initial operation screen of the patient support for caster control.

As shown in FIG. 40, a sequence of caster operation is described beginning from an exemplary level position of the patient support 10. The casters 470 of the patient support 10 are presently in a locked state as indicated by the caster icon 218 and the current caster information (right of icon 218).

Figure 41:
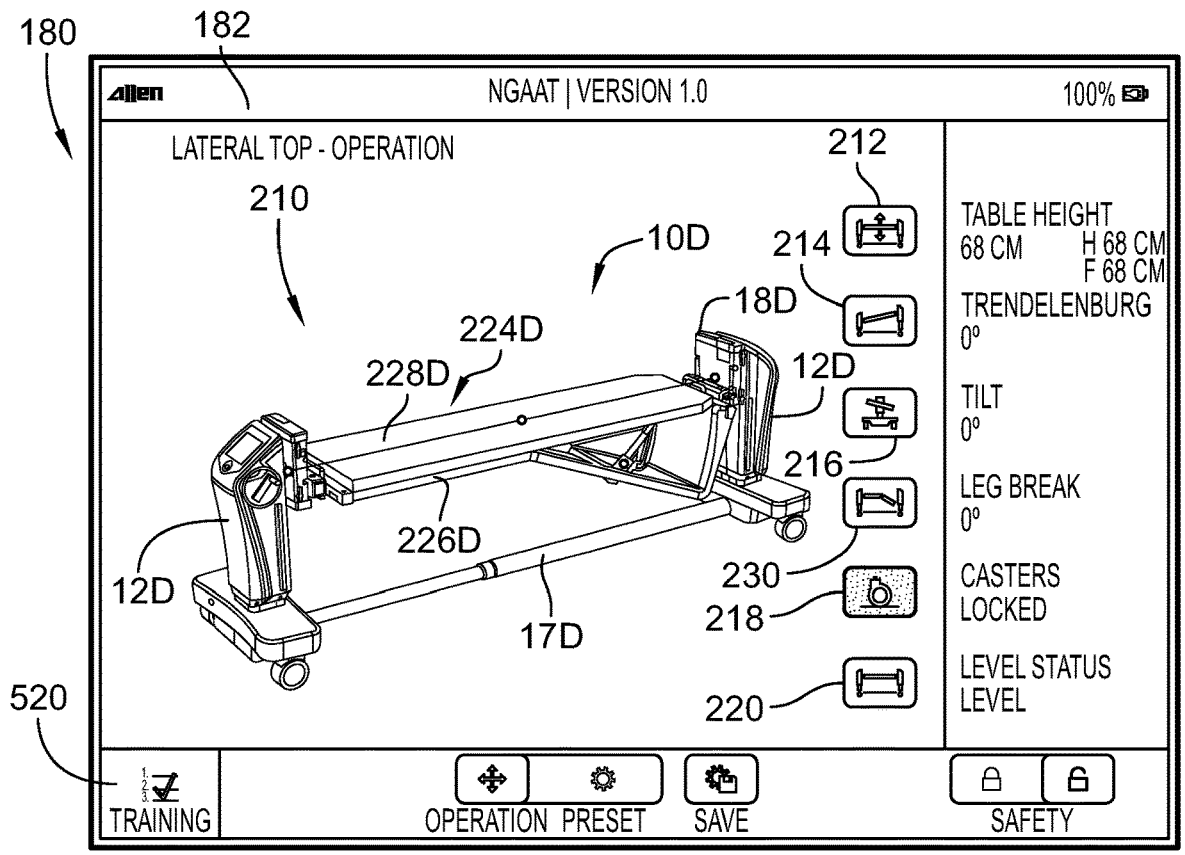
FIG. 41 is a screen shot of the display of the patient support of FIGS. 1-4 similar to FIG. 32 showing that the patient support has determined that the patient support top is a lateral support top, and showing that the caster adjustment has been selected and indicating the selection of the caster adjustment by highlighting a caster status icon.

Referring to FIG. 41, the user has selected the caster icon 218 as indicated by highlighting of the icon 218 (represented by fill of icon 218). A momentary indication of the height of the head end "H" and foot end "F" tower bases 12 is in the table height information to the right of the table height icon 212.

Figure 42:
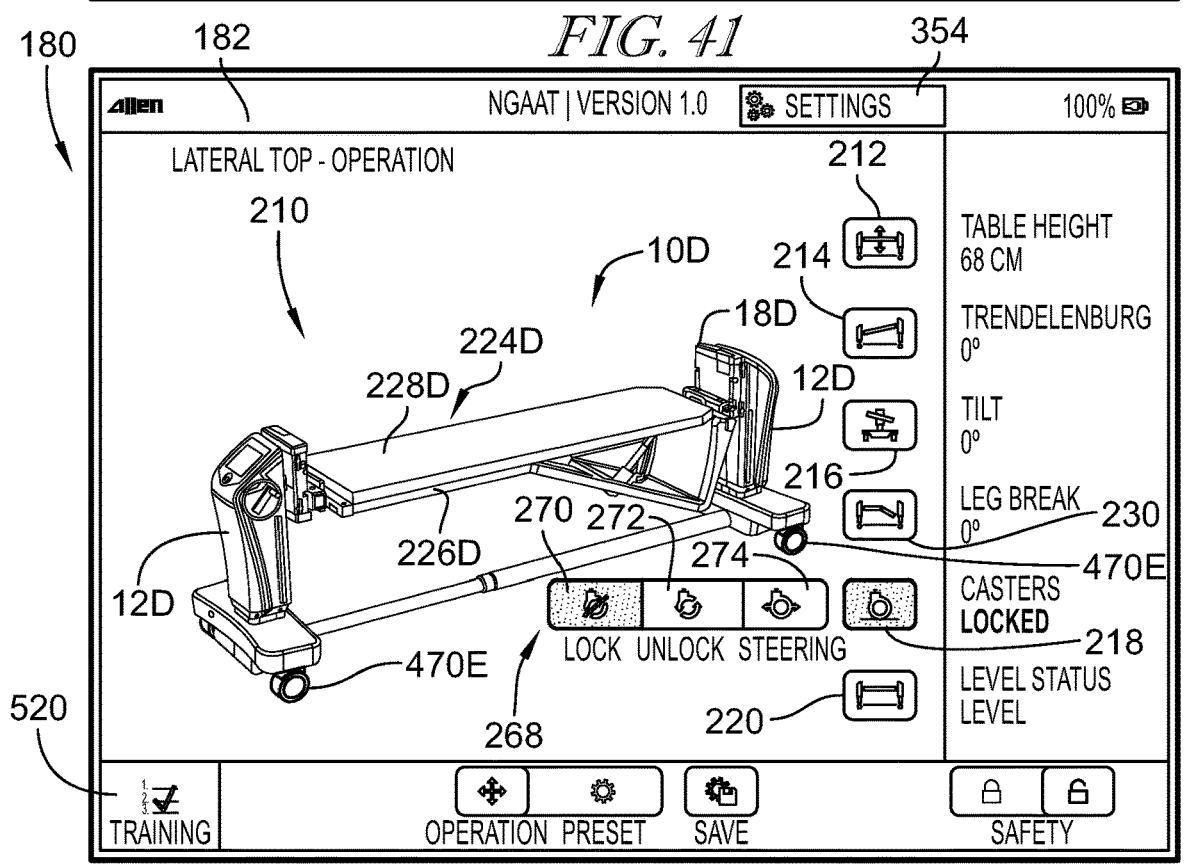
FIG. 42 is a screen shot of the display of the patient support of FIGS. 1-4 similar to FIG. 32 showing that the patient support has determined that the patient support top is a lateral support top, and showing that upon caster adjustment selection the casters of the depiction are highlighted and a caster adjustment bar is displayed for user interface near the caster status icon indicating that a locked option of the caster adjustment bar is currently selected to lock the casters and block against moving of the patient support along the floor.

As shown in FIG. 42, responsive to selection of the caster icon 218, a caster selection bar 268 is presented for user selection of a caster mode. The caster modes for selection illustratively include a locked mode 270 blocking against rolling of the caster wheels 472, an unlock mode 272 permitting rolling of the caster wheels 472, and a steering mode 274. In the steering mode 274, the wheels 472 of the all of the casters 470 are permitted to roll, but the casters 470 at the head end of the patient support 10 are locked to prevent swiveling, while the wheels 472 of the two casters 470 at the foot end are permitted to swivel. Each of the modes is selectable by a corresponding icon 270, 272, 274, and the present selection is indicated by highlighting on the selection bar (represented by fill, presently the locked mode icon 270 in FIG. 42) and in the information to the right of the icon 218 (represented in bolding).

Figure 43:
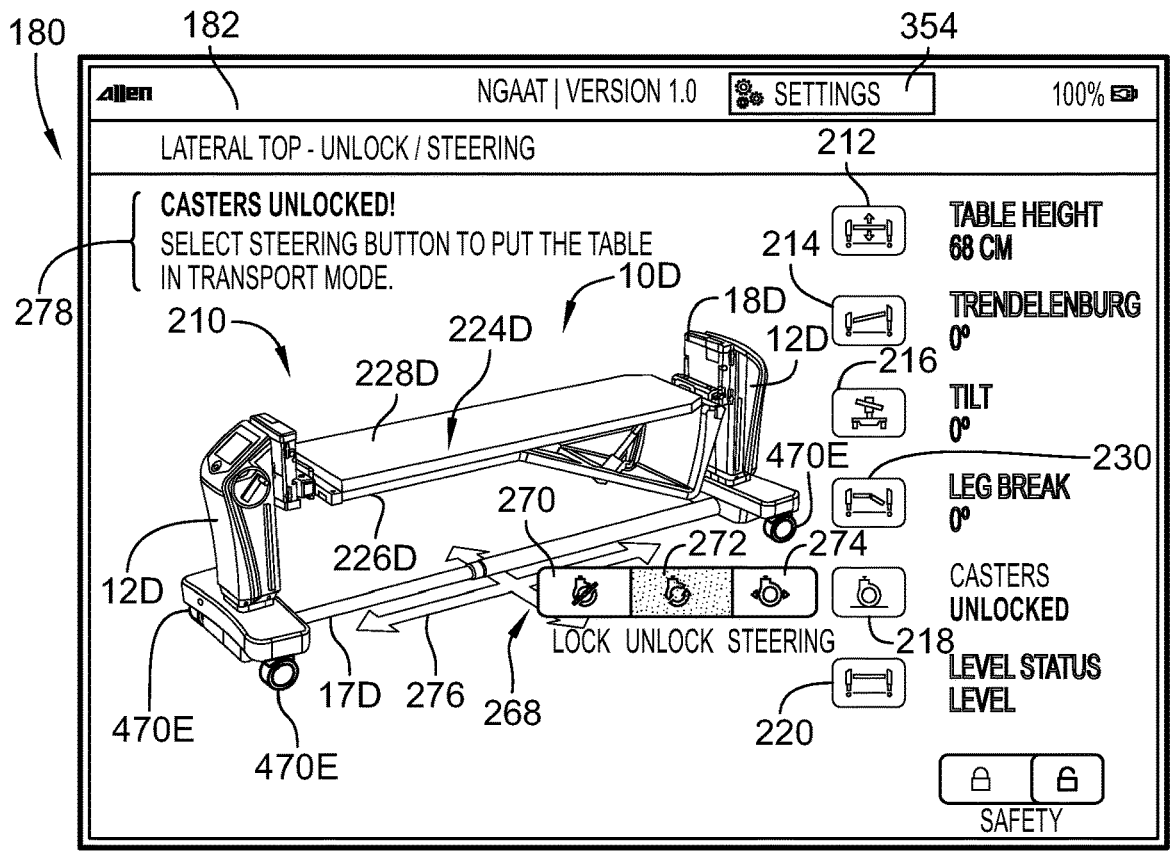
FIG. 43 is a screen shot of the display of the patient support of FIGS. 1-4 similar to FIG. 32 showing that the patient support has determined that the patient support top is a lateral support top, and showing that an unlock option of the caster adjustment bar has been selected to unlock the casters to permit rolling the patient support along the floor.

As shown in FIG. 43, the unlock icon 272 of the caster selection bar 268 has been selected. The unlock icon 272 indicates its present selection by remaining highlighted (represented by fill in icon 272), and the information to the right of the icon 272 indicates unlocked as the caster status. A set of arrows 276 are displayed beneath the patient support 10D having four directions and indicating that all casters 470 are unlocked for rolling and swiveling to allow movement of the patient support 10. An alert script 278 is shown on the GUI 180 indicating that the casters 470 are unlocked.

Figure 44:
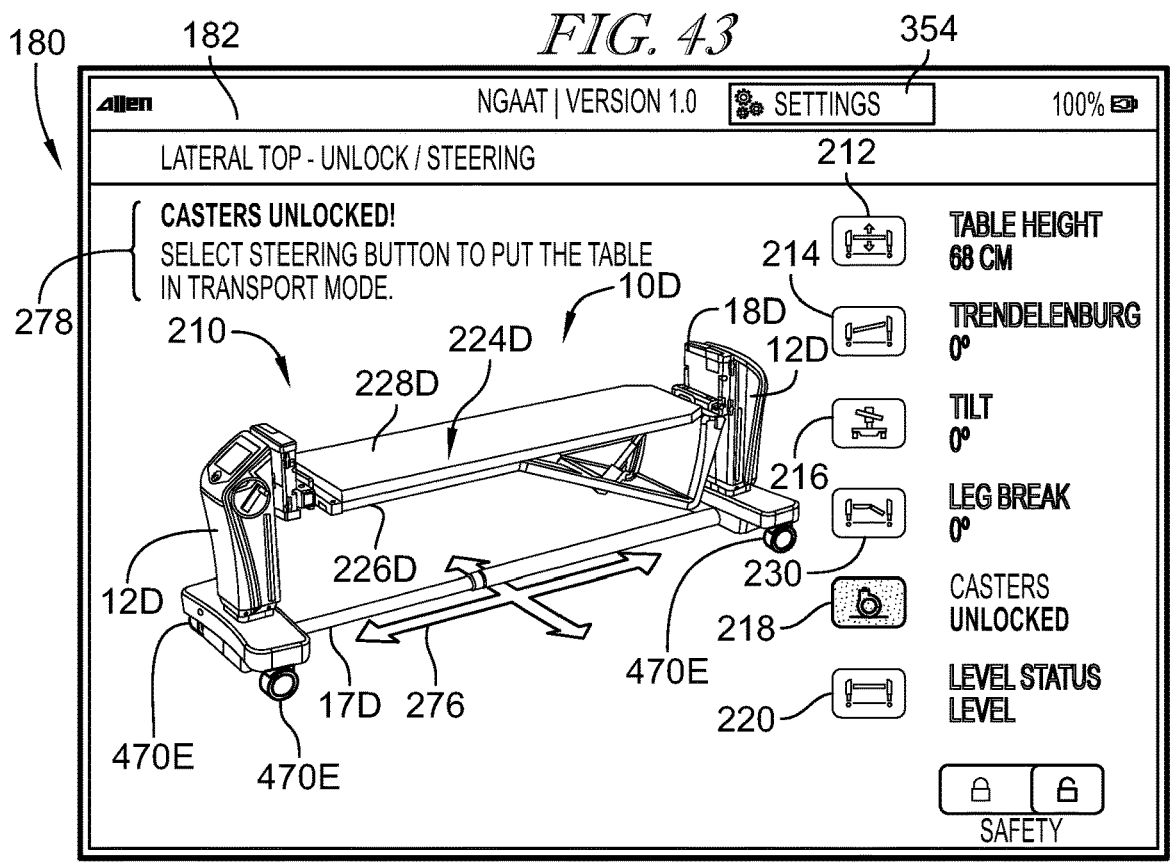
FIG. 44 is a screen shot of the display of the patient support of FIGS. 1-4 similar to FIG. 32 showing that the patient support has determined that the patient support top is a lateral support top, and showing that the casters are unlocked and indicating the same by display of arrows beneath the patient support and changing the caster status indication icon to read "UNLOCKED"

As shown in FIG. 44, after a predetermined period of time without engagement with the caster selection bar 268, the selection bar 268 is removed from the GUI 180. The casters 470 remain unlocked until the user executes alternative configuration allowing movement of the patient support 10 for transport.

Figure 45:
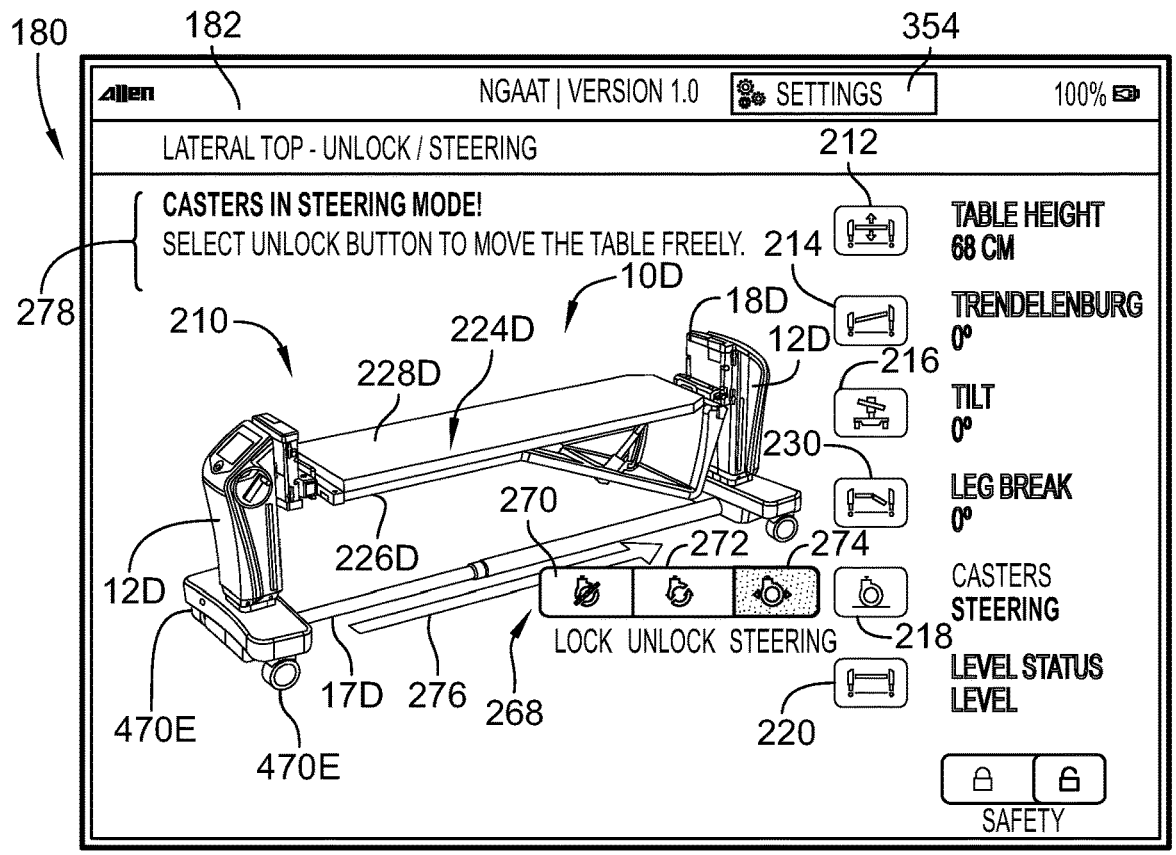
FIG. 45 is a screen shot of the display of the patient support of FIGS. 1-4 similar to FIG. 32 showing that the patient support has determined that the patient support top is a lateral support top, and showing that a steering option of the caster adjustment bar has been selected to unlock the head side casters for linear (non-swivel) rolling and to unlock the foot side casters for variable (swivel) rolling and indicating the steering selection by highlighting the corresponding option on the caster adjustment bar to permit steering the patient support along the floor.

As shown in FIG. 45, the user has illustratively selected the caster icon 218 to display the caster selection bar 268. The user has selected the steering icon 274 as indicated by its highlighting (represented by fill in icon 274), the information to the right of the caster icon 218 (also highlighted as represented by bolding), and the alert script 278 to indicate that the steering mode has been activated.

Figure 46:
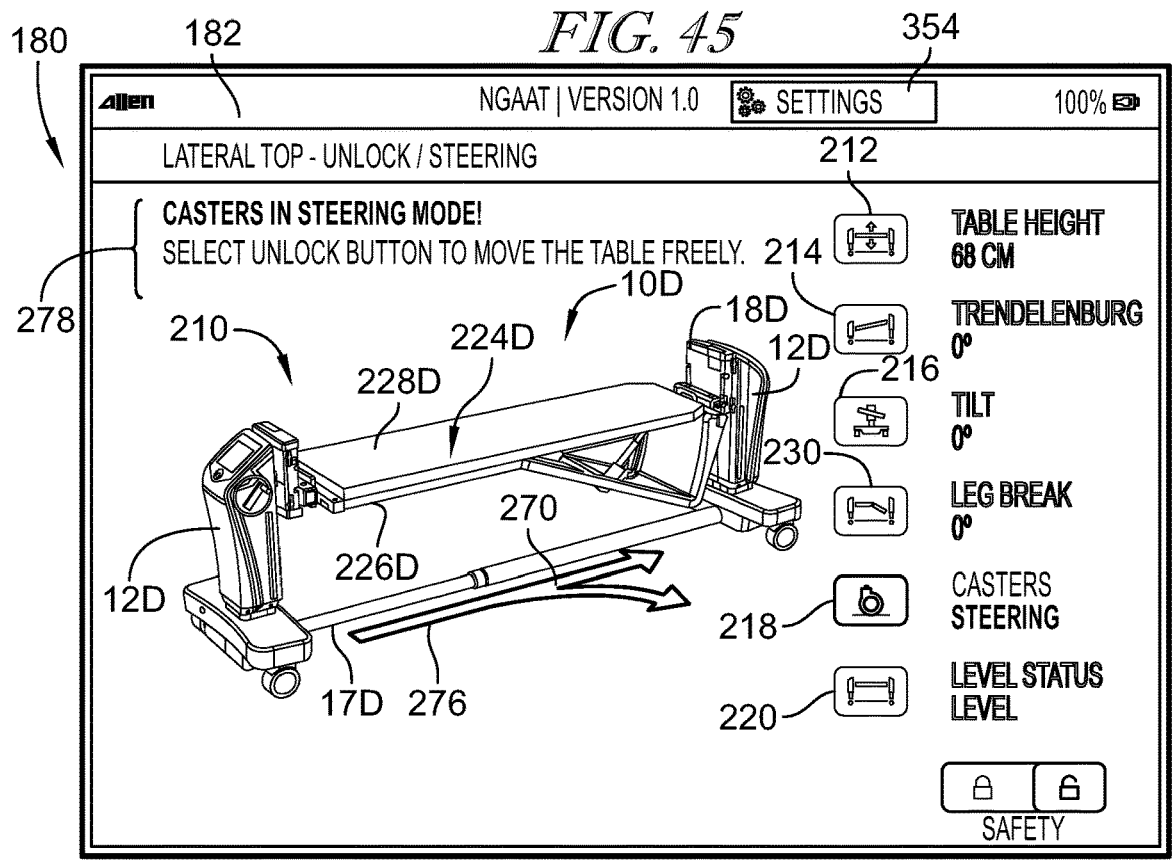
FIG. 46 is a screen shot of the display of the patient support of FIGS. 1-4 similar to FIG. 32 showing that the patient support has determined that the patient support top is a lateral support top, and showing that a steering option of the caster adjustment bar has been selected to permit steering the patient support along the floor, and indicating the steering selection by highlighting and changing the caster status indication icon to read "STEERING" and by displaying steering arrows beneath the patient support.

As shown in FIG. 46, after a predetermined period of time without engagement with the caster selection bar 268, the selection bar 268 is removed from the GUI 180. Notably, the set of arrows 276 have been changed to show only two directions/paths indicating the steering mode. Accordingly, the GUI 180 indicates that the patient support 10 can be steered for transport.

The height, tilt, Trendelenburg, leg break, casters, and level adjustments as disclosed relative to the lateral support top 224, apply equally to other types of support tops, such as the prone top 24 and/or supine top 14, as applicable, although support top-specific features may not be available for support tops which do not support those features. For example, the leg break adjustment is not available for the supine and prone tops 14, 24.

Figure 47:
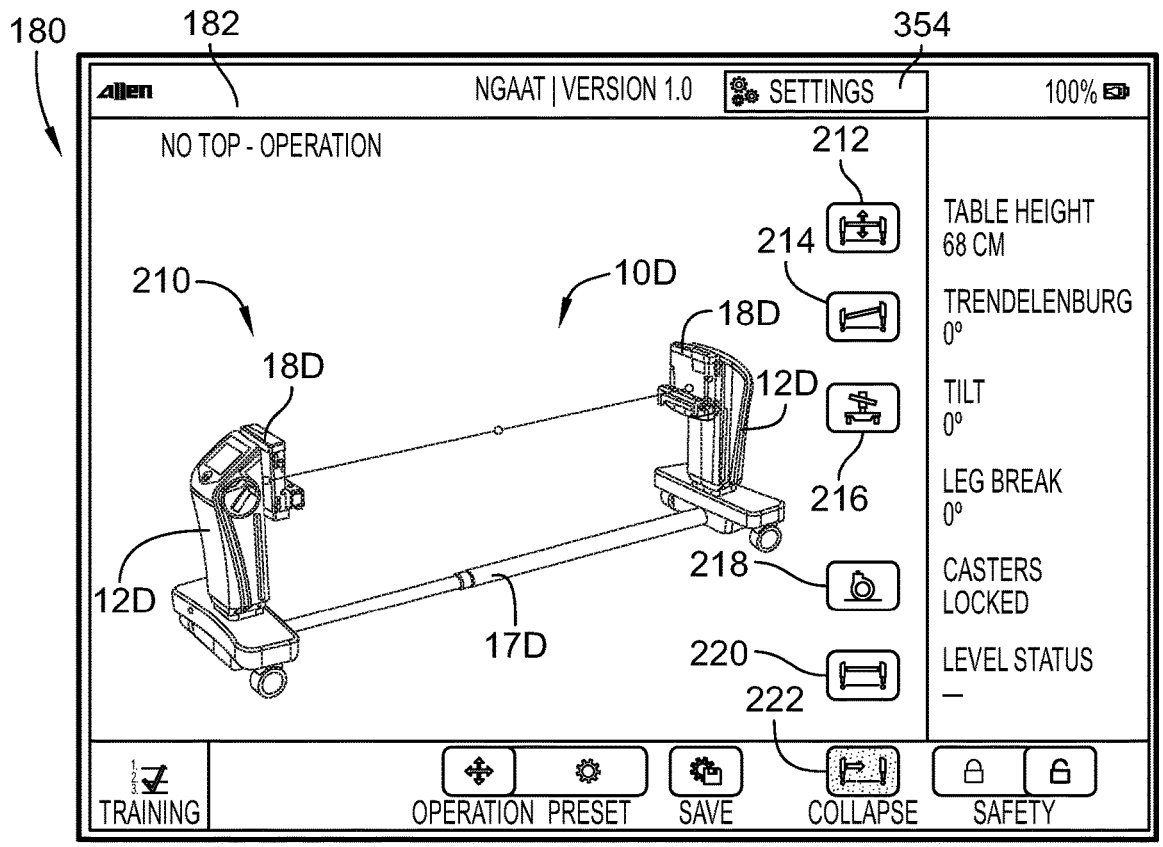
FIG. 47 is a screen shot of the display of the patient support of FIGS. 1-4 showing that a depiction of the patient support is presented on the display including the tower bases with the connection assemblies and without a patient support top connected, and showing that an initial operation screen of a collapse mode of the patient support for collapsing the patient support along the longitudinal dimension, and showing that a collapse icon has been selected.

As shown in FIG. 47, the depiction 210 indicates that no support top is attached with the connection assemblies 18.

When no support top is connected, the collapse icon 222 is available for selection. As indicated by highlighting (represented as fill of icon 222), the collapse icon 222 has been selected by the user to permit collapsing of the patient support 10 along its longitudinal dimension.

Figure 48:
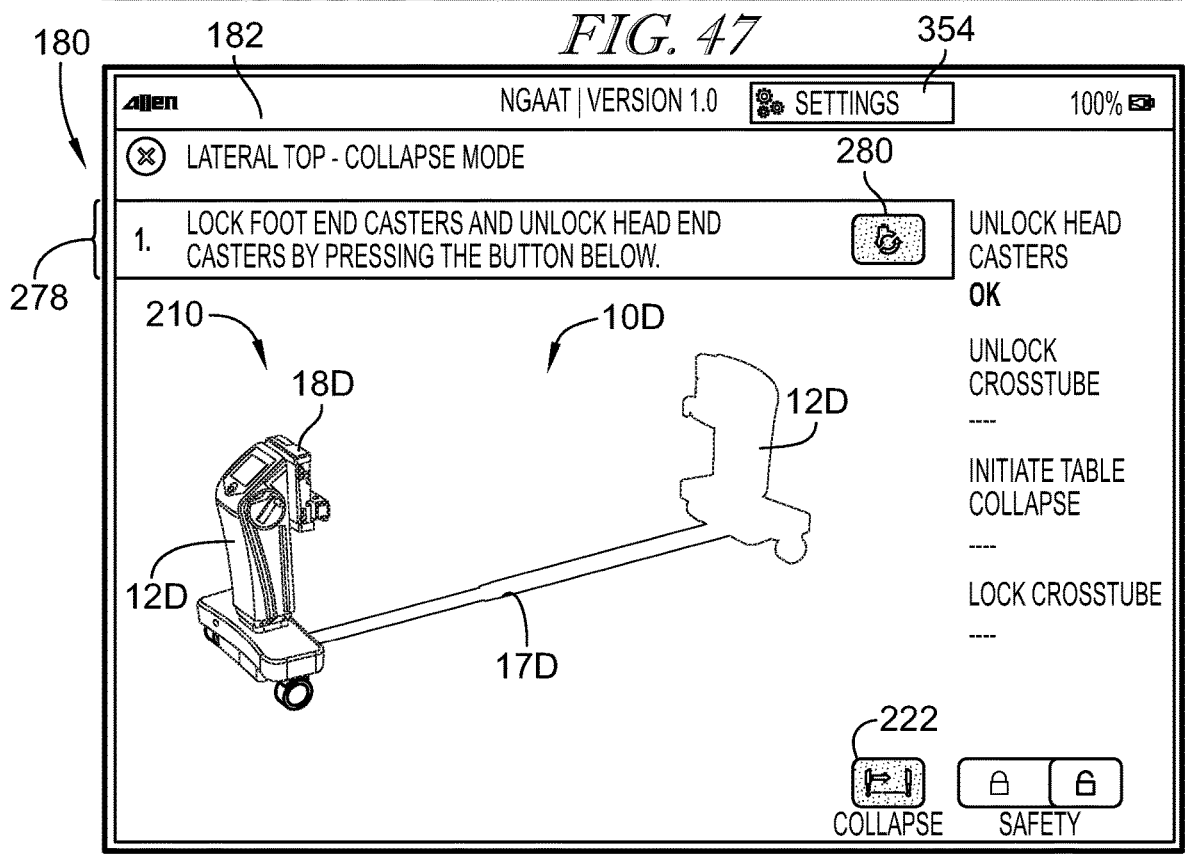
FIG. 48 is a screen shot of the display of the patient support of FIGS. 1-4 similar to FIG. 47 showing that responsive to the selection of the collapse icon, a request to lock the foot ends casters and unlock the head end casters is presented together with a caster operation icon to facilitate collapsing.

As shown in FIG. 48, responsive to the user's selection of the collapse icon 222, the alert script 278 indicates an instruction to lock the foot end casters 470 and unlock the head end casters 470 to allow translation of the head end tower base 12 towards the foot end tower base 12 for collapse. The alert script 278 includes an unlock icon 280 to allow one-touch actuation of the desired locking/unlocking of the casters 470 to allow collapsing. The foot end tower base 12D is shown in outline to draw attention and to invite motion of the head end tower base 12D for collapsing the patient support 10.

Figure 49:
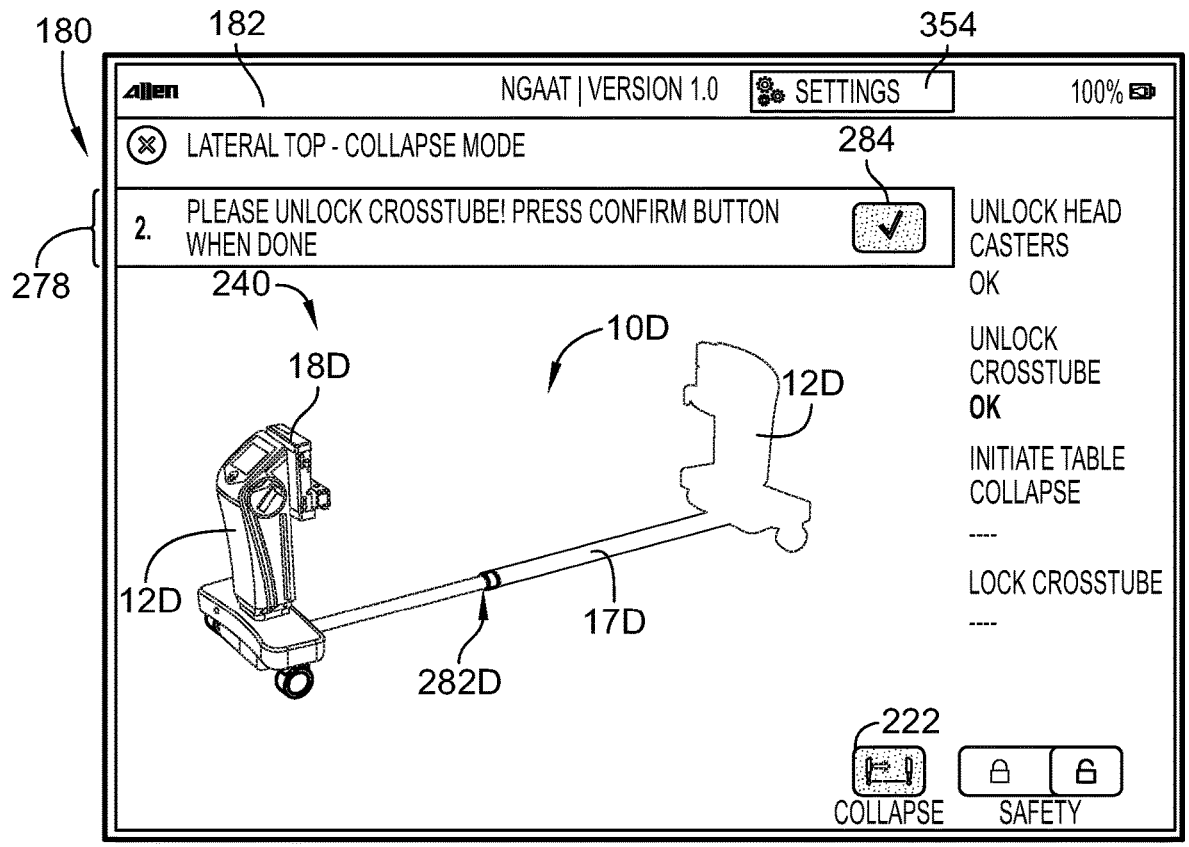
FIG. 49 is a screen shot of the display of the patient support of FIGS. 1-4 similar to FIG. 48 showing that responsive to the selection of the caster operation icon to lock the foot ends casters and unlock the head end casters, a request to unlock a cross-tube is presented including a cross-tube operation icon for user selection upon successful cross-tube unlocking to facilitate collapsing, and showing that a cross-tube unlock device is highlighted.

As shown in FIG. 49, the user has previously selected the unlock icon 280 to configure the casters 470 for collapsing. Responsive to the user's selection of the unlock icon 280, the alert script 278 indicates a request to unlock the cross tube 17 at the cross tube lock 282 to allow telescopic collapse. The depiction 210 indicates the cross tube lock 282D as highlighted (represented by bolding). The alert script 278 illustratively includes a confirmation button 284 for user selection to indicate that the cross tube lock 282 has been unlocked. Upon user selection of the confirmation button 284, the GUI 180 proceeds.

Figure 50:
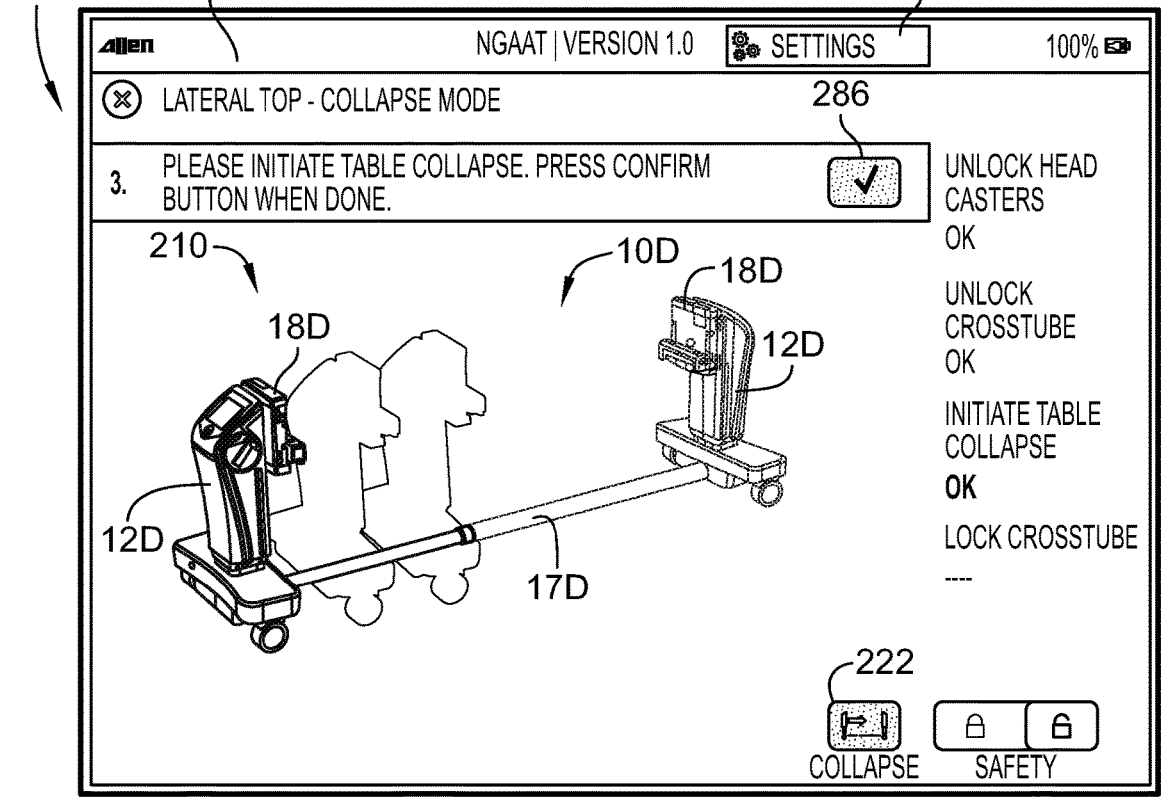
FIG. 50 is a screen shot of the display of the patient support of FIGS. 1-4 similar to FIG. 49 showing that responsive to the selection of the cross-tube operation icon to confirm that the cross-tube is unlocked, a request to manually collapse the patient support is presented along with a collapse operation icon for user selection upon successful collapsing and a graphic of the collapsing process is shown.

As shown in FIG. 50, the user has previously selected the confirmation button 284. The alert script 278 indicates a request for manual movement of the head end tower base 12D towards the foot end tower base 12D to collapse the patient support 10. An outlined trail of the head end tower base 12D indicates the request by illustrating movement. The alert script 278 includes a confirmation button 286 for user selection to indicate that movement of the head end tower base 12D to the desired collapsed state has been achieved. Upon user selection of the confirmation button 286, the GUI 180 proceeds.

Figure 51:
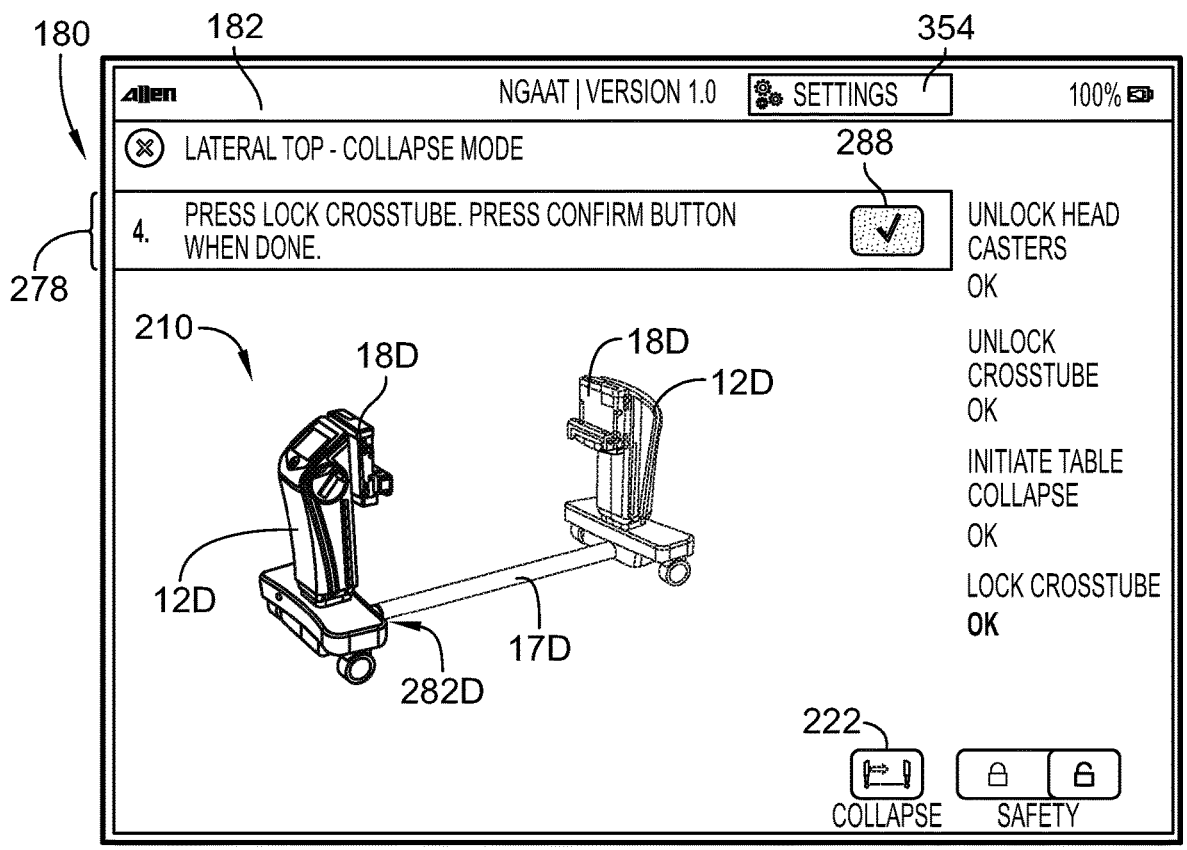
FIG. 51 is a screen shot of the display of the patient support of FIGS. 1-4 similar to FIG. 50 showing that responsive to the selection of the collapse operation icon to confirm that the patient support has been collapsed, the patient support is depicted in a collapsed state, and a request to lock the cross-tube is presented along with a cross-tube operation icon for user selection upon successful locking of the cross-tube.

As shown in FIG. 51, the user has previously selected the confirmation button 286. The alert script 278 indicates that the patient support 10 has been collapsed and requests that the user relock the cross tube lock 282 to complete collapsing operation. The alert script 278 includes a confirmation button 288 for user selection upon completion of relocking the cross tube lock 282. Upon user selection of the confirmation button 288, the GUI 180 proceeds.

Figure 52:
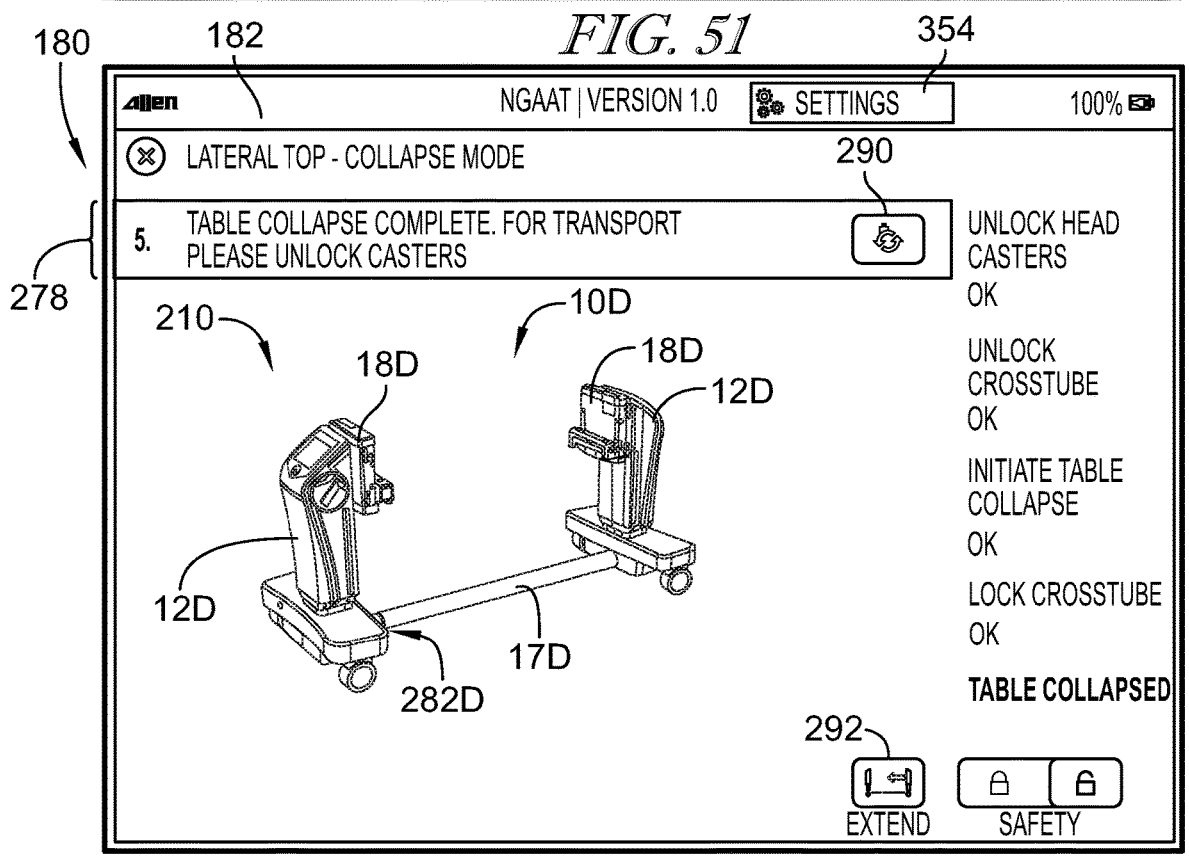
FIG. 52 is a screen shot of the display of the patient support of FIGS. 1-4 similar to FIG. 51 showing the patient support has been collapsed and confirming completion of the collapsing operation, and presenting a caster unlock operation icon for unlocking the casters for transport of the patient support.
Figure 53:
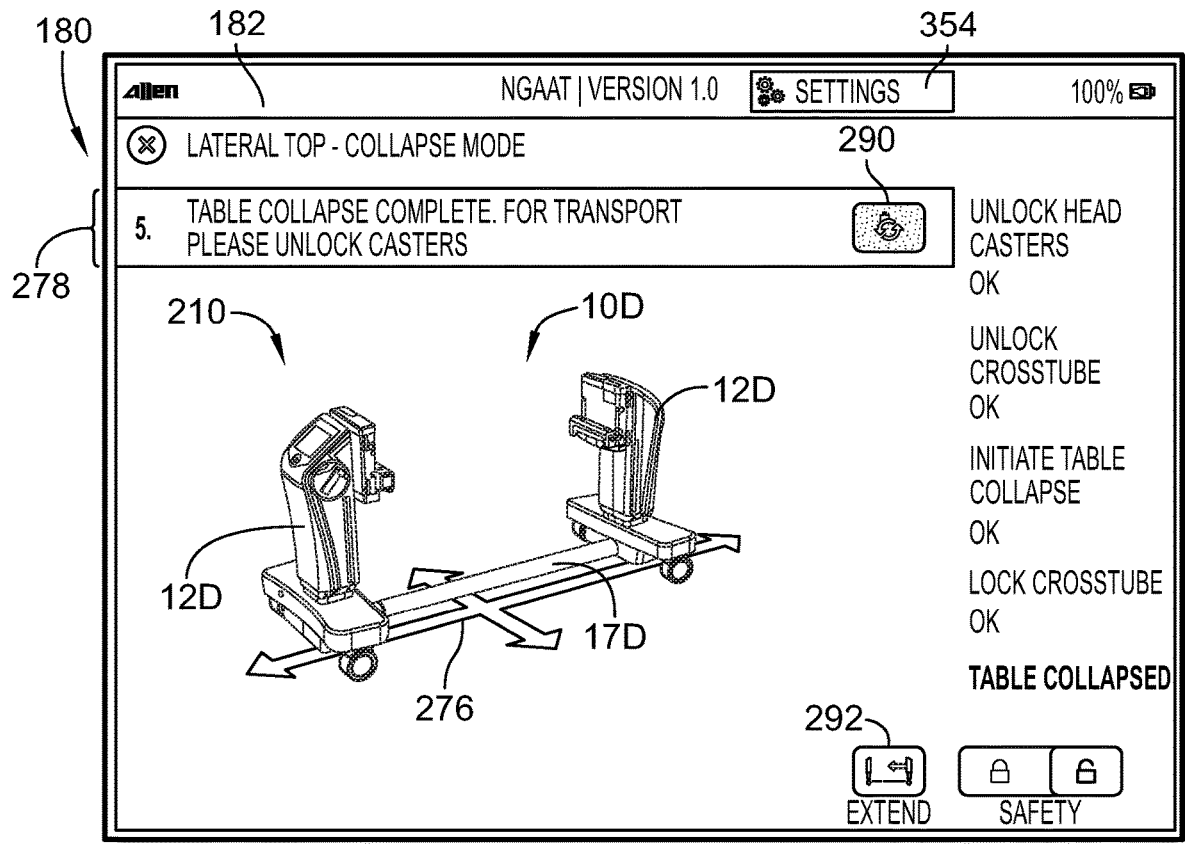
FIG. 53 is a screen shot of the display of the patient support of FIGS. 1-4 similar to FIG. 52 showing the caster unlock operation icon has been selected for unlocking the casters for transport of the patient support, and indicating the selection by highlighting the caster unlock operation icon and displaying arrows beneath the patient support.
Figure 54:
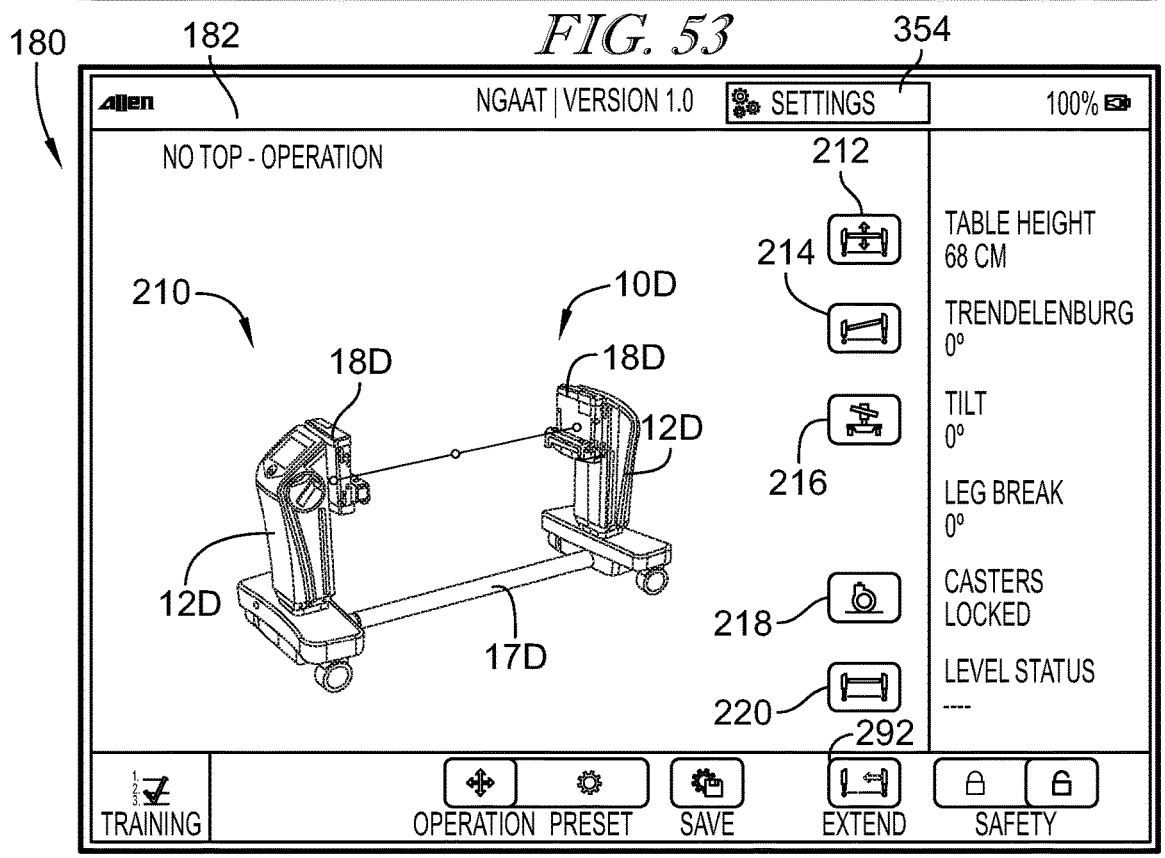
FIG. 54 is a screen shot of the display of the patient support of FIGS. 1-4 similar to FIG. 47 in a main view showing that the patient support is in a collapsed state.

As shown in FIG. 52, the depiction 210 shows a collapsed patient support 10D. The alert script 278 indicates that the collapse of the patient support 10 is complete and invites the user to unlock the casters 470 using an unlock icon 290. Responsive to collapse of the patient support 10, an extend icon 292 is shown for initiating an extend sequence. Upon selection of the unlock icon 290, the casters 470 are unlocked for transport of the patient support 10. As shown in FIG. 53, the user has selected the unlock icon 290 as indicated by highlighting (represented by fill in icon 290). Selection of the unlock icon 290 unlocks the casters 470 for transport and presents arrows 276 beneath the patient support 10D. As shown in FIG. 54, the casters 470 have been locked and main screen options have returned.

Figure 55:
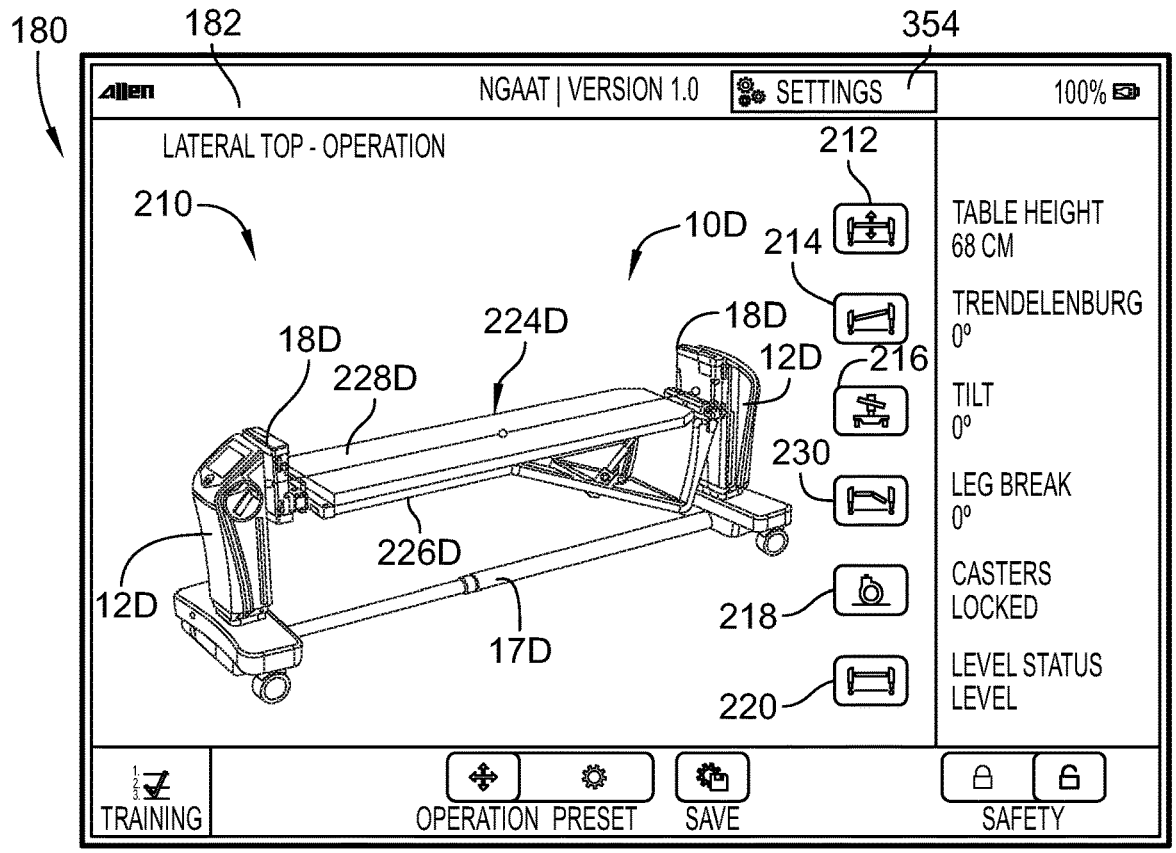
FIG. 55 is a screen shot of the display of the patient support of FIGS. 1-4 in a main view showing that the patient support has determined that the connected patient support top is a lateral support top, and presenting an initial operation screen for height check of the lateral support top.

As shown in FIG. 55, the lateral top 224 has been attached to the connection assemblies 18 as represented in the depiction 210 to demonstrate a main screen for providing height check. As shown to the right of height icon 212 the table height is presently 68 cm, which is illustratively representation of the height defined from the bottom of the frame 226 to the floor, but in some embodiments may be any suitably defined height of the support top, for example, the height of a top surface of the padding 228 above the floor.

Figure 56:
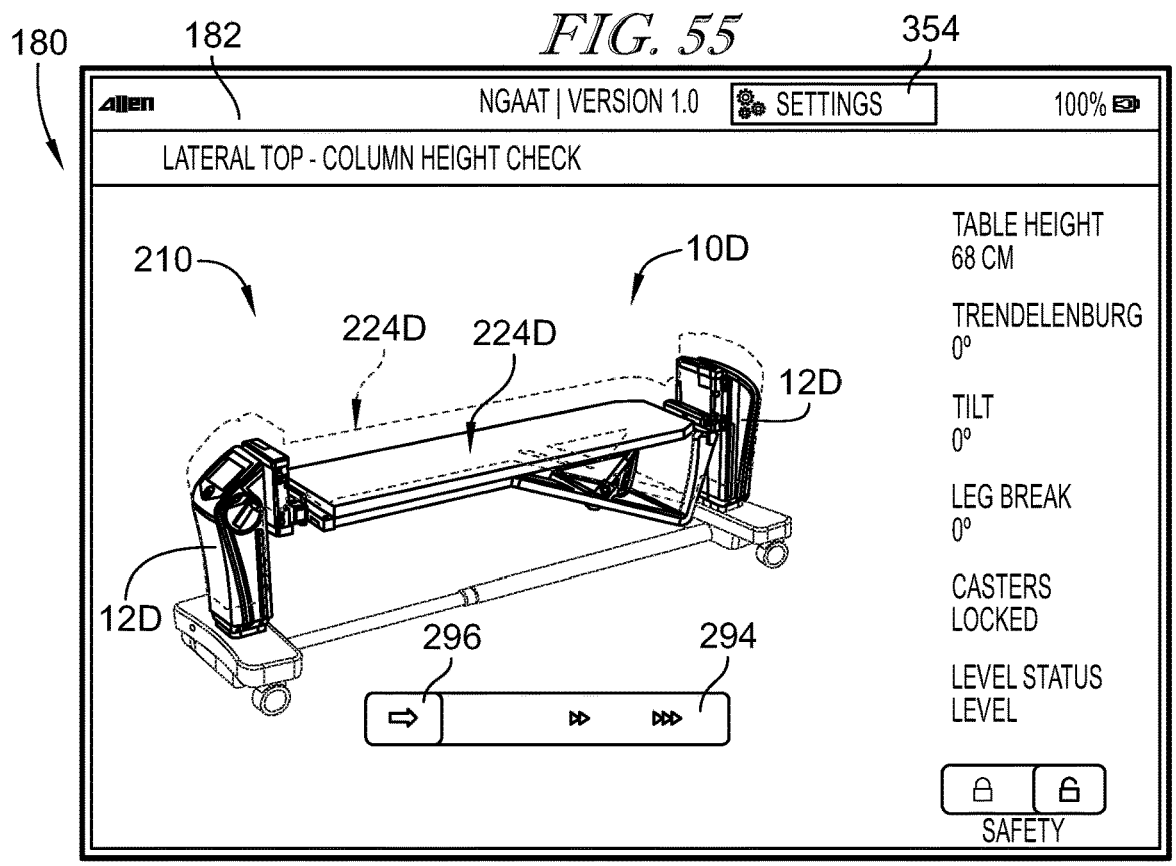
FIG. 56 is a screen shot of the display of the patient support of FIGS. 1-4 similar to FIG. 55 showing that a table height icon has been selected to enter a height check mode as indicated by highlighting of the lateral support top and the tower bases, and a desired height for the lateral support top indicated as a transparent overlay (shown in broken line), and showing that a height adjustment bar is presented for user interface for height adjustment.

As shown in FIG. 56, upon attachment of the lateral top 224 having insufficient height for tilting, the height check process is indicated by outline of the appropriate support top height in the depiction 210 (represented in dashed line) to allow tilting without interference. For purposes of the description, the tilt angle is provided generally as an axial angle of controlled mechanical rotation within a limited range (e.g., +/−30 degrees) of the connection rods 16 under a drive mechanism of the tower base 12, compared with the free rotation of the connection rods 16 when unlocked for flip rotation. However, tilt check can include both tilt and flip rotation clearances to avoid collision between portions of the support top and the other components of the patient support. Required heights may vary according to the connected support top. In some embodiments, the height check made be initiated upon a specific user, such as selection of the tilt icon 216 or release of the rotation lever 306, while an insufficient height is present, according to the particular support top presently attached. A height adjustment slider bar 294 is presented to adjust the table height. A user can drag the slider 296 (to the right) with increasing actuation speed in the execution direction to adjust the height of the support top 224. The depiction 210 illustratively tracks the actual current height of the support top 224 and indicates the transitioning height in the depiction 210 and the status information, on the GUI 180.

Figure 57:
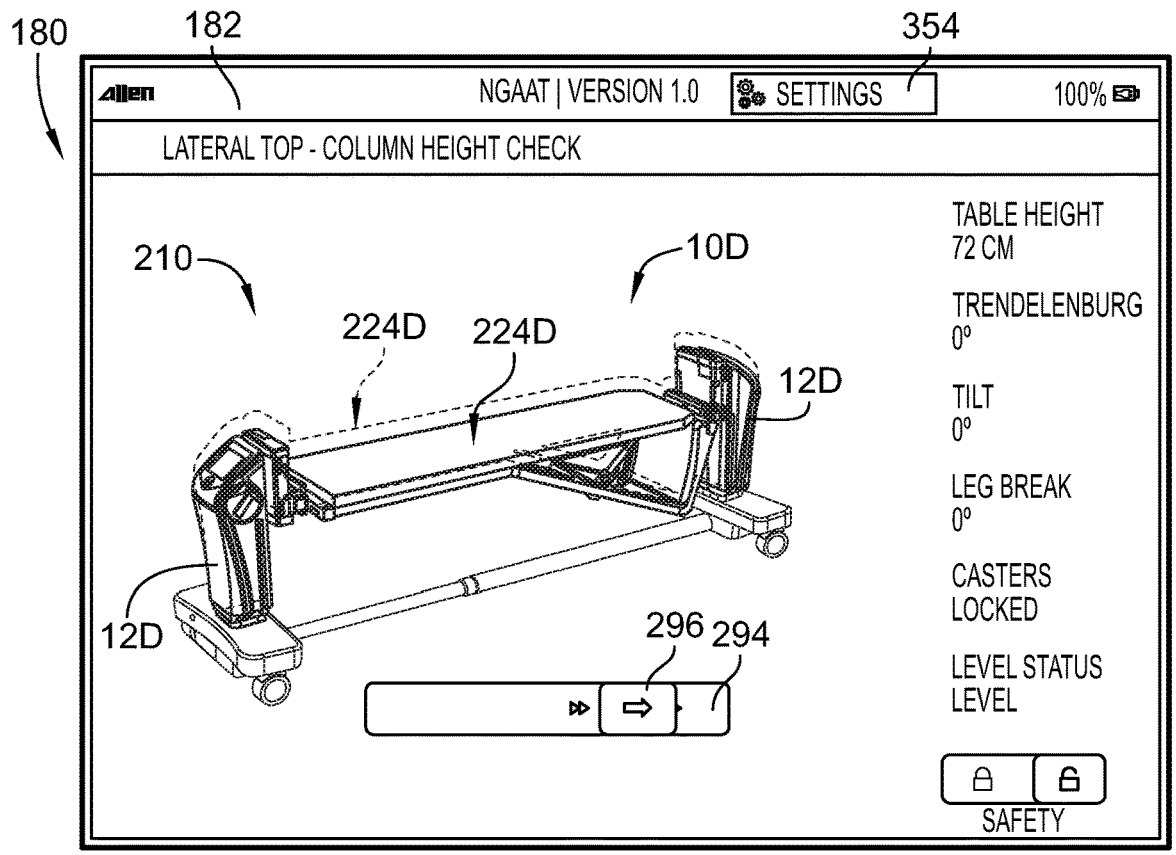
FIG. 57 is a screen shot of the display of the patient support of FIGS. 1-4 similar to FIG. 56 showing that the height adjustment bar has been dragged partly to the right to commence execution of height adjustment and showing that the depiction tracks with the actual position of the patient support.

As shown in FIG. 57, a user has dragged the slider 296 partly to the right to activate height adjustment. The support top 224 begins height adjustment by extension of the tower bases 12 and the depiction 210 illustrates the current height as the height adjustment proceeds toward the outlined position 224D. The table height information to the right of the table height icon 212 indicates the current height as 72 cm.

Figure 58:
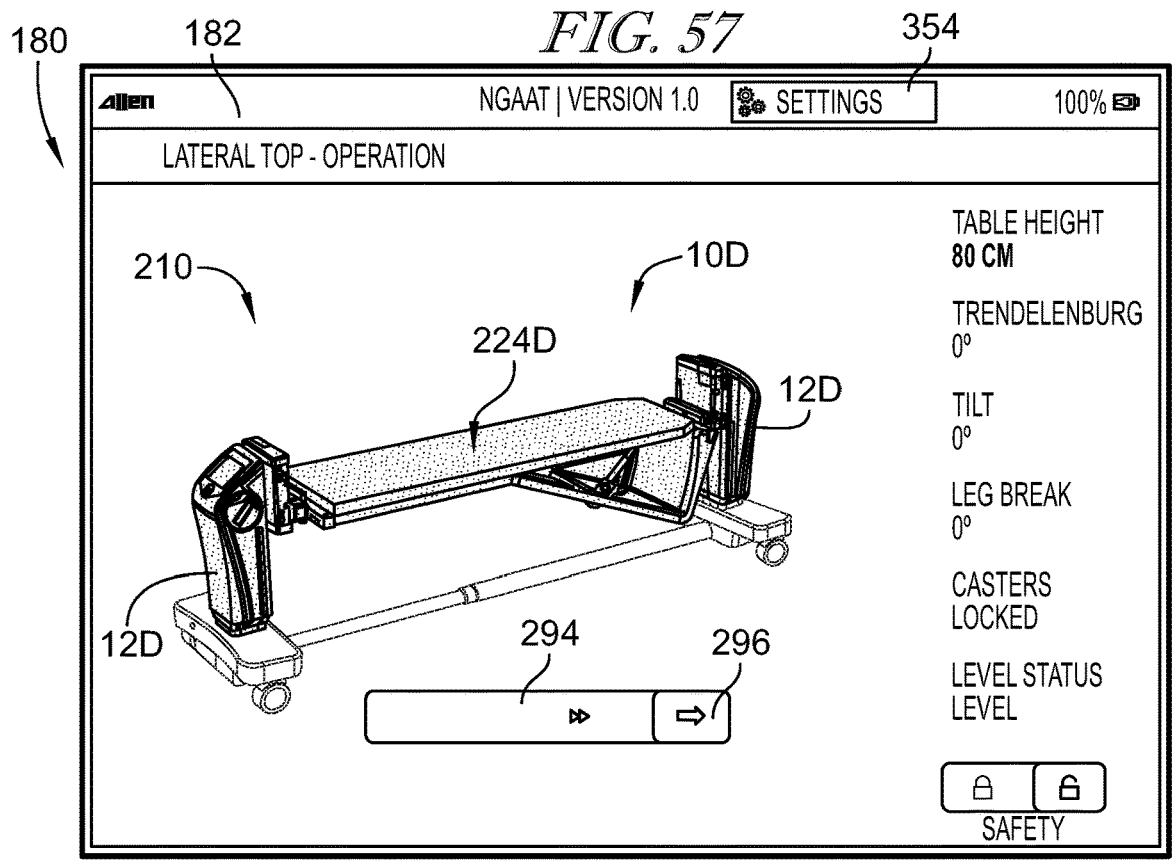
FIG. 58 is a screen shot of the display of the patient support of FIGS. 1-4 similar to FIG. 57 showing that the height adjustment has been completed by displaying the lateral support table at the desired height and momentarily changing the color and/or brightening the support top and tower bases upon achievement of the desired height.

As shown in FIG. 58, the desired table height of 80 cm has been reached as indicated by the position of the lateral support 224D and the height information to the right of the height icon 212. Upon reaching the desired height of 80 cm, the lateral support 224D momentarily flashes (green) as indicated by highlighting the patient support 10D (represented by fill of the patient support 10D) to indicate completion. The user had elected to drag the slider 296 entirely to the right of the slider bar 294 to effect maximum adjustment speed to the desired height. The user can release the slider 296 on confirmation flashing of patient support 10D.

Figure 59:
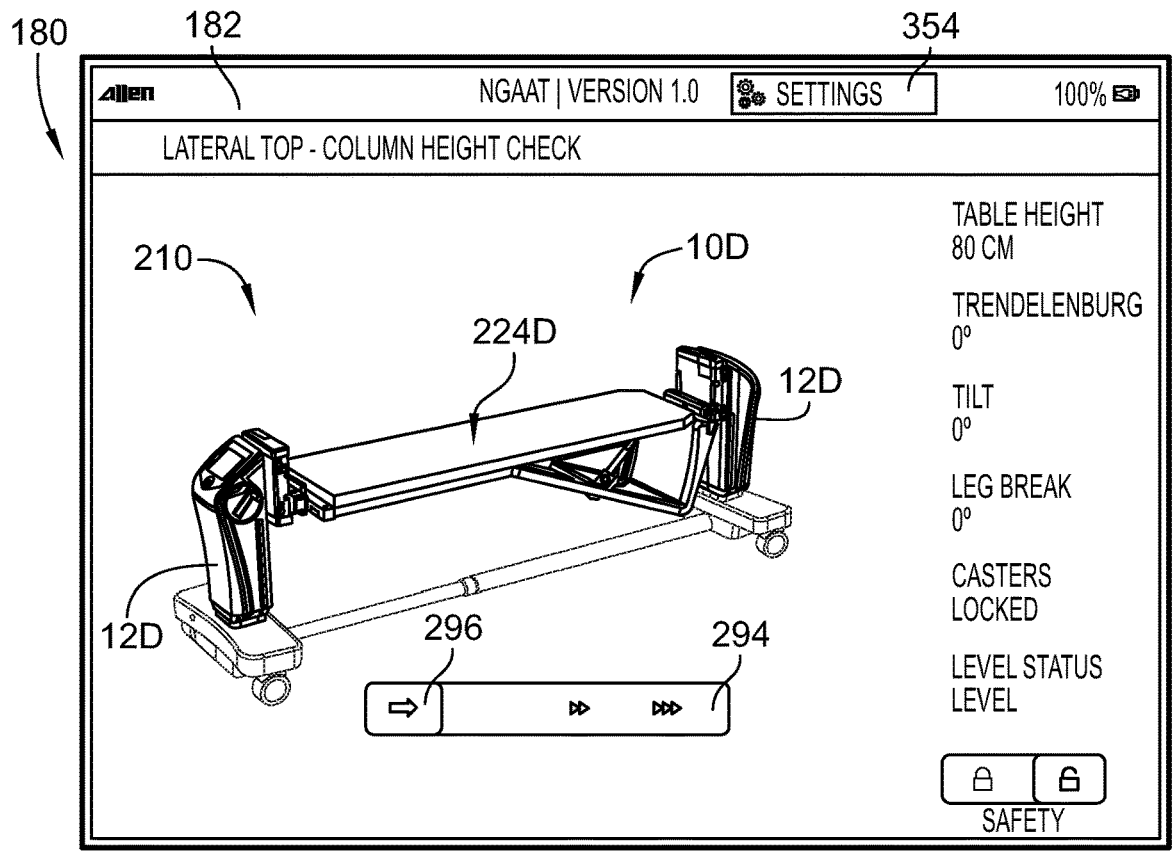
FIG. 59 is a screen shot of the display of the patient support of FIGS. 1-4 similar to FIG. 58 after the momentary color change and/or brightening of the tower bases and support tops indicated in FIG. 58, before timeout of the display to a main screen, and showing the table height status as "80 cm"
Figure 60:
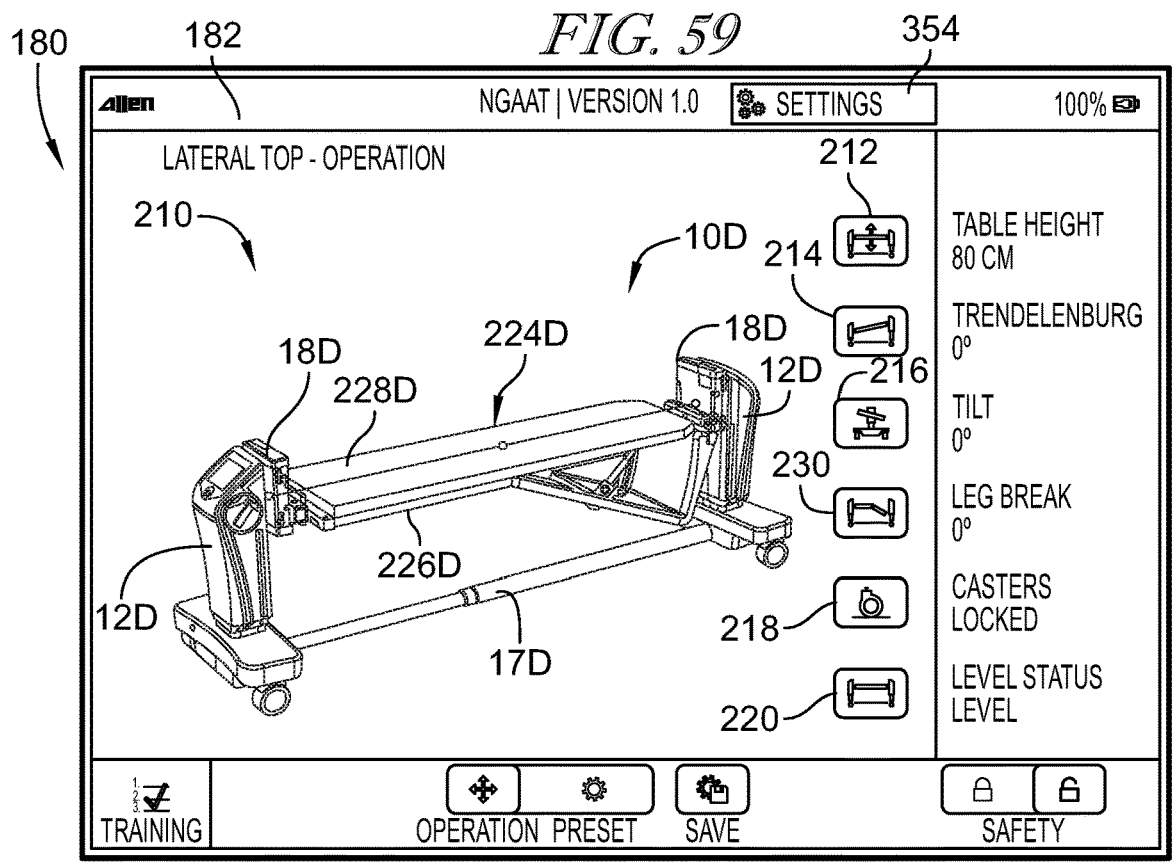
FIG. 60 is a screen shot of the display of the patient support of FIGS. 1-4 similar to FIG. 59 showing that a table height adjustment operation has been completed and a main view is returned.

As shown in FIG. 59, the flashing (to green) has ceased and the desired height of 80 cm is indicated. The slider 296 has returned to its default (left) position. The height information to the right of the height icon 212 indicates the current height as 80 cm. As shown in FIG. 60, on completion of the height (check) adjustment operation, the GUI 180 returns to the regular screen including the adjustment icons 212-220,230.

Figure 61:
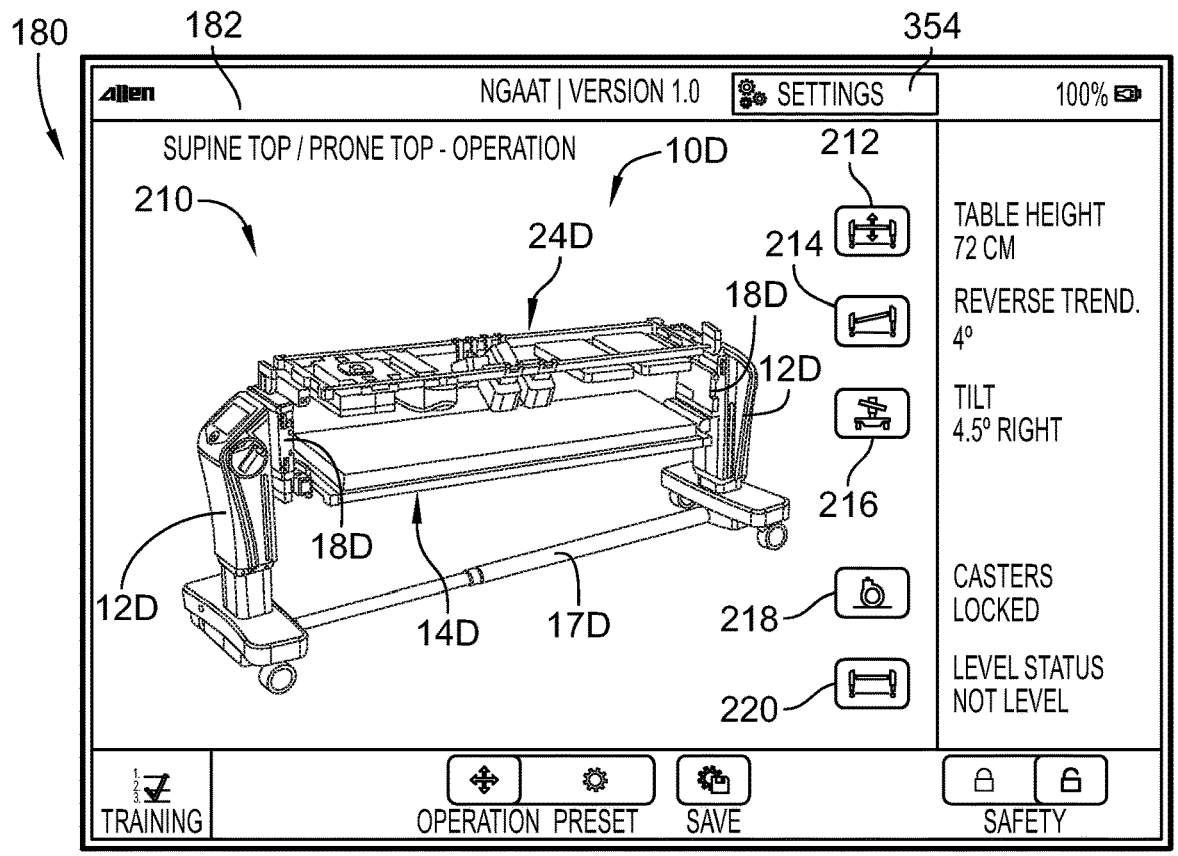
FIG. 61 is a screen shot of the display of the patient support of FIGS. 1-4 in a main view showing that a depiction of the patient support is presented including the tower bases with the connection assemblies connected with a pair of patient support tops and showing that the patient support has determined that the patient support tops include a prone support top (upper) and a supine support top (lower), and showing that the support tops are arranged with a 4 degree reverse Trendelenburg angle and a tilt of 4.5 degrees right, and presenting an initial operation screen for rotation of the support tops to perform a supine-to-prone flip under selection of an operation icon.

As shown in FIG. 61, the GUI 180 indicates that a supine top 14 and a prone top 24 have been attached with the connection assemblies 18 as represented by the depiction 210. As seen in the information to the right of the icons 212-220, the Trendelenburg angle is −4 degrees, the tilt angle is 4.5 degrees right, the casters 470 are locked, and the level status is not level. Responsive to attachment of the complimentary supine 14 and prone 24 tops, the GUI 180 initiates a flip rotation operation, although the user can cancel and/or call up the flip rotation operation as appropriate.

Figure 62:
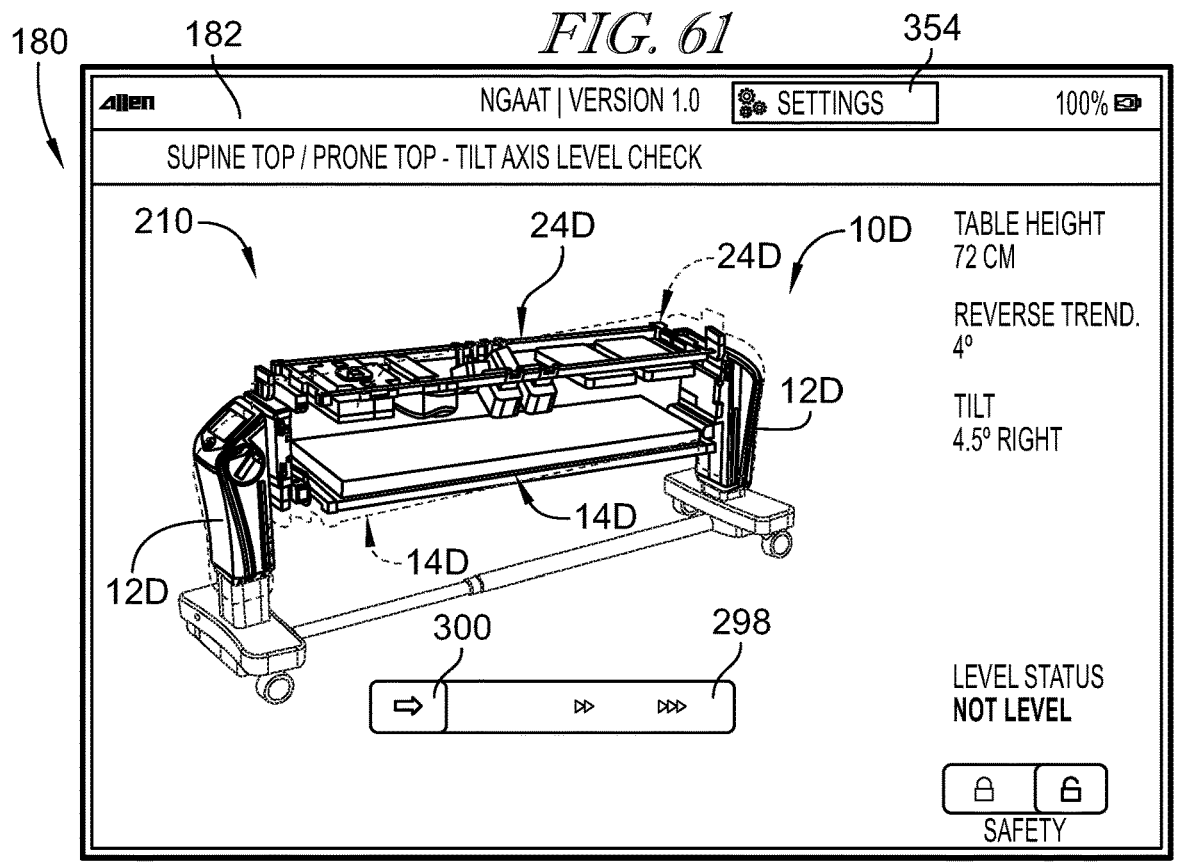
FIG. 62 is a screen shot of the display of the patient support of FIGS. 1-4 similar to FIG. 61 showing the response of attachment of the supine and prone tops including a level check operation indicating a level status as "Not Level" and presenting a level activation bar for adjustment of the tilt and Trendelenburg angle of the support tops and displaying the current position of the support tops as highlighted and a translucent overlay of the desired (level) position of the support tops.

As shown in FIG. 62, upon attachment of each of the supine and prone tops 14, 24 with "not level" positioning, the tilt axis check is triggered. Upon triggering of the tilt axis check, an outline of the level position of the support tops 14D, 24D is shown in outline (represented in dashed line). A slider bar 298 is presented including a slider 300 for user operation to adjust the support tops 14, 24 to level.

Figure 63:
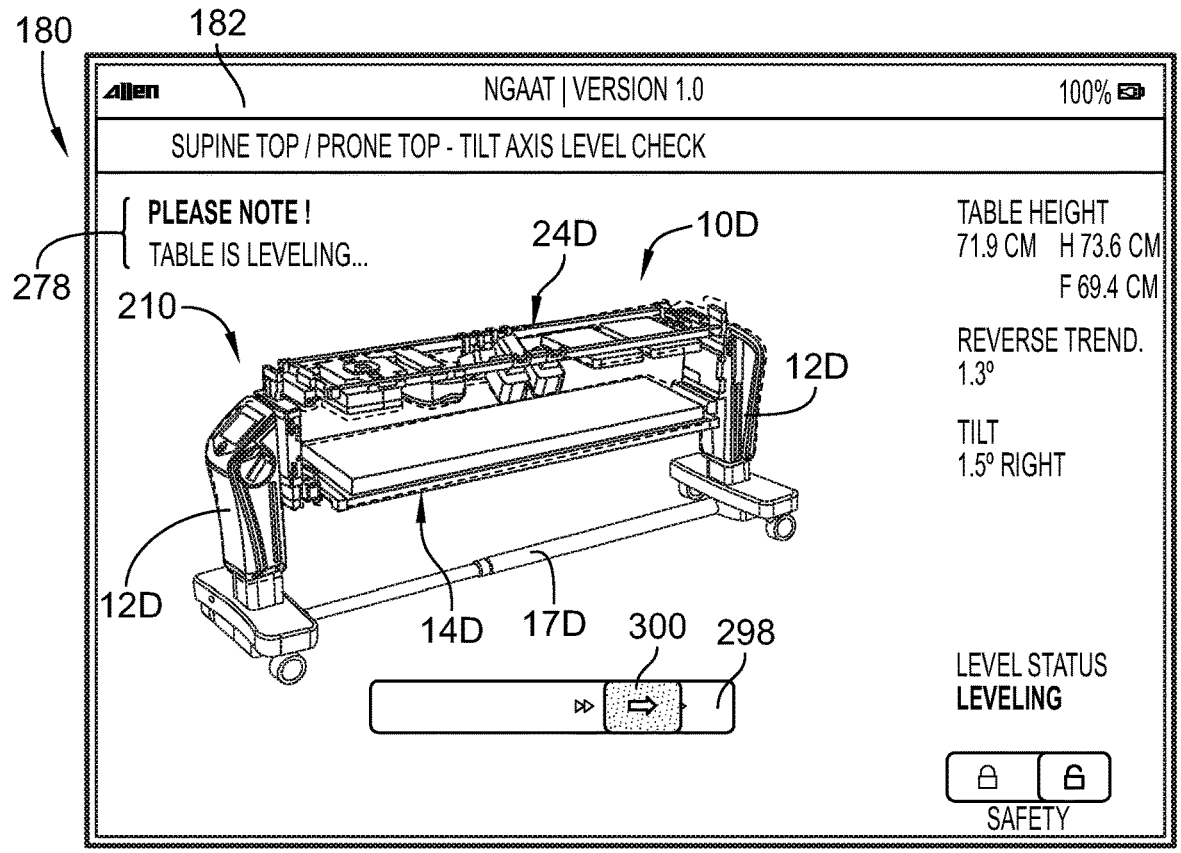
FIG. 63 is a screen shot of the display of the patient support of FIGS. 1-4 similar to FIG. 62 showing a transition of the support tops to the desired level position responsive to user actuation of the level activation bar and indicating a level status as "Leveling . . . " and depicting the current position of support tops as the highlighted support tops overlaid with the desired (level) position of the support tops.

As shown in FIG. 63, the user has dragged the slider 300 partly to the right to begin adjustment of the support tops 14, 24 to level. The selection of the slider 300 is indicated by highlighting (represented by fill of slider 300). The depiction 210 indicates the current position of the support tops 14, 24 during the adjustment, and the information on the right hand side indicates the numerical values as the support tops 14, 24 move to level. Notably, the height of the head end tower base 12 is indicated as 73.6 cm while foot end tower base 12 is presently indicated as 69.4 cm. The leveling operation is actuated by a single slider bar 298 to return all degrees of freedom (height, tilt, Trendelenburg angle) to desired (level) status for flip rotation. The alert script 278 indicates that the patient support 10 is in motion for leveling.

Figure 64:
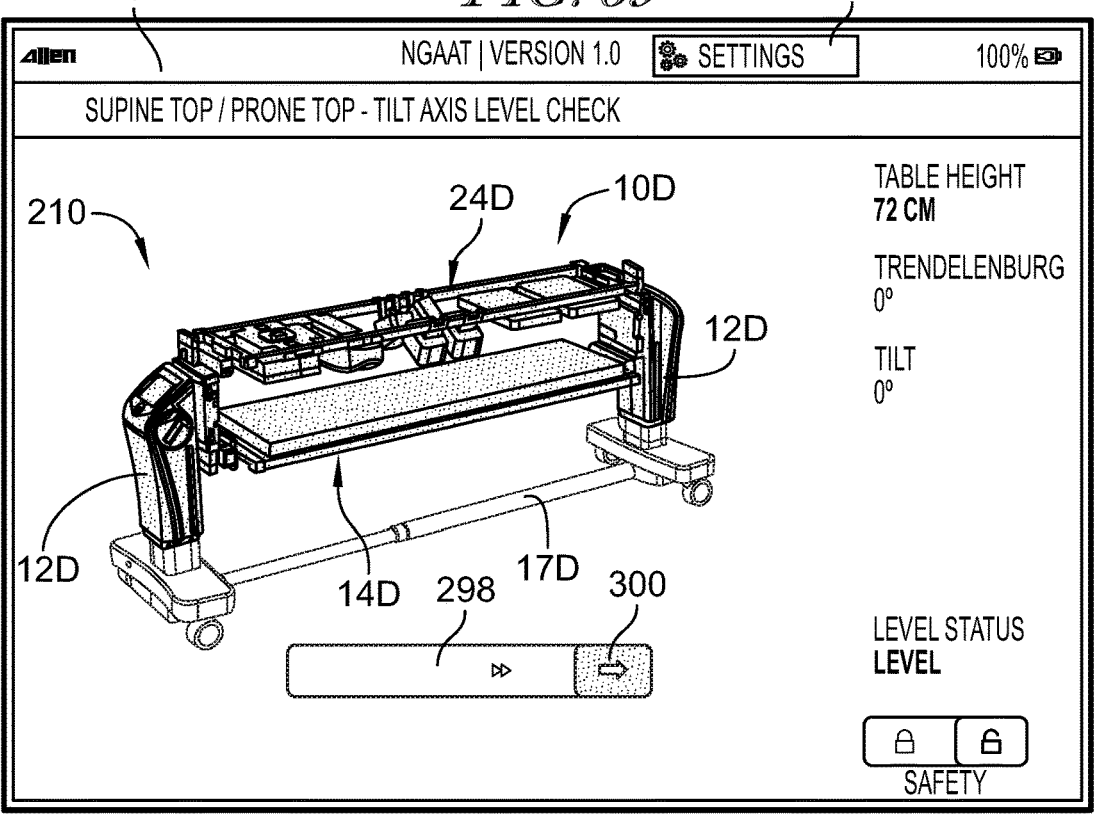
FIG. 64 is a screen shot of the display of the patient support of FIGS. 1-4 similar to FIG. 63 showing that the support tops have achieved the desired (level) position and indicating the achievement by momentarily changing the color and/or brightening the tower bases and support tops.

As shown in FIG. 64, upon achievement of the desired level status for flip rotation the patient support 10D momentarily flashes (green, as represented by fill of the patient support 10D). The momentary flashing provides a visual indicator to the user that the desired level status has been reached. The slider 300 has been dragged completely to the right to provide maximum adjustment speed.

Figure 65:
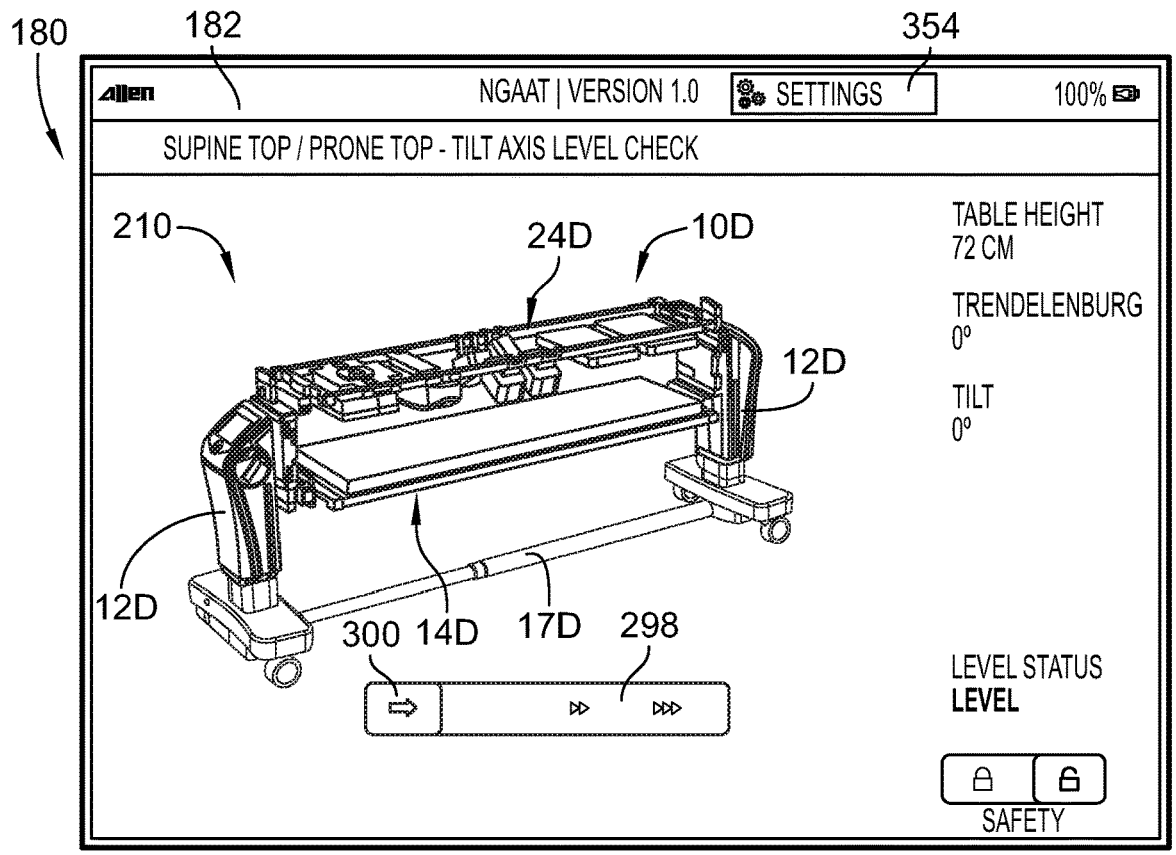
FIG. 65 is a screen shot of the display of the patient support of FIGS. 1-4 similar to FIG. 64 after the momentary color change and/or brightening of the tower bases and support tops indicated in FIG. 64, and showing the level status as "Level"

As shown in FIG. 65, the flashing (to green) has ceased and the level status of the patient support 10 is indicated. The slider 300 has been released to return to its default (left) position. On completion of the level (check) adjustment operation, the GUI 180 advances the flip operation.

Figure 66:
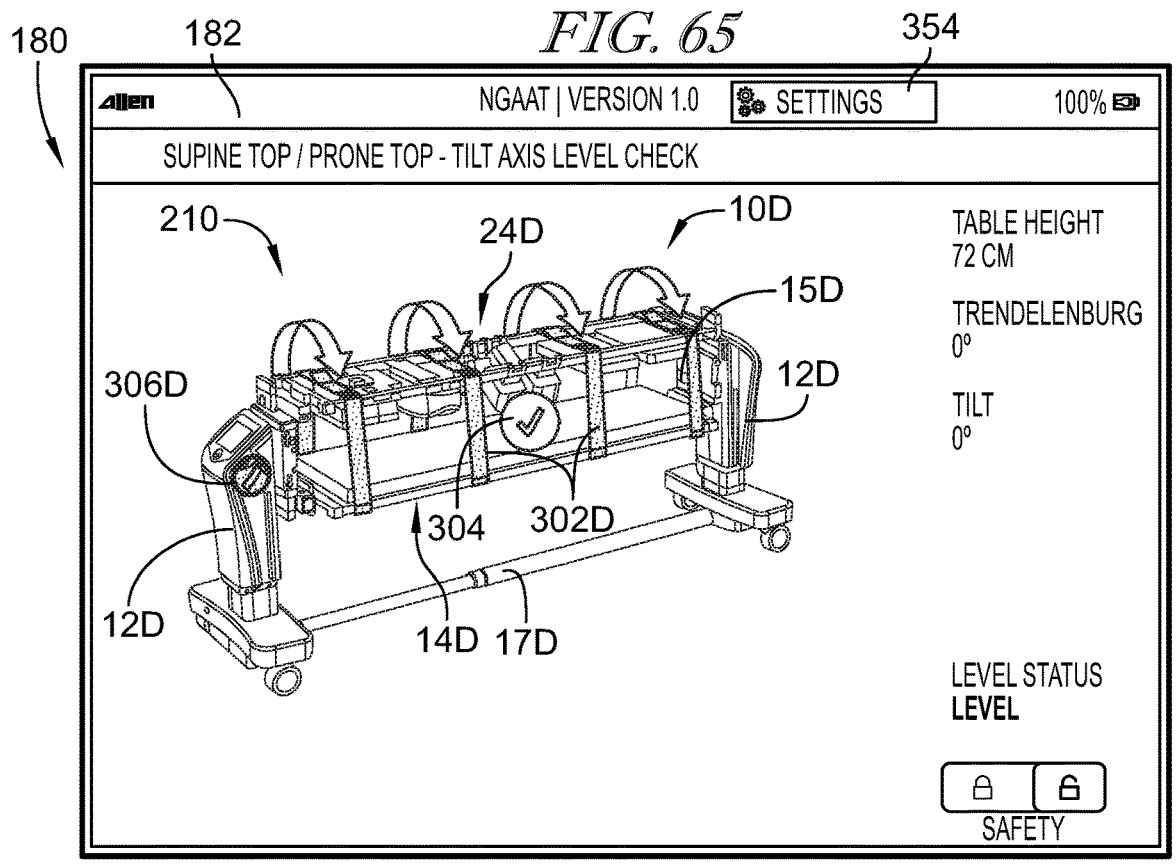
FIG. 66 is a screen shot of the display of the patient support of FIGS. 1-4 similar to FIG. 65 after the support tops have achieved the desired (level) position, showing that a request is presented to apply rotation straps to the patient support tops and a rotation strap operation icon is displayed as a check box in the center of the patient support for activation by the user upon successful application of the rotation straps to enable flip rotation.

As shown in FIG. 66, once the level status has been achieved, the GUI 180 illustratively prompts the user to apply safety straps 302 about the support tops 14, 24 to prepare for rotation flip about the axis 15. A confirmation button 304 is presented for user selection upon successful application of the safety straps 302. A rotation lever 306D is highlighted (green, as represented by fill in lever 306D) to draw attention to unlocking for the flip rotation actuation.

Figure 68:
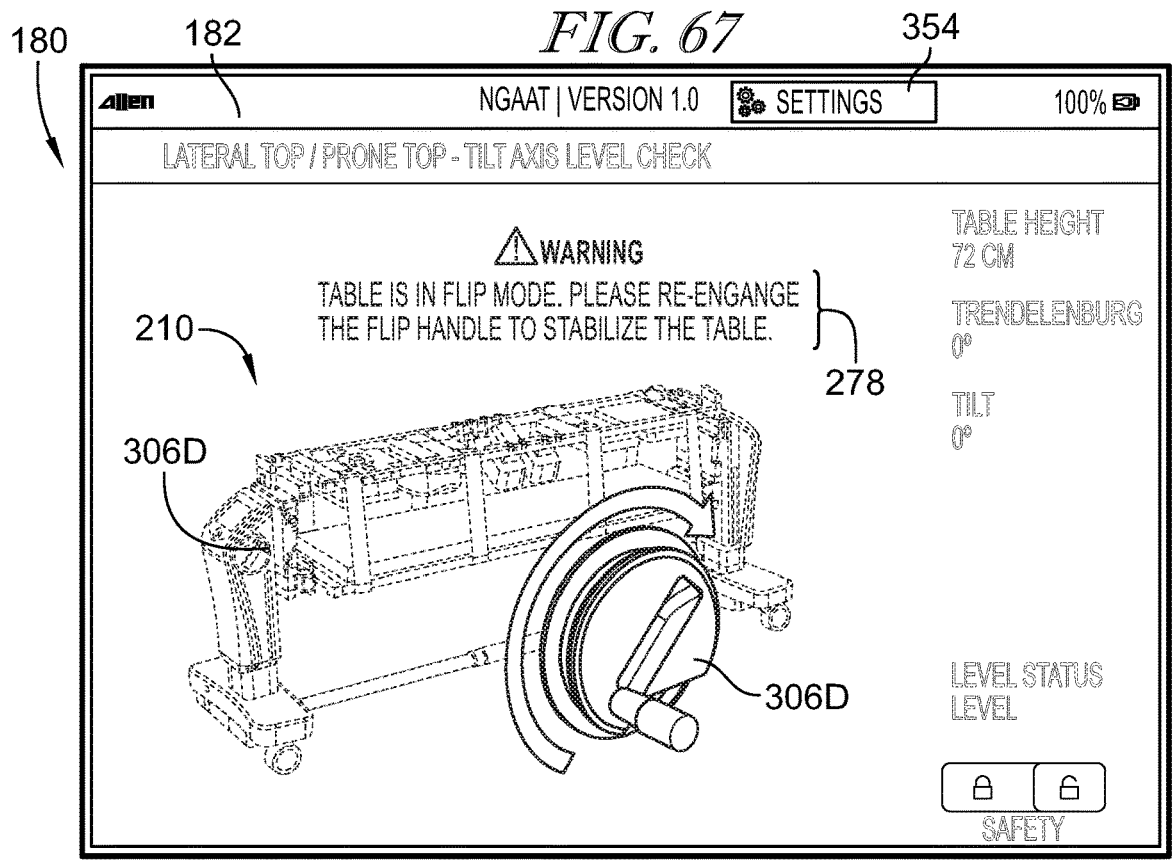
FIG. 68 is a screen shot of the display of the patient support of FIGS. 1-4 showing a warning window overlay indicating a flip mode in which the user operated a rotation handle to allow rotation of the connection assemblies to permit manual rotation the patient support tops about the longitudinal axis to provide supine to prone rotation, the warning screen indicating that clockwise rotation of the rotation handle reengages the connections assembly to prevent rotation.

As shown in FIG. 68, upon selection of the confirmation button 304, the button 304 is removed from the GUI 180 and the rotation lever 306D remains highlighted. As discussed in additional detail below, the user can rotate the rotation lever to unlock rotation flip, i.e., disengage a lock mechanism to allow the connection rods 16 to rotate freely under manual control of the user. Once the flip rotation is unlocked, the user can manually rotate the support tops 14, 24 together about axis 15 to perform the flip rotation. Upon user actuation of the rotation lever 306 to unlock rotation of the connection assemblies 18 about the axis 15, the GUI 180 presents a closer depiction of the rotation lever 306D overlaid over the patient support 10D (shown in dashed line to indicate background darkening). The alert script 278 indicates that the patient support 10 is in flip mode. The overlaid, closer depiction of the rotation lever 306D and the flip mode indication of the alert script remains until the rotation lever 306 is rotated back to reengage the lock mechanism of the connection rod 16. In some embodiments, the overlaid rotation lever 306D may be an animation indicating the desired direction of rotation of the rotation lever 306.

Figure 67:
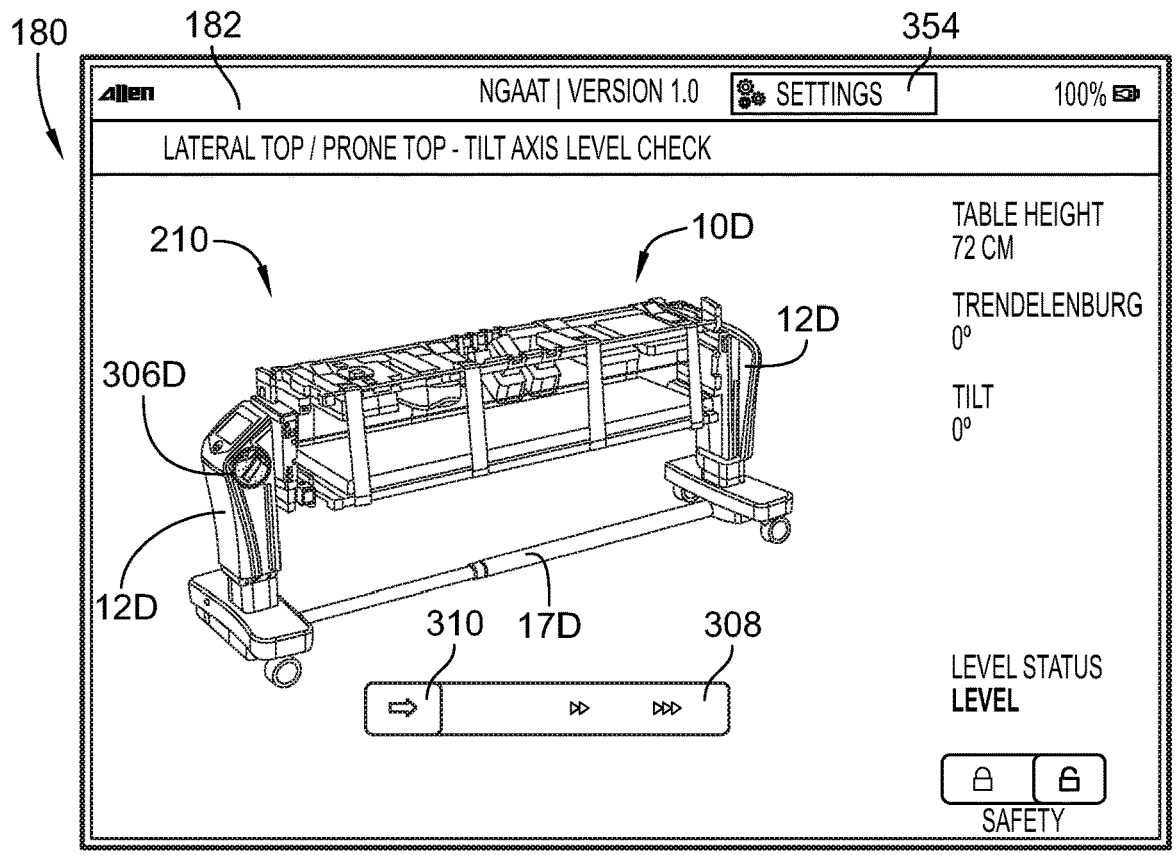
FIG. 67 is a screen shot of the display of the patient support of FIGS. 1-4 similar to FIG. 66 showing that the depiction includes rotation straps applied responsive to user activation of the rotation strap icon and a rotation handle is highlighted to draw the user's attention to the location of the rotation handle to enable flip rotation.

Referring briefly to FIG. 67, in the illustrative embodiment, the rotation flip operation is manually performed by the user. However, in embodiments in which the patient support 10 is enabled for powered rotation flip about the axis 15, a slider bar 308 is presented including a slider 310 for selective actuation by the user to execute rotation flip operation. In some embodiments, the slider 310 may be arranged biased into the center of the slider 308 allowing dragging to either left or right corresponding with clockwise or counterclockwise rotation of the patient support tops 14, 24 about the axis 15.

Figure 69:
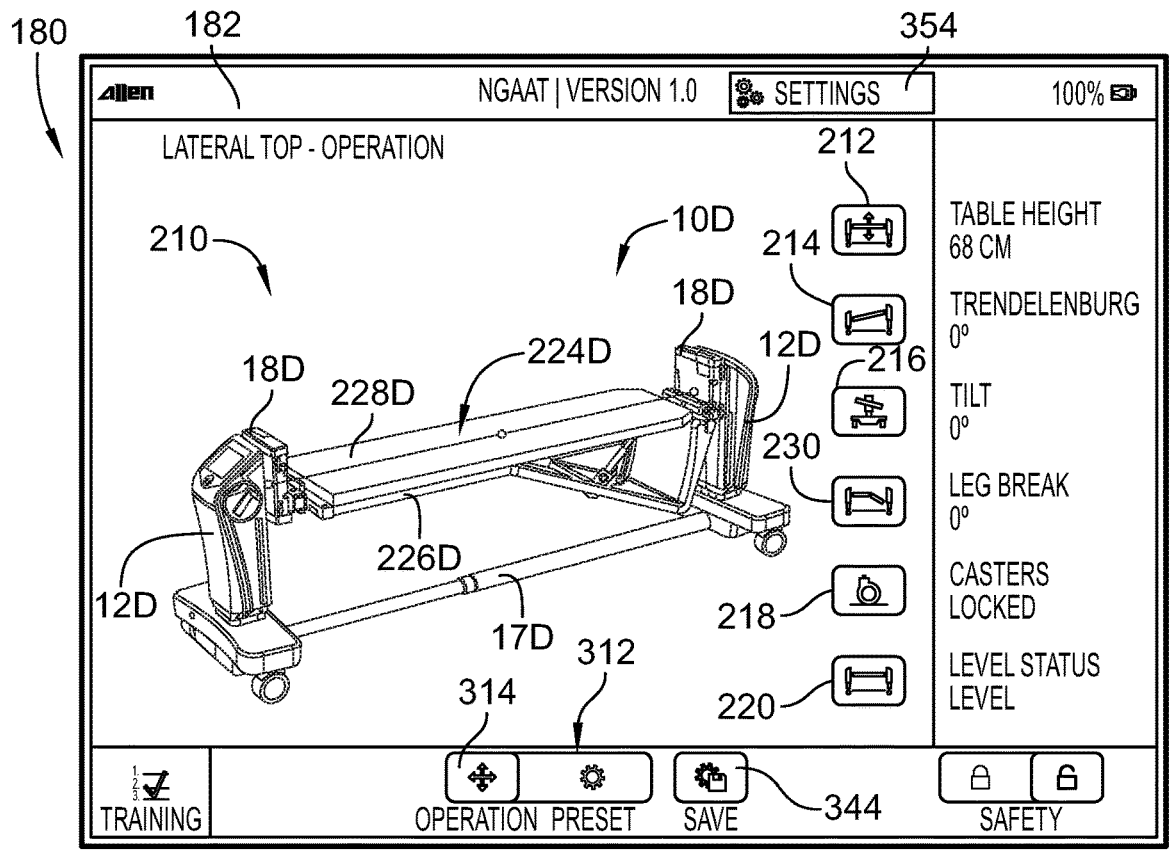
FIG. 69 is a screen shot of the display of the patient support of FIGS. 1-4 showing that the patient support has determined that that a lateral support top is connected and showing an initial operation screen in which the user can select a preset icon to selectively arrange the support top into preset configurations.

As shown in FIG. 69, a regular screen of the GUI 180 is shown in preparation for a preset position operation of the patient support 10. An operation slider bar 312 is illustratively shown in the footer area of the screen 182. The operation slider bar 312 includes a slider 314 operable by dragging between an operation position (left) for enabling position controls as discussed above, and a preset position (right) for enabling the preset position operation. For the purpose of example descriptions, the GUI 180 presents the lateral support top 224D attached to the connection assemblies 18D responsive to the detection of the presence of the lateral top 224.

Figure 70:
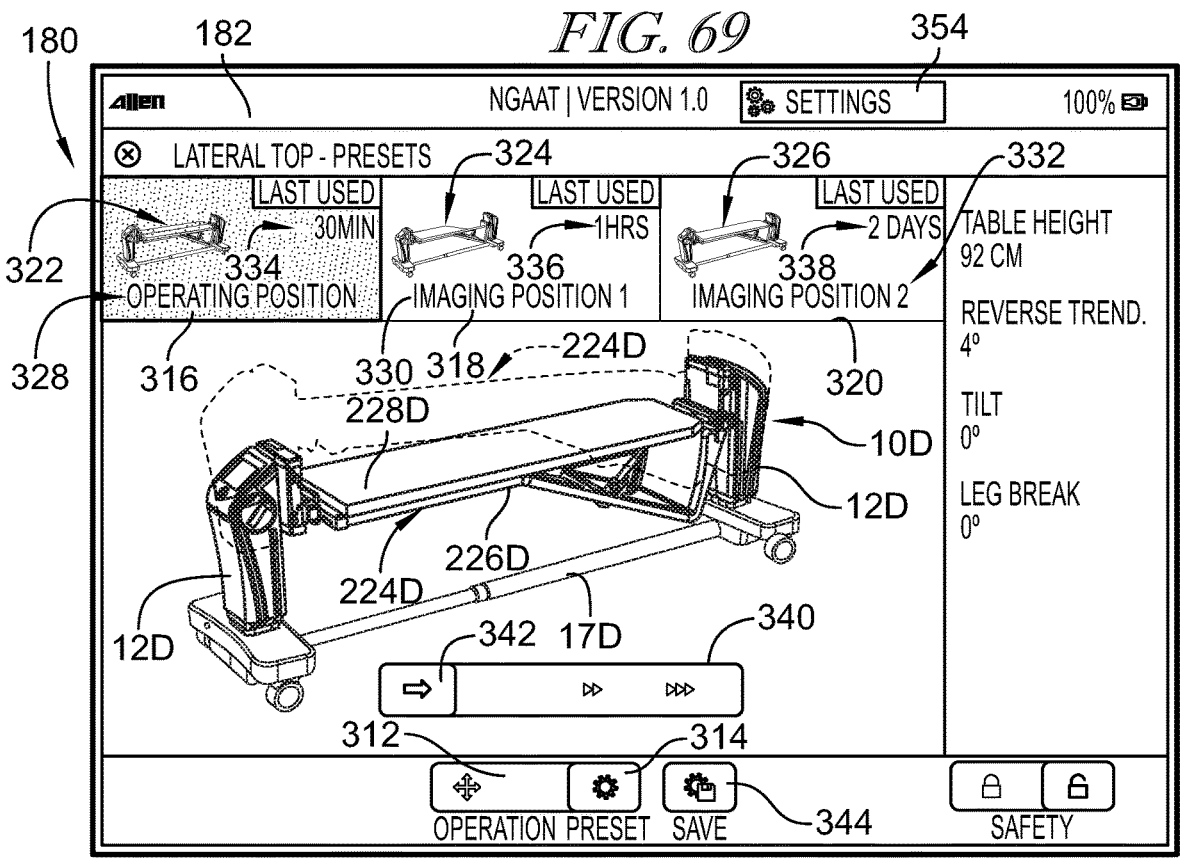
FIG. 70 is a screen shot of the display of the patient support of FIGS. 1-4 similar to FIG. 69 showing that the preset icon has been selected to responsively display a preset selection bar having a number of preset configuration icons, and showing that a preset operating position icon is presently selected as indicated by highlighting (fill) of the corresponding icon on the preset selection bar, and showing that a preset activation slider bar is presented for operation by the user to activate the selected preset operating position.

As shown in FIG. 70, a user has set the slider 314 to the present position (right) to enable the preset position operation. A user can illustratively drag the slider 314 to the operation position (left) to disable preset position operation in favor of adjustment operation. A number of preset position icons 316, 318, 320 are presented for user selection. The position icons 212-220, 230 have been illustratively removed from the screen 182.

The present position icons illustratively include an operating position icon 316, a first imaging position icon 318, and a second imaging position icon 320. In some embodiments, the preset position icons may include any suitable number, style, and/or combination of features for preset positioning of the patient support 10 and/or may include support top-specific positions, for example, position having a leg break angle for the lateral support top 224 when appropriately detected. In the present example, the operating position icon 316 is preset for an operating position of the support top 224 having a table height of 92 cm, 0 degrees of leg break, 0 degrees of tilt, 4 degrees of reverse Trendelenburg angle (or −4 degrees of Trendelenburg angle). The operating position of the support top 224D and tower bases 12D is indicated on the GUI 180 in outline (dashed line) and the corresponding parameters of the operating position are indicated by the information on the right hand side of the screen 182 (table height, reverse Trend., tilt, leg break).

Each position icon 316, 318, 320 illustratively includes a depiction 322, 324, 326 of the support top 10 having the corresponding preset position and a script 328, 330, 332 indicating the corresponding position title, and an indication of the amount of elapsed time from the last use of the corresponding position 334, 336, 338. For example, the operating position icon 316 illustratively includes the depiction 322 of the support top 10 having the preset operating position, the script 328 indicating "Operating Position", and an indication 334 that the operating position was last used about 30 minutes prior. The operating position icon 316 is presently selected as indicated by highlighting on the GUI 180 (represented by fill in icon 316).

A preset slider bar 340 is presented on the GUI 180 including a slider 342 for actuation by the user to adjust the patient support 10 to obtain the position of the presently selected preset icon. In the illustrative embodiment, by dragging the slider 342 partly to the right, the user can actuate the patient support 10 to begin adjustment to the presently selected preset position, and by further dragging the slider 342 to the right the speed of adjustment can be increased, although in some embodiments, a single speed of adjustment may be available and/or dragging the slider 342 to the far right may activate complete movement to the preset position even with release by the user. Once the slider 342 is activated, the information to the right indicates the current position of the patient support 10 and the depiction 210 tracks accordingly. In the present example, the operating position is the presently selected position and thus actuation of the slider 342 adjusts the patient support 10 towards the operating position.

Figure 71:
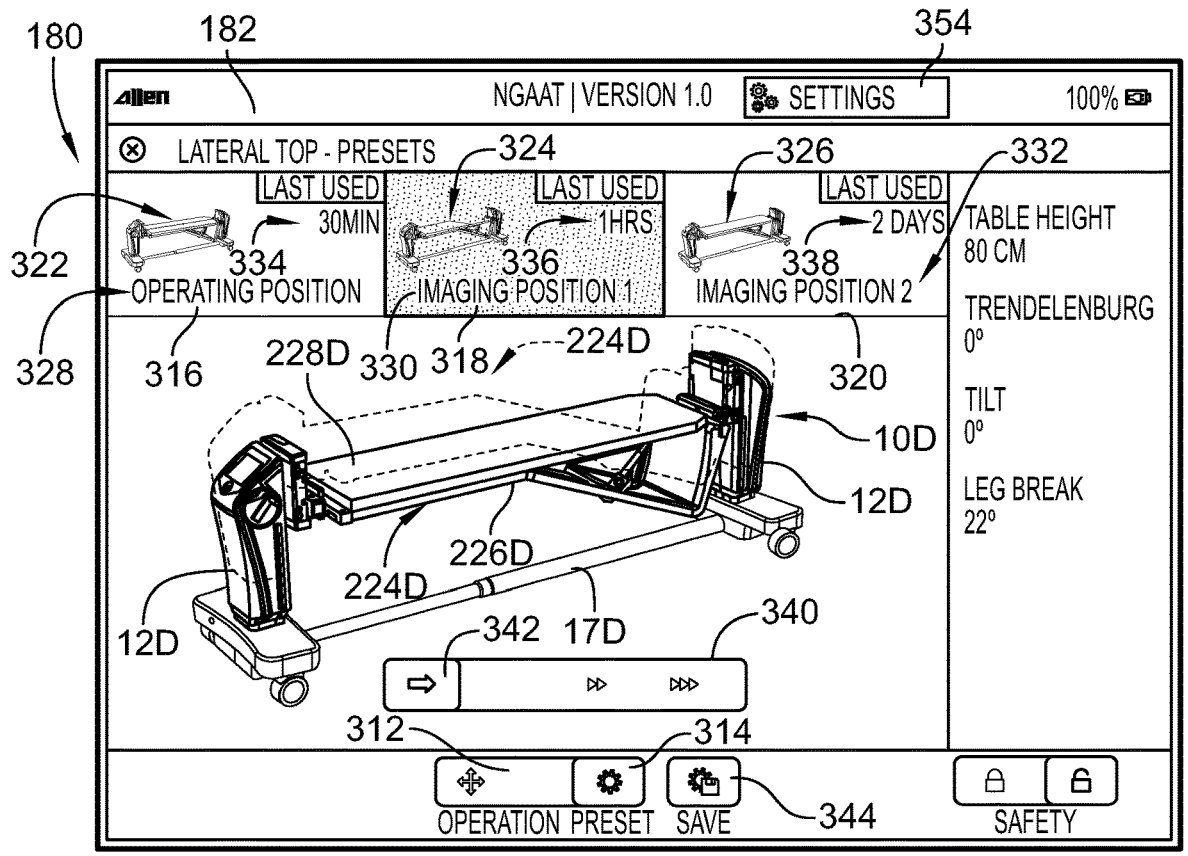
FIG. 71 is a screen shot of the display of the patient support of FIGS. 1-4 similar to FIG. 70 showing that a preset imaging position icon has been selected as indicated by highlighting (fill) of the corresponding icon on the preset selection bar, and showing that a preset activation slider bar is presented for operation by the user to activate the selected preset imaging position.

As shown in FIG. 71, the user has selected the first imaging position icon 318 as indicated by highlighting the icon 318 on the GUI 180 (represented by fill in icon 318). The position of the patient support 10D remains unchanged from the example as discussed relative to FIG. 69, yet the outlined position (dashed line) of the support top 224D and tower bases 12D is now presented as the preset first imaging position. The preset first imaging position illustratively includes a table height of 80 cm, a Trendelenburg angle of 0 degrees, a tilt angle of 0 degrees, and 22 degrees of leg break. The user can operate the patient support 10 to adjust the patient support 10 towards the first imaging position, as the presently selected position, by dragging the slider 342 towards the right side of the slider bar 340, similar to preceding descriptions of slider bars. Once the slider 342 is activated, the information to the right indicates the current position of the patient support 10 and the depiction 210 tracks accordingly. Accordingly, the position of the patient support 10 can be adjusted towards the preset position using the single drag action.

Figure 72:
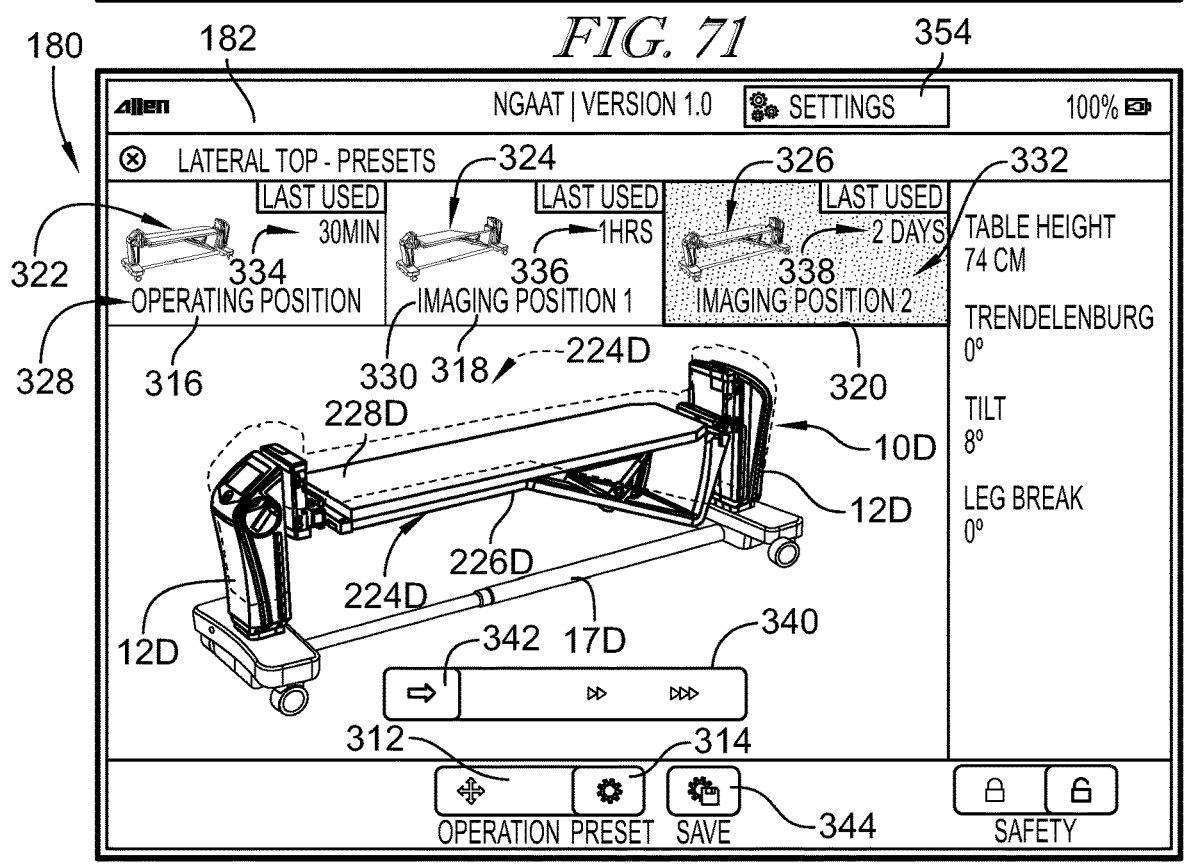
FIG. 72 is a screen shot of the display of the patient support of FIGS. 1-4 similar to FIG. 71 showing that another preset imaging position has been selected as indicated by highlighting (fill) of the corresponding icon on the preset selection bar, and showing that a preset activation slider bar is presented for operation by the user to activate the selected other preset imaging position.

As shown in FIG. 72, the user has selected the second imaging position icon 320 as indicated by highlighting the icon 320 (represented as fill of icon 320) on the GUI 180. The position of the patient support 10DE remains unchanged from the example as discussed relative to FIG. 69, yet the outlined position (dashed line) of the support top 224D and tower bases 12D is now the preset second imaging position. The preset second imaging position illustratively includes a table height of 74 cm, a Trendelenburg angle of 0 degrees, a tilt angle of 8 degrees, and 0 degrees of leg break. The user can operate the patient support 10 to adjust towards the second imaging position, as the presently selected position, by dragging the slider 342 towards the right side of the slider bar 340, similar to preceding descriptions of slider bars. Once the slider 342 is activated, the information to the right indicates the current position of the patient support 10 and the depiction 210 tracks accordingly. Accordingly, the position of the patient support 10 can be adjusted towards the preset position using the single drag action.

Figure 73:
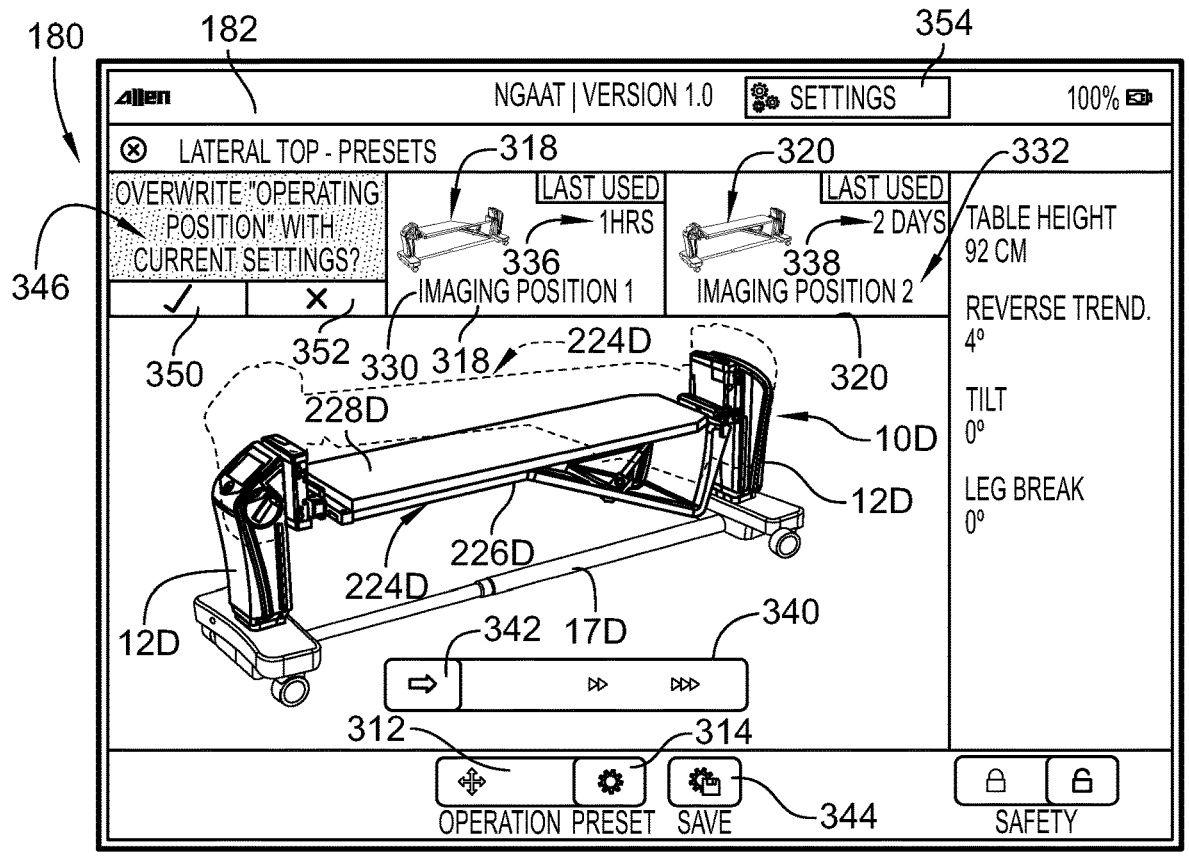
FIG. 73 is a screen shot of the display of the patient support of FIGS. 1-4 similar to FIGS. 69-72 showing that a preset save button has been selected to redefine the selected preset configuration to have the current configuration of the patient support, and showing that responsive to user selection of the preset save button, an overwrite confirmation window is displayed including a confirmation icon and a cancellation icon for user selection.

As shown in FIG. 73, the operating position icon 316 is presently selected, and from the present selection, the user has selected a save button 344 to initiate overwriting of the configuration of the preset operating position. Responsive to the user selection of the save button 344, an overwrite icon 346 is presented, illustratively overlapping the location of the operating position icon 316. The overwrite icon 346 illustratively includes a script requesting a confirmation to overwrite the presently selected preset position (the preset operating position) with the current position settings of the patient support 10, a yes button 350 for selection by the user to confirm the overwrite, and a cancel button 352 for selection by the user to cancel the overwrite.

Figure 74:
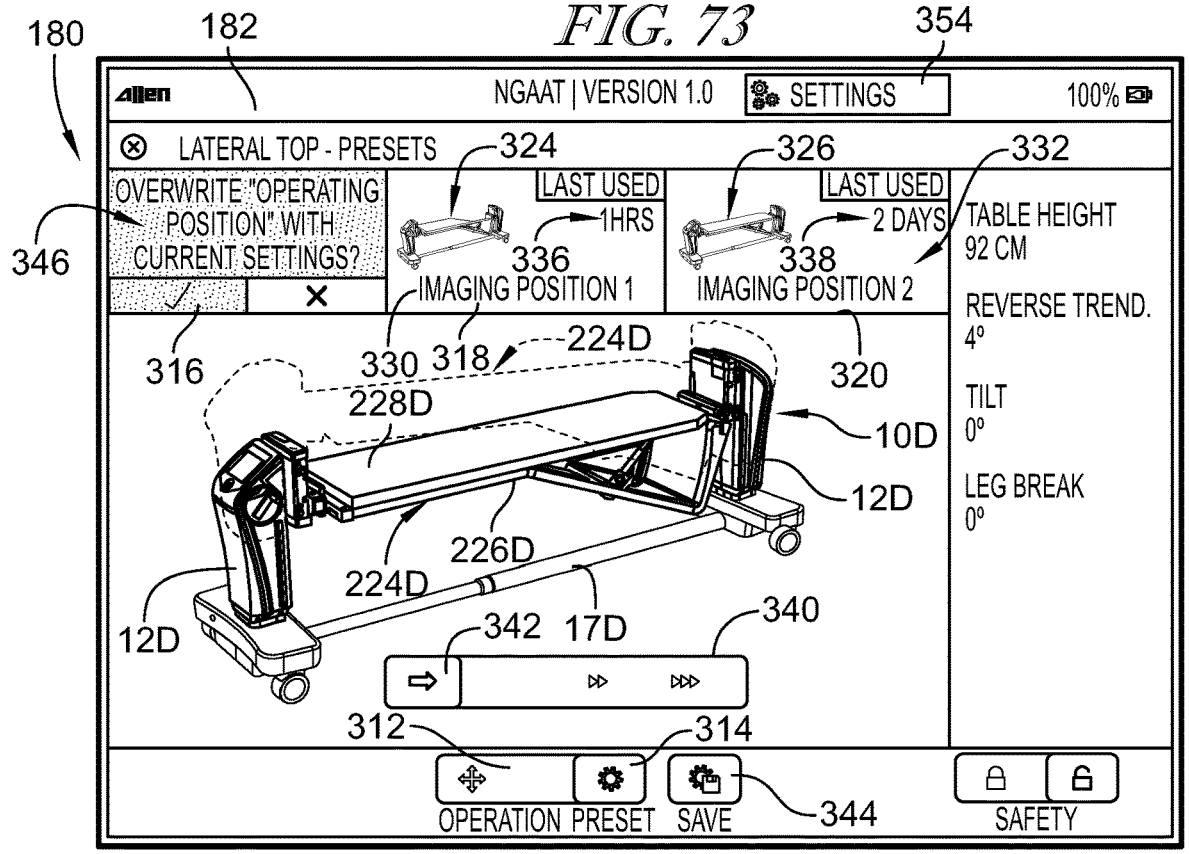
FIG. 74 is a screen shot of the display of the patient support of FIGS. 1-4 similar to FIG. 73 showing that the user has selected the confirmation icon to overwrite the previous operating position with the current configuration.

As shown in FIG. 74, the user has selected the yes button 350 to confirm saving of the current position of the patient support 10 as the newly defined operating position in place of the previous operating position. Selection of the yes button 350 is indicated by highlighting the button 350 (represented by fill of button 350). After saving is completed, the preset operating icon 316 returns indicating the new presets. The preset positions of the first and second imaging position icons 318, 320 can be redefined by similar overwriting process as disclosed regarding the operating position icon 316, by selection of the save button 344 when the corresponding icon 318, 320 is presently selected.

Figure 75:
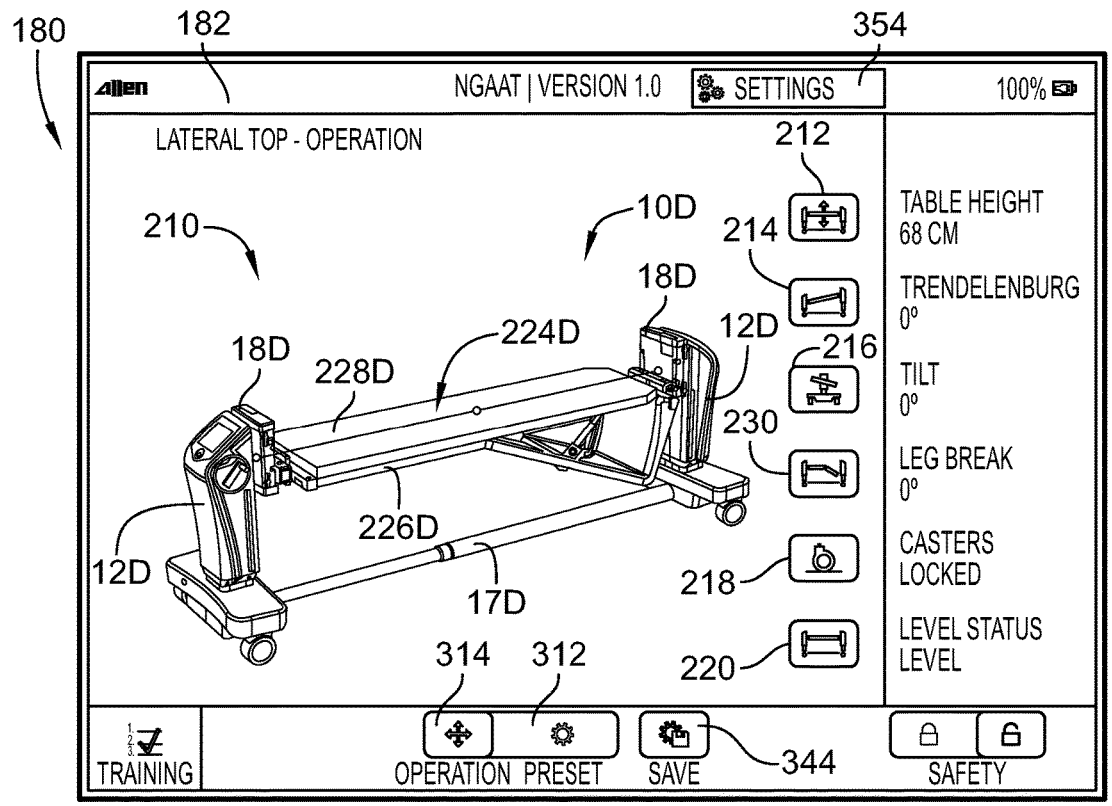
FIG. 75 is a screen shot of the display of the patient support of FIGS. 1-4 similar to FIG. 74 showing that a settings icon is available for user selection to access various settings.

As shown in FIG. 75, the user has dragged the slider 314 to the operation position. The GUI 180 responsively terminates the preset position operation and presents the main screen.

Figure 76:
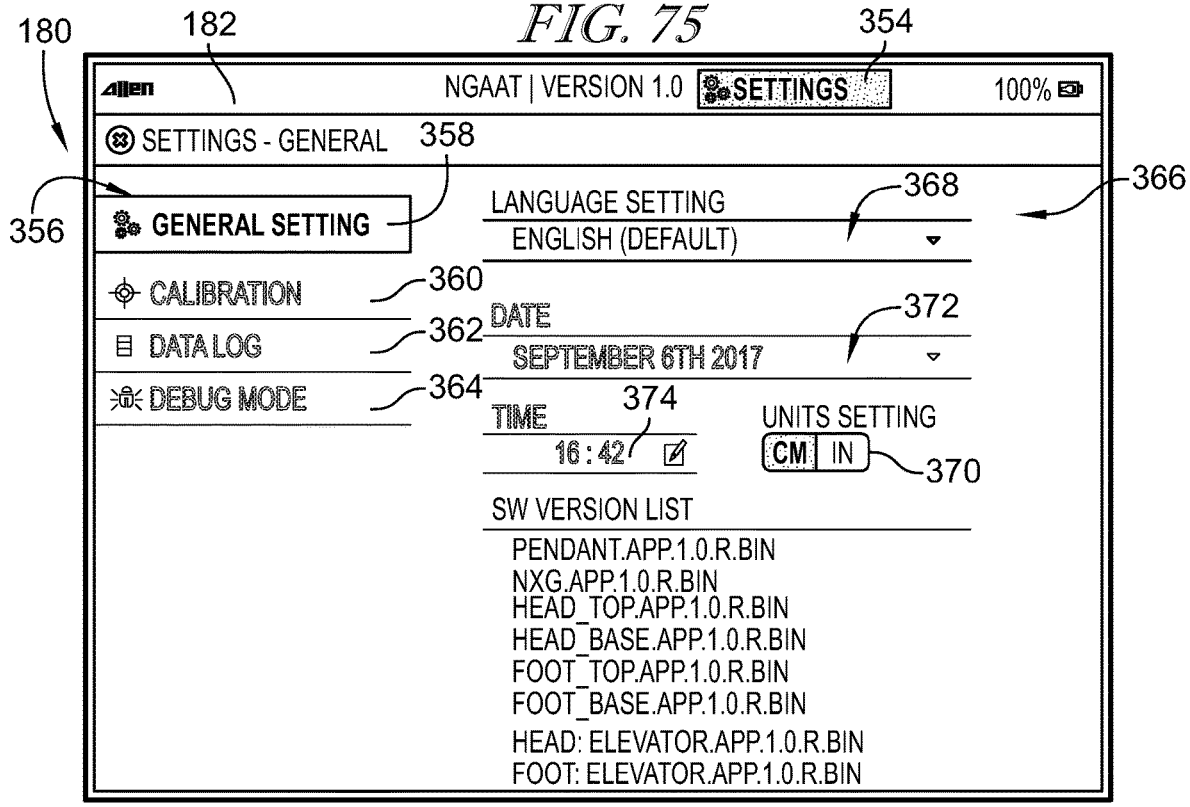
FIG. 76 is a screen shot of the display of the patient support of FIGS. 1-4 similar to FIG. 75 showing that responsive to user selection of the settings icon a settings menu is displayed including various settings tabs for user selection, and showing that a general settings tab is currently highlighted to display general settings options such as language, date, and time.

Referring now to FIG. 76, a settings button 354 is available in the header of the screen 182 for user selection to adjust various parameters. User selection of the settings button 354 advances the GUI 180 to a settings menu.

As shown in FIG. 76, the settings button 354 has been selected by the user as indicated by highlighting (represented as fill of button 354) to present the settings menu. In the settings menu, a navigation bar 356 is presented including tabs 358-364, having a general settings tab 358, a calibration tab 360, a data log tab 362, and a debug tab 364. As shown in FIG. 76, the general settings tab 358 is presently selected as indicated by highlighting the tab 358 (represented as bolding). As the general settings tab 358 is presently selected, a number of general parameters 366 are displayed such as language, date, time, and units, as well as the software version, corresponding to the general settings tab 358.

Figure 77:
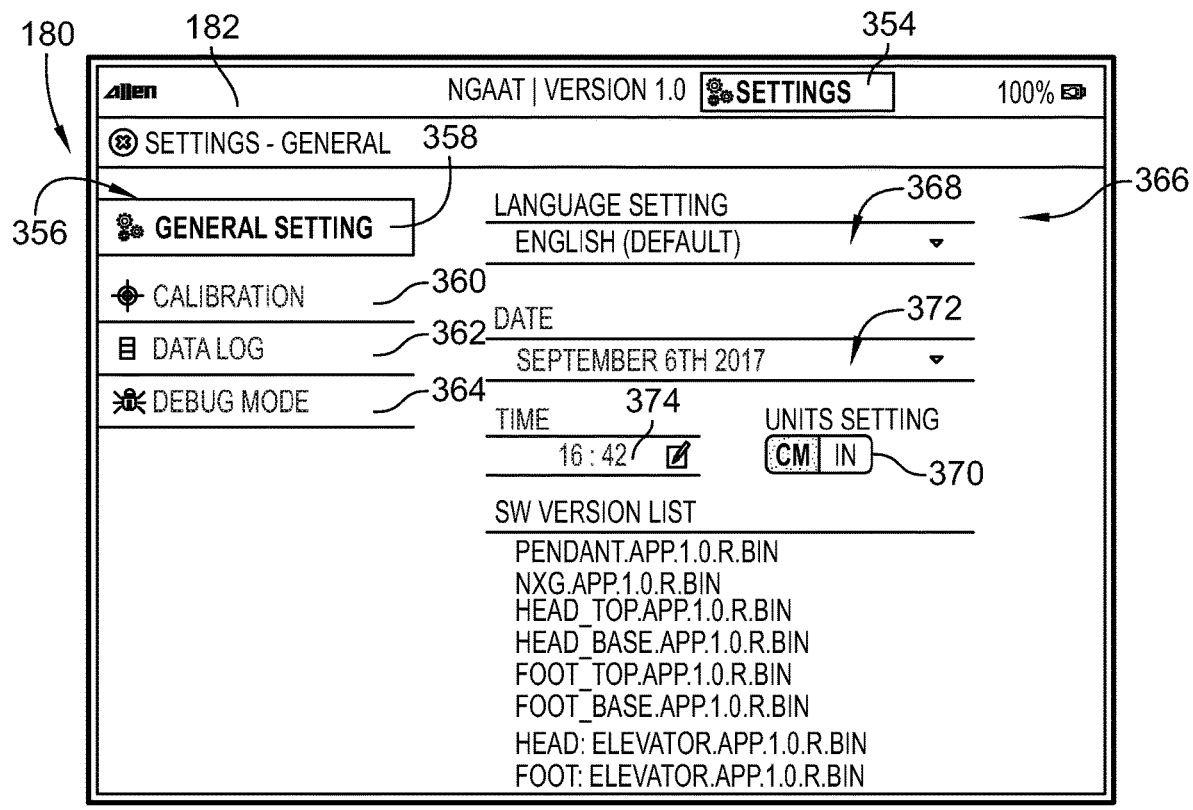
FIG. 77 is a screen shot of the display of the patient support of FIGS. 1-4 similar to FIG. 76 showing that, responsive to user selection of a general settings tab of the settings menu, language, date/time, and units data is displayed.

As shown in FIG. 76, the generic features, including the general settings tab 358 and a few of the general parameters 366 (e.g., language parameter 368, units parameter 370), are presently available (active) for user adjustment. Availability for adjustment is indicated by their solid text, while other features including the other tabs 360, 362, 364 and other general parameters 366 (e.g., date 372, time 374) are presently unavailable (inactive) for user adjustment as indicated by their outlined (hollow) text. The generic features are always available from the general settings tab 358 while the other features are only available on activation of a switch 375 (as shown in FIG. 1) illustratively embodied as a physical switch. As shown in FIG. 77, the user has activated the switch 375 to make active the other features including the tabs 360, 362, 364, and the date 372 and time 374 features, as indicated by their change to solid text (from previously hollow text).

Figure 78:
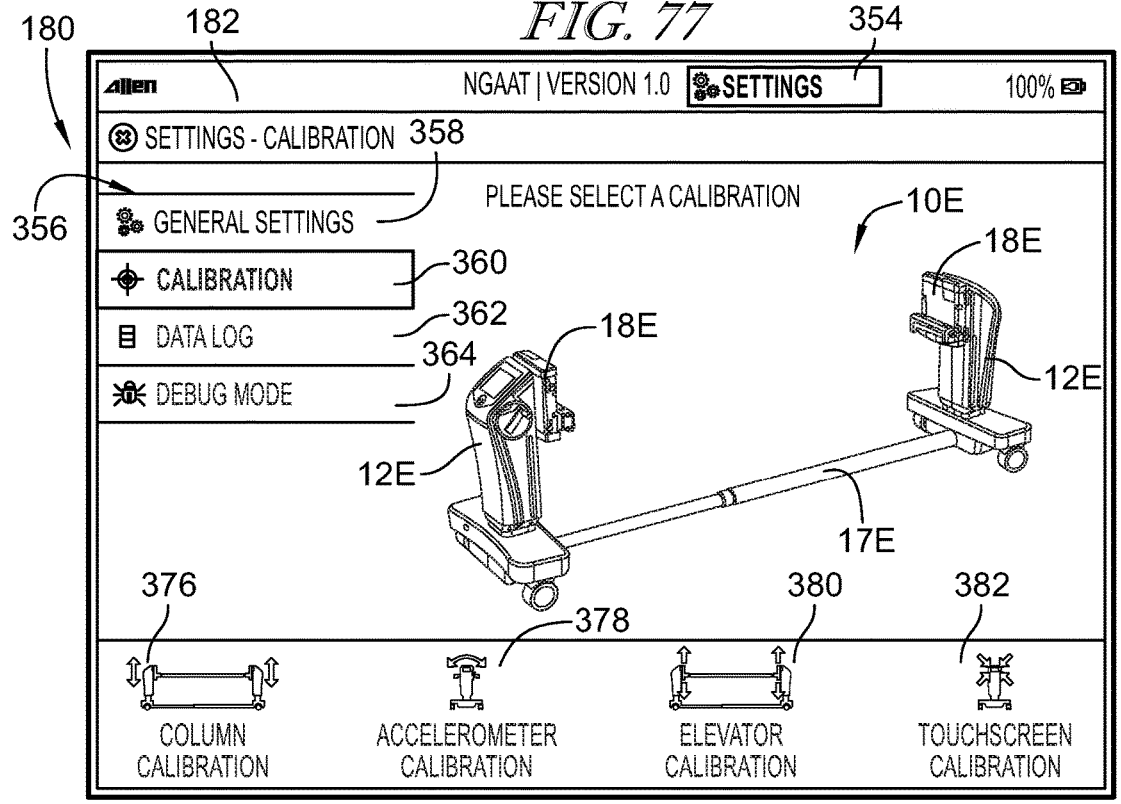
FIG. 78 is a screen shot of the display of the patient support of FIGS. 1-4 similar to FIG. 76 showing that, responsive to user selection of a calibration tab of the settings menu, calibration options including column, accelerometer, elevator, and touchscreen calibrations are displayed for user selection to perform respective calibration operations.

As shown in FIG. 78, the user has selected the calibration tab 360 as indicated by highlighting the tab 360 (represented by bolding) to enable a calibration operation. Responsive to selection of the calibration tab 360, the GUI 180 presents a depiction of the patient support 10 (indicated as 10E) having no support tops attached and a number of calibration icons 376, 378, 380, 382 for selection by the user. The calibration icons 376-382 illustratively include a tower base (column) calibration, an accelerometer calibration icon 378, a slide plate (elevator) calibration icon 380, and a touch screen calibration icon 382, as discussed in additional detail below.

Figure 79:
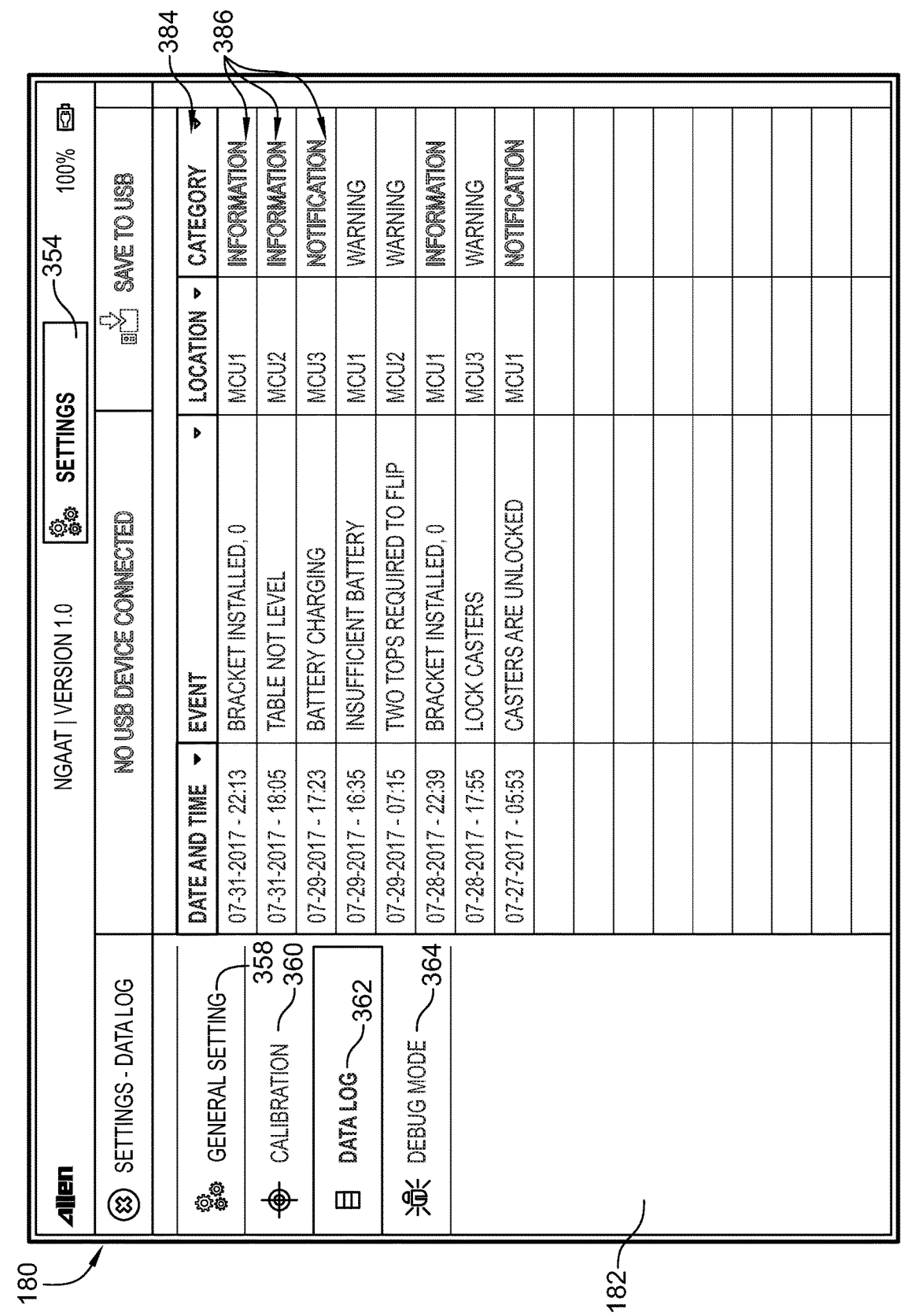
FIG. 79 is a screen shot of the display of the patient support of FIGS. 1-4 similar to FIG. 76 showing that, responsive to user selection of a data log tab of the settings menu, a log of event data is displayed.

As shown in FIG. 79, the user has selected the data log tab 362 as indicated by highlighting the tab 362 (represented by bolding). Responsive to selection of the data log tab 362, the GUI 180 presents a list of data entries 384 indicating historical data events 386. The historical data events (individual rows) 386 each illustratively include date and time information, event names, location information, and category information presented as sortable columns. The GUI 180 illustratively indicates that no USB is connected with the control system 184 and presents a save to USB button (currently inactive) for saving to external universal serial bus connected devices.

Figure 80:
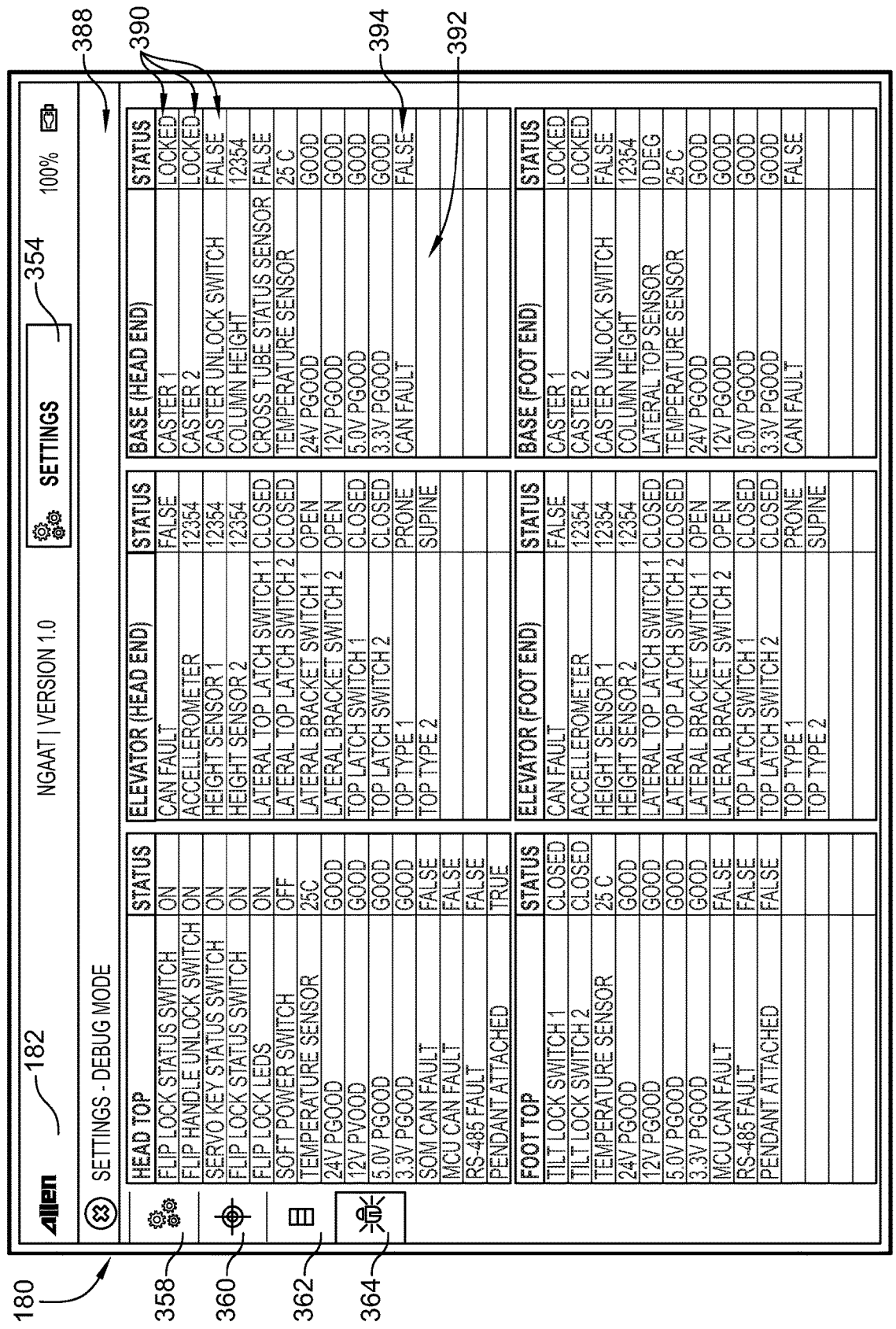
FIG. 80 is a screen shot of the display of the patient support of FIGS. 1-4 similar to FIG. 76 showing that responsive to user selection of a debug tab of the settings menu, a debugging mode is entered.

As shown in FIG. 80, the user has selected the debug tab 364 as indicated by highlighting the debug tab 364 (represented by bolding). Responsive to selection of the debug tab 364, the GUI 180 enters a debugging mode and presents a menu of areas 388 of the patient support 10, including the head end base tower top (head top), head end slide plate (elevator (head end)), head end base tower base (base (head end)), foot end base tower top (foot top), head end slide plate (elevator (foot end)), foot end base tower base (base (foot end)). The areas 388 each include a list of sub-features 390 each including an identifier (name) 392 and a status 394. For example, the base (head end) illustratively includes two casters 470 and each caster 470 includes an identifier 392 (caster 1, caster 2) and a status 394 (locked).

Figure 81:
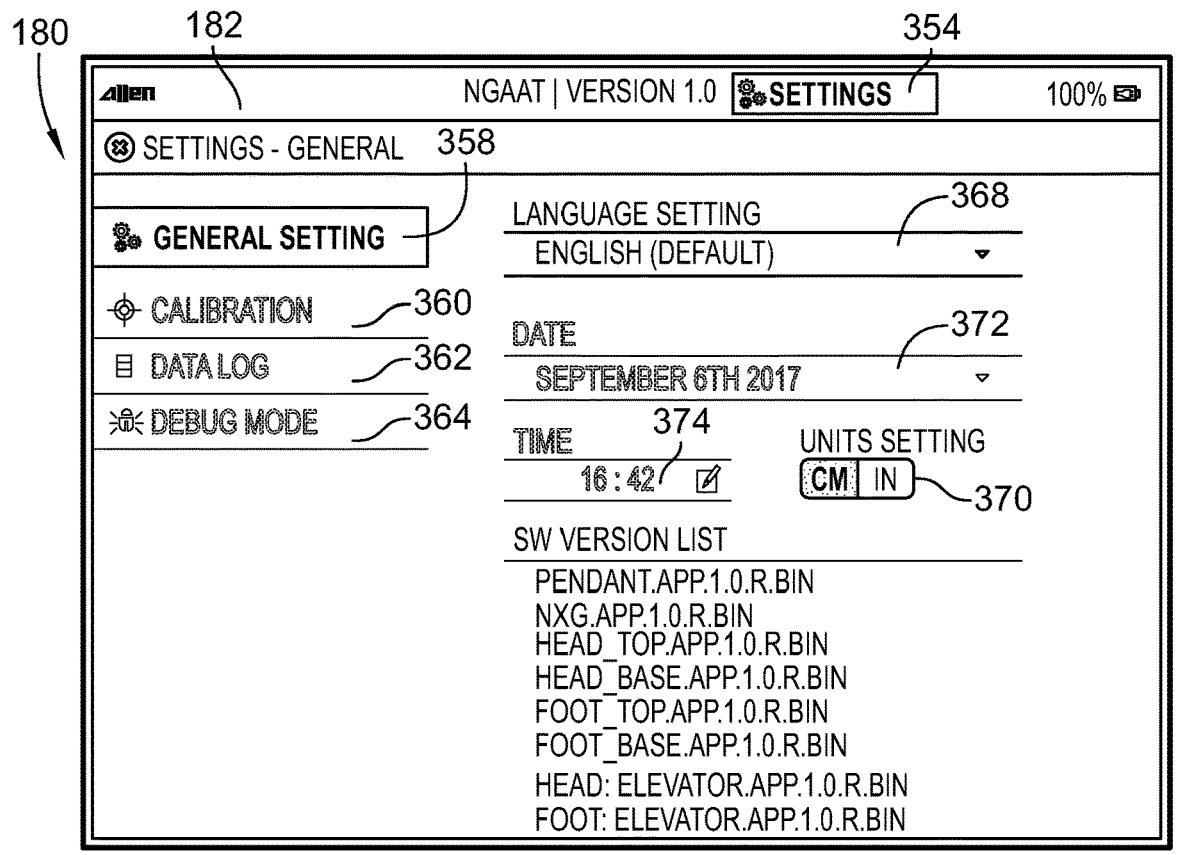
FIGS. 81-86 are screen shots of the display of the patient support of FIGS. 1-4 showing a number of settings for selective user adjustment.
Figure 82:
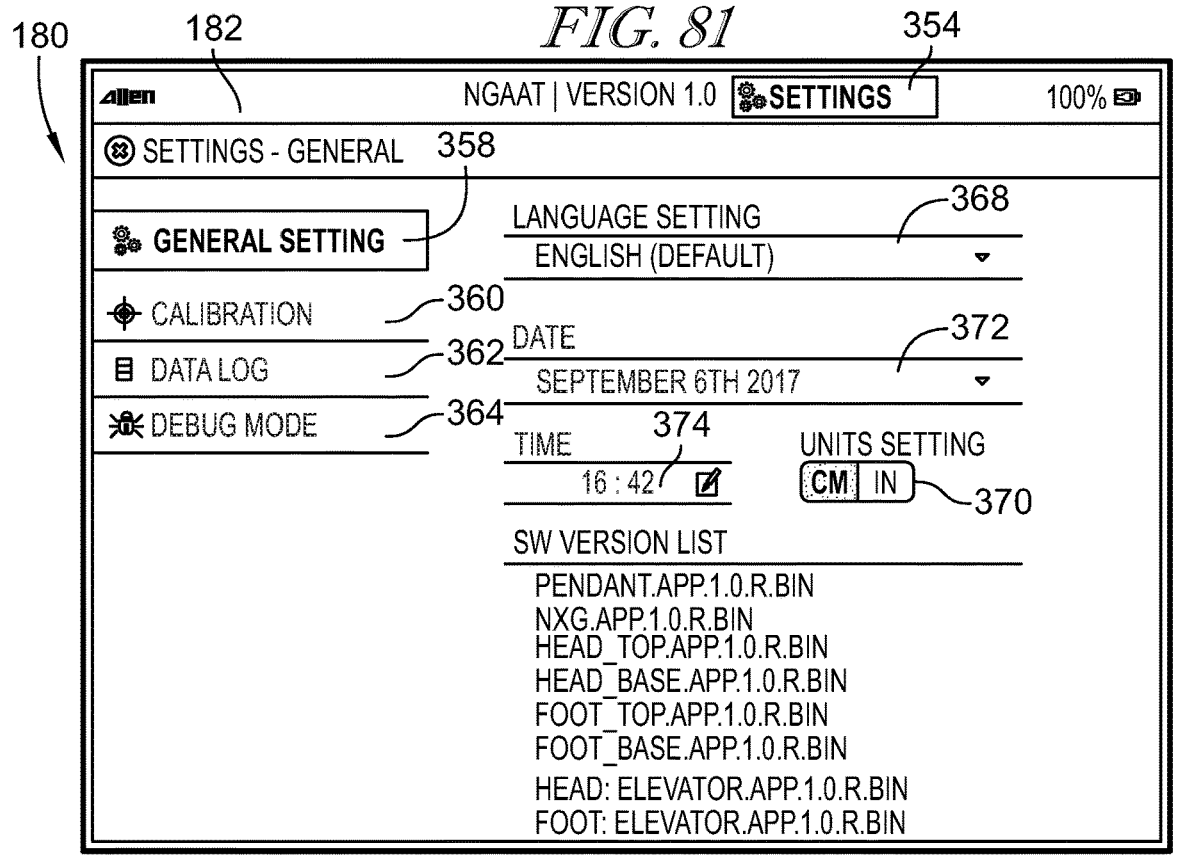

Referring to FIG. 81, a process of adjusting general settings is disclosed. The user has selected the settings button 354 to present the menu and has selected the general settings tab 358. The switch 375 has not been activated as indicated by the inactiveness of the other features (e.g., the date and time are inactive). The user can select active features for adjustment such as the language and units. As shown in FIG. 82, the user has activated the switch 375 to make active the other features as indicated by their solid text.

Figure 83:
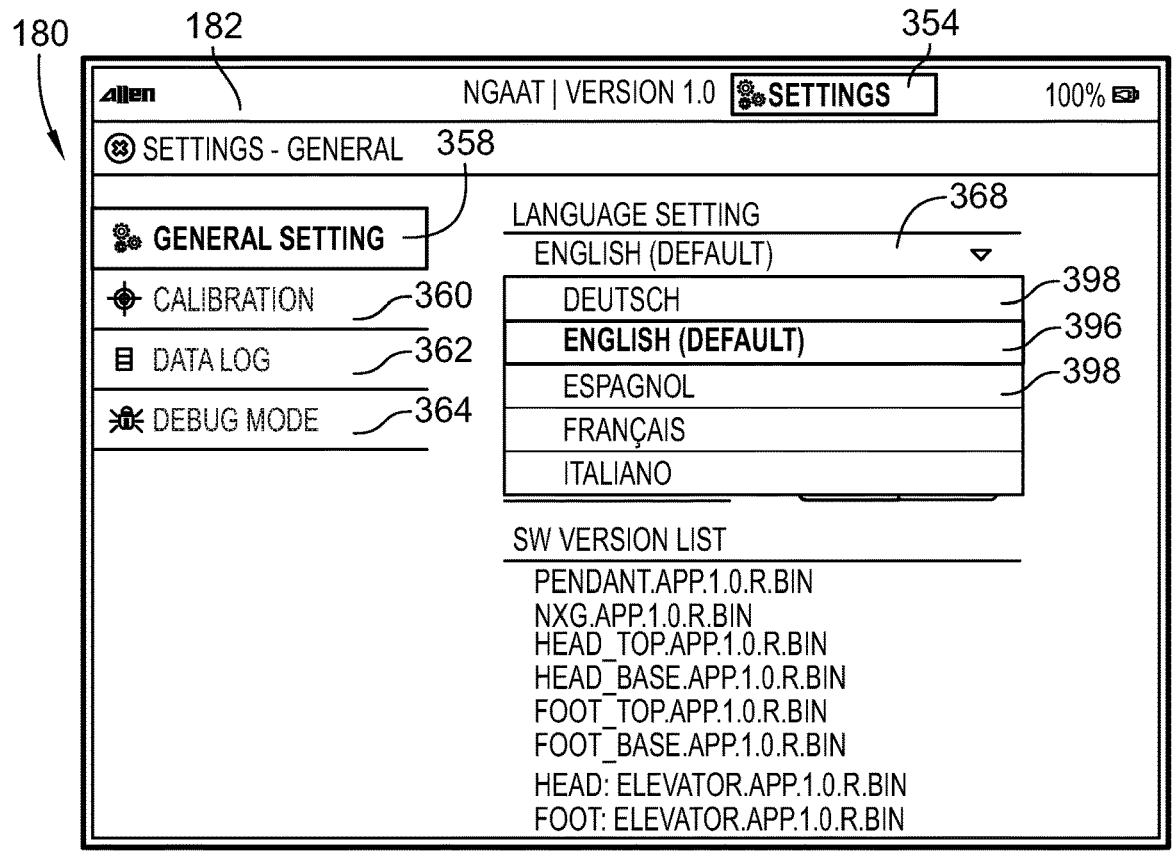

As shown in FIG. 83, the user has selected the language parameter 368 which is presently set to English. User selection of the language parameter 368 presents a drop down menu 396 including language options 398 for selection by the user to define the present language of the GUI 180. The presently selected option on the menu 396 (English) is indicated on the GUI 180 by highlighting (represented by bolding). Upon user selection of a language option 398, the menu 396 is collapsed.

Figure 84:
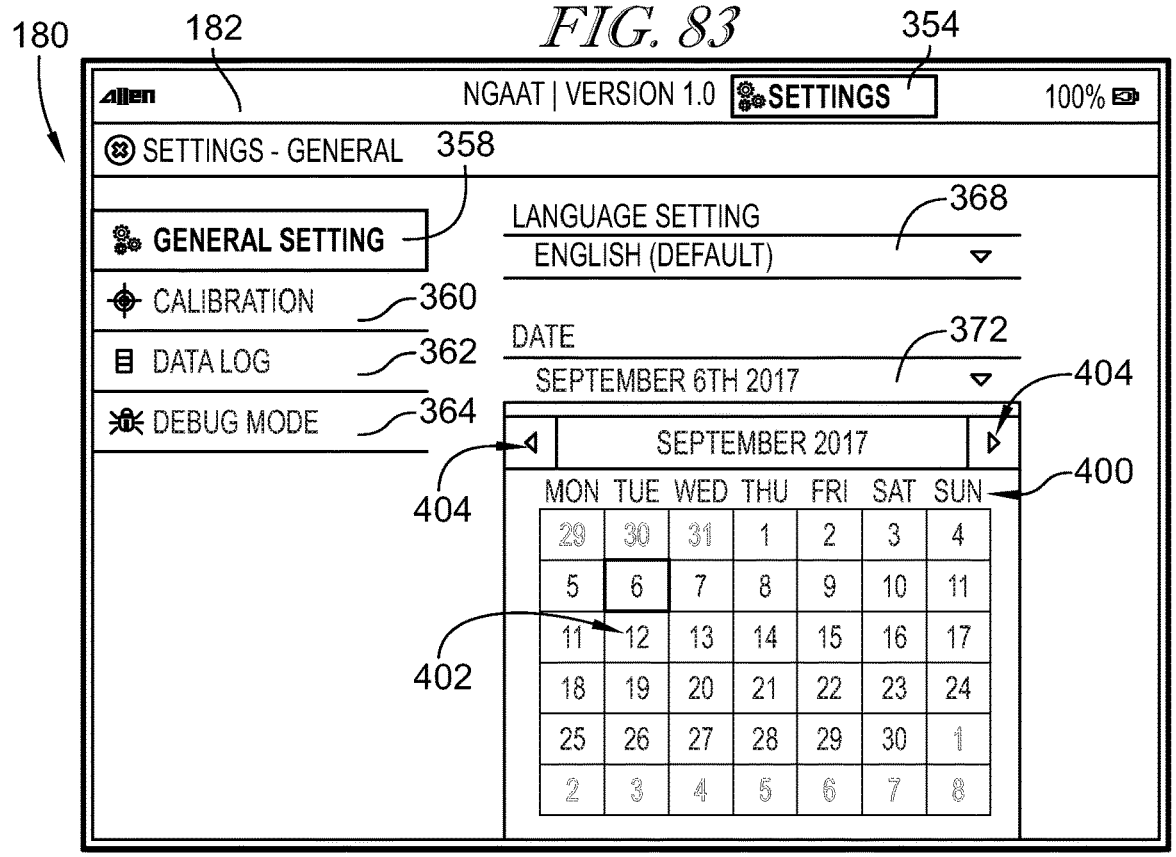

As shown in FIG. 84, the user has selected the date parameter 372 presently set as Sep. 6, 2017. User selection of the date parameter 372, the GUI 180 presents a drop down calendar menu 400 including date options 402 for user selection to define the present date. The menu 400 indicates the presently selected date option 402 by highlighting the corresponding date (i.e., September 6, as represented by bolding the box for Sep. 6, 2017). A user can navigate the menu 400 to other months by selection of the arrows 404. Upon user selection of a date option 402, the menu 400 is collapsed.

Figure 85:
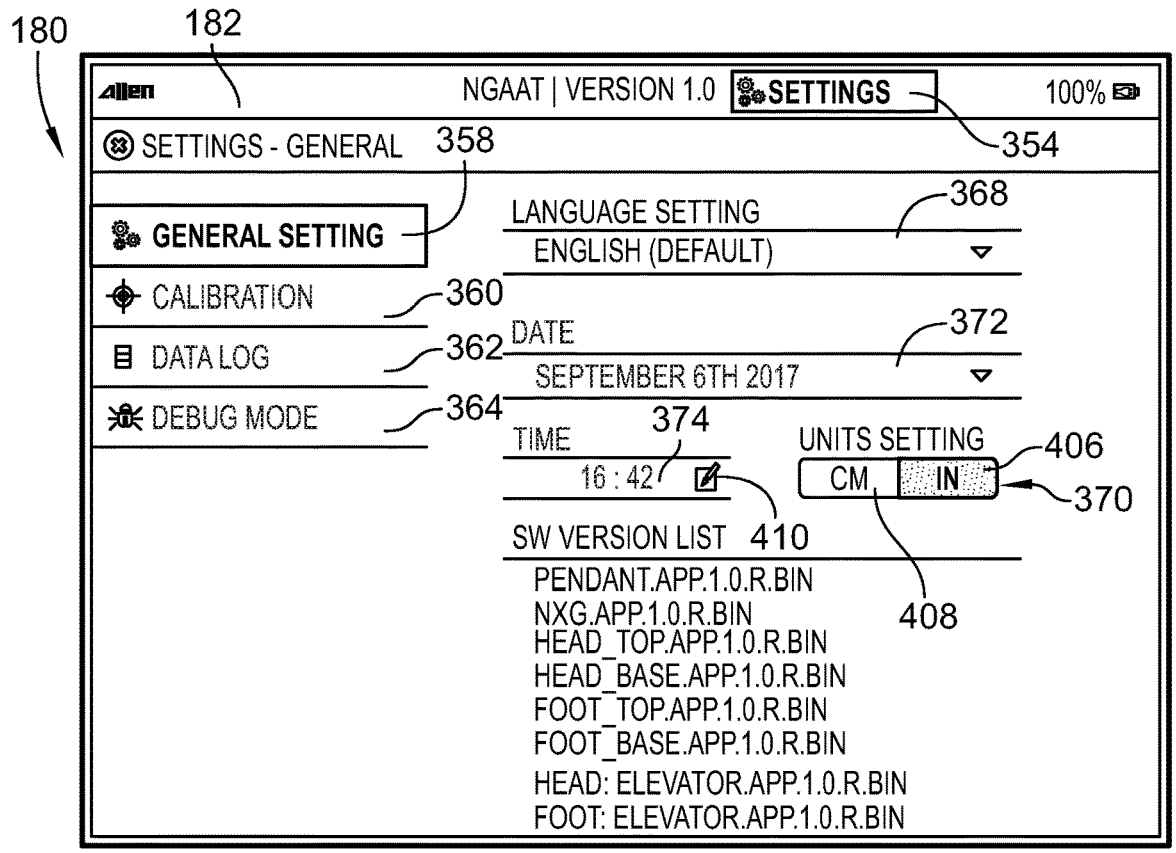

As shown in FIG. 85, the general settings tab 358 has been selected and switch 375 has been activated. The units parameter 370 is presently set to inches as indicated by highlighting the IN option 406 (as represented by bold and fill of option 406). The time parameter 374 illustratively includes an edit button 410 for user selection to edit the current time.

Figure 86:
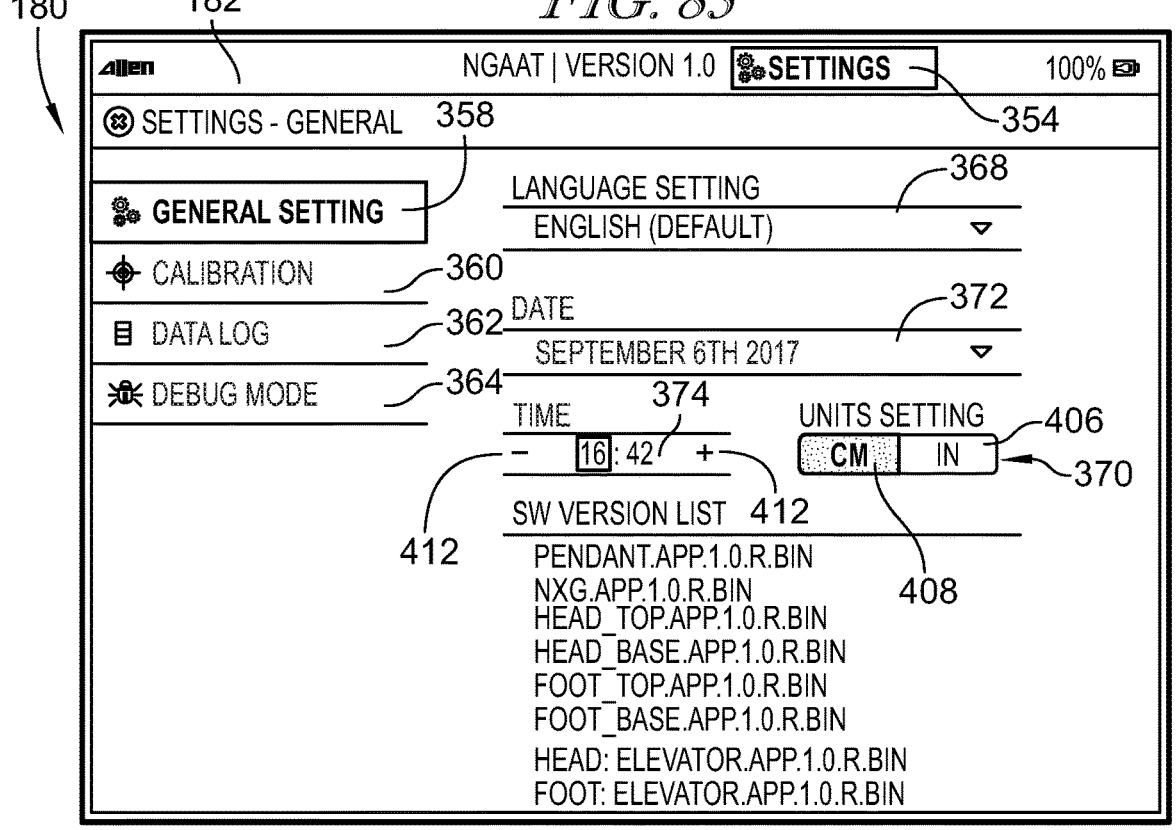

Referring to FIG. 86, the user has selected the CM option 408 to set centimeters as the units as indicated by highlighting the CM option 408 (as represented by bold and fill). The user has selected the edit button 410 to allow editing the current time. The hour numeral (16) is presently selected for adjustment as indicated by highlighting on the GUI 180 (represented by outline box) and the user can select the minutes numeral (42) for adjustment as desired. The user can operate the increment buttons 412 to increase or decrease the selected time numeral. In the illustrative embodiment, time editing can be completed by user selection of any other feature, but in some embodiments, may be completed upon touch by the user of any area outside of the time parameter 374.

Figure 87:
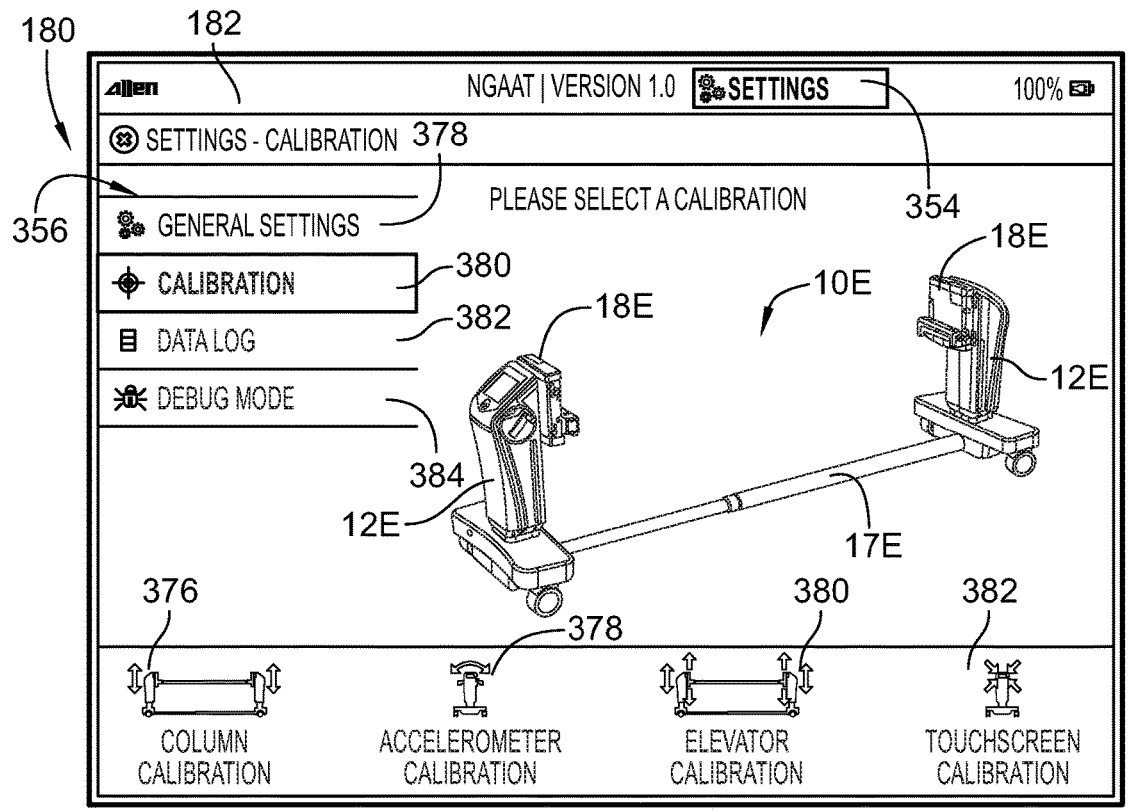
FIGS. 87-109 are screen shots of the display of the patient support of FIGS. 1-4 showing a number of calibration operations for calibrating the actual motion of features of the patient support with the depiction of those features upon the display.
Figure 88:
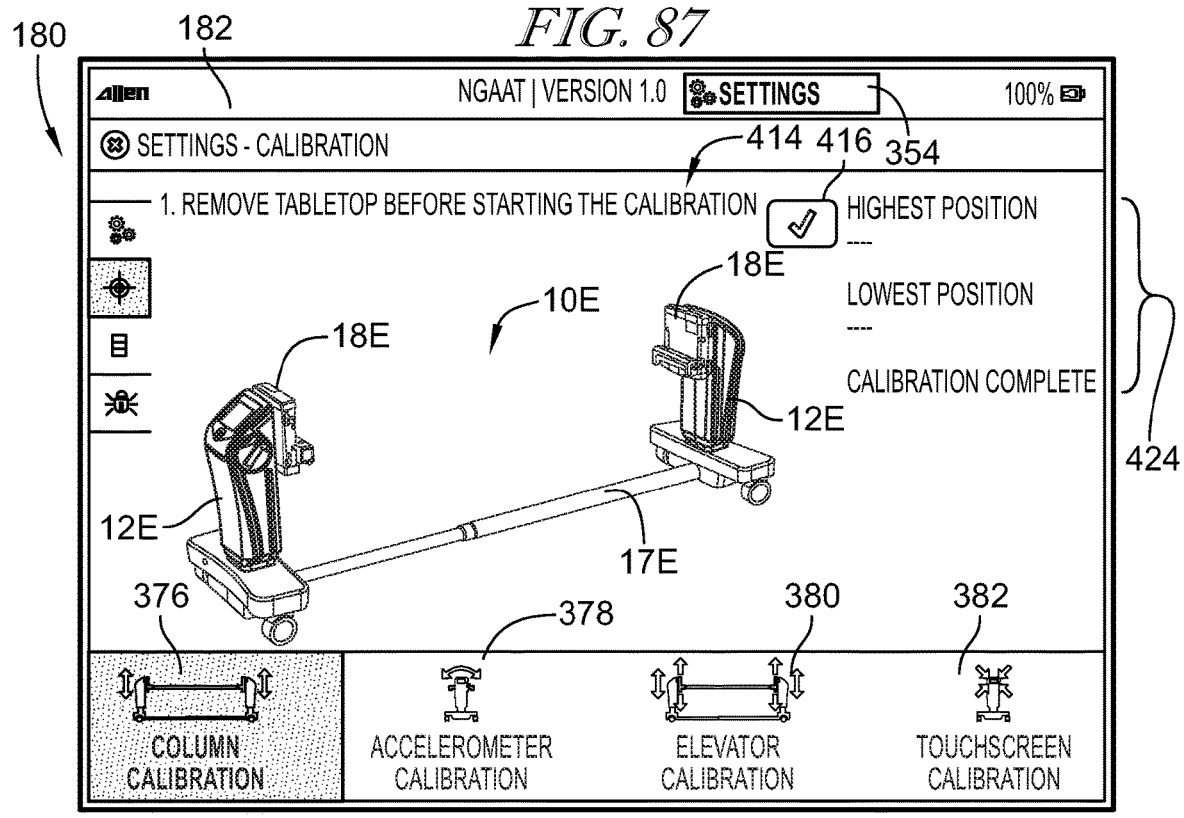

As shown in FIG. 87, the calibration tab 380 has been selected to enable calibration operation for any of the tower bases (columns), accelerometers, elevators (slide plates), and touchscreen. As shown in FIG. 88, the user has selected the column (tower base) calibration icon 376 as indicated on the GUI 180 by highlighting of the icon 376 and tower bases 12E (represented by bolding and fill of the icon 376 and bolding of the tower bases 12E). Upon user selection of the icon 376, an alert script 414 is presented indicating instructions to remove any attached support top and including a confirmation button 416 for user selection upon successful removal of all attached support tops. Status information 424 is presented to indicate the state of the calibration operation including a highest position stage, lowest position stage, and complete stage. User selection of the confirmation button 416 advances the calibration operation.

Figure 89:
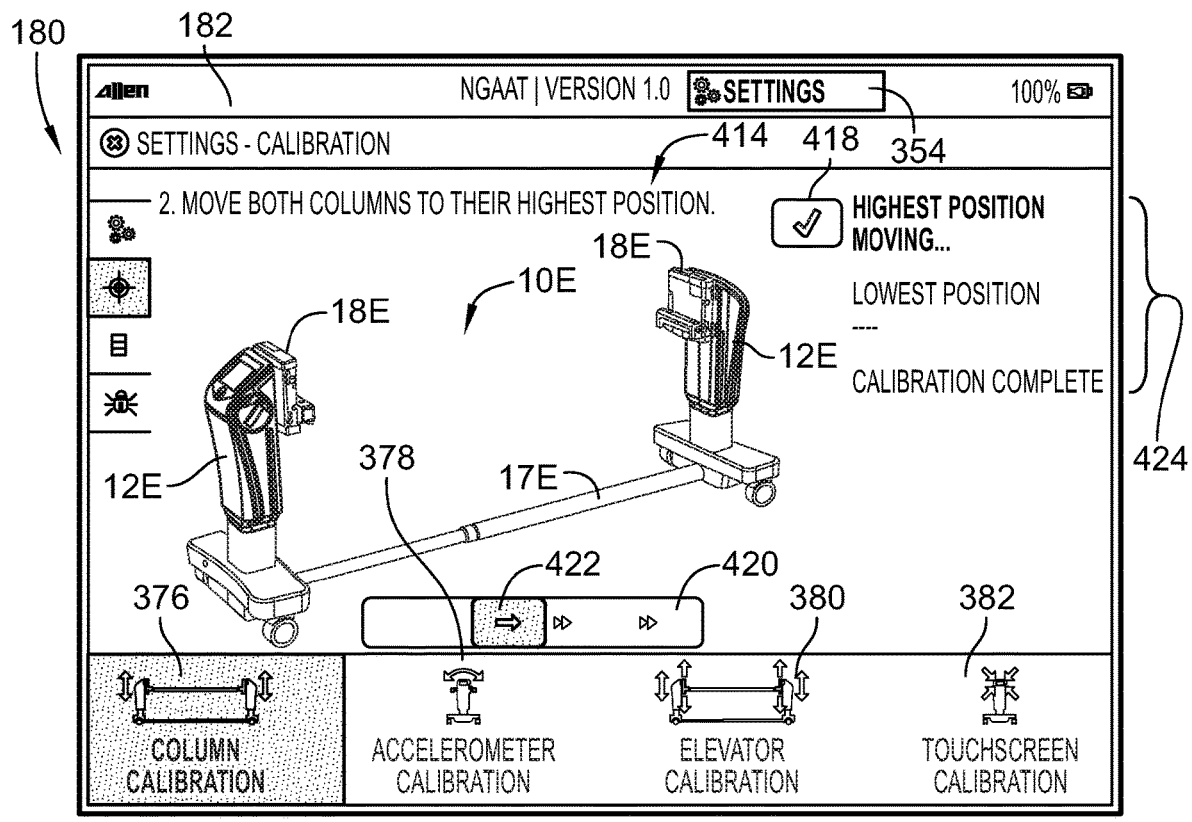

As shown in FIG. 89, upon user selection of the confirmation button 416, the alert script 414 is changed to indicate instructions to adjust both tower bases 12 (columns) to their highest positions. A confirmation button 418 is presented for user selection upon successful adjustment of the tower bases 12 to their highest positions. A slider bar 420 is presented having a slider 422 for dragging (to the right) by the user to activate height adjustment of the tower bases 12. The highest position stage of the status information 424 is highlighted (represented as bolding) and an information script of the highest position stage that reads "moving . . . " is presented to indicate active adjustment of the height of the tower bases 12. The depiction 10E illustratively tracks the actual movement of the patient support 10 as the height adjustment is performed. User selection of the confirmation button 418 advances the calibration operation.

Figure 90:
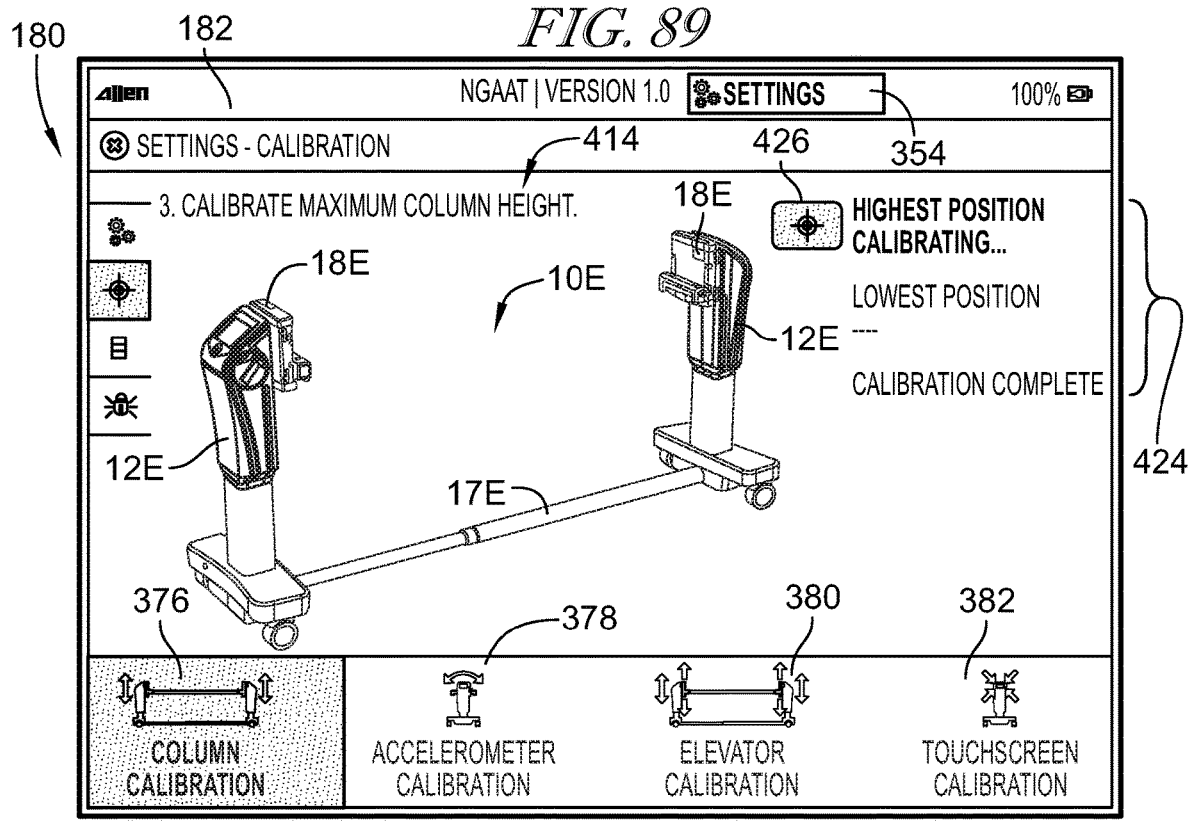

As shown in FIG. 90, the user has previously selected the confirmation button 418 and the alert script 414 is changed to indicate that a maximum height calibration can be performed. A calibration button 426 is presented for user selection to initiate calibration, and has illustratively been selected as indicated by its highlighting on the GUI 180 (represented by fill of button 426) and the information script of the highest position stage of the status information 424 reading as "calibrating . . . ". Upon successful calibration of the highest position, the highest position stage information script reads "calibrated" and the GUI 180 automatically advances to FIG. 91.

Figure 91:
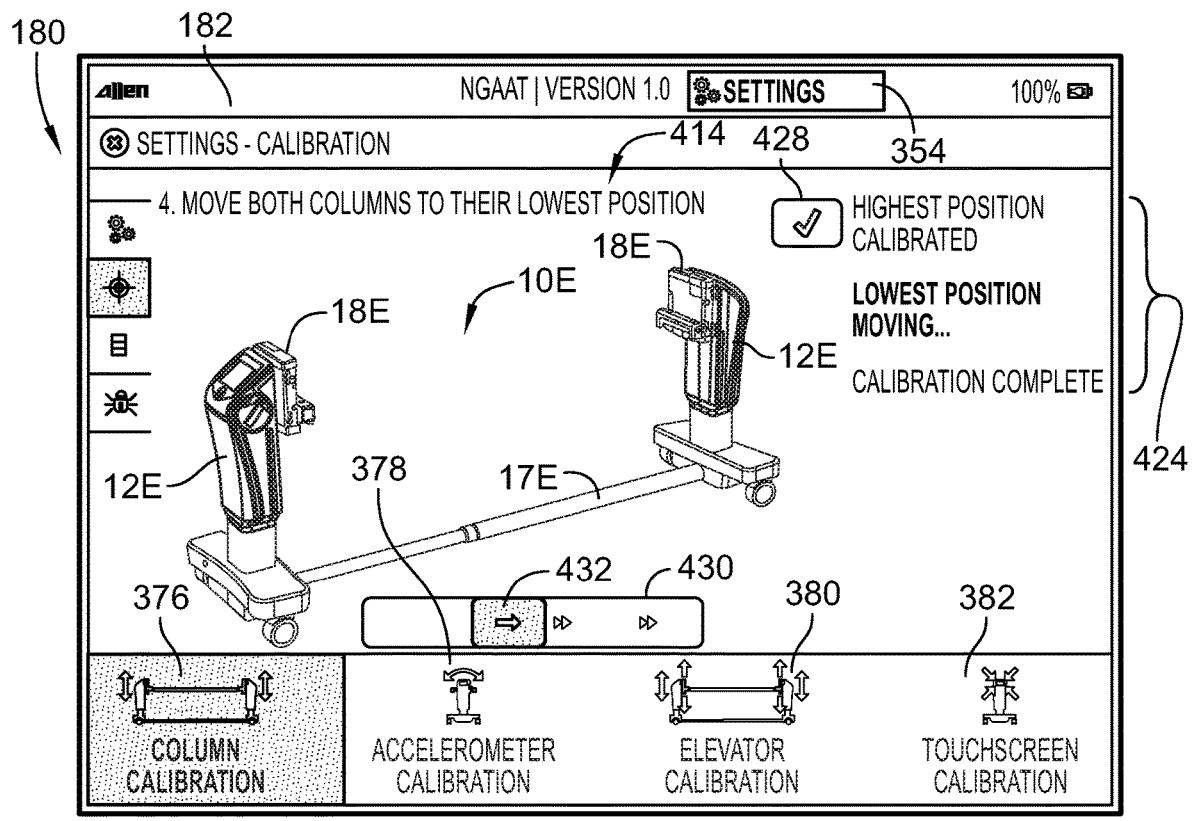

As shown in FIG. 91, the lowest position stage has been initiated as indicated by highlighting the lowest position stage (represented by bolding). The alert script 414 has changed to indicate instructions to move the tower bases 12 to their lowest position and a confirmation button 428 is presented for user selection upon successful adjustment of the tower bases 12 to their lowest position. A slider bar 430 includes a slider 432 is presented for user dragging (to the right) to adjust the position of the tower bases 12 to their lowest position. On adjustment of the tower bases 12, an information script of the lowest position stage that reads "moving . . . " is presented to indicate active adjustment of the tower base 12 height. The depiction 10E illustratively tracks the actual movement of the patient support 10 as the height adjustment is performed. Upon user selection of the confirmation button 428 advances the calibration operation.

Figure 92:
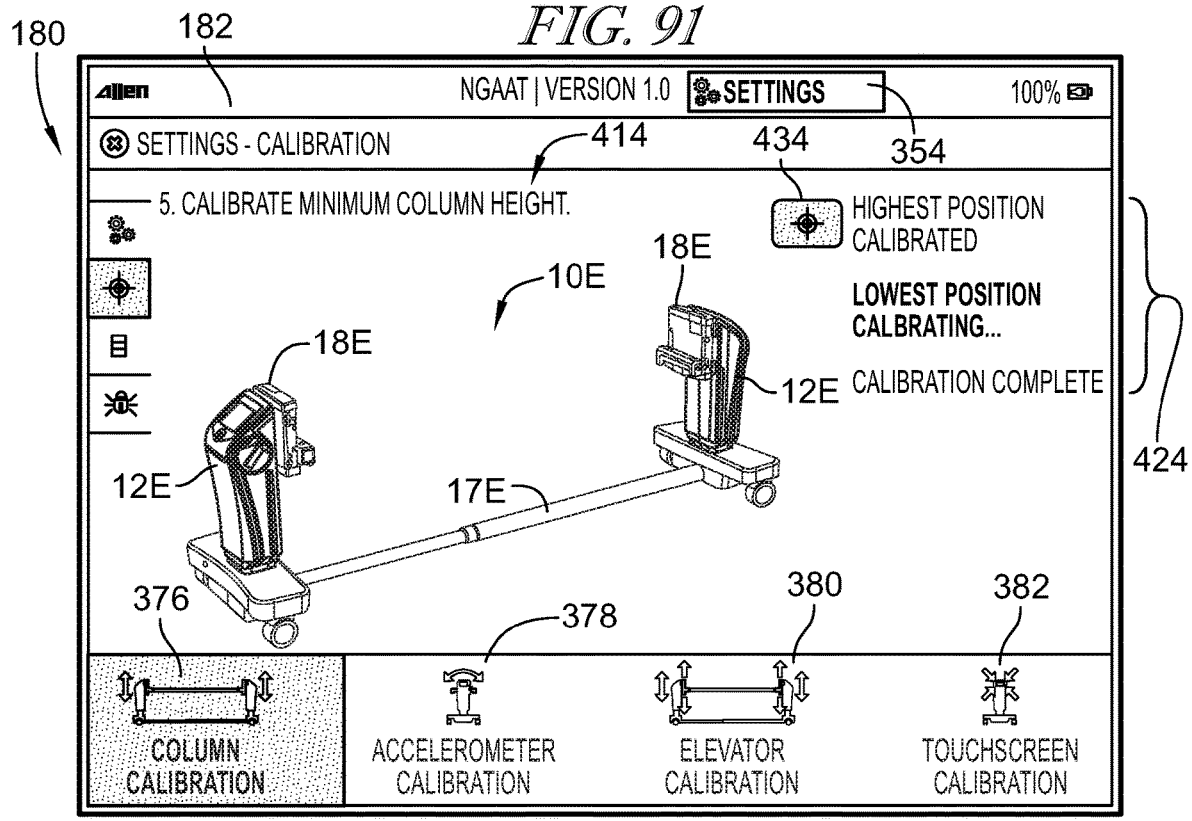

As shown in FIG. 92, the user has previously selected the confirmation button 428 and the alert script 414 has changed to indicate that a minimum height calibration can be performed. A calibration button 434 is presented for user selection to initiate lowest position calibration, and has illustratively been selected as indicated by its highlighting on the GUI 180 (represented by fill of button 434). During calibration and responsive to user selection of the calibration button 434, the information script of the lowest position stage of the status information 424 changes to read "calibrating . . . " indicating that calibration of the lowest position is in progress. Upon successful calibration of the lowest position, the lowest position stage information script reads "calibrated" and the GUI 180 automatically advances to FIG. 93.

Figure 93:
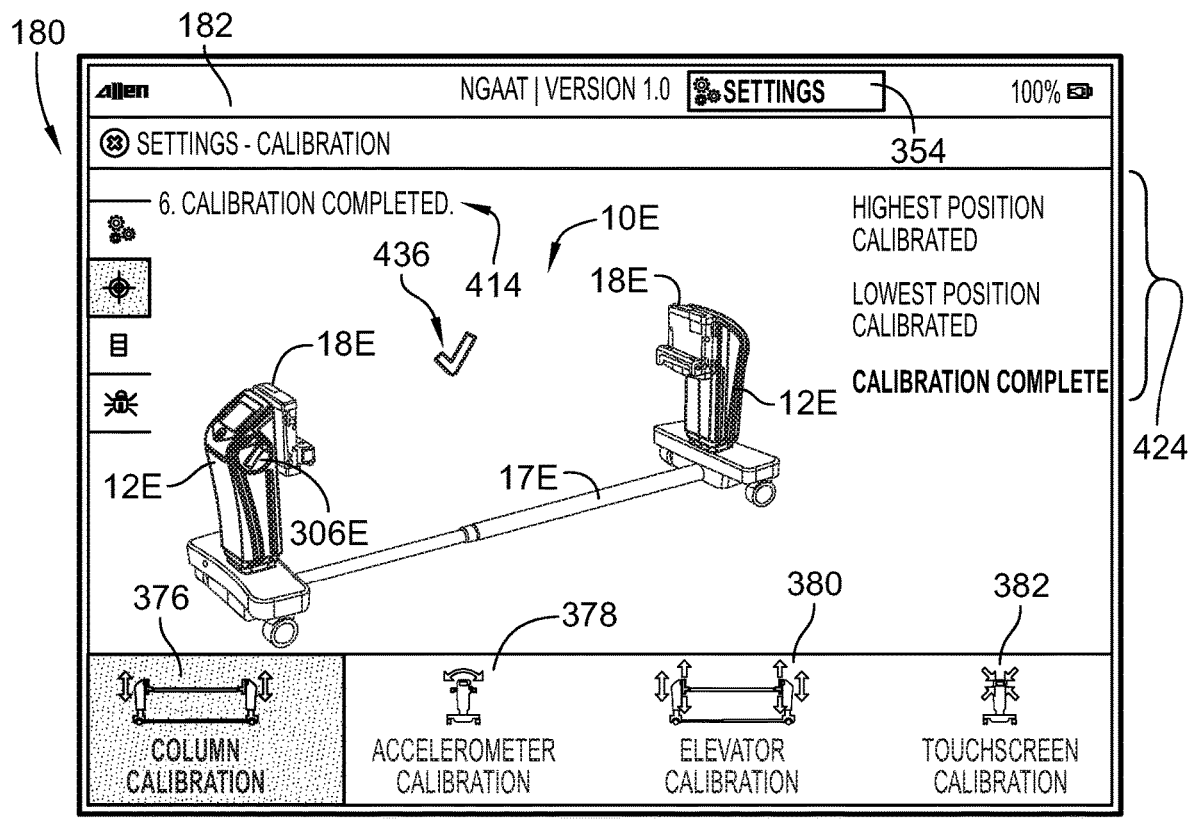

As shown in FIG. 93, upon successful completion of the tower base calibration, the calibration complete stage of the status information 424 is activated as indicated by highlighting on the GUI 180 (represented by bolding). A visual checkmark 436 is displayed near the depiction 10E and the alert script 414 indicates that calibration is completed. Accordingly, the actual position of the tower bases 12 can be calibrated with the sensors, systems, and the GUI 180 of the patient support 10.

Figure 94:
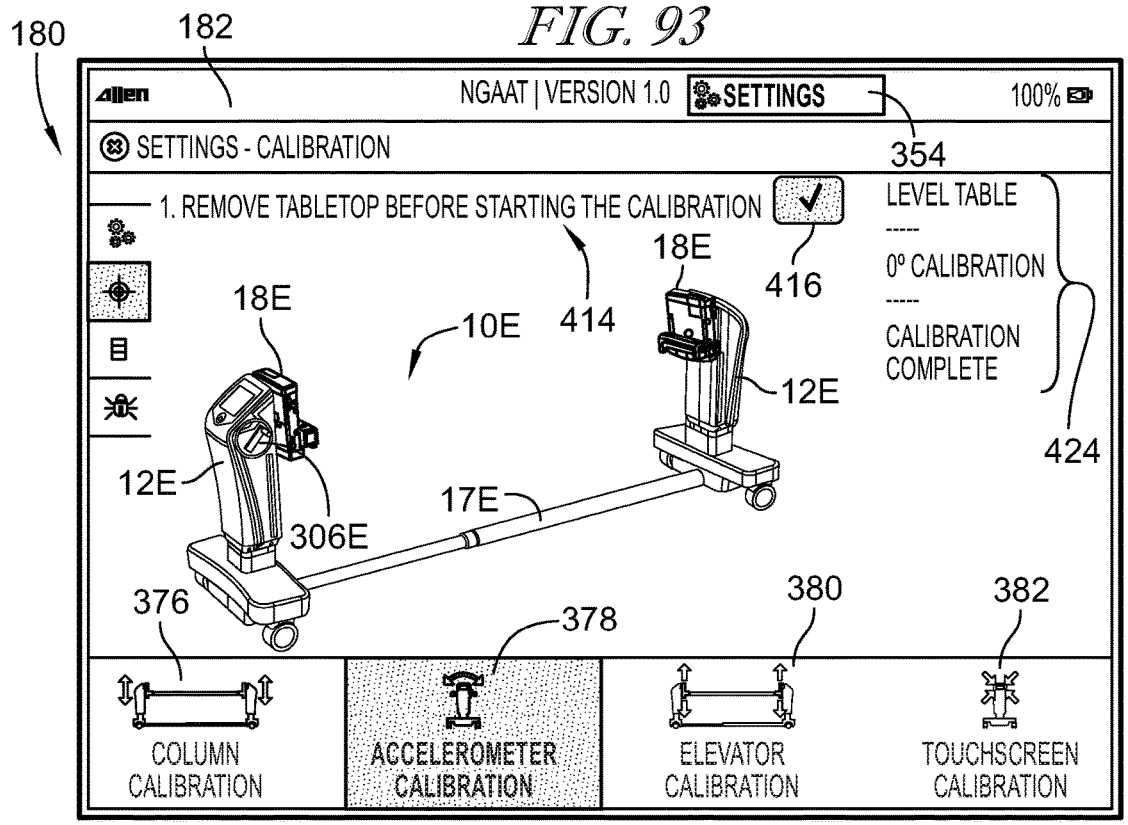

As shown in FIG. 94, the calibration tab 380 has been selected and the user has selected the accelerometer calibration icon 378 as indicated on the GUI 180 by highlighting of the icon 378 and connection assemblies 18E (represented by bolding and fill of the icon 378 and bolding of the connection assemblies 18E). Upon user selection of the icon 378, the alert script 414 is presented indicating instructions to remove any attached support top and including a confirmation button 416 for user selection upon successful removal of all attached support tops. Status information 424 is presented to indicate the state of the calibration operation including a level position stage, a zero-degree calibration stage, and complete stage. User selection of the confirmation button 416 advances the calibration operation.

Figure 95:
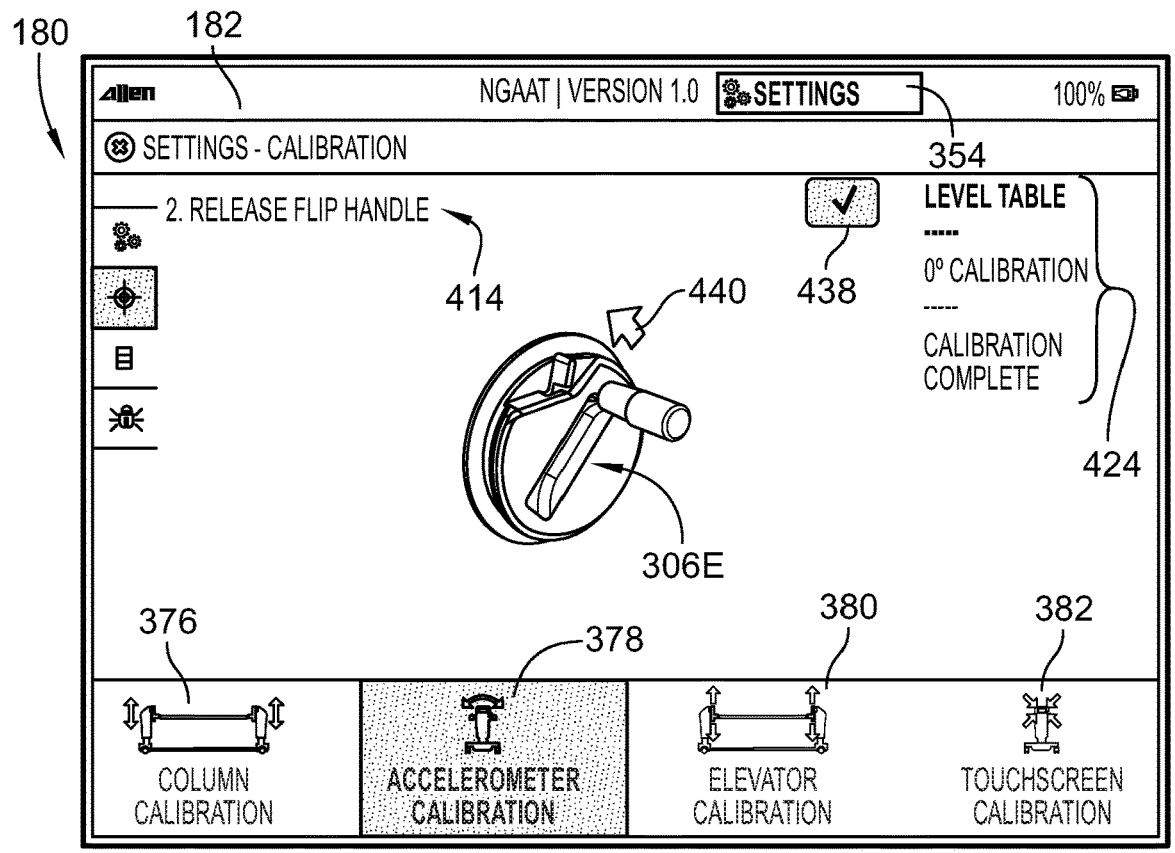
Figure 96:
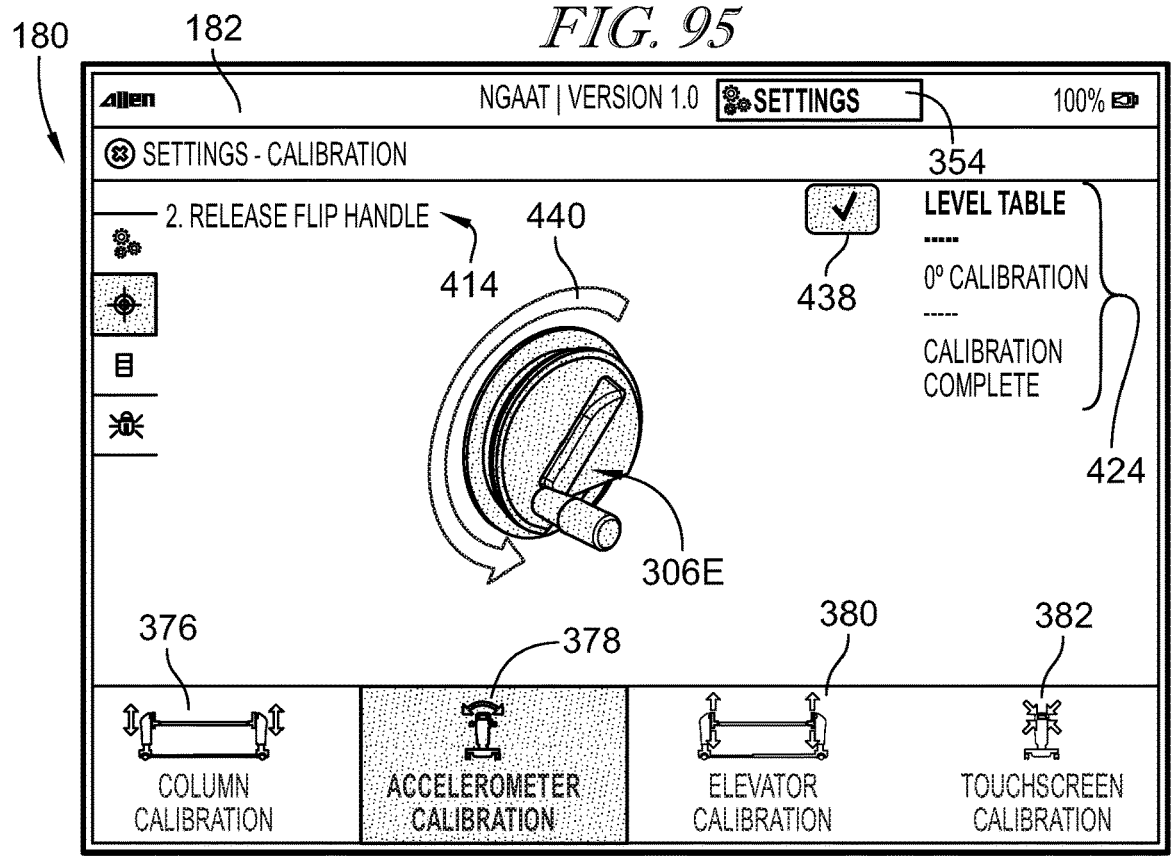

As shown in FIG. 95, the user has previously selected the confirmation button 416 and the alert script 414 has changed to indicate instructions to release the rotation lever (flip handle) 306. A confirmation button 438 is presented for user selection upon successful release of the rotation lever 306. A depiction of the rotation lever 306E is presented with an arrow 440 indicating counterclockwise rotation of the lever 306 to release the connection rod 16 to allow rotation of the connection assemblies 18. As illustrated by the FIGS. 95 and 96, the depiction of the rotation lever 306E is an animation of the rotation lever 306 rotating in the desired direction for releasing the flip rotation about the axis 15, and when the animation reaches the released position, the depiction 306E momentarily flashes with color (represented by fill in FIG. 96) before restarting the animation. Once the rotation lever 306 has been released to allow flip rotation of the connection assemblies 18 about the axis 15, the user can select the confirmation button 438 to advance the calibration operation.

Figure 97:
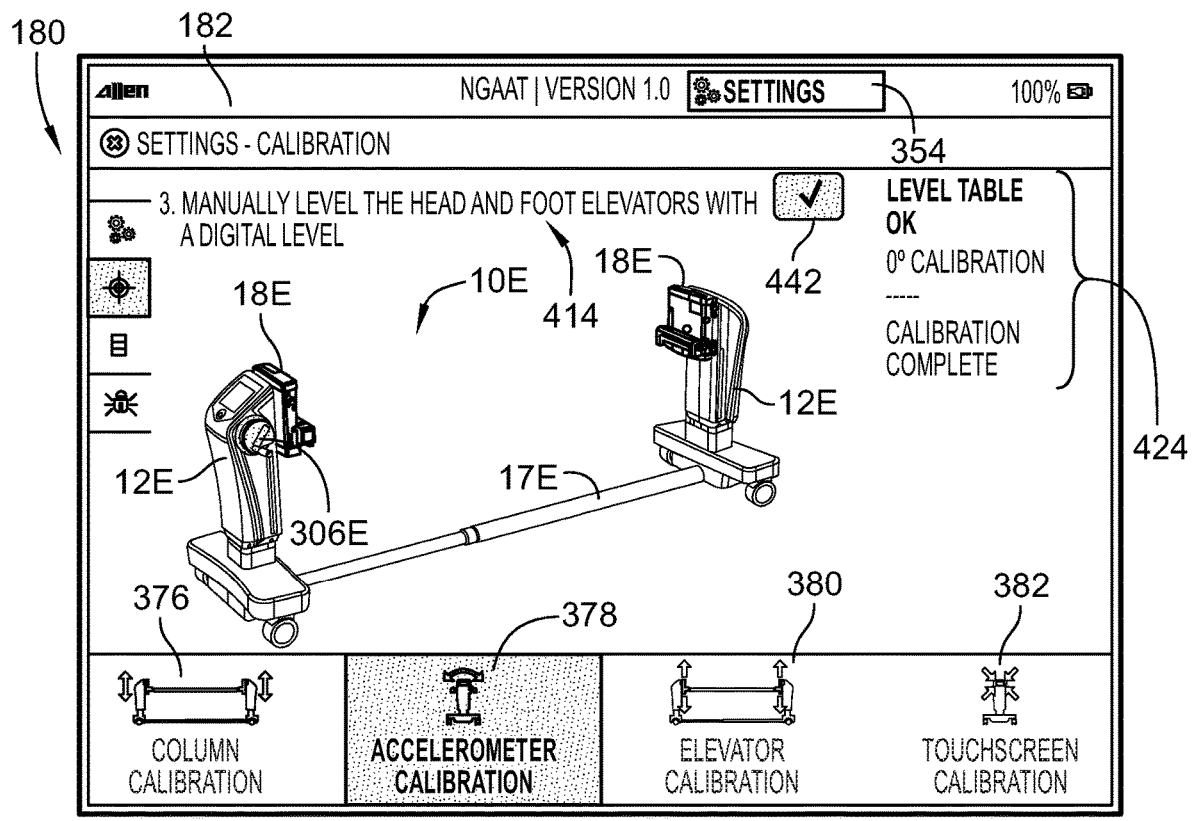

As shown in FIG. 97, the user has previously selected the confirmation button 438 and the level position stage script of the status information 424 has changed to indicate that leveling is "OK". The alert script 414 changes to indicate instruction to perform manual leveling of the head and foot connection assemblies 18. The GUI 180 presents the depiction 10E of the patient support 10. A confirmation button 442 is presented for user selection upon successful complete of manual leveling of the connection assemblies 18. User selection of the confirmation button 442 advances the calibration operation.

Figure 98:
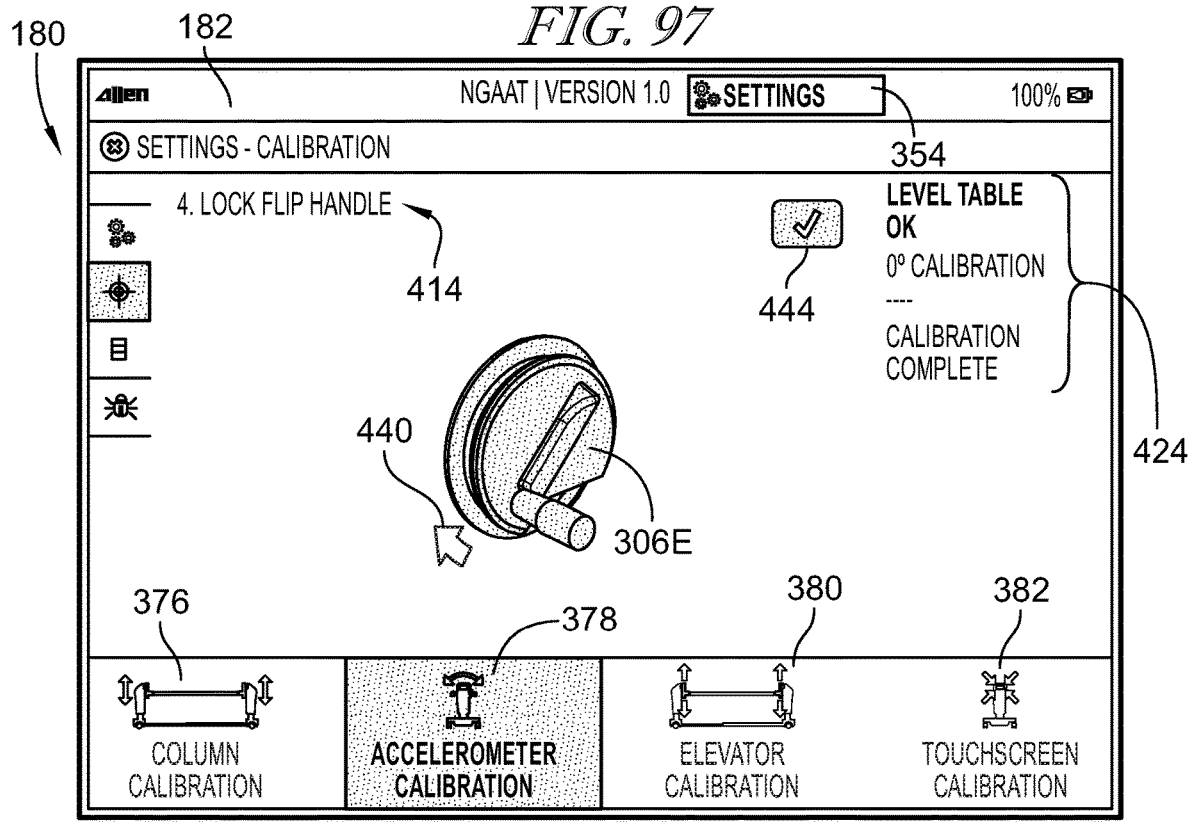
Figure 99:
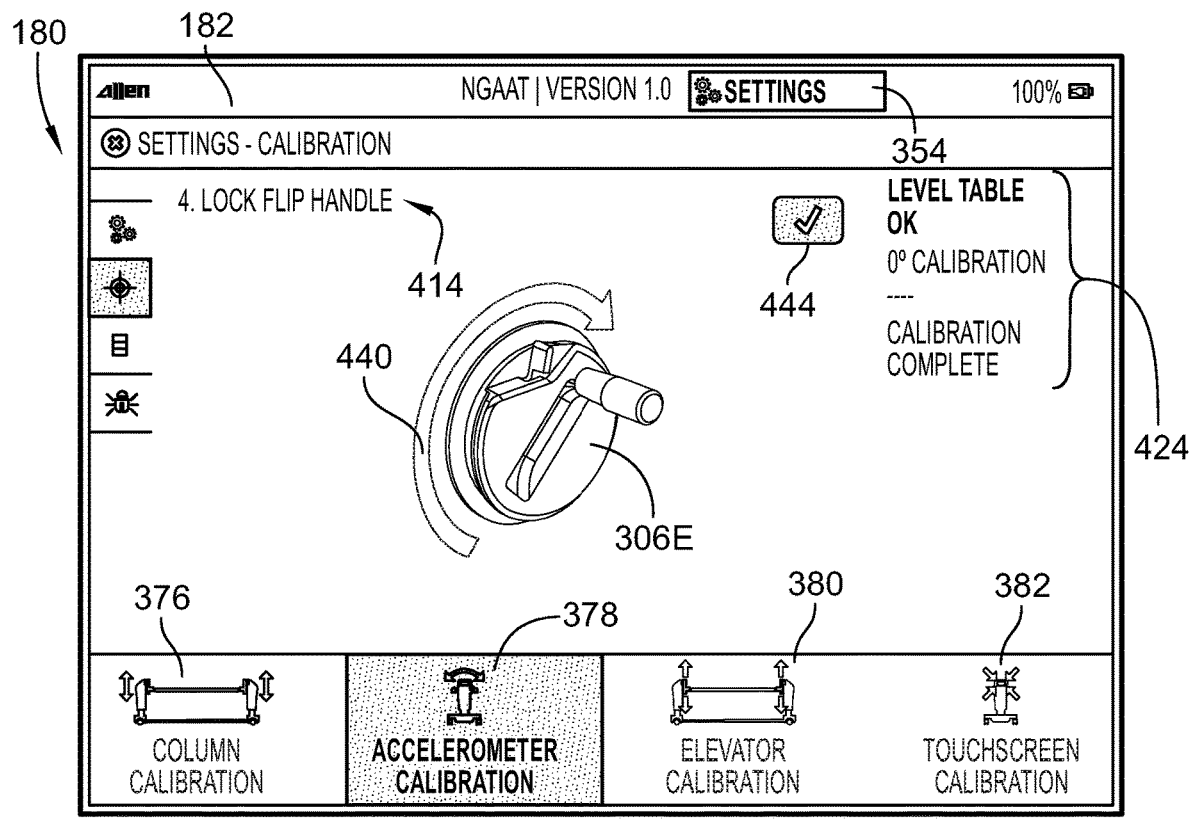

As shown in FIG. 98, the user has previously selected the confirmation button 442 and the alert script 414 has changed to indicate instruction to lock the rotation lever (flip handle) 306. The depiction of the rotation lever 306E is presented with the arrow 440 indicating clockwise rotation to lock the rotation lever 306. A confirmation button 444 is presented for user selection upon successful locking of the rotation lever 306. As shown in FIG. 99, the depiction of the rotation lever 306E is an animation similar to that disclosed regarding release as to FIGS. 95 and 96, to illustrate the clockwise rotation to lock the rotation lever 306. Upon successful locking of the rotation lever 306, the user can select the confirmation button 444 to advance the calibration operation.

Figure 100:
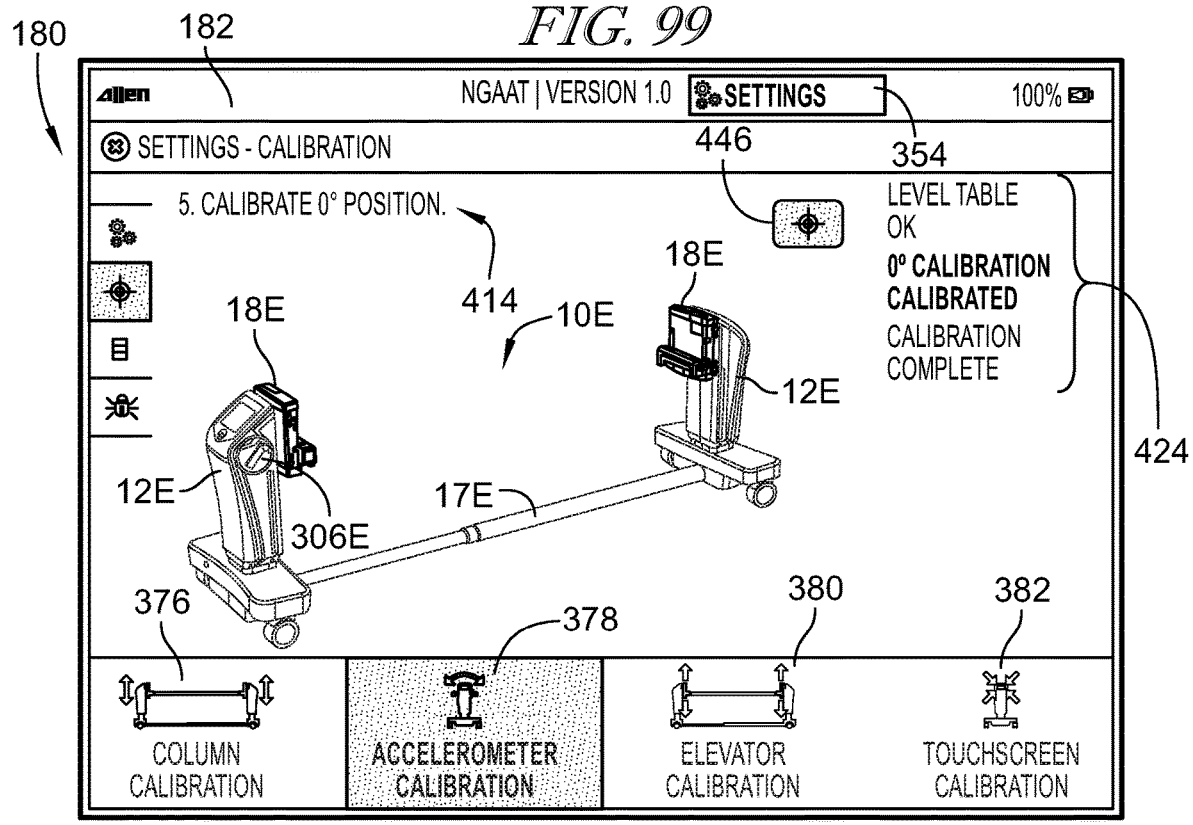

As shown in FIG. 100, the user has previously selected the confirmation button 444 and the zero degree calibration stage has been activated as indicated by highlighting the stage in the status information 424 on the GUI 180 (represented by bolding the text). The alert script 414 changes to indicate instruction to calibrate the zero degree position and a confirmation button 446 is presented for user selection to perform zero degree calibration. The user can calibrate the zero degree tilt position of the connection assemblies manually, for example, by digital level. In FIG. 100, the user has already selected the calibration button 446 as indicated by highlighting the button 446 (represented by fill of button 446) and the calibration has been completed as indicated by the script of the stage reading "calibrated".

Figure 101:
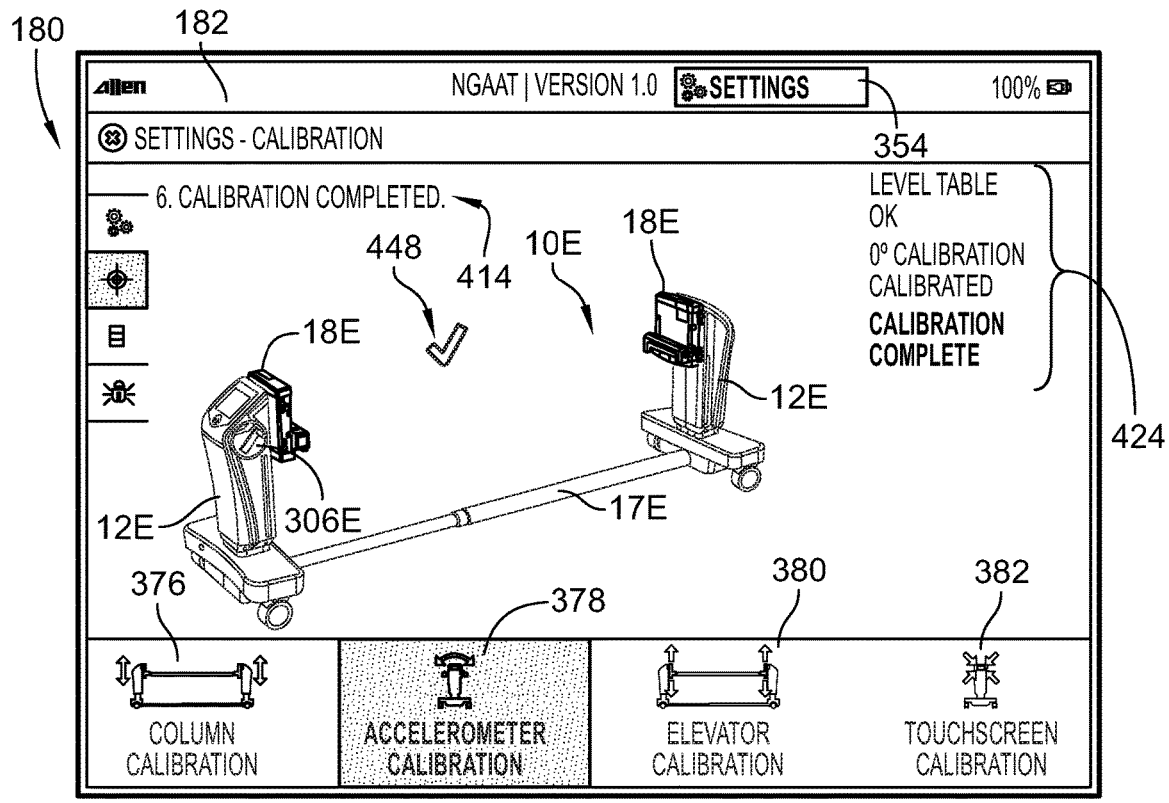

As shown in FIG. 101, the user has selected the confirmation button 446 to indicate successful completion of the zero degree calibration. Upon successful completion of the zero degree calibration the calibration complete stage of the status information 424 is highlighted as indicated by bolding. A visual checkmark 448 is displayed near the depiction 10E and the alert script 414 indicates that calibration is completed. Accordingly, the accelerometers of the connection assemblies 18 can be calibrated with the sensors, systems, and the GUI 180 of the patient support 10.

Figure 102:
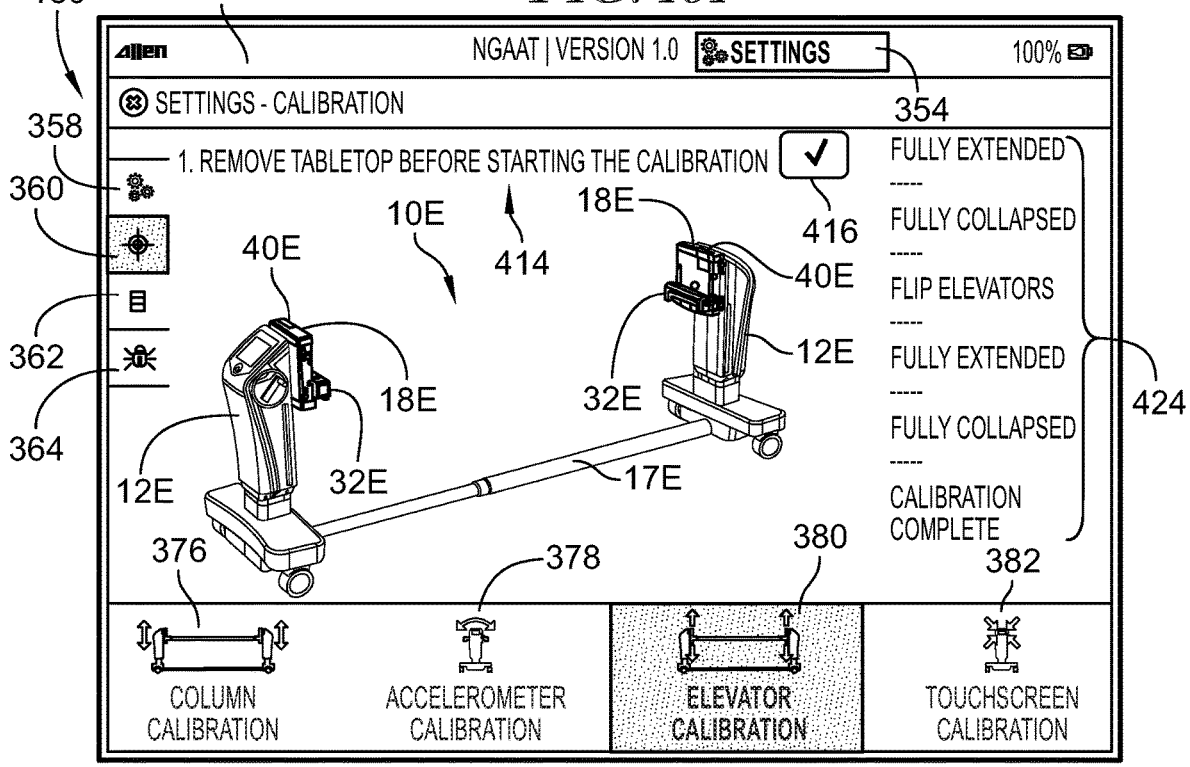

Referring now to FIG. 102, the user has selected the calibration tab 360 and the elevator calibration icon 380 as indicated by highlighting on the GUI 180 (represented by fill of the tab 360 and icon 380) to initiate a slide plate (elevator) calibration operation. In response, the connection assemblies 18E are highlighted (represented by bolding), the alert script 414 indicates instruction to remove any attached tops, and the confirmation button 416 is presented for user selection upon successful removal of any attached support tops. The status information 424 for the elevator calibration operation illustratively indicates stages including a first fully extended stage, a first fully collapsed stage, a flip elevators stage, a second fully extended stage, a fully collapsed stage, and a calibration complete stage. Each of the stages, other than the calibration complete stage, includes a script presently indicated as "----". User selection of the confirmation button 416 advances the calibration operation.

Figure 103:
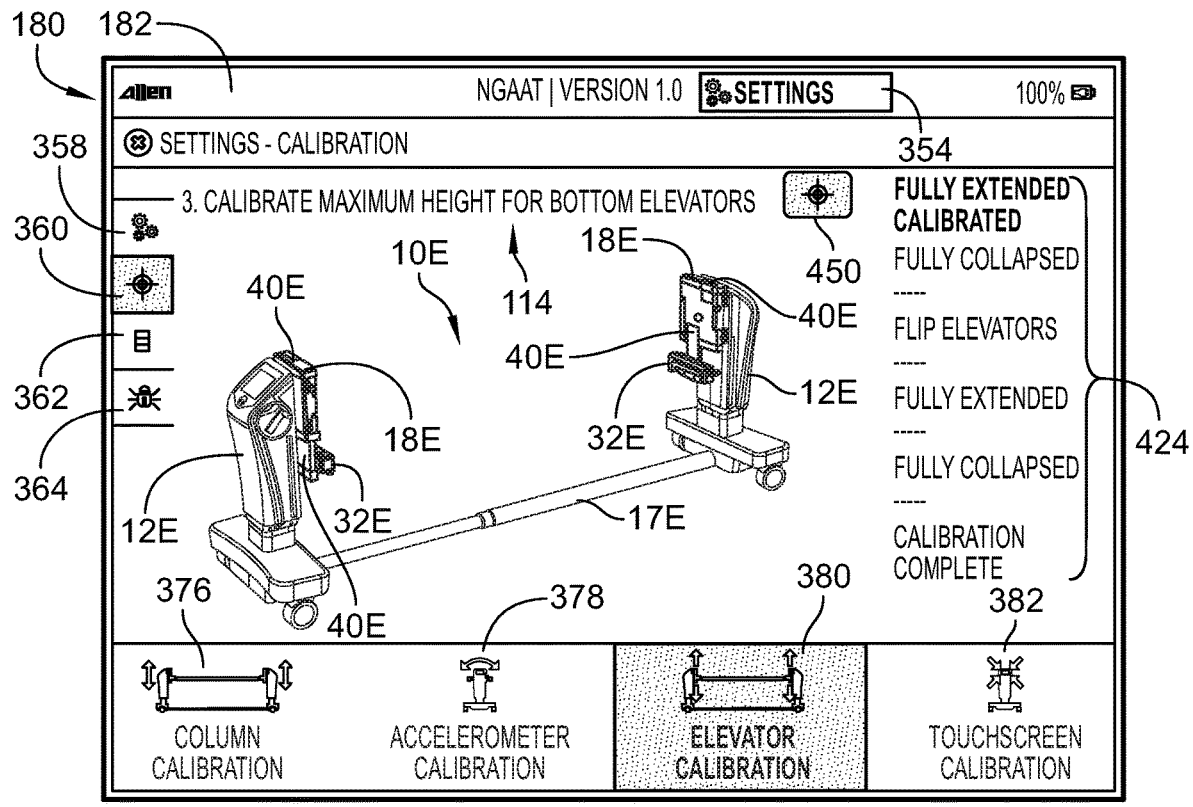

As shown in FIG. 103, the user has previously selected the confirmation button 416 and the alert script 414 responsively changes to indicate calibration of the maximum height (full extension of the slide plate 40 corresponding to the docking receiver 32). In the illustrative embodiment, before advancing to the screens as shown in FIG. 103, the GUI 180 prompts the user to manually extend the first (lower) slide plates 40 into the extended position and to select a confirmation button to indicate that such extension is complete to advance to the screens shown in FIG. 103. In the illustrative embodiment as shown in FIG. 103, the lower slide plates 40 are identifiable by their attached docking receivers 32E in the depiction, while the upper slide plates 40E are shown without docking receivers 32 attached.

A confirmation button 450 is presented for user selection to initiate first fully extended calibration. As shown in FIG. 103, the button 450 has illustratively been previously selected as indicated by its highlighting on the GUI 180 (represented by fill of button 450) and the calibration of the first fully extended stage has completed as indicated by the information script of the first fully extended stage of the status information 424 reading "calibrated." During calibration, the information script of the first fully extended position stage of the status information 424 reads "calibrating . . . ". Upon successful calibration of the first fully extended position, the GUI 180 automatically advances to FIG. 104.

Figure 104:
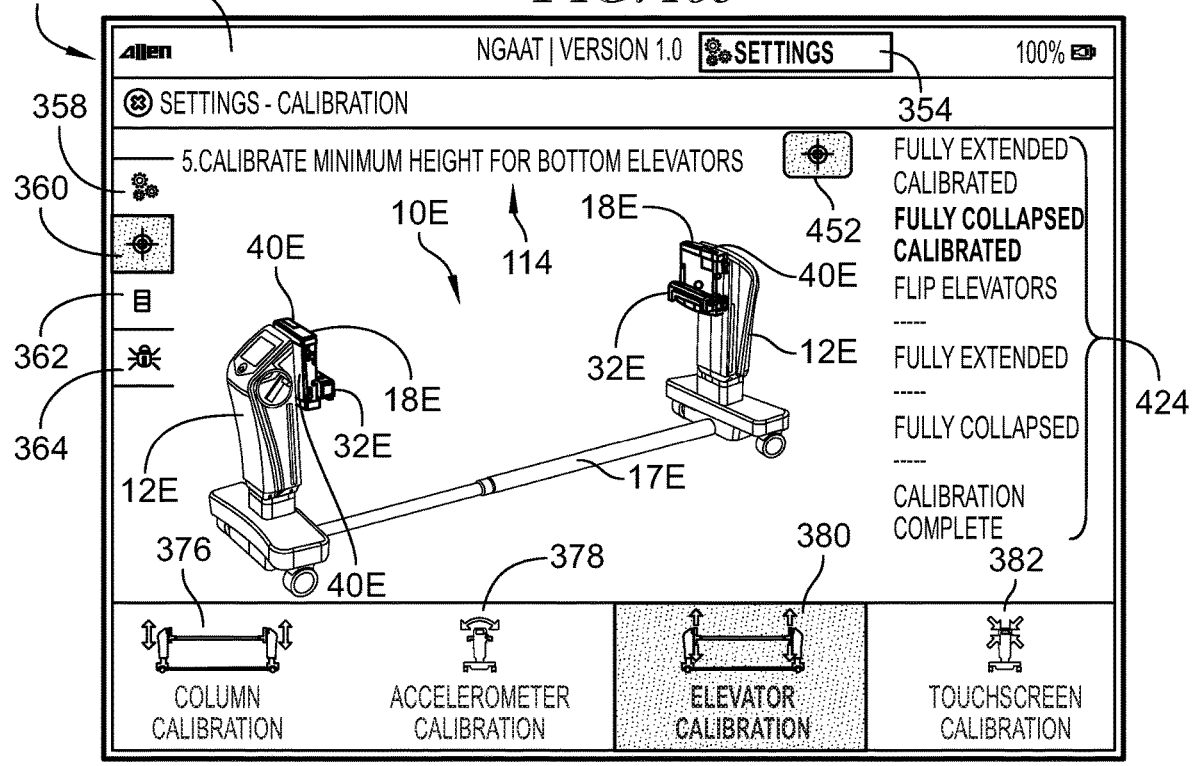

In the illustrative embodiment of FIG. 104, the user has already been prompted to manually retract the slide plates 40 to the retracted position and to confirm the retracted position (collapsed position) by selecting a confirmation button. Responsive to the confirmation of the retracted position, the alert script 414 is changed to indicate instructions to calibrate the minimum (retracted) position for the lower slide plates 40 (bottom elevators) and a calibration button 452 is presented for user selection to initiate first fully retracted calibration. As indicated by highlighting the button 452 on the GUI 180 (represented as fill in the button 452), the user has already selected the calibration button 452 and the first fully collapsed stage has completed according to the "calibrated" text of the corresponding information script of the status information 424. Upon successful calibration of the first fully extended position, the GUI 180 automatically advances to FIG. 105.

Figure 105:
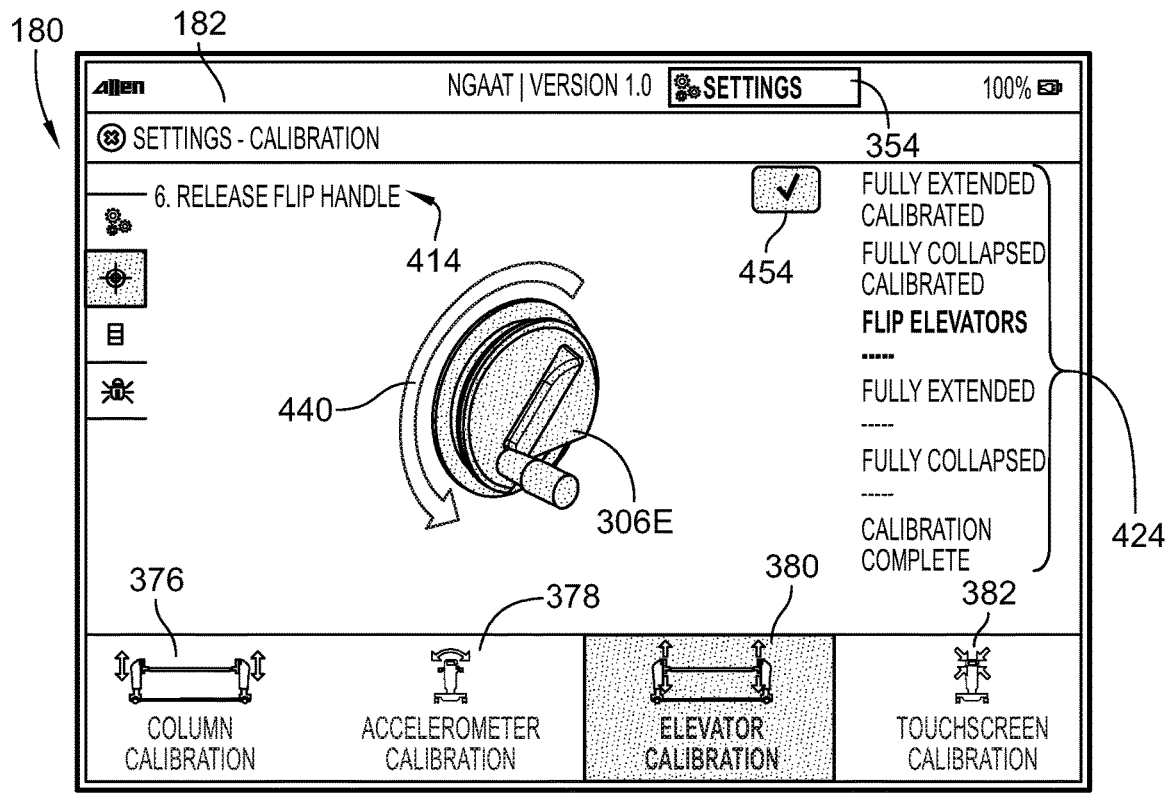

As shown in FIG. 105, responsive to successful calibration of the first fully extended position, the alert script 414 changes to indicate instructions to release the rotation lever (flip handle) 306 and the flip elevator information script of the status information 424 is highlighted (as represented by bolding). A depiction of the rotation lever 306E as an animation is presented with indication by arrow 440 to perform rotation release by rotating the rotation lever counterclockwise. Upon successful rotation of the rotation lever 306 to release the flip rotation of the connection assemblies 18, the user can select a confirmation button 454 to advance the calibration operation.

Figure 106:
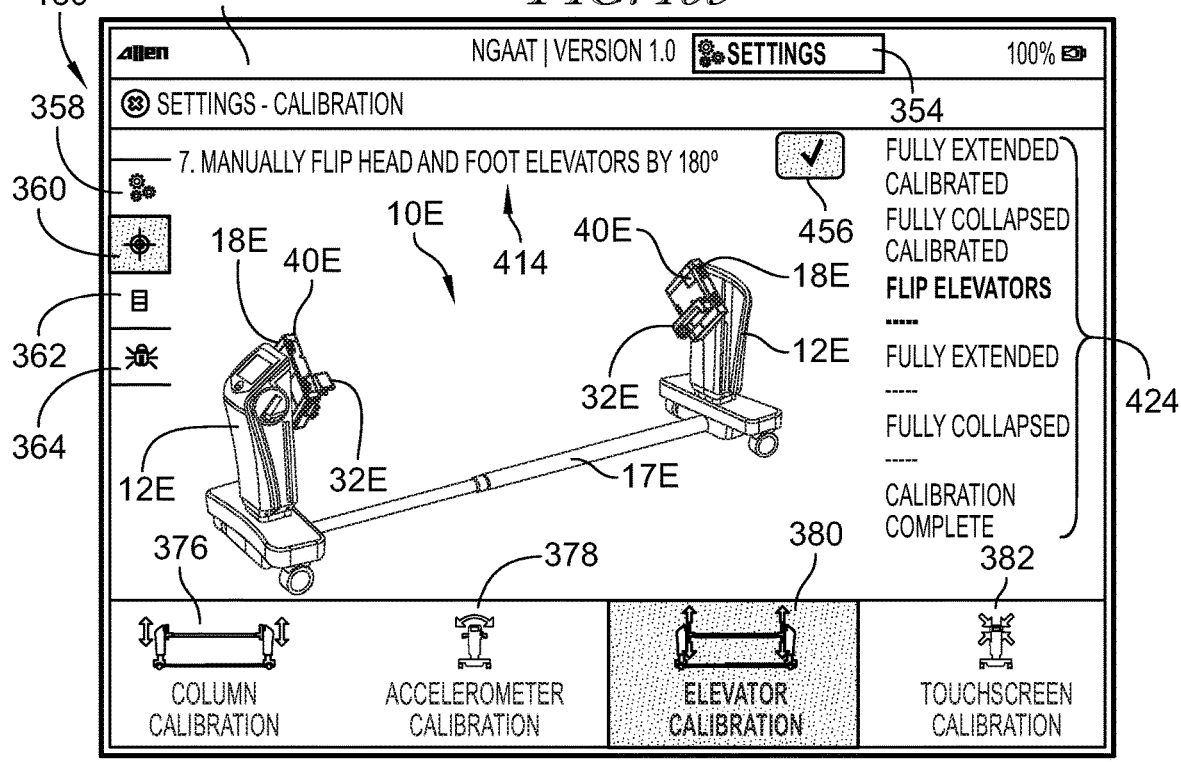

As shown in FIG. 106, responsive to the selection of the confirmation button 454, the alert script 414 is changed to indicate instruction to manually rotate (flip) the head and foot end connection assemblies by 180 degrees such that the formerly lower slide plates 40 of the head and foot end connection assemblies 18 with the docking receivers 32 attached, are now rotated to the upper position above the other slide plates 40. A confirmation button 456 is presented for user selection upon successful completion of manual rotation of the connection assemblies 18 by 180 degrees. Responsive to user selection of the confirmation button 456, the GUI 180 illustratively indicates instruction for the user to manually extend the (now) lower slide plates 40 and to confirm extension.

Figure 107:
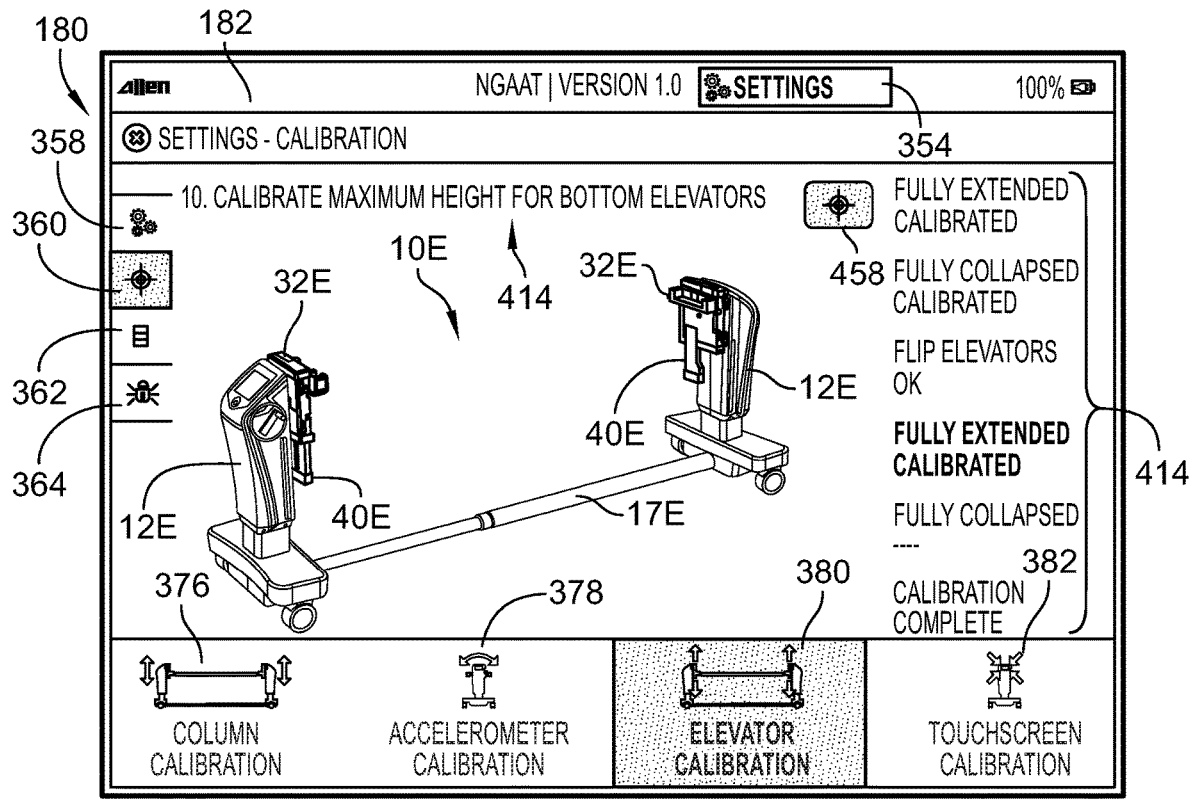

As shown in FIG. 107, upon successful extension of the lower slide plates 40, the alert script 414 is changed to indicate instruction to calibrate the second fully extended position by selection of the calibration button 458 (presently, due to the previous flip of the connection assemblies 18, the lower slide plates 40 are those slide plates 40 without docking receivers 32 attached, as indicated by the depiction 10E). In FIG. 107, the calibration button 458 has already been selected (as indicated by highlighting, represented by fill of the button 458) and the calibration completed as indicated by the corresponding information script of the status information 424. Upon successful calibration of the second fully extended position, the GUI 180 automatically advances to FIG. 108.

Figure 108:
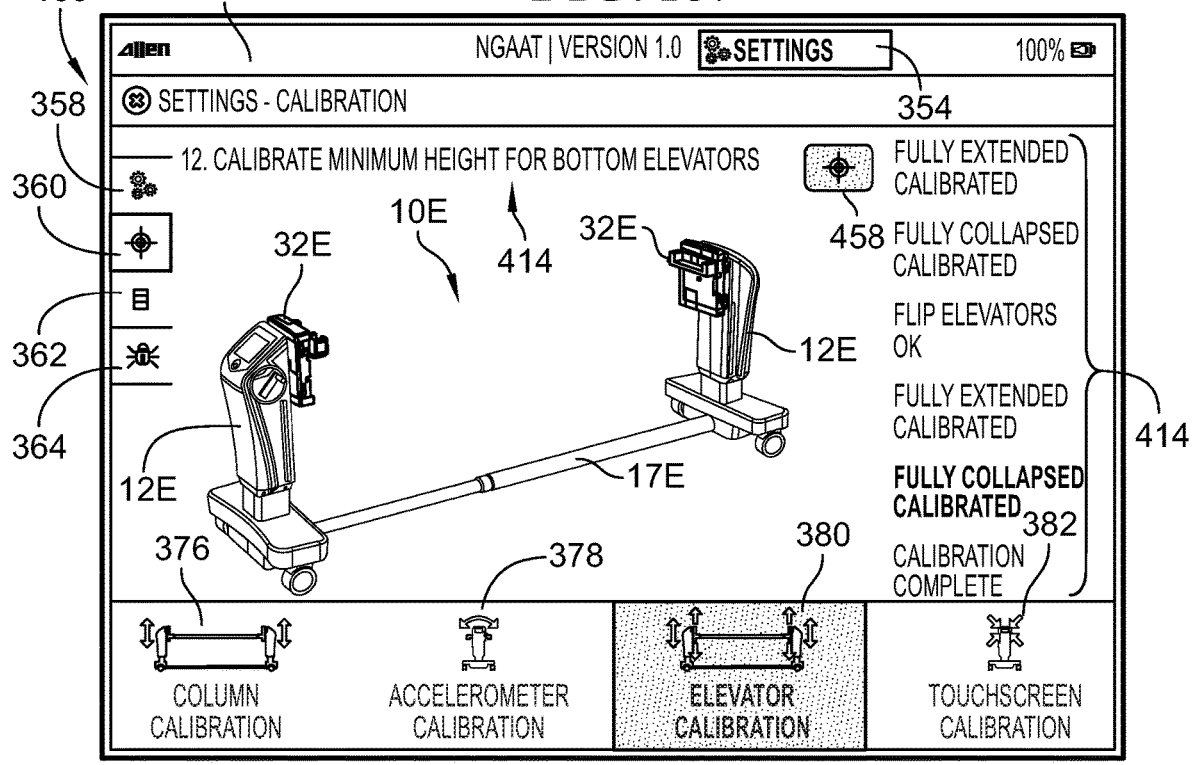

Referring to FIG. 108, upon successful completion of the second fully extended stage, the GUI 180 may prompt the user to manually retract the lower slide plates 40 and to confirm successful retraction. Upon successful retraction of the lower slide plates 40, the alert script 414 is changed to indicate instruction to calibrate the second fully retracted position by selection of the calibration button 458 (presently, the lower slide plates 40 are those without docking receivers 32). In FIG. 107, the calibration button 458 has already been selected (as indicated by highlighting the button 458, represented by fill of the button 458) and the calibration completed as indicated by the corresponding information script of the status information 424. Upon successful calibration of the second fully collapsed position, the GUI 180 automatically advances to FIG. 109.

Figure 109:
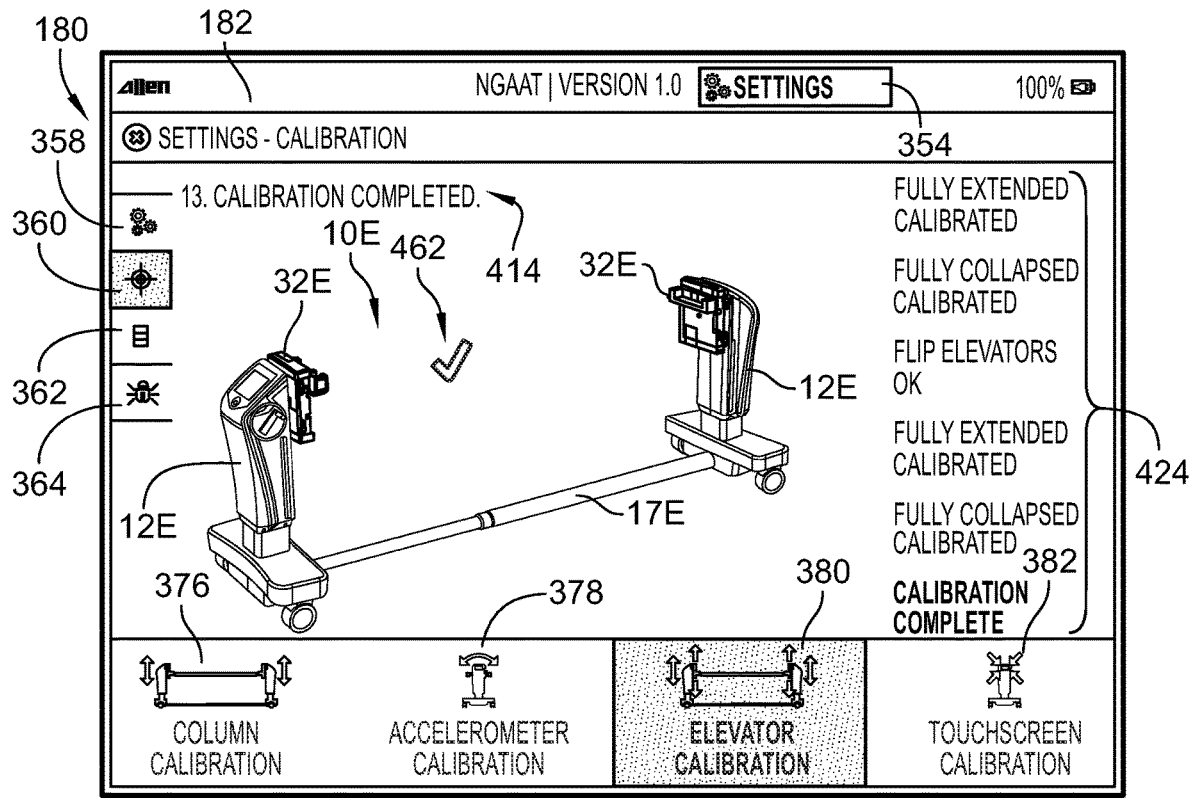

As shown in FIG. 109, responsive to successful calibration of the second fully collapsed position stage, the calibration complete stage of the status information 424 is highlighted as indicated by bolding. A visual checkmark 462 is displayed near the depiction 10E and the alert script 414 indicates that calibration is completed. Accordingly, the actual position of the slide plates 40 can be calibrated with the sensors, systems, and the GUI 180 of the patient support 10. From the screen of FIG. 109, after momentary indication of completion, the calibration operation illustratively returns to a main calibration screen as shown in FIG. 110.

Figure 110:
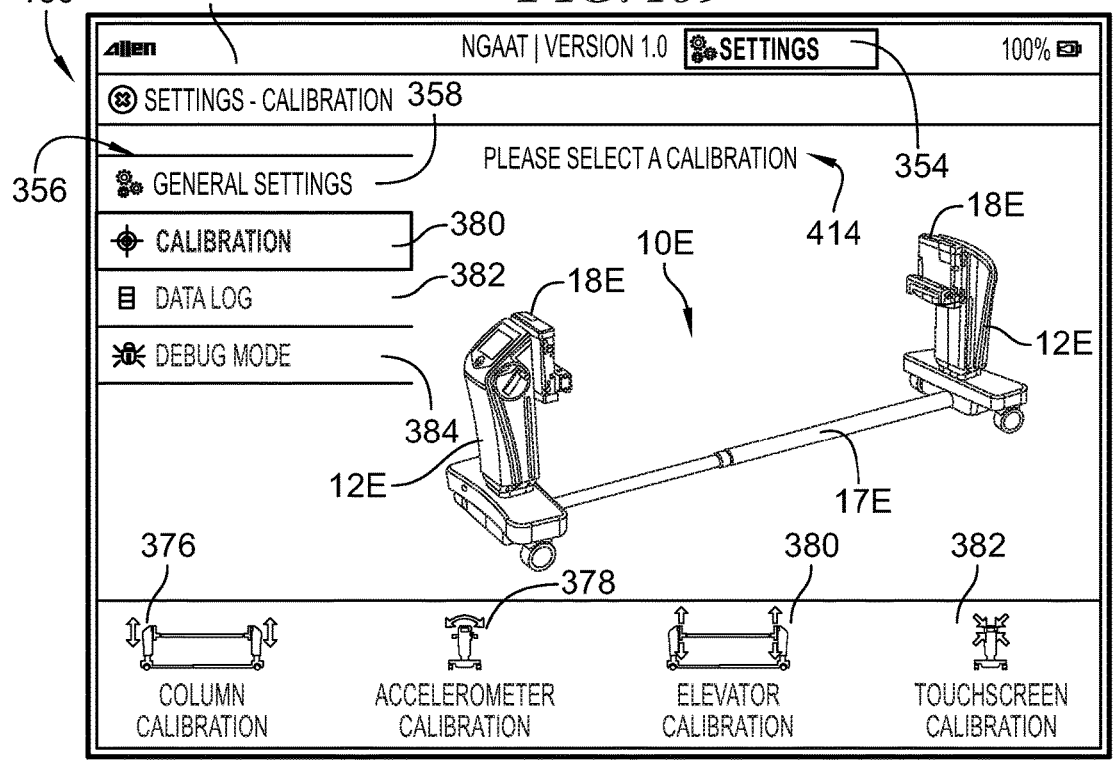
FIGS. 110-116 are screen shots of the display of the patient support of FIGS. 1-4 showing a calibration operation for calibrating a touch screen input of the display.

As shown in FIG. 110, the calibration tab 360 has been selected and the alert script 414 indicates instruction to select a calibration icon. Upon user selection of the touch screen calibration icon 382, calibration of the touchscreen 182 of the GUI 180 is initiated.

Figure 111:
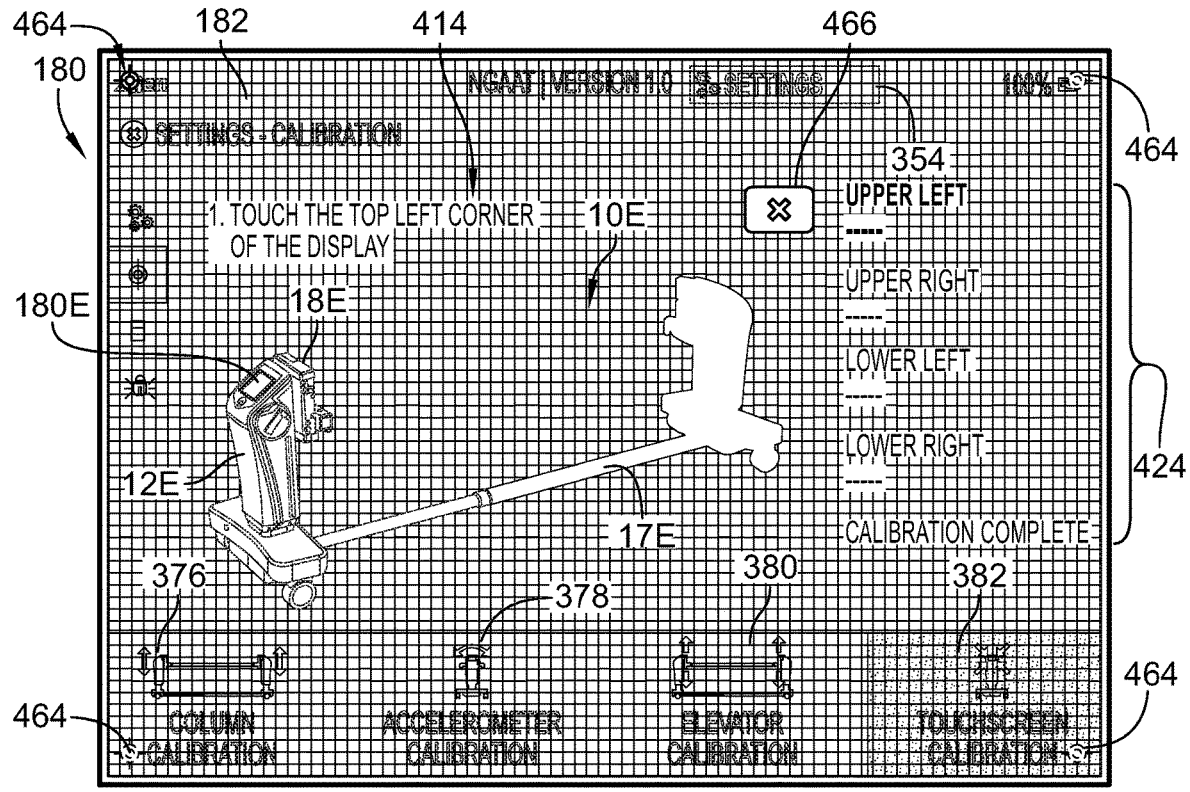

As shown in FIG. 111, responsive to user selection of the touch screen calibration icon 382, the GUI 180 presents the screen 182 with checkering for visual accuracy. The GUI 180 presents the patient support 10E with the GUI 180E highlighted (represented by bolding) and a number of targets 464. The status information 424 indicates five stages including an upper left stage, which is presently active as indicated by highlighting on the GUI 180 (represented by bolding), an upper right stage, a lower left stage, a lower right stage, and a calibration complete stage. The alert script 414 indicates instruction for the user to touch an assigned one of the targets, presently shown as the upper left target 464 that is positioned in the upper left corner of the screen 182 which is active as indicated by highlighting on the GUI 180 (as represented by bolding). A cancellation button 466 is presented for user selection to exit the calibration stage and return to the main screen.

Figure 112:
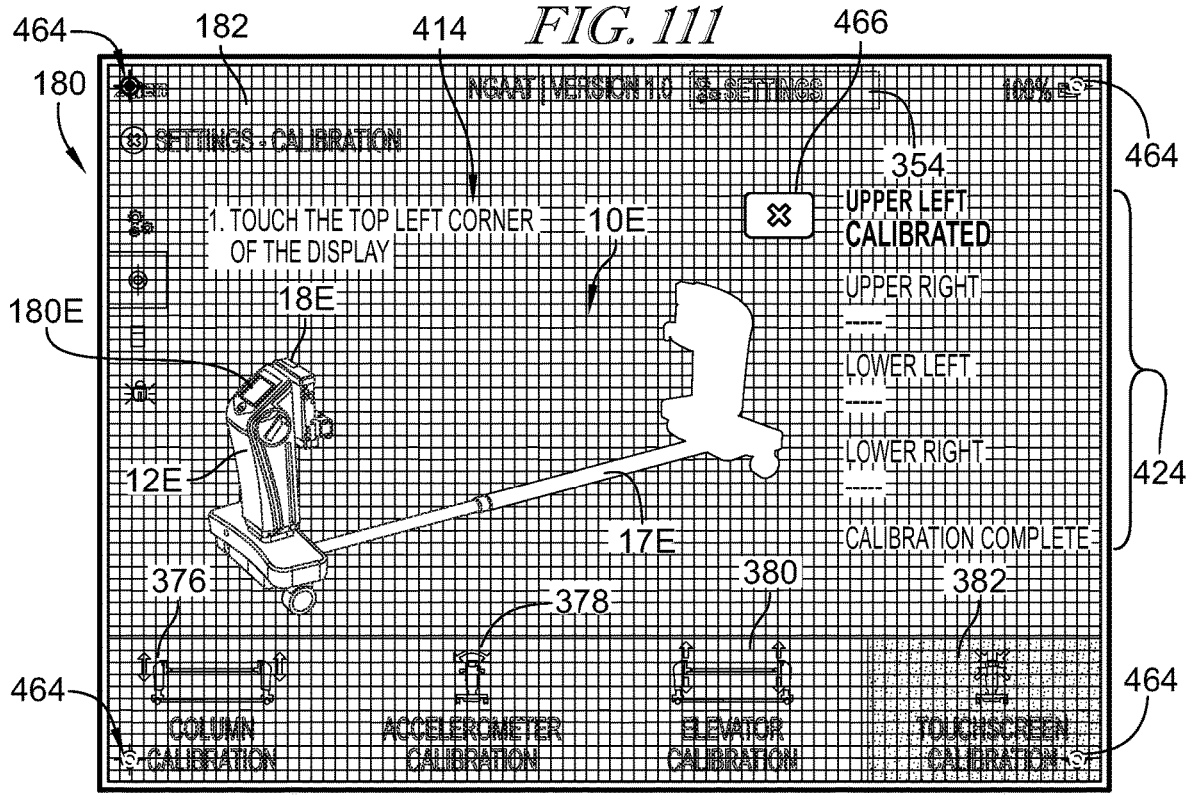

As shown in FIG. 112, the user has successfully selected the upper left target 464 as indicated by change in color of the upper left target 464 (represented by solid inner circle of the target symbol) to activate corresponding calibration. The corresponding information script illustratively indicates successful calibration of the upper left stage by reading "calibrated." Upon successful completion of the upper left stage calibration, the calibration operation advances.

Figure 113:
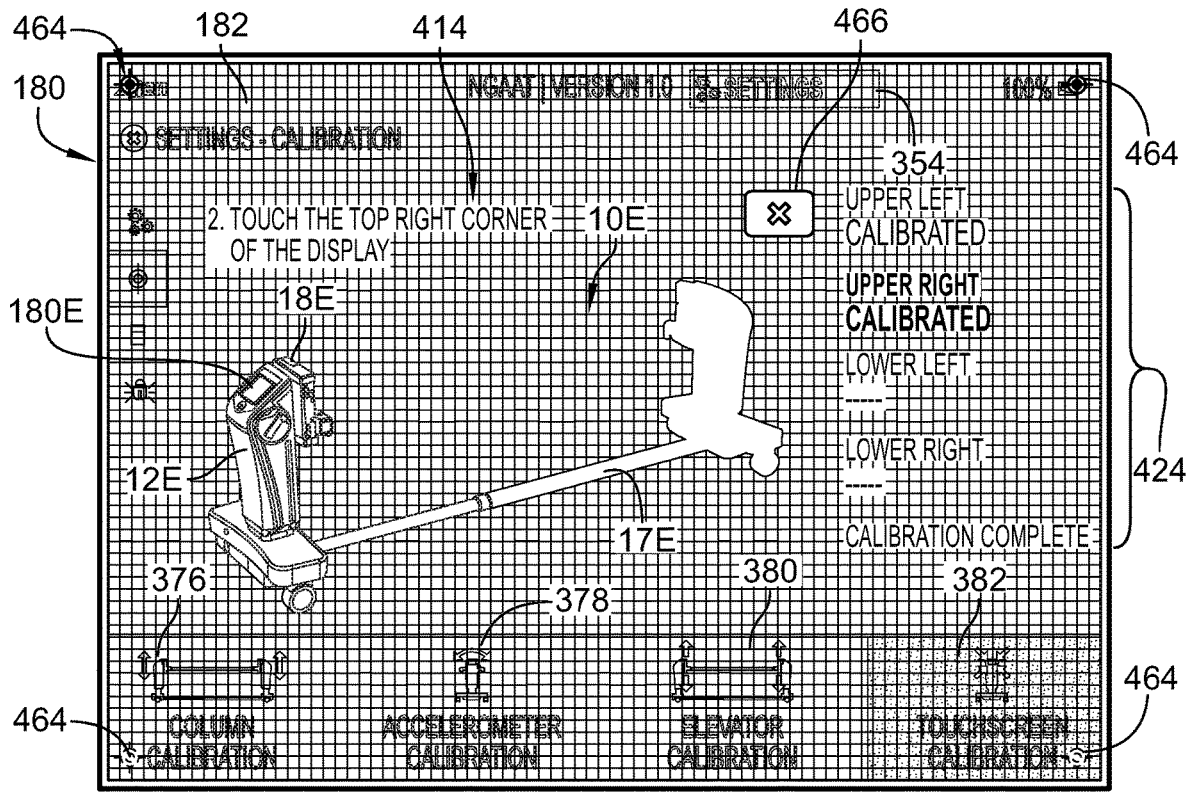

As shown in FIG. 113, responsive to completion of the upper left stage calibration, the upper right stage of the status information 424 is activated as indicated by highlighting on the GUI 180 (represented by bolding). Notably, the upper left target 464 remains changed in color (solid inner circle of target symbol) to indicate its recent calibration. The alert script 414 indicates instruction for the user to touch the newly assigned upper right target 464. Prior to touching by the user, the upper right target 464 is indicated as assigned by merely highlighting (represented by bolding), but in FIG. 113, the user has already selected the upper right target 464 as indicated by its color change (represented by solid inner circle of target symbol). Responsive to the user's selection of the upper right target 464, the corresponding calibration is performed, and on completion, the status information 424 indicates that the upper right stage is "calibrated".

Figure 114:
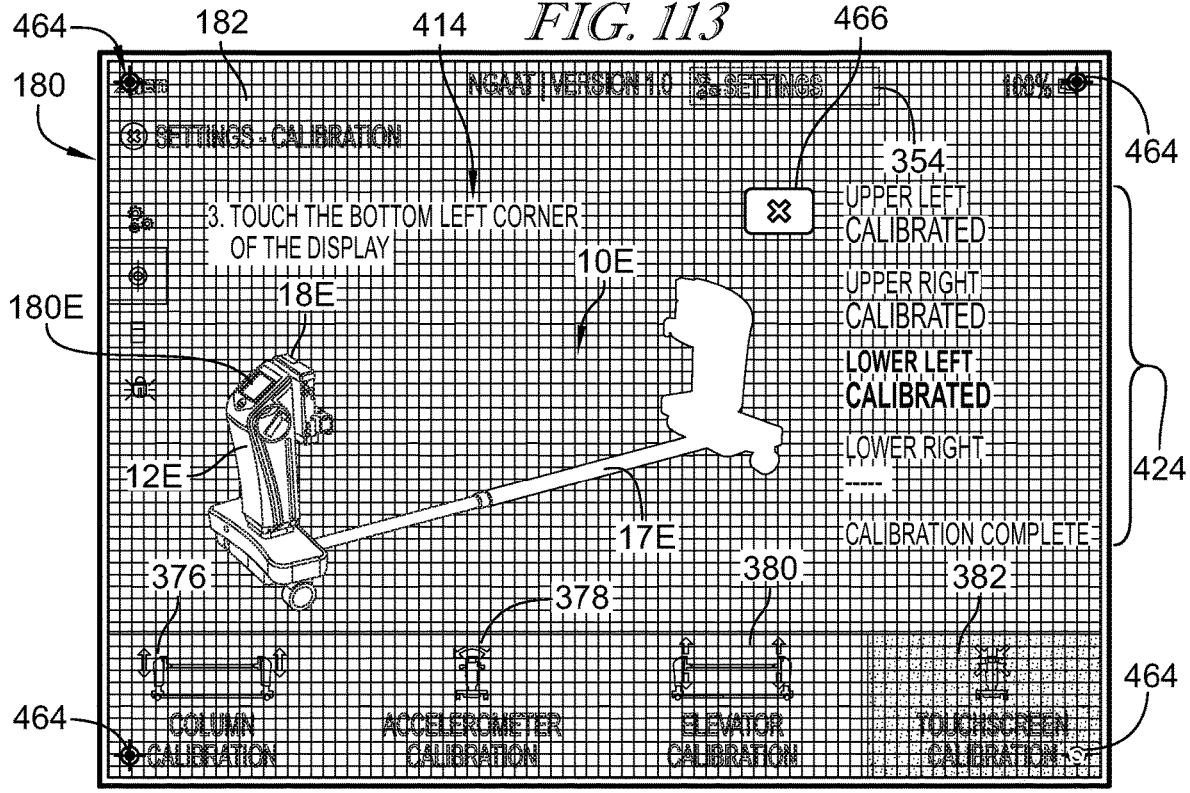

As shown in FIG. 114, responsive to successful completion of the upper right stage calibration, the lower left stage of the status information 424 is activated as indicated by highlighting on the GUI 180 (represented by bolding). Notably, the upper targets 464 remain changed in color (solid inner circle of target symbol) as already calibrated. The alert script 414 indicates instruction for the user to touch the newly assigned lower left target 464. Prior to touching by the user, the lower left target 464 is indicated as assigned by merely highlighting (represented by bolding), but in FIG. 114, the user has already selected the lower left target 464 as indicated by its color change (represented by solid inner circle of target symbol). Responsive to the user's selection of the lower left target 464, the corresponding calibration is performed, and on completion, the status information 424 indicates that the lower left stage is "calibrated".

Figure 115:
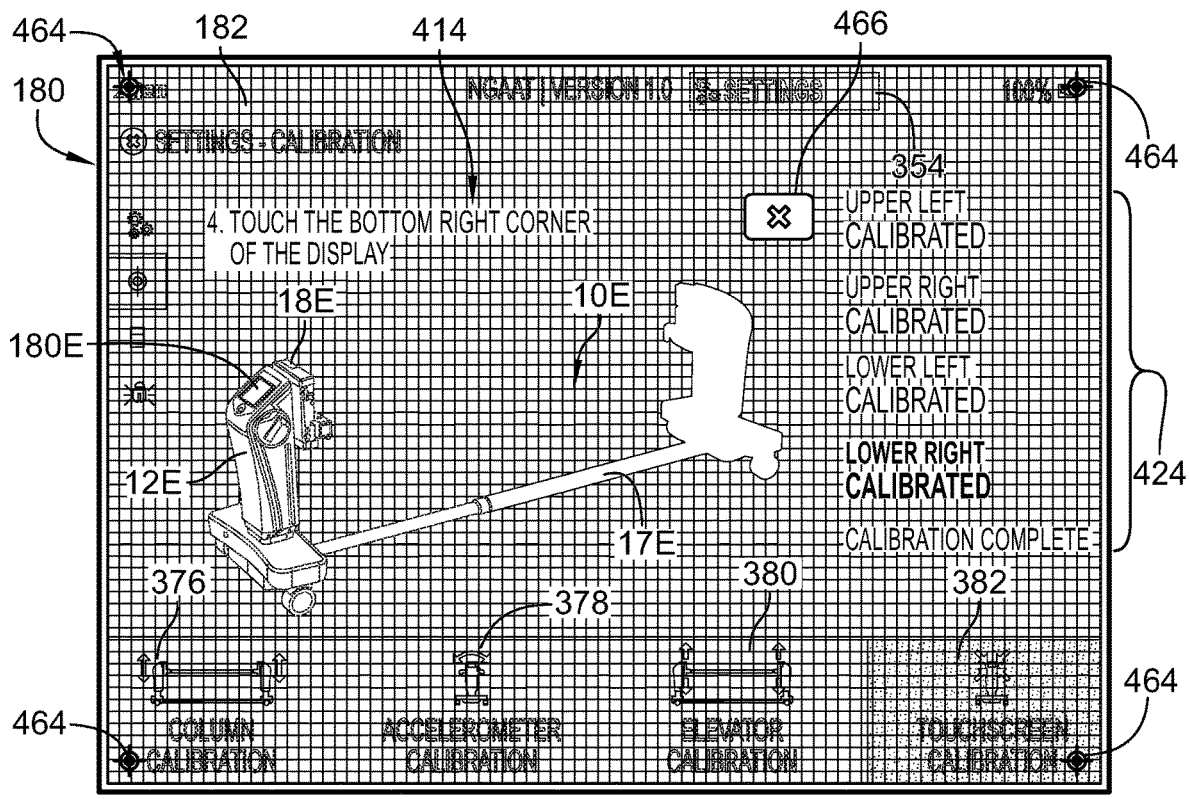

As shown in FIG. 115, responsive to successful completion of the lower left stage calibration, the lower right stage of the status information 424 is activated as indicated by highlighting on the GUI 180 (represented by bolding). Notably, the upper targets and the lower left target 464 remain changed in color (solid inner circle of target symbol) as already calibrated. The alert script 414 indicates instruction for the user to touch the newly assigned lower right target 464. Prior to touching by the user, the lower right target 464 is indicated as assigned by merely highlighting (represented by bolding), but in FIG. 115, the user has already selected the lower right target 464 as indicated by its color change (represented by solid inner circle of target symbol). Responsive to the user's selection of the lower right target 464, the corresponding calibration is performed, and on completion, the status information 424 indicates that the lower right stage is "calibrated".

Responsive to completion of the upper and lower calibration stages, the GUI 180 presents a completion screen as shown in FIG. 116. The calibration complete stage of the status information 424 is active as indicated by highlighting (represented by bolding). The alert script 414 indicates that calibration is complete and a checkmark 468 is presented. Accordingly, the touchscreen 182 and the GUI 180 can be calibrated with the sensors and systems of the patient support 10. In some embodiments, calibration stages of a particular calibration icon, and the various calibration processes of each calibration icon, may be performed in any suitable order.

Returning briefly to FIG. 27, the GUI 180 illustratively includes a header section in which the settings button 354 is presented. In the header section the GUI 180 illustratively displays the power life (100%) of a portable energy storage device (battery) and a graphical indication as to whether a permanent power source is connected (e.g., electrical plug within battery outline). The GUI 180 illustratively includes a footer section in which the collapse button 222 is presented. In the footer section the GUI 180 illustratively includes the operation and preset icons, the save button 344. In the footer, the GUI 180 illustratively presents a training button 520 for user selection to enter a training module for instruction on patient support control and operations, and a safety lockout slider bar including a slider operable between an unlocked state to permit changes patient support status and a locked state to block against changes to the current patient support status, including status features that are adjustable via GUI 180. Referring to FIG. 48, immediately below the header section, the GUI 180 illustratively includes a title of the current operation (Lateral Top—Collapse Mode) and includes a cancel button (represented by an X within a circle) for user selection to cancel the current operation and return to an earlier general screen, such as that shown in FIG. 47. The screen for return can vary according to the particular operation from which cancellation is selected.

Figure 117:
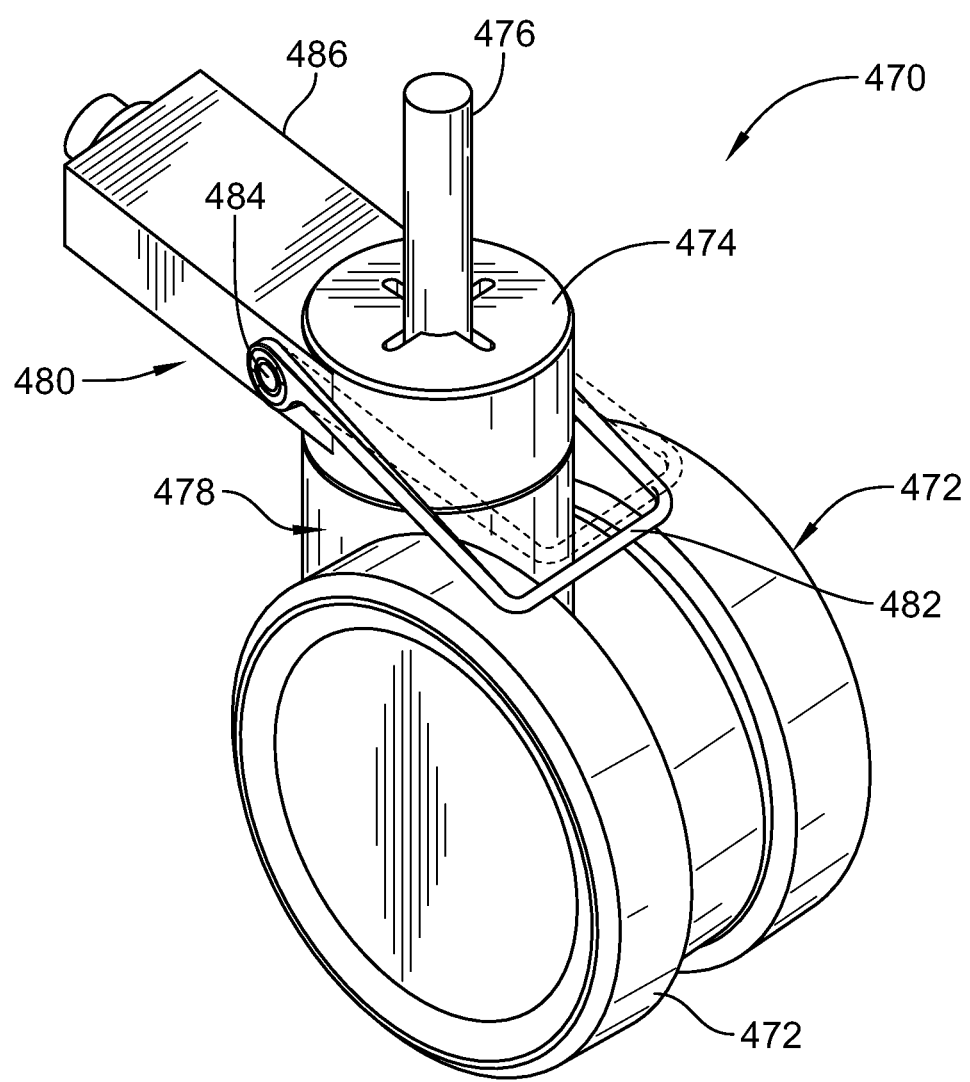
FIG. 117 is perspective view of a caster of the patient support of FIG. 1 showing that the caster includes swiveling wheels for assisting in moving the patient support across the floor, and showing that the caster includes an electrical actuator for selectively operating the caster to brake and release rotation of the wheels, and an actuation handle for engagement with a user's foot to manually operate the caster to release braking of the wheels.

Referring to FIG. 117, a caster 470 of the patient support 10 illustratively includes a pair of wheels 472 for supporting the patient support 10 on the floor. The wheels 472 are mounted to a column 474 for selective rolling to allow movement of the patient support 10 along the floor. The column 474 illustratively includes a post 476 projecting vertically for connection with the corresponding tower base 12. A lower portion 478 of the column 474 to which the wheels 472 are mounted is selectively releasable for swiveling about the longitudinal axis of the column 474 to allow steering. One example of a caster may include that disclosed within U.S. Pat. No. 8,205,297, the contents of which are hereby incorporated by reference in their entirety, and including at least those details related to caster operation and control.

The caster 470 illustratively includes a lock assembly 480. The lock assembly 480 includes a foot actuation lever 482 that is illustratively arranged to extend about the column 474. The foot actuation lever 482 is operable between a rest position (solid line in FIG. 117) and an unlock position (dashed line in FIG. 117) to unlock the wheels 472 of the caster 470 for rolling. The lever 482 illustratively connects on either side of the column 474 with a rotation shaft 484 that extends through a housing 486 that projects from the column 474. The rotation shaft 484 is operable between an unlocked position to allow rolling of the wheels 472 for movement of the patient support 10, and a locked position preventing rolling of the wheels 472 to block against movement of the patient support across the floor. As explained in additional detail below, the lever 482 is operable to drive the rotation shaft 484 into the unlocked position, but is unable to drive the rotation shaft 484 into the locked position.

Figure 118:
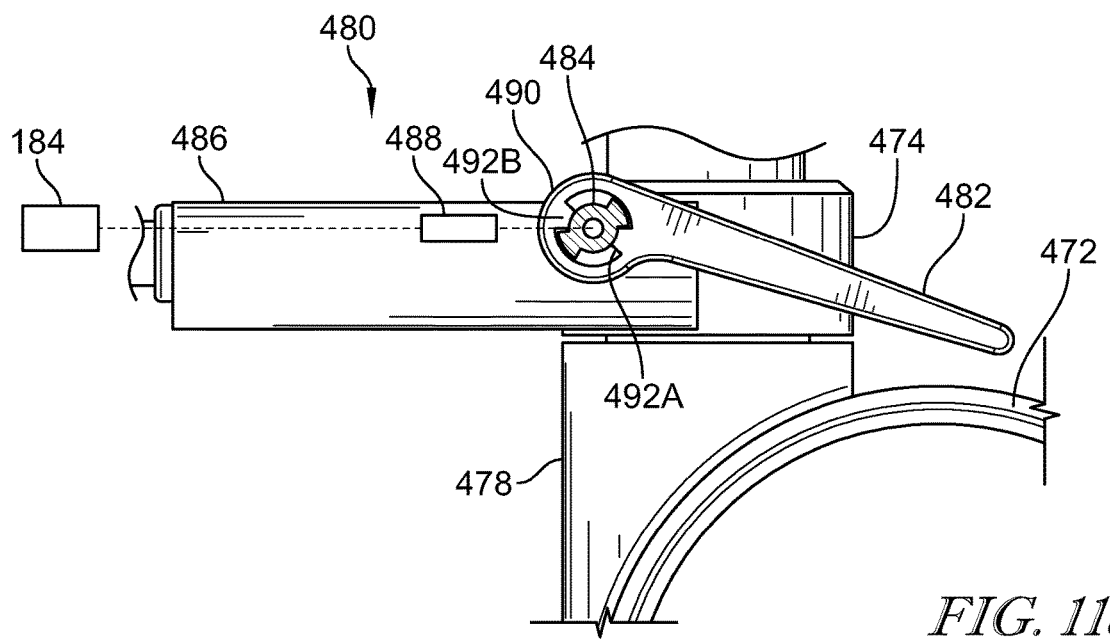
FIG. 118 is a side elevation view of the caster FIG. 117 having a portion cutaway to show that a rotation shaft (crosshatch for identification) is arranged in a locked position to actuate a breaking device to block against rotation of the caster wheels to brake the patient support, and showing that an actuation handle is arranged in a rest position and is movable to rotate the rotation shaft (counter-clockwise) into an unlocked position to release the caster wheels for rotation.

As shown in FIG. 118, the rotation shaft 484 is arranged in the locked position preventing the wheels 472 from freely rolling. The lock assembly 480 illustratively includes an actuator 488 arranged in communication with the control system 184 and engaged with the rotation shaft 484 to operate the rotation shaft 484 between the locked and unlocked positions as directed by the control system 184. In the illustrative embodiment, the user can perform locking and unlocking of the caster wheels 472 via the GUI 180, as discussed above, via the actuator 488.

As shown in FIG. 118, the lever 482 includes a base 490 that illustratively encircles a portion of the rotation shaft 484. The base 490 illustratively includes a pair of teeth 492A,B projecting radially inwardly for selective engagement with the rotation shaft 484. The teeth 492A,B are arranged spaced apart from each other circumferentially to selectively engage the rotation shaft 484 to drive the shaft 484 into the unlocked position, but cannot engage the shaft 484 to drive the rotation shaft 484 into the locked position.

Figure 119:
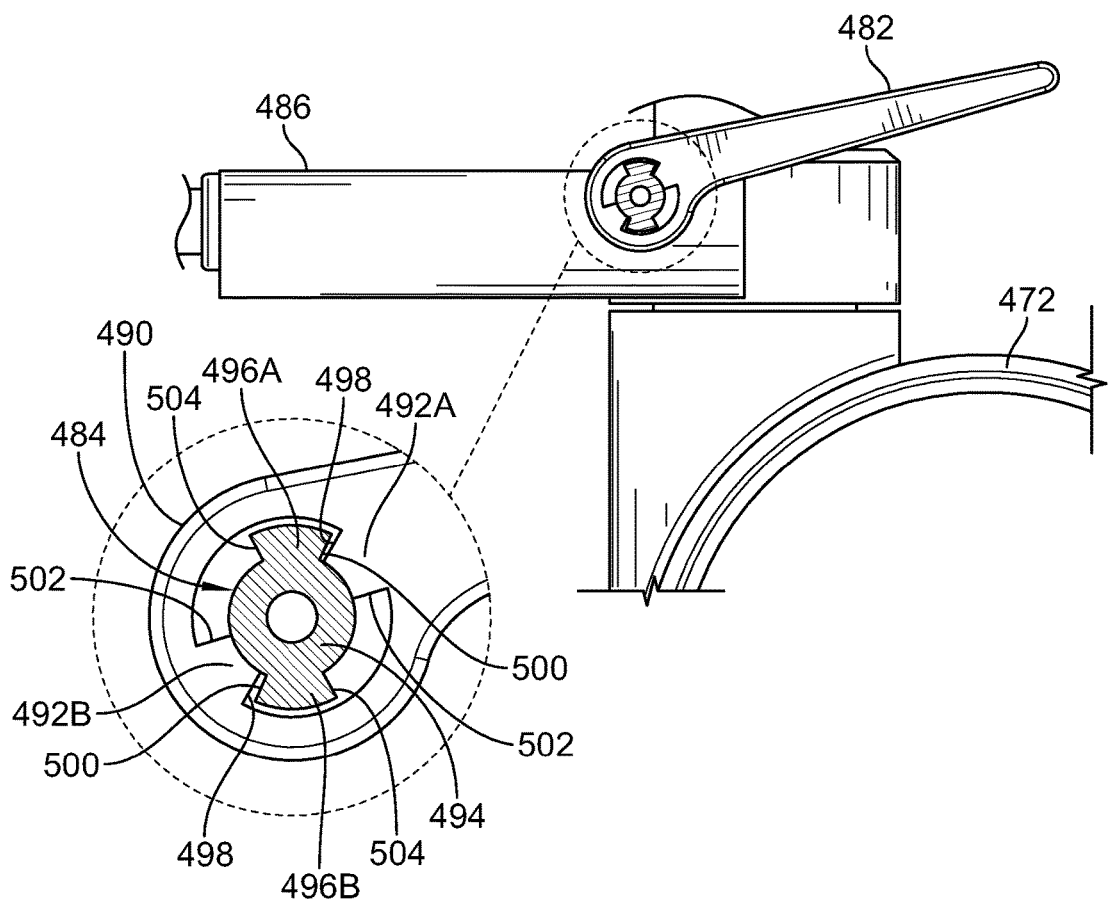
FIG. 119 is the side elevation view of the caster of FIG. 118 showing that the rotation shaft has been rotated (counter-clockwise) into the unlocked position by moving the actuation handle into an unlock position, and showing that the actuation handle includes a pair of teeth extending radially inward for selective engagement with teeth of the rotation shaft, and showing that the teeth of each of the actuation handle and rotation shaft are arranged with spacing to permit engagement with the teeth of the actuation handle and the rotation shaft only for counter-clockwise rotation of the shaft to permit the actuation handle to drive the rotation shaft for counter-clockwise rotation from the locked position into the unlocked position, but not for clockwise rotation into the locked position.

As shown in FIG. 119, the lever 482 has been moved into the unlock position to drive the rotation shaft 484 into the unlocked position. The rotation shaft 484 illustratively includes a hub 494 and teeth 496A,B extending radially outward from the hub 494 arranged for selective engagement by a respective tooth 492A,B of the lever 482. The teeth 496A,B of the rotation shaft 484 are illustratively spaced apart from each other and are each arranged relative to the teeth 492A,B to allow engagement with the corresponding tooth 492A,B only to drive rotation towards the unlocked position (i.e., counter-clockwise). For example, the tooth 492A illustratively includes an engagement surface 498 arranged for selective engagement with an engagement surface 500 of the tooth 492A, and another surface 502 opposite the engagement surface 498 which does not engage the rotation shaft 484 (e.g., the surface 498 does not engage another surface 504 of the tooth 496A, nor the other tooth 496B, to drive the shaft 484 clockwise, in any position between the rest and the locked positions of the lever 482). The tooth 492B is arranged similarly with respect to the tooth 492B. Thus, the lever 482 cannot drive clockwise rotation of the rotation shaft 484, through the complimentary arrangement of the teeth 496A,B with the teeth 492A,B of the shaft 484. The lever 482 illustratively includes a similar base 490 and toothed engagement with the rotation shaft 484 on the opposite side of the column 474. Accordingly, the lever 482 is operable to drive the rotation shaft 484 to the unlocked position, but is incapable of driving the rotation shaft 484 into the locked position.

By requiring the user to lock the casters 470 only by use of the GUI 180, the risk of inadvertent locking can be reduced, which can prevent uncomfortable stopping of a patient support 10 in movement. However, the ability to switch the casters 470 into an unlocked position by physical lever, in addition to the GUI 180 controls, can provide a speedy and simple manner to enable motion of the patient support 10 along the floor. In some embodiments, the lever 482 may be operable to drive the rotation shaft 484 to the locked position, but is incapable of driving the rotation shaft 484 into the unlocked position, for example, by transposing the actuation positions of the locked and unlocked position (and thereby the direction of rotation, clockwise-versus-counterclockwise) of the rotation shaft 484.

Figure 121:
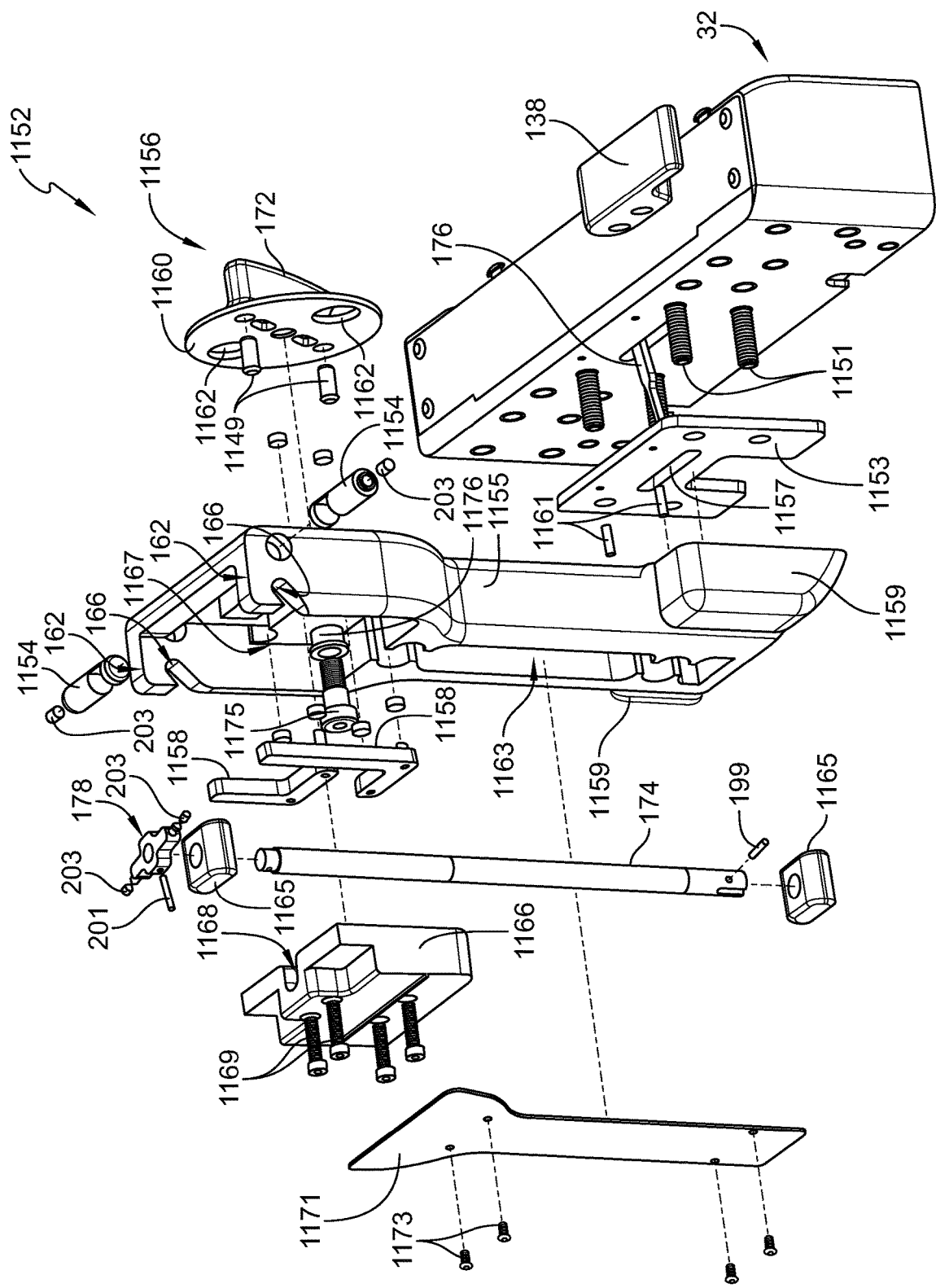
FIG. 121 is an exploded perspective view of a side arm assembly, similar to the lateral extension of FIG. 14, of the connection assembly of FIGS. 2 and 3 for extending laterally with an additional docking receiver for connection with a prone support top to enable a lateral-to-prone transfer of the patient.

Referring now to FIG. 121, a side arm assembly 1152, similar to the lateral extension 152, is shown in exploded perspective view. The disclosure of the lateral extension 152 applies equally to the side arm assembly 1152 except in instances of conflict with the specific disclosure of the side arm assembly 1152. The side arm assembly 1152 includes a body 1155 having a connection end on which a docking receiver 32 is mounted by threaded fasteners 1151 extending through a plate 1153. The plate 1153 includes an elongated slot 1157 through which the linkage 176 extends for connection with the shaft 174 through the body 1155. The body 1155 includes wings 1159 extending in opposite directions to receive the fasteners 1151 for connection of the docking receiver 32. Retainer pins 1161 extend through holes of the plate 1153 and engage holes of the body 1155 and docking receiver 32 for guiding connection of the body 1155 with the docking receiver 32.

The body 1155 defines an elongate cavity 1163 for receiving the shaft 174. The cavity 1163 is shaped on both ends to receive mounts 1165 for supporting the rotation of the shaft 174, and shaped on one end for accommodating connection of the linkage 176 with the shaft 174, via pin 199, with clearance to avoid impedance of their coordination movement. The shaft 174 illustratively includes the connector 178 connected to an end opposite the linkage 176, via pin 201, the connector 178 having a t-shape and including magnetic elements 203 on opposite ends of the t-shape for interaction with sensors. The body 1155 is adapted to connect on an opposite end from the docking receiver 32 with the connection assembly 18 to position the docking receiver 32 for reception of a support top, laterally and perpendicularly relative to the support top 14, for assisting in changing a patient's body position, for example, rotating a patient from a lateral recumbent position to a prone position. The side arm assembly 1152 includes a pair of lever actuated engagement pins 1154 housed within a depression 1167 of the body 1155. The engagement pins 1154 are selectively movable between a retracted position within the side arm assembly 1152 and out from engagement with the connection assembly 18, and an extended position extended out from the extension arm 154 and into engagement with the connection assembly 18 to secure the side arm extension 1152 with the connection assembly 18. The body 1155 includes a casing 1166 for receipt by the depression 1167 and having a slot 1168 for receiving the shaft 174. The casing 1166 is fastened to the body 1155 by threaded fasteners 1169. A cover 1171 is secured with the body 1155 by threaded fasteners 1173 to cover the elongate cavity 1163 and at least a portion of the casing 1166

A rotatable dial 1156 engages with levers 1158 via pins 1149 which extend from the dial 1156 through the body 1155 to actuate each of the engagement pins 1154 between the retracted and extended positions. The dial 1156 includes a base 1160 and a pair of view ports 1162 penetrating through the base 1160. The view ports 1162 allow visual inspection of the body 1155 through the dial 1156. The body 1155 includes visual indication that the engagement pins 1154 are in the extended position, visible through the view ports 1162 only when the dial 1156 is correspondingly positioned. For example, the extension arm 153 may include a color indication that is sized, shaped, and/or positioned with correspondence with each of the view ports 1162 such that only when the pins 1154 are in the engagement position, the color indication is fully visible through view ports 1162 based on corresponding position of the dial 1156, and such that when the pins 1154 are not in the engaged position, the color indication is not fully visible through the view ports 1162. Accordingly, the user can be alerted to occurrence of partial seating of the engagement pins 1154 within the complimentary holes 167 of the connection assembly 18 and inadvertent disconnection of the side arm assembly 1152 can be avoided. The base 1160 is rotatably connected with the body 1155 by a threaded fastener 1175 and bushing 1176.

Referring now to FIG. 122, a connection assembly 2018 is shown, similar to the connection assembly 18, in an exploded perspective view, and without the docking receiver 32 secured thereto. The disclosure of the connection assembly 18 applies equally to the connection assembly 2018 except in instances of conflict with the specific disclosure of the connection assembly 2018. The connection assembly 1018 illustratively includes the frame 30 having a body 2020. The body 2020 includes a base 2022 and end caps 2024 attached via threaded fasteners 2011 on opposite lateral sides of the base 2022 (in the orientation of FIG. 122) for receiving connection of a lateral attachment such as the lateral extension 152 or side arm assembly 1152 in the orientation of FIG. 122, and end caps 2025 attached to the base 2022 via threaded fasteners 2013 on opposite vertical sides of the base 2022 (in the orientation of FIG. 122). The end caps 2025 each include a slot 2027 extending vertically therethrough for passage of the slide plate 40 throughout its range of translation. Each slot 2027 is shaped to correspond with the profile of the slide plate 40 to allow passage of the slide plate 40 throughout the range of its translation between extended and retracted positions.

As shown in FIG. 122, the base 2022 includes an I-shape having spaces 2080 defined in each lateral side (in the orientation of FIG. 122). The spaces 2080 are formed to receive a corresponding portion 2082 of the end caps 2024. The base 2022 includes a number of recesses 2028 defined in a front side 2030. The recesses 2028 each house one of the racks 48 of the dampening assembly 44 and a pawl 2032 of a ratchet assembly 2034. The ratchet assembly 2034 is illustratively similar to the ratchet assembly 46 and the disclosure of the ratchet assembly 46 applies equally to the ratchet assembly 2034 except in instances of conflict with the specific disclosure of the ratchet assembly 2034.

As shown in FIG. 122, a central support bar 2015 is secured with the base 2022 via threaded fasteners 2017 and defines tracks 2019 on opposite lateral rear sides (in the orientation of FIG. 122) for receiving translatable contact with each of the slide plates 40. The support bar 2015 includes rollers 2021 rotatably pinned to support translation of the slide plates 40 along the tracks 2019. The slide plates 40 each include rollers 2021 rotatably pinned on each lateral side at an inner end 2081 of the slide plate 40 to engage the corresponding track 2019. A number of covers 2062 connect with the base 2022 via threaded fasteners 2064. A cover 2066 is secured to the rear side 2031 of the base 2022 via threaded fasteners 2067. The cover 2066 includes an opening 2068 defined therethrough for receiving the adapter 31 for connection of the base 2022 with the connection rod 16.

As shown in FIG. 123, each ratchet assembly 2034 controls the position of the respective slide plate 40 of the slide assembly 38. The ratchet assembly 2034 includes a ratchet track 2036 and the corresponding pawl 2032. The pawl 2032 is selectively engageable with the ratchet track 2036 to define the positon of the slide plate 40 relative to the frame 30.

Figure 124:
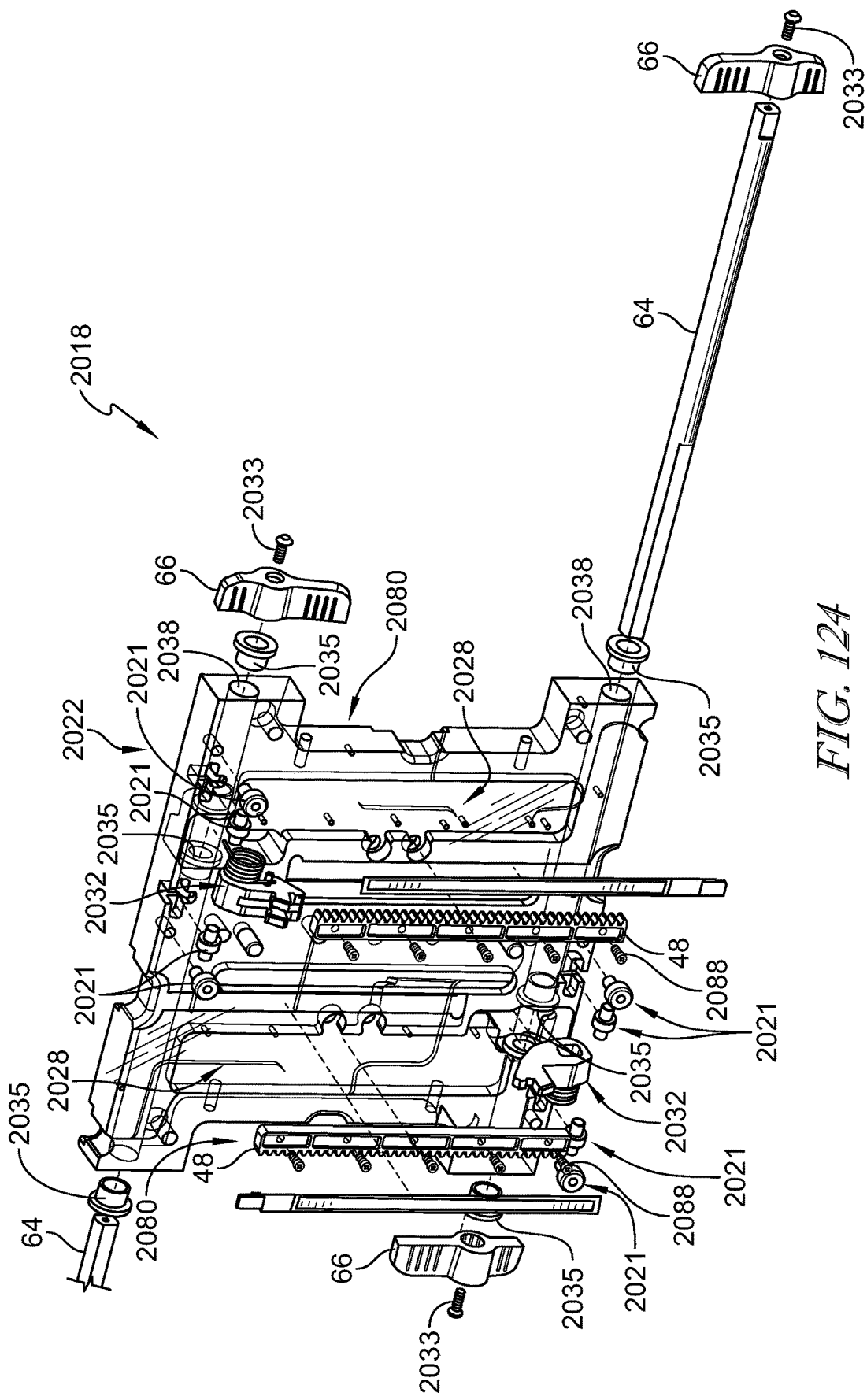
FIG. 124 is a closer exploded perspective view of portions of the connection assembly of FIG. 122 showing that the slide assemblies include a ratchet system includes a pair of handles for disengaging a ratchet mechanism to allow translation of the slide plate, and showing that the ratchet system includes a pawl formed as a split pawl.

Referring to FIG. 124, the base 2022 includes mount receptacles 2038, each for receiving one of the shafts 64 on which the pawls 2032 are secured for rotation. The user can selectively rotate the handles 66 which are secured with the corresponding shaft 64 via threaded fasteners 2033 supported by bushing 2035, to rotate the shaft 64 and to pivot the position of the pawl 2032 between engaged and disengaged positions relative to the ratchet track 2036. Each pawl 2032 is supported on the corresponding shaft 64 by bushings 2035 for pivoting and includes a torsional spring 2031 for biasing into the engaged position with the track 2036. Pivoting the pawl 2032 to the disengaged position allows the slide plate 40 to be released for linear repositioning relative to the base 2022. The racks 48 are engaged the damper 56 and secured with the base 2022 by threaded fasteners 2088. Rollers 2021 are rotatably pinned to the base 2022 to engage the slide plates 40 on lateral and front and rear sides, to guide translation of the slide plates 40.

As shown in FIG. 125, the end caps 2024 each include a body 2090 having the portion 2082 extending therefrom for insertion into the spaces 2080 of the base 2022. The end caps 2024 each define a track 2092 for guiding the corresponding slide plate 40 throughout its translation range opposite the corresponding track 2019 of the central support bar 2015. The end caps 2024 include rollers 2021 for rollably engaging the corresponding slide plate 40.

The end caps 2024 each define slots 2040 for receiving the hooks 162 of the side arm extension 1152. The hooks 162 are arranged for engagement with the shafts 165 (shown displaced) to secure the side arm extension 1152 with the connection assembly 2018. The hooks 162 being engaged with the shafts 165 are counterpoised from the engagement pins 1154 of the side arm extension 1152 to block against the articulated movement required to disengage the hooks 162 from the shafts 165 to secure the side arm extension 1152 in place.

The ends caps 2024 each include a sensor 2042 arranged near the midsection for determining the state of the docking receiver 32 of the side arm extension 1152. The sensor 2042 is secured within a recess 2093, defined by the body 2090 and portion 2082, with a cover 2094 via threaded fasteners 2096. The sensor 2042 senses the rotational position of the connector 178 and therefore the rotational position of the shaft 174 which indicates whether the translatable shaft 136 of the docking receiver 32 is positioned to engage the locking pins 102 with the gate latches 90 to prevent movement of the docking gate 88 out from the locked position to prevent removal of a connection tube 36 from the docking slot 34. One example of a suitable sensor 2042 includes a magnetic reed switch for determining the position of the connector 178 which includes magnetic elements 203 to interact with the sensor 2042.

The end caps 2024 each include a cavity 2044 arranged near the complimentary pin hole 167 for at least one of the engagement pins 1154 of the side arm extension 1152. The ends caps 2024 each include a sensor 2046 arranged in the cavity 2044 in proximity to the hole 167 to detect the presence of the corresponding pin 1154 when in the engaged position within the hole 167. The sensor 2046 is illustratively secured to an inner side of a cover 2104 via threaded fasteners 2106, and the cover 2104 is secured with the body 2090 within the cavity 2044 to accurately locate the sensor 2046 relative to the body 2090. One example of a suitable sensor 2046 includes a magnetic reed switch for determining the position of the pin 1154 which may include magnetic elements 203 to interact with the sensor 2046. Covers 2049, 2098 are adapted for securement to the end caps 2024 via threaded fasteners 2102 to conceal and/or protect the sensor 2042, 2046.

Referring to FIG. 126, the slide plate 40 includes cavities 2048, 2050 for receiving the ratchet track 2036 and the damper 56 of the dampening assembly 44. The ratchet track 2036 is similar to the ratchet track 58, but unlike the single teeth 62 of the ratchet track 58, the ratchet track 2036 includes corresponding pairs of teeth 62 arranged adjacent and oriented parallel to each other. The teeth 62 of each pair are illustratively spaced apart from each other by a wall 2052 that extends longitudinally along the successive pairs of teeth 62. The ratchet track 2036 is secured within the cavity 2048 of the slide plate 40 by threaded fasteners 2108. The damper is secured within the cavity 2050 via threaded fasteners 2110. A cover 2112 is secured to an opposite side of the slide plate 40 from the ratchet track 2036 via threaded fasteners 2114 and includes a tab 2116 extending across an underside (in the orientation of FIG. 126) of the slide plate 40.

Figure 127:
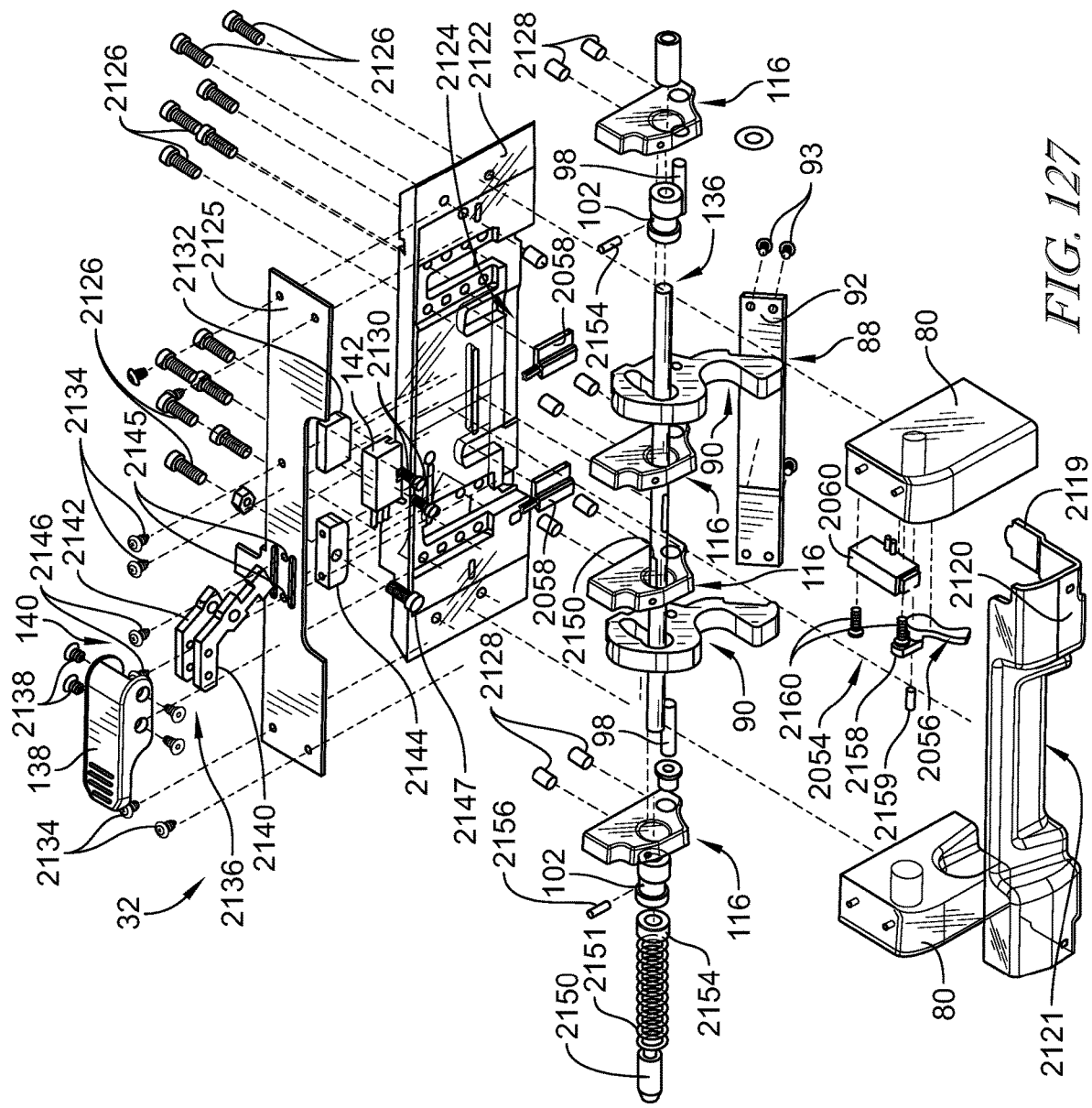
FIG. 127 is an exploded perspective view of a docking receiver of the connection assembly of FIG. 3 showing that a docking gate is movably secured within the docking receiver.

Referring to FIG. 127, a docking receiver 32 is shown in exploded view illustrating that its includes a front housing 2120 connecting with each of the end stops 80, and a rear wall 2122 and a lower wall 2125 each joined at opposite ends with the ends stops 80 by threaded fasteners 2126. The front housing 2120 includes a depression 2121 on an outer side therefore, and a number of tabs 2119 extending towards the end stops 80. The rear wall 2122 includes a depression 2124 formed to receive various components such as the sensors 2058 and the support walls 116 secured within the depression 2124 of the rear wall 2122 by threaded fasteners, and portions of the docking gate 88 (e.g., portion of the gate latches 90 and the gate bar 92 fastened to each gate latch 90 by threaded fasteners 93) when arranged in the unlocked position. Guide pins 2128 guide components, such as the support walls 116, to connect with the rear wall 2122. The position sensor 142 for the shaft 174 is connected by threaded fasteners 2130 with a support mount 2132 which is connected with the lower wall 2125 by threaded fasteners 2134.

As shown in FIG. 127, linkage 2136 of the lever assembly 140 is connected on one end with the handle 138 by threaded fasteners 2138. The linkage 2136 includes a pair of armatures 2140, 2142, one of which 2140 connects with the shaft 136. Each armature 2140, 2142 has a bent shape extending from connection with the handle 138 and each extends through a corresponding slot 2145 in the lower wall 2125. Each armature 2140, 2142 connects with a pivot support 2144 via threaded fastener 2147 for pivoting about the fastener 2147 under force from the handle 138. The pivot support 2144 is secured with an inner side of the lower wall 2125 by threaded fasteners 2146 that extend through the lower wall 2125. The armature 2140 includes a t-shaped end 2148 which engages the shaft 136 by insertion in a slot 2150 of the shaft 136 to transfer pivoting motion of the armature 2140 into translation of the shaft 136.

A stopper 2152 is illustratively engaged with a spring 2151 including a spring head 2154 which engages with the shaft 136 to biasing the shaft 136 into the unlocked position. The latch pins 102 are connected with the shaft 136 by receiving the shaft 136 through their axial center and pinning by pins 2156 extending through the locking pins 102 and the shaft 136 across the axial dimensional of each to fix the pins 102 for translation with the shaft 136.

The docking receiver 32 includes a top presence sensor 2054 including a trigger arm 2056 formed as a rotating lever and a physical switch 2060. The trigger arm 2056 extends into the docking slot 34 when no connection tube 36 is present. The trigger arm 2056 engages connection tubes 36 entering the docking slot 34 and pivots out of the path to permit the connection tube 36 to be seated under the force of the entering connection tube 36 to indicate the presence of the connection tube 36 within the docking slot 34. A fulcrum end 2055 of the trigger arm 2056 engages and depresses the switch 2060 as a cam when a connection tube 36 pivots the trigger arm 2056 sufficiently to indicate that the connection tube 36 is fully seated in the docking slot 34. The trigger arm 2056 is pivotably supported by a mount 2158 on a pivot rod 2159. The mount 2158 and the physical switch 2060 are secured with one of the end stops 80 by threaded fasteners 2160.

The docking receiver 32 includes a pair of top type sensors 2058 for sensing the type of support top connected. The sensor 2058 illustratively sense coded information embedded onto the support top indicating the type of support top. Each sensors 2058 are illustratively embodied as a magnetic sensor, such as a reed switch, responding to magnetic force indicating a particular identification code of the support top type, however, in some embodiments, the sensors 2058 may comprise bar code, optical, and/or any other suitable manner of sensing the support top type according to corresponding indication by the support top.

Figure 128:
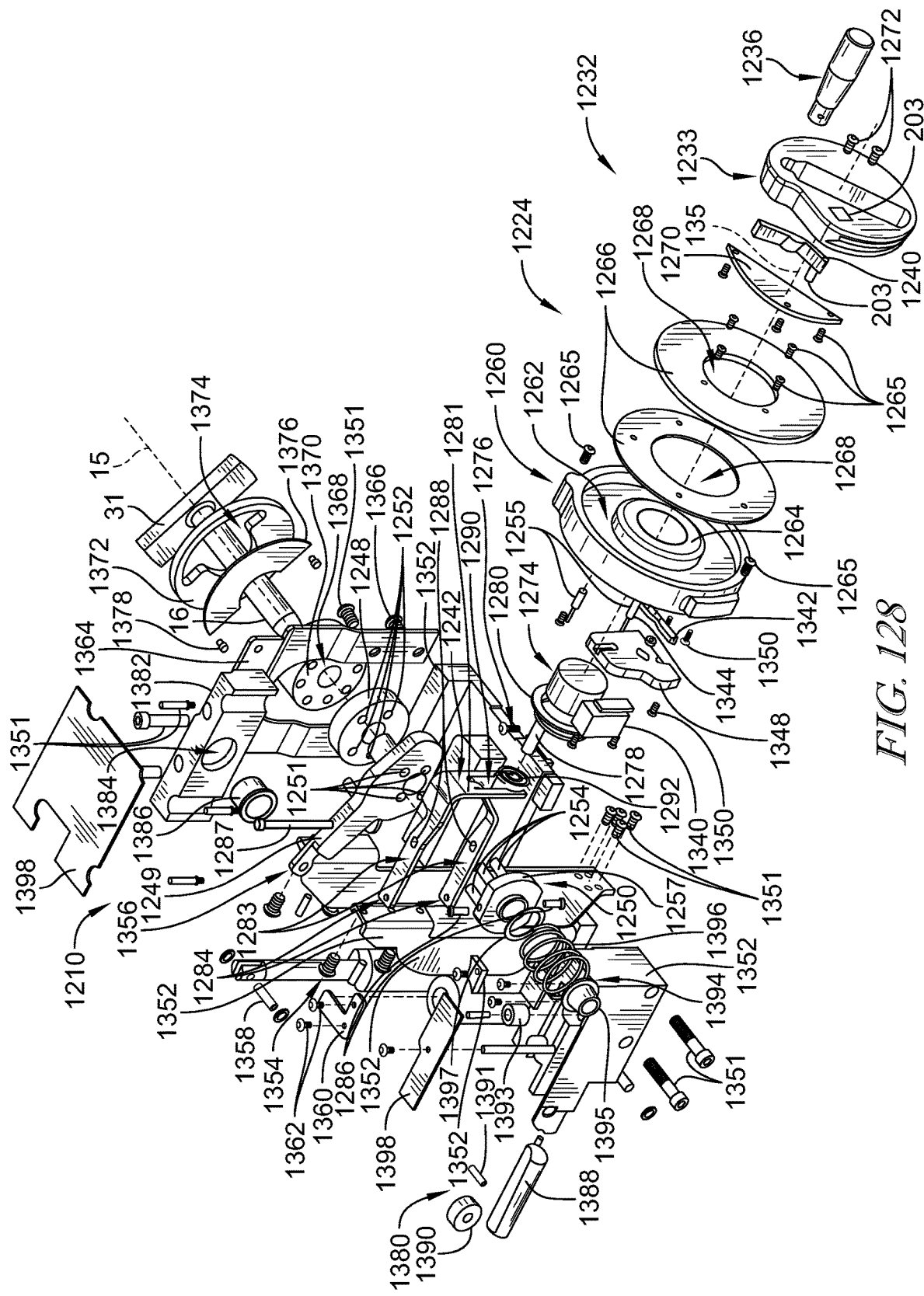
FIG. 128 is an exploded perspective view of a portion of the head end tower base showing that a connection rod is arranged for controlled rotation, and showing that a lockout system provides for selective operation of a lock mechanism between locked and unlocked states to allow free rotation of the connection rod.

Referring now to FIG. 128, an upper portion of one of the tower bases 12 is shown to provide controlled rotational support to the support top. In the illustrative embodiment, the head end tower base 12 includes a rotation lockout assembly 1210 for supporting the connection assembly 18 for controlled rotational. The rotation lockout assembly 1210 is illustratively similar to the rotation lockout assemblies 22, 122 as disclosed within U.S. Patent Application Publication No. 2019/0029906, filed Jul. 18, 2018, the contents of which are hereby incorporated by reference in their entirety, including at least those portions directed to devices, systems, and methods of patient support. The disclosure of the rotation lockout assemblies 22,122 is applicable to the rotation lockout assembly 1210, except in instances of conflict with the particular disclosure of rotation lockout assembly 1210.

The rotation lockout assembly 1210 includes the connection rod 16 which connects to support the patient support top via the connection assembly 18. On one end, the connection rod 16 includes the adapter 31 formed as a plate mounted on the rod 16 for rotation together. The adapter 31 is arranged for mounting of the connection assembly 18 as previously discussed above with respect to FIG. 3. The rotation lockout assembly 1210 enables two distinct controlled rotational movements of the connection rod 16 about the axis 15 including a limited angle adjustment and a free rotation.

A flange 1248 is fixedly connected with the connection rod 16 and includes holes 1251 formed to selectively receive pins 1254 to block against rotation of the connection rod 16. A translatable locking collar 1250 includes a body 1257 formed concentric with axis 15 and the pins 1254 extending axially from the body 1257. The locking collar 1250 is translatable along the connection rod 16 to selectively engage the pins 1254 within the holes 1252 of the flange 1248.

The pins 1254 serve as engagement keys between the flange 1248 and a lever 1249 formed as a plate having holes 1252 for receiving the pins 1254 therethrough for circumferential rotation about the axis 15. The lever 1249 is embodied as a power activated lever providing precisely controlled selective revolution of the pins 1254 circumferentially about the axis 15, sliding in a track of the locking collar 1250. The pins 1254 can be inserted through the lever 1249 and into engagement with the flange 1248 to fix the rotational position of the lever 1249 relative to the flange 1248 (and thus the connection rod 16). The lever 1249 is controlled for lever action about the axis 15 by an actuator 1354, as discussed in additional detail below. By controlled lever action of the lever 1249 about the axis 15 with the pins 1254 engaged with the flange 1248, the lever 1240 provides controlled power rotation of the connection rod 16 for controlled rotation of the connected patient support top.

A manual interface 1224 provides a platform for the user to actively operate the rotation lockout assembly 1210 to translate the locking collar 1250 to engage and disengage the pins 1254 from the flange 1248. By depressing a trigger 1240 and manually operating a handle 1236, the locking collar 1250 can be translated along the axis 15. The handle 1236 extends from a rotational disk assembly 1232 for operable for rotation about axis 135. The disk assembly 1232 includes a disk body 1233 connected with a pivoting lever arm 1242 which connects with the locking collar 1250 to transfer the rotational movement of the disk body 1233 into translational movement of the locking collar 1250.

The manual interface 1224 illustratively includes a housing 1260 and the disk assembly 1232 mounted onto the housing 1224 for selective rotation. The housing 1260 is secured by threaded fasteners 1265 to the tower base 12, and includes a circumferential rotation track 1262 defined therein for receiving portion of the disk body 1233 and a hub 1264 for guiding rotation of the disk body 1233. The disk assembly 1232 includes the disk body 1233 and a number of disk plates 1266 secured with the disk body 1233 via threaded fasteners 1265. The disk plates 1266 formed for insertion into the rotation track 1262, and each plate 1266 having an opening 1268, at least one of which corresponding with the size of the hub 1264 for rotational guidance of the disk body 1233. The disk body 1233 includes a trigger plate 1270 secured thereto by threaded fasteners 1265 between the trigger 1240 and the disk plates 1266.

The disk body 1233 is secured via thread fasteners 1272 with a rotation body 1274 which is arranged within an opening of the hub 1264. The rotation body 1274 extends from connection with the disk body 1233 through the housing 1260 and connects with the lever arm 1242 via yolk joint 1276. The yolk joint 1276 is formed by an eccentric shaft 1278 extending from a ring 1280 of the rotation body 1274 and engaging the lever arm 1242 with a pinned connection 1282 to transfer the eccentric motion of the shaft 1278 into pivoting motion of the lever arm 1242. The lever arm 1242 includes a yolk base 1281 proximal to the manual interface 1224 and a pair of connection arms 1283 each defining a distal end 1284. Each of the connection arms 1283 is pinned as a fulcrum at its distal end 1284 to a support structure 1352 via threaded fasteners 1286 and pinned with an opposite (upper and lower) side of the locking collar 1250 by fastener 1287 at a connection 1288 to communicate pivoting of the lever arm 1242 into translation of the locking collar 1250 along the axis 15. The yolk joint 1276 is formed by a slot 1290 defined in the yolk base 1281. The yolk slot 1290 receives a bushing 1292 which in turn receives the eccentric shaft 1278 for rotation. The slot 1290 is elongated vertically to absorb vertical movement of the bushing 1292. The bushing 1292 translates vertically along the slot 1290 and allows rotation and/or penetration of the shaft 1278 in the bushing 1292, while remaining fixed with the lever 1242 for motion in the direction along the axis 15 to transfer arced motion of the eccentric shaft 1278 into pivoting movement of the lever arm 1242 and translation of the locking collar 1250 along the axis 15.

The locking collar 1250 is biased towards the flange 1248 to engage the pins 1254 and prevent the connection rod 16 from rotating relative to the lever 1249. However, the manual interface 1224 can be operated to disengage the locking collar 1250 to permit the user to freely rotate the connection rod 16, for example, to perform a flip rotation of attached patient support tops. A trigger 1240 can be operated to unlock the manual interface 1224 for rotation to disengage the locking collar 1250. A switch 1255 illustratively detects the position of the trigger 1240 and activates a servo motor 1340 to operate a lock pin 1342 to disengage from a normally engaged position with the disk assembly 1232 for rotation. The switch 1255 is illustratively embodied as a reed switch arranged to interact with a magnetic element 203 of the trigger 1240 in one position and to cease interaction in another position to provide a binary indication of the position of the trigger 1240. When the trigger 1240 is depressed, the switch 1255 detects the position of the trigger 1240 in the depressed position and issues a disengagement request (via a controller) to the solenoid to withdrawal the lock assembly and allow rotation of the disk assembly 1232 to translate the locking collar 1250, although in some embodiments, depressing the trigger 1240 may deactivate a signal causing the disengagement request. The servo motor 1340 may require confirmation from other systems prior to activation to disengage the lock assembly, for example, confirmation that appropriate patient support tops are connected with the connection assembly 18. Another reed switch 1344 communicates with a magnetic element 203 of the disk body 1233 when the disk body 1233 is rotated to an unlocked position retracting the pins 1254 from engagement with the flange 1248. The servo motor 1340 and pin 1342 are mounted on a mounting plate 1348 via threaded fasteners 1350 for engagement with the disk assembly 1232.

As shown in FIG. 128, the upper portion of the tower base 12 includes structural portions 1352 secured with the connection post 1422 of the tower base 12 via various threaded fasteners 1351. A solenoid 1354 is connected with an end 1356 of the lever 1249, and is selectively operable between retracted and extended positions (vertically in the orientation of FIG. 128) to pivot the lever 1249 to adjust the tilt position of the connection rod 16 about axis 15. The solenoid 1354 is secured with at least one of the structural portions 1352 via retaining plate 1360 and threaded fasteners 1362. The structural portions 1352 include arched frame member 1364 receiving the connection rod 16 through its arch 1368, and secured with other structural portions 1352 via threaded fasteners 1366. The structural portions 1352 include a bushing 1370 for supporting the connection rod 16, and a cover assembly including disk plate 1372 having a crescent opening 1374 and cover shield 1376 for covering the opening 1374 by securing with the plate 1372 via threaded fasteners 1378. A brace 1382 includes a hole 1384 for receiving a bushing 1386 for supporting the connection rod 16 therethrough.

A traction assembly 1380 is arranged to provide traction to a patient head support on a connection support top. The traction assembly 1380 includes a traction arm 1388 extending horizontal and perpendicular to the axis 15. The traction arm 1388 includes a roller 1390 rotatably pinned by a pin 1391 within a slot of the arm 1388 to guide a traction line from within the connection rod 16, bending (laterally) along roller 1393, which is mounted with the structural portion 1352, and (vertical) along roller 1390 for providing suspended traction weights. A spring assembly 1394 includes a head 1395 engaged with the structural portion 1352 and a spring 1396 engaged with the head 1395 and providing a biasing force against the locking collar 1250 via a ring 1397. The traction line extends through the spring assembly 1394 and the connection rod 16 to provide traction to the patient's head. A number of covers 1398 are connected with structural portions 1352.

Figure 129:
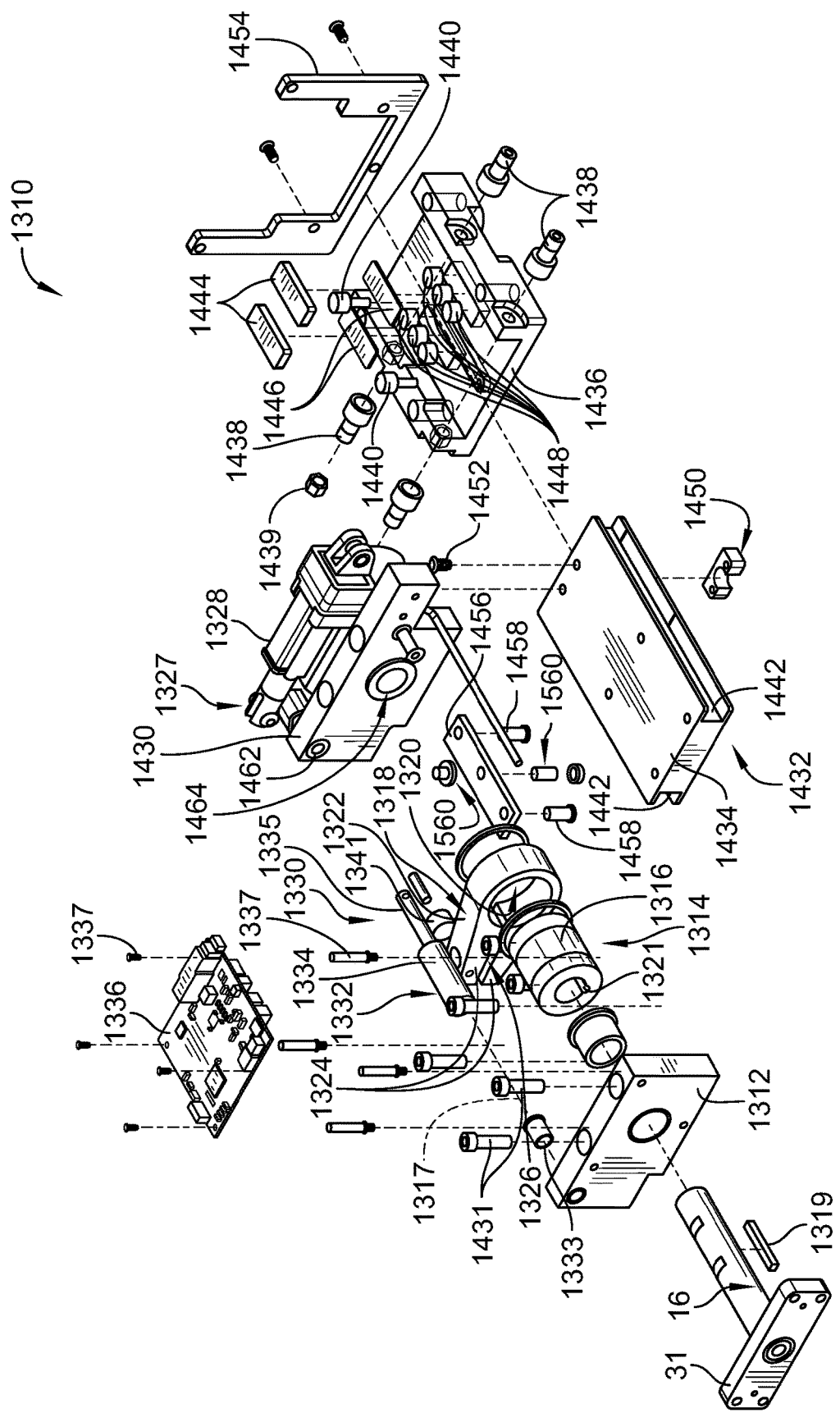
FIG. 129 is an exploded perspective view of a portion of the foot end tower base showing that a connection rod is arranged for selective operation between locked and unlocked states to permit rotation of the connection rod complimentary to the connection rod of the head end tower base.

Referring to FIG. 129, a rotational connection 1310 of the foot end tower base 12 is shown. The rotational connection 1310 includes the connection rod 16 and adapter 31 for connection with the connection assembly 18 of the foot end base tower 12. The connection rod 16 extends through a support wall 1312 for rotational connection with a lockout assembly 1314.

The lockout assembly 1314 provides rotational support of the connection rod 16. The lockout assembly 1314 includes a band clamp 1318 operable for selective clamping to block against rotation of the connection rod 16. The lockout assembly 1314 illustratively includes a bushing 1316 and the band clamp 1318 that supports the bushing 1316. The bushing 1316 is rotationally fixed with the connection rod 16 by a key 1319 and corresponding keyhole 1321 within the bushing 1316. The bushing 1316 resides within an opening 1320 of the band clamp 1318. The band clamp 1318 is selectively operable to clamp the bushing 1316 to block against rotation.

The band clamp 1318 includes a body 1322 defining the opening 1320 and having a pair of wings 1324 spaced apart by a slit 1326. When the wings 1324 are compressed towards each other to reduce the size of the slit 1326, the opening 1320 is reduced in size to clamp the bushing 1316 (and the connection rod 16) against rotation. The band clamp 1318 is selectively operable between an open position (as shown in FIG. 129) having the wings 1324 spaced apart to permit rotation of the bushing 1316 within the opening 1320, and a clamped position having reduced size of the opening 1320 to block against rotation of the bushing 1316.

An actuation assembly 1327 is arranged to operate the band clamp 1318 between the open and clamped positions. The actuation assembly 1327 illustratively includes an actuator 1328 and a cam 1330 in communication with the actuator 1328 to selectively operate the band clamp 1318.

The actuator 1328 is embodied as a linear actuator connected by linkage with the cam 1330 to rotate the cam 1330 along a central axis 1317. The cam 1330 includes a body 1332 defining a radial cam surface 1334 offset from the central axis 1317 to provide eccentric rotation and selective engagement with a roller 1341 the band clamp 1318. The cam 1330 includes a shaft 1335 concentric with the central axis 1317 and linked with the actuator 1328 to receive actuation force for rotation. The cam 1330 includes a bushing connector 1333 extending opposite the shaft 1335 for connection with the support wall 1312. The cam 1330 is operable between an engaged position in which the cam surface 1334 is rotated into engagement with the band clamp 1318 to reduce the size of the slit 1326 to clamp the bushing 1316, and a disengaged position in which the cam surface 1334 does not compress the slit 1326 enabling rotation of the bushing 1316 within the opening 1320. The actuator 1328 is arrangement in communication with other controllers of the patient support via a local controller 1336 which is mounted to the support wall 1312 via fasteners 1337 to provide coordinated locking of the connection rod 16 against rotation. The actuator 1328 is mounted to a plate 1430. The plate 1430 includes a bushing 1462 for receiving the shaft 1335 of the cam 1330 through the plate 1430 for connection with the actuator 1328. The plate 1430 includes rod bushing 1464 for receiving and supporting the connection rod 16 for rotation.

As shown in FIG. 129, the support wall 1312 and plate 1430 are mounted to a slide assembly 1432 via threaded fasteners 1431. The slide assembly 1432 includes a slide rig 1434 connected with the support wall 1312 and plate 1430 on top, slidably mounted on a slide base 1436 to provide translatable positioning of the connection rod 16. The slide rig 1434 is formed as a plate structure having an I-shaped cross-section receiving connection of the wall 1312 and plate 1430. The slide rig 1434 is slidably mounted on the slide base 1436 via rollers 1438, 1440 mounted via nuts 1439 to the slide base 1436. The roller 1438 engage the bottom of the slide rig 1434 (in the orientation of FIG. 129) and rollers 1440 engage a web 1442 of the slide rig 1434.

The slide base 1436 is secured with the connection post 1422 of the tower base 12 to support the slide rig 1434 for sliding. The slide base 1436 includes slide plates 1444 formed as shear bearings supported on spacers 1446. The spacers 1446 are supported by the slide base 1436 by springs 1448, embodied as wave springs providing a resiliently snug fit with the slide rig 1434. A stopper 1450 is illustratively secured via threaded fasteners 1452 to the bottom of the slide rig 1434 to engage the slide base 1436 to prevent over translation of the slide rig 1434. A mounting bracket 1454 is connected with the slide base 1436 for receiving connection with outer coverings of the tower base 12. A mounting platform 1456 is secured spaced apart from the top of the slide rig 1434 via fasteners 1458 to support the band clamp 1318 via a support foot 1560 for arrangement between the clamped and unclamped positions.

Figures 130, 131:
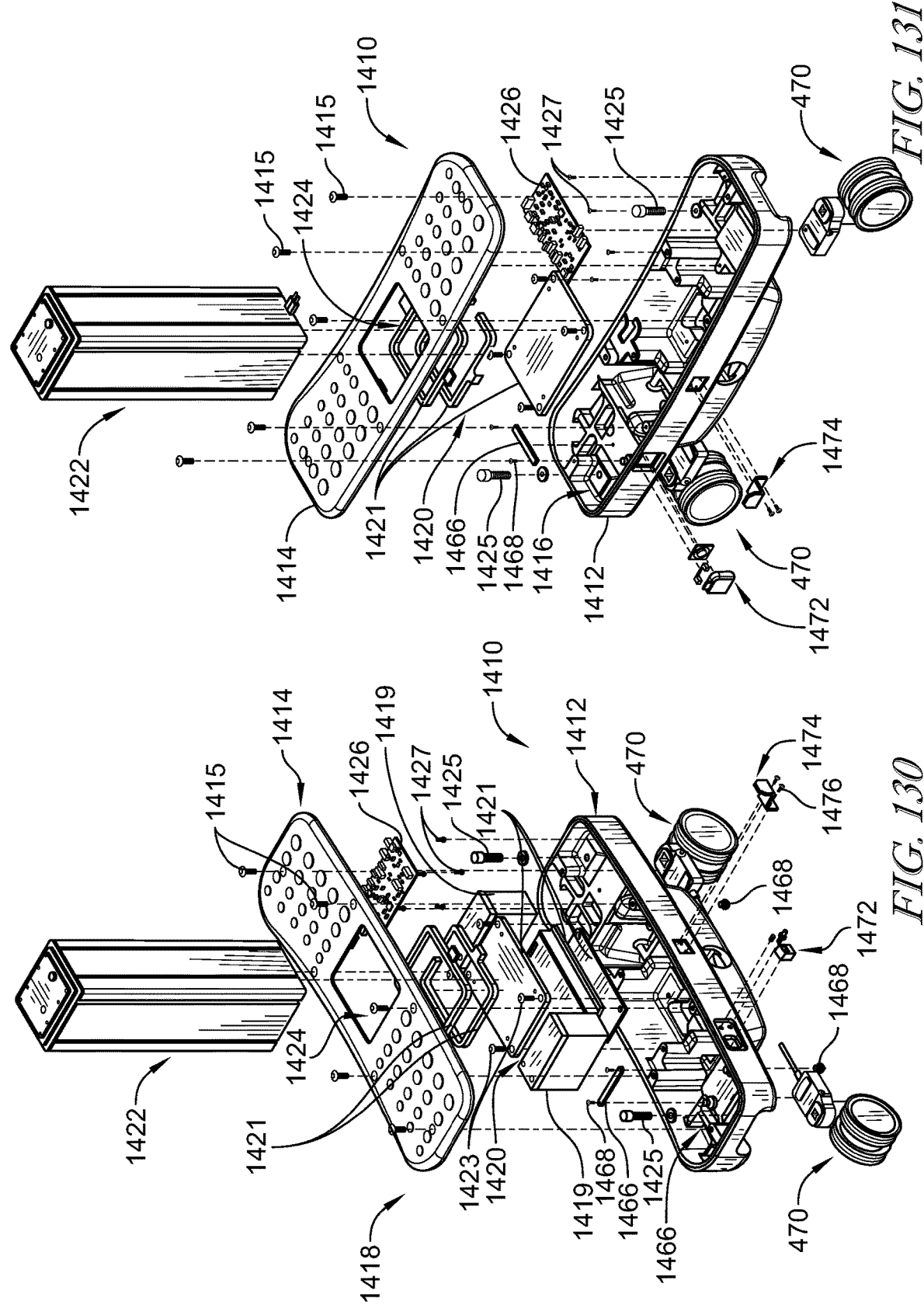
FIGS. 130 and 131 are exploded perspective views of a lower portion of the tower bases showing their internal support structure.

Referring now to FIG. 130, a lower portion of the head end tower base 12 is shown in exploded view. The tower base 12 includes a base member 1410 having a lower member 1412 and an upper member 1414 secured together via threaded fasteners 1415 to define an enclosed space 1416. The enclosed space 1416 can house a variety of components, for example, power components, such as batteries 1419 and/or converters. A support assembly 1418 connects with the lower member 1412 within the enclosed space 1416.

The support assembly 1418 illustratively includes a connection platform 1420 and a connection post 1422. The connection platform 1420 includes stacked portions 1421 secured via threaded fasteners 1423 with the lower member 1412 within the enclosed space 1416 and the connection post 1422 is connected with the connection platform 1420 and extends through an opening 1424 in the upper member 1414 to provide height of the tower base 12 to support the upper portion.

A pair of casters 470 are connected with the base member 1410 via threaded fasteners 1425 extending through the base member 1410 for connection with each caster 470 to support the tower base 12 above the floor. A counter brace 1466 is secured with an end of the each caster 470 through the base member 1410 via threaded fasteners 1468. The casters 470 are operable between their locked and unlocked states using the GUI 180 via a local controller 1426 and the control system 184. The local controller 1426 is illustratively mounted via threaded fasteners 1427 within the enclosed space 1416 and arranged in communication with the casters 470 and the control system 184. A number of ports 1472 may be connected with the base member 1410 for receiving connection with other systems, such as electrical power systems and/or communication systems. A bracket 1474 is mounted via threaded fasteners 1476 with the base member 1412 to support accessories.

Referring to FIG. 131, a lower portion of the foot end tower base 12 is shown in exploded view. The tower base 12 includes the base member 1410 having lower and upper members 1412, 1414 similar to the head end tower base 12. The tower base 12 includes a pair of casters 470 operable between their locked and unlocked states by the GUI 180 via a local controller 1426 and control system 184. The base member 1410 of each head end and foot end base towers 12 illustratively includes sensors for determining a state of the casters 470 between their locked and unlocked states for communication to the control system 184.

Referring to FIG. 132, an outer covering 1510 of the head end tower base 12 provides exterior protection of the tower base internals. The outer covering 1510 includes a front section 1512 and pair of side sections 1514, 1515. The front section 1512 is formed as a molded panel including a base section 1516 extending from connection with the base member 1410 and an interface section 1518 extending from the base section 1516 having an upward angle to face towards a user for ergonomic access. The interface section 1518 defines an opening 1520 having an interface bezel assembly 1522 fitted therein for receiving the GUI 180 for access by the user. The front section includes a connection edge 1524 defined collectively by the base and interface sections 1516,1518 for engagement with the side sections 1514.

The side sections 1514, 1515 are each formed as molded panels having a lateral section 1526 and rear section 1528 connected with each other to define a corner 1530. The lateral sections 1526 each define a front edge 1532 and the rear sections 1528 each define an inner edge 1534. The front edges 1532 each engage with the front section 1512. The inner edges 1534 of each side section 1514, 1515 engage with each other to connect the side sections 1514, 1515 together. Each of the side sections 1514, 1515 defines a portion 1535 of an opening for allowing penetration of the connection rod 16 through the outer covering 1510. The lateral section 1526 of the side section 1515 illustratively includes an opening 1537 for receiving the manual interface 1224 of the rotational lockout assembly 1210 for access by the user. The outer covering 1510 defines an interior space 1538 for housing the internals, such as the upper portion of the tower base 12 and certain portions of the lower portion of the tower base 12. The outer covering 1510 includes a base ring 1539 for engaging the interior of the lower ends of each of the front and side sections 1542, 1544 to reinforce their connection with the base member 1410. A number of trim sections 1545 are mounted with the side sections 1514, 1515. A data port 1547 is mounted in a receptacle 1551 of the side section 1514 for receiving connection with other communication systems such as diagnostic tools.

As shown in FIG. 133, an outer covering 1540 of the foot end tower base 12 is similar to the outer covering 1510 and includes front 1542 and side sections 1544 for collectively defining an interior space 1546. The front section 1542 is formed as a molded panel including a base section 1548 extending from connection with the base member 1410 and an interface section 1550 extending from the base section 1548 having an upward angle, however, in the illustrative embodiment, the interface section 1550 does not include an interface opening as the GUI 180 is arranged only in the head end tower base 12. The side sections 1544 each include front edges 1552 for engagement with the front section 1540, and interior edges 1554 for engagement with each other to define the interior space 1546. The side sections 1544 each define a portion of an opening 1556 to allow penetration of the connection rod 16 through the outer covering 1540. The outer covering 1540 includes a base ring 1549 for engaging the interior of the lower ends of each of the front and side sections 1542, 1544 to reinforce their connection with the base member 1410.

Figure 134:
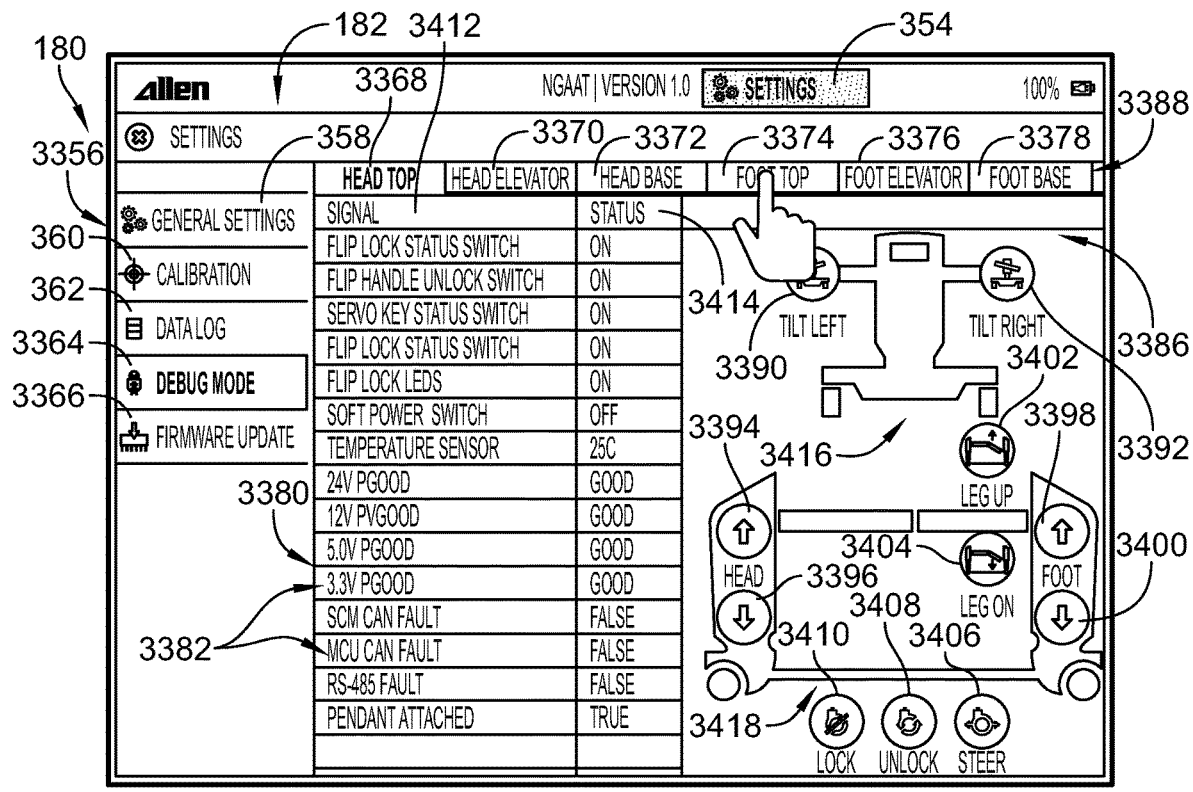
FIGS. 134 and 135 are screen shots of the display of the patient support of FIGS. 1-4 similar to FIG. 80 showing that responsive to user selection of a debug tab of the settings menu, a debugging mode is entered, and showing that a number of debugging systems are available for user selection including head top, head elevator, head base, foot top, foot elevator, foot base, and showing that upon selection of one of the debugging systems, a debugging list (left) is presented together with a debugging operation screen (right)

Referring to FIG. 134, the settings button 354 has been selected as indicated by the highlighting of the button 354 (indicated by fill and bolding in FIG. 134) to present another embodiment of a settings menu, similar to settings menu disclosed with respect to FIGS. 76-116. The disclosure regarding the settings menu of FIGS. 76-116 applies equally to the settings menu disclosed in FIGS. 134-136, except in instances of conflict with the specific disclosure of the settings menu of FIGS. 134-136.

As shown in FIG. 134, a navigation bar 3356 offers the user selection of the general settings tab 358, calibration tab 360, and data log tab 362. The navigation bar 3356 includes a debug tab 3364 similar to the debug tab 364, and a firmware tab 3366. Responsive to selection of the debug tab 3364, the GUI 180 enters a debugging mode and presents a menu of area tabs 3388 indicating areas of the patient support 10 for debugging.

The menu tabs 3388 includes a head top tab 3368, head elevator tab 3370, head base tab 3372, foot top tab 3374, foot elevator tab 3376, and foot base tab 3378. Each of the menu tabs 3388 are selectable by touch activation to present a debugging menu corresponding with the selected tab. For example, the head top tab 3368 is presently active (as indicated by bolding in FIG. 134) which presents a debugging menu 3380 having corresponding debug features 3382 of the head end portion of the support top presently attached. For example, the debug features 3382 of the head end portion include a signal column 3412 and status column 3414 indicating a feature and its corresponding status, including a signal such as flip lock status switch, flip handle unlock switch, servo key status switch, flip lock status switch, flip lock LEDS, soft power switch, temperature sensor, 24 volt power, 5 volt power, 3.3 volt power, SCM Can fault, MCU Can fault, RS-485 fault, and pendant attached, and a corresponding status such as on/off, good/bad, temperature reading, and true/false, as appropriate to the signal type.

As shown in FIG. 134, a debugging control map 3386 is presented having selectable control buttons 3390-3410 for adjustment of the patient support position while in the debugging mode. The debugging control map 3386 includes graphical depictions of the patient support 3416, 3418. The depictions include a 2-dimensional representation of the patient support as a plan view from the head end 3416 having tilt left and tilt right buttons 3390, 3392 positioned on corresponding sides of the representation to selectively adjust the lateral tilt of the support top while in the debugging mode, and a 2-dimensional representation of the patient support as a plan view from a lateral side 3418 having head end elevator tower raise and lower buttons 3394,3396 to selectively adjust the height of the head end tower base 12, foot end elevator tower raise and lower buttons 3398, 3400 to selectively adjust the height of the foot end tower base 12, and leg up and down buttons 3402, 3404 to selectively adjust the position of the leg drop portion, each button being positioned at locations relative to the representation corresponding to its operation.

Figure 135:
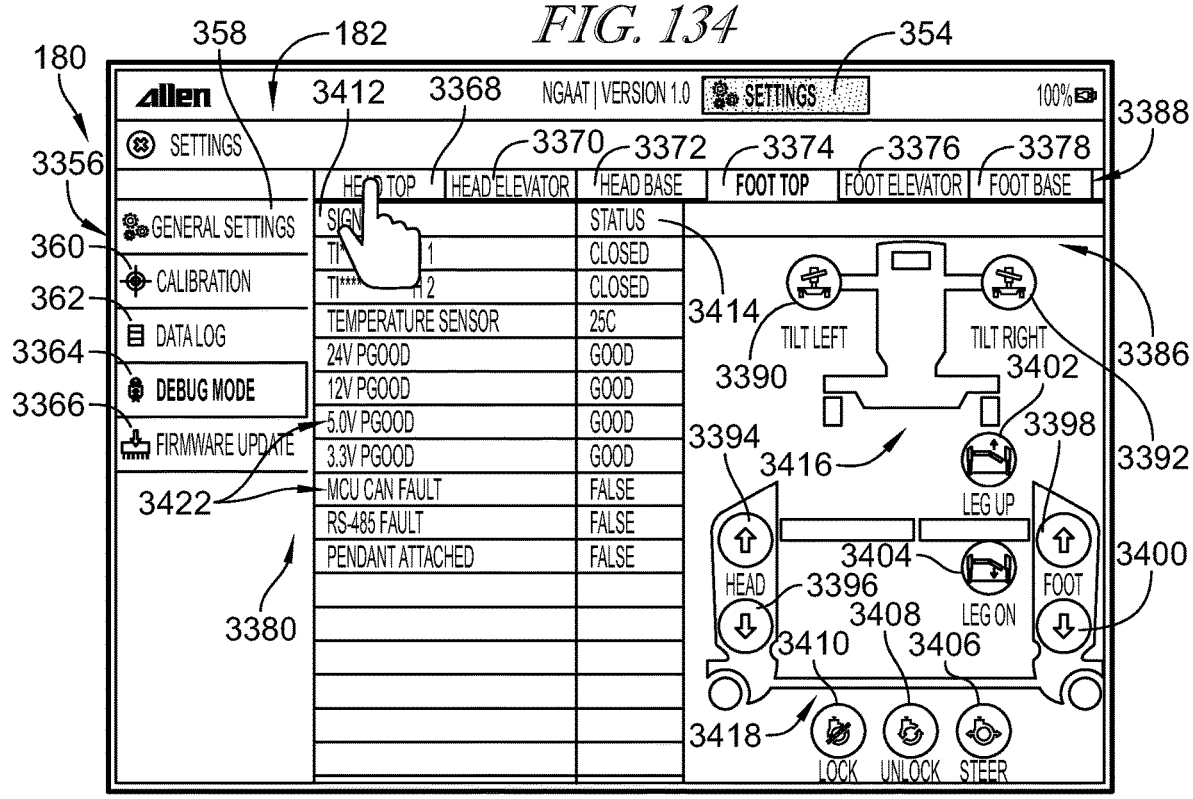

Referring to FIG. 135, the foot top tab 3374 has been activated (as indicated by bolding in FIG. 135) which presents the debugging menu 3380 having corresponding debug features 3422 of the foot end portion of the support top presently attached. For example, the debug features 3422 of the foot end portion include a signal column 3412 and status column 3414 indicating a feature and its corresponding status, including a signal such as tilt lock status switch 1, tilt lock status switch 2, temperature sensor, 24 volt power, 5 volt power, 3.3 volt power, MCU Can fault, RS-485 fault, and pendant attached, and a corresponding status such as on/off, temperature reading, good/bad, and true/false, as appropriate to the signal type.

The debugging control map 3386 is presented having selectable control buttons 3390-3410 for adjustment of the patient support position while in the debugging mode. The debugging control map 3386 includes graphical depictions of the patient support 3416, 3418. The depictions include a 2-dimensional representation of the patient support as a plan view from the head end 3416 having tilt left and tilt right buttons 3390, 3392 positioned on corresponding sides of the representation to selectively adjust the lateral tilt of the support top while in the debugging mode, and a 2-dimensional representation of the patient support as a plan view from a lateral side 3418 having head end elevator tower raise and lower buttons 3394,3396 to selectively adjust the height of the head end tower base 12, foot end elevator tower raise and lower buttons 3398, 3400 to selectively adjust the height of the foot end tower base 12, and leg up and down buttons 3402, 3404 to selectively adjust the position of the leg drop portion, each button being positioned at locations relative to the representation corresponding to its operation.

Figure 136:
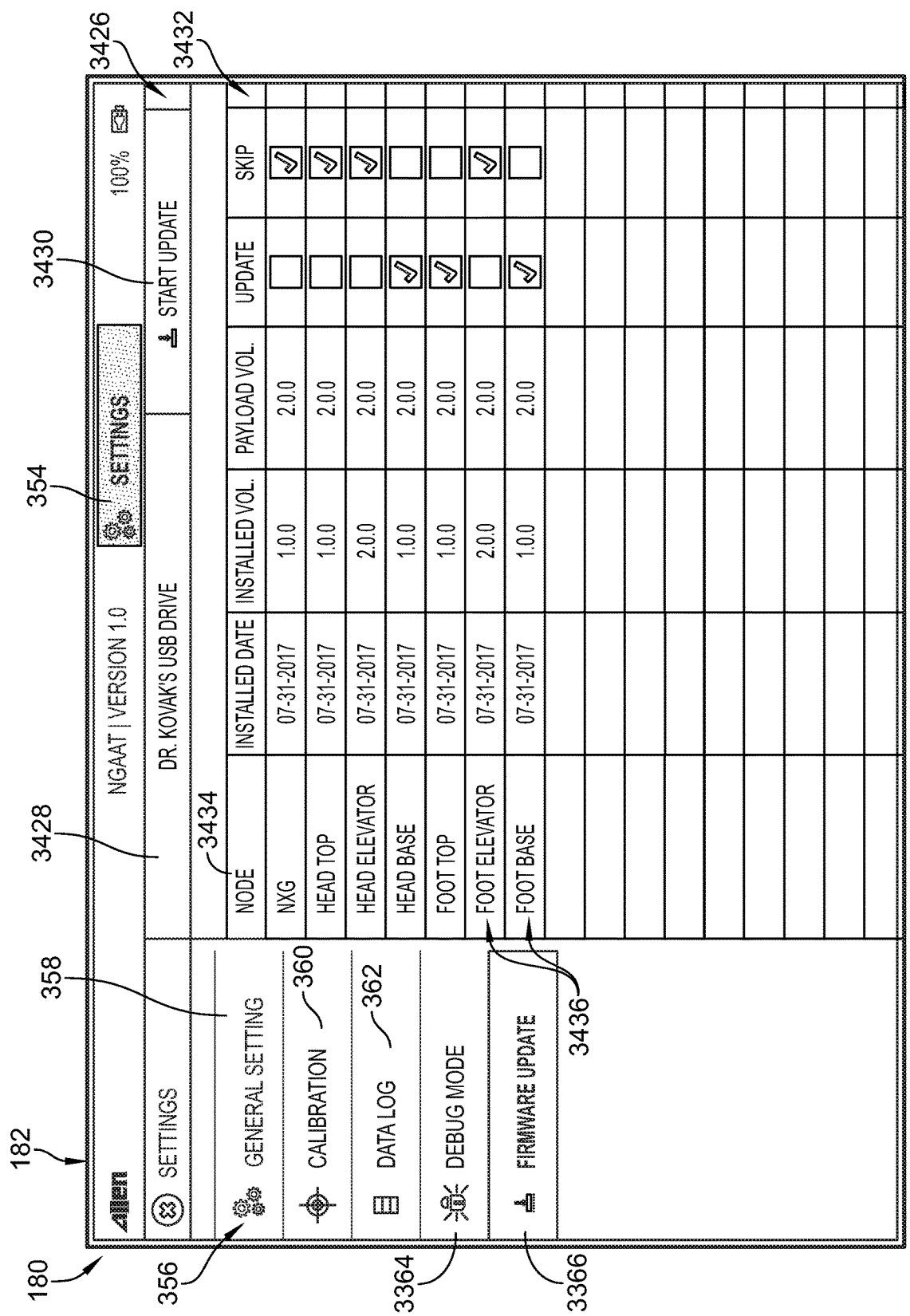
FIG. 136 is a screen shot of the display of the patient support of FIGS. 1-4 similar to FIG. 76 showing that responsive to user selection of a firmware tab of the settings menu, a update mode is entered, and showing that an update list is presented for user selection of firmware for update.

As shown in FIG. 136, the firmware update tab 3366 has been selected presenting a firmware update menu 3426. The firmware update menu 3426 includes a USB box 3428 indicating the name of the attached universal serial bus (USB) storage device as "Dr. Kovak's USB Drive" which illustratively stores the payload firmware updates for consideration, although firmware updates can also be provided via any suitable medium, including but without limitation via a network. The firmware update menu 3426 includes a start update button 3430 for user selection to initiate payload firmware updating according to the selected configuration.

The firmware update menu 3426 includes a configuration menu 3432 including a table of columns including a node identifier 3434 column having rows of update features 3436 including NXG, head top, head elevator, head base, foot top, foot elevator, and foot base features. The columns include an installation date column 3438, installed version 3440, payload version 3442 to be installed, and selectable options of update 3444 and skip 3446. The menu 3426 illustratively default to select the update option for each feature which has a less recent installed version than the payload version and illustratively defaults to the skip option for features having an installed version equal to or later than the payload version, and the user can selective alter the selected option for each feature as desired. For example, the user has opted to skip the firmware update for the head top feature to maintain the installed version 1.0.0 by touch activating the corresponding skip option. Similarly, the user observing that the foot elevator firmware is up-to-date with installed version 2.0.0 equal to the payload version 2.0.0 may elect to still update this portion of the firmware by touch activation of the update option. Upon preferred configuration of the configuration menu 3432, the user can select the start update button 3430 to initiate firmware update by touch activation.

Figure 137:
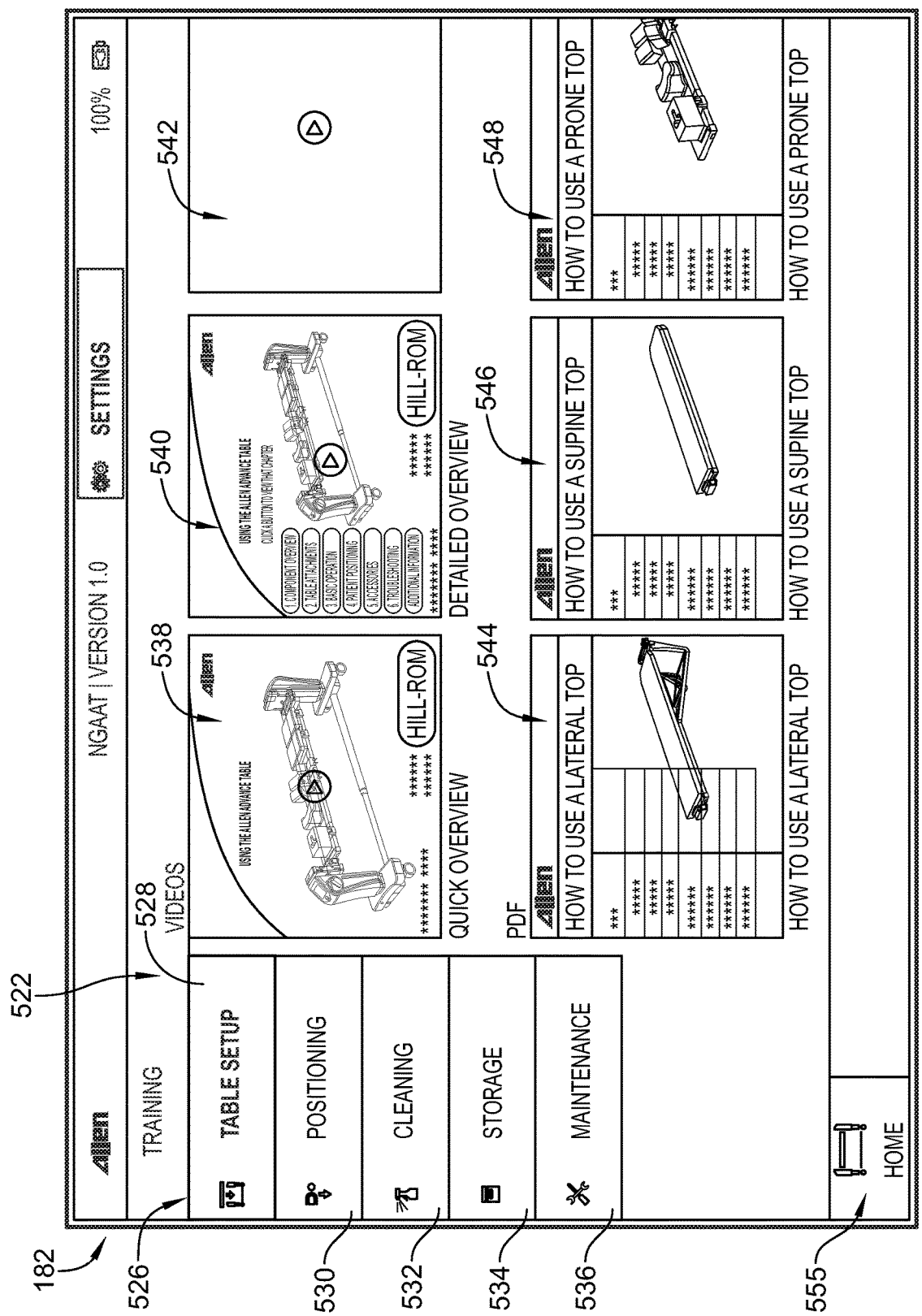
FIG. 137 is a screen shot of the display of the patient support of FIGS. 1-4 showing that responsive to user selection of a training button, a training mode is entered to provide selectable tabs for training including the presently selected table setup, positioning, cleaning, storage, and maintenance training information, and showing that a number of video recordings and reading materials are available for user selection regarding the presently selected tab.

Referring to FIG. 137, responsive to user selection of the training button 520 (for example, from FIG. 27), a training mode is entered presenting a training menu 522. In the training menu 522, a navigation bar 526 is presented including tabs 528-536, having a table setup tab 528, a positioning tab 530, a cleaning tab 532, a storage tab 534, and a maintenance tab 536. The table setup tab 528 is presently selected as indicated by highlighting the tab 528 (represented as bolding). As the setup tab 528 is presently selected, a number of video recordings selections 538-542 and slide show materials 544-548 are displayed for user selection. The video recordings selections include quick overview 538 and detailed overview 540 and the slide show materials include lateral top 544, supine top 546, and prone top 548 instructions. A home button 555 is presented which upon selection, exits the training mode to the previous screen.

Figure 138:
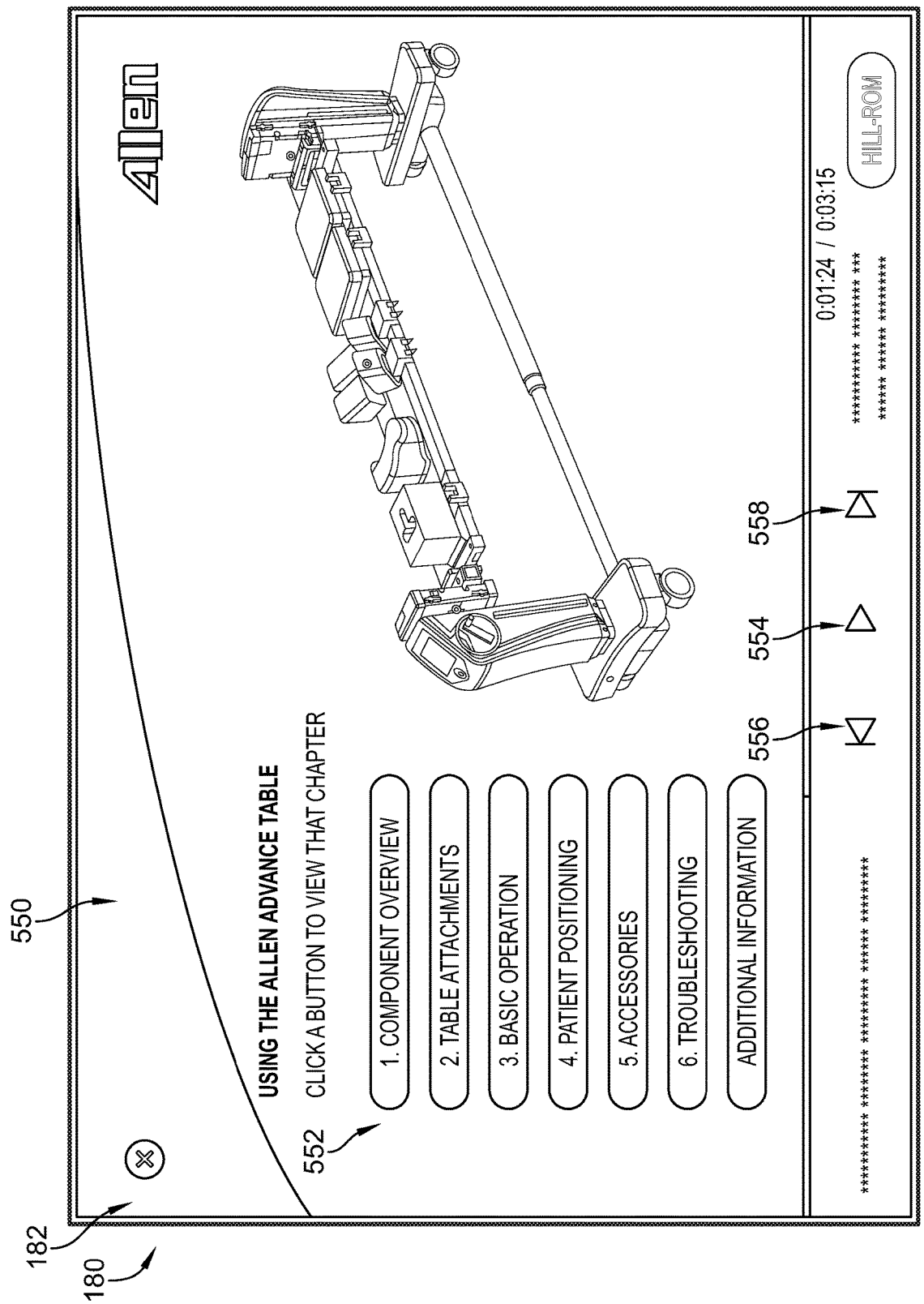
FIG. 138 is a screen shot of the display of the patient support of FIGS. 1-4 showing that a video recording has been selected by the user and that the video recording has begun playing.

Referring to FIG. 138, the detailed overview selection 540 has been selected to present a detailed overview screen 550. The detailed overview screen 550 includes a number of selectable chapters 552 which can responsively skip to the appropriate section of the video. The selectable chapters illustratively include components overview, table attachments, basic operation, patient positioning, accessories, troubleshooting, and additional information. An elapsed time compared with the run time is displayed and navigation icons for play 554, backward 556, and forward 558 navigation are presented for user selection. A cancel button 560 is presented in the top left hand corner and upon selection returns to the training menu 522.

Figure 139:
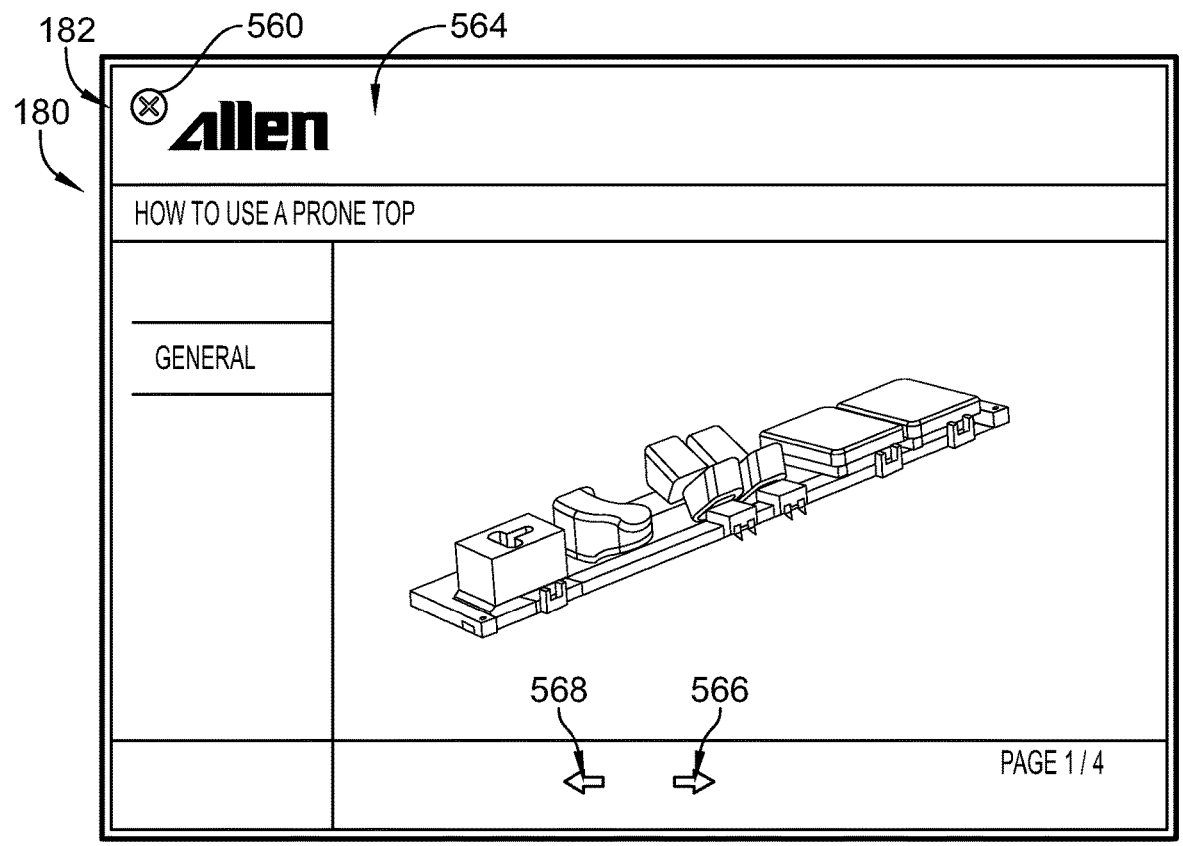
FIG. 139 is a screen shot of the display of the patient support of FIGS. 1-4 showing that one of the reading materials as a slide show of the table setup tab of FIG. 137 has been selected to provide a slide sequence of materials indicating how to use a prone top of the patient support.

Referring to FIG. 139, supine top instructions 546 have been selected to present a supine top instruction screen 564. The number of the present slide over the total slides is shown and navigation controls including forward and reverse tabs 566, 568. Selection of the cancel button 560 returns to the training menu 522.

Figure 140:
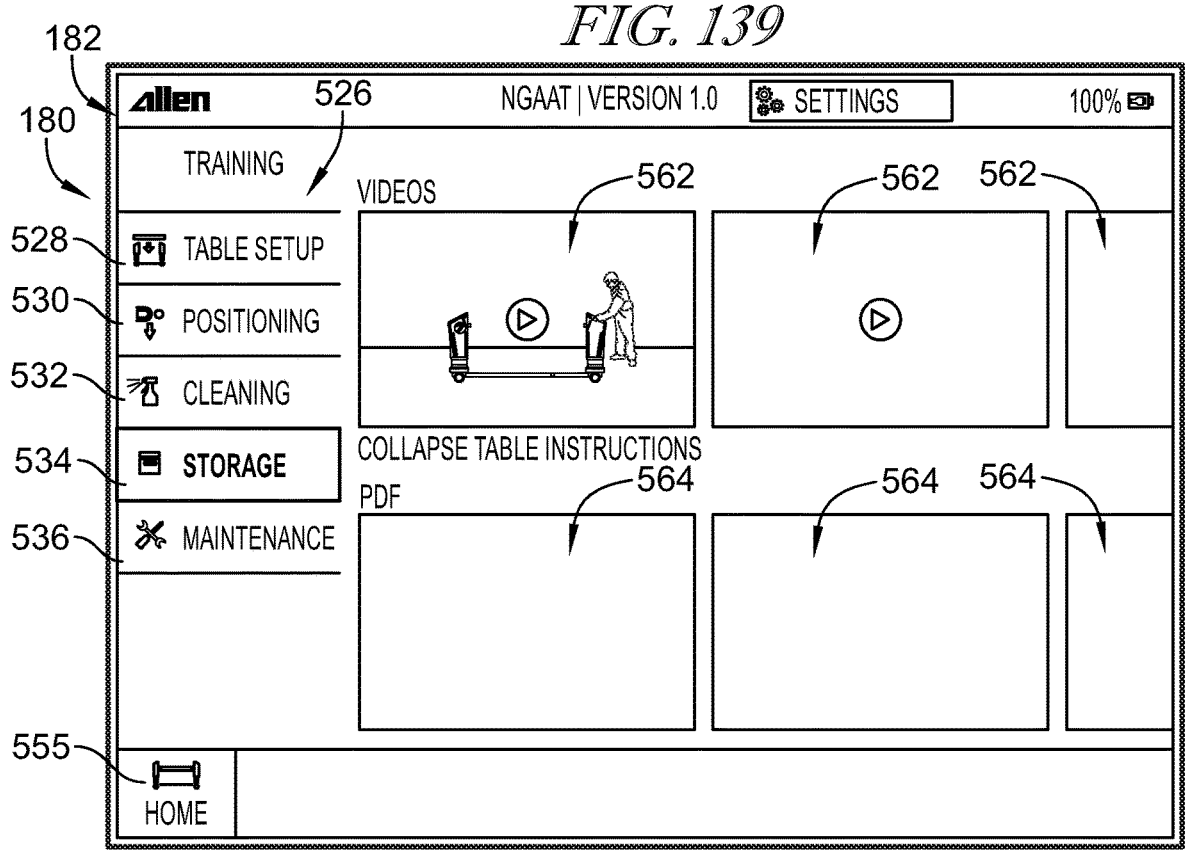
FIG. 140 is screen shot of the display of the patient support of FIGS. 1-4 showing that the user has selected the storage tab to present a number of storage-related video recordings and reading materials.

Referring to FIG. 140, the storage tab 534 has been selected to present video recording selections 562 related to storage operations, such as table collapse instructions, and slide show materials 564. Additional materials may be revealed by panning right (by swipe). Selection of the particular video recording 562 or slide show materials 564 advances to display the corresponding information in similar manner as described regarding the table setup tab 528.

Referring to FIGS. 141-146, a number of screen shots are shown for positioning the patient support, similar to the manner described as to FIGS. 33-39. However, in the alternative to the various adjustment bars, adjustment buttons are provided to control the position of the patient support 10. The adjustment buttons are generally represented with a body having at least partially transparent form to allow visually rearward components to be seen and a directional arrow corresponding to the direction of movement adjustment upon activation of that particular button. Each of the buttons operate to adjust the corresponding parameter of the patient support as indicated below between its operational limits with continued engagement (contact or near contact) of the respective button, and adjustment is halted upon disengagement (release or removal from close proximity) with the respective button. Engagement of a particular button is graphically depicted by highlighting the particular button (indicated by fill and/or bolding). The GUI 180 depicts the transitioning position of the tower base 12D as the adjustment is performed.

Figure 141:
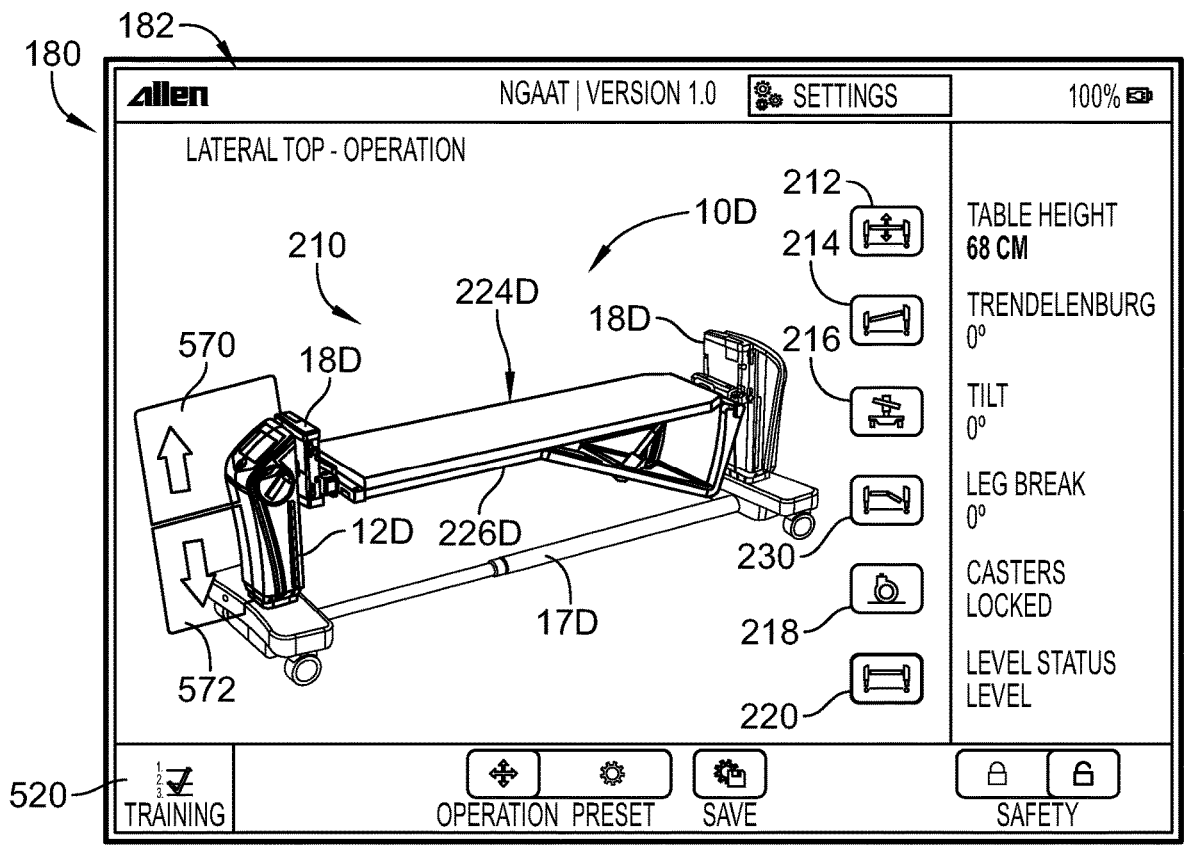
FIGS. 141-146 are a number screen shots of the display of the patient support of FIGS. 1-4, similar to FIGS. 33-39, showing alternative interface options including position adjustment tabs for adjusting the position of the patient support according to user preference.

As shown in FIG. 141, the 3D depiction 210 is shown similar to FIG. 33, including adjustment buttons 570, 572. The user has selected the tower base 12 at the head end for adjustment. The user has selected the head end tower base 12 by directly touching on (or hovering near for a minimum time) the indication of the head end tower base 12D on the screen 182. Selection of the head end tower base 12D is indicated by highlighting the head end tower base 12D and support top 224D (represented by bolding in FIG. 141).

As shown in FIG. 141, responsive to the user's selection of the head end tower base 12D, the adjustment buttons 570, 572 are displayed near the head end. The adjustment buttons 570, 572 is embodied as a selectable upward button 570 and a selectable downward button 572 arranged in a stacked configuration similar to the intended direction of movement of each respective button. The user can selectively engage (contact or near contact) the upward button 570 to adjust the height of the head end tower base 12 higher, and can selectively engage the downward button 572 to adjust the height of the head end tower base 12 lower (independently from the height of the foot end tower base 12). The GUI 180 depicts the transitioning height of the head end tower base 12D as the height adjustment is performed.

Figure 142:
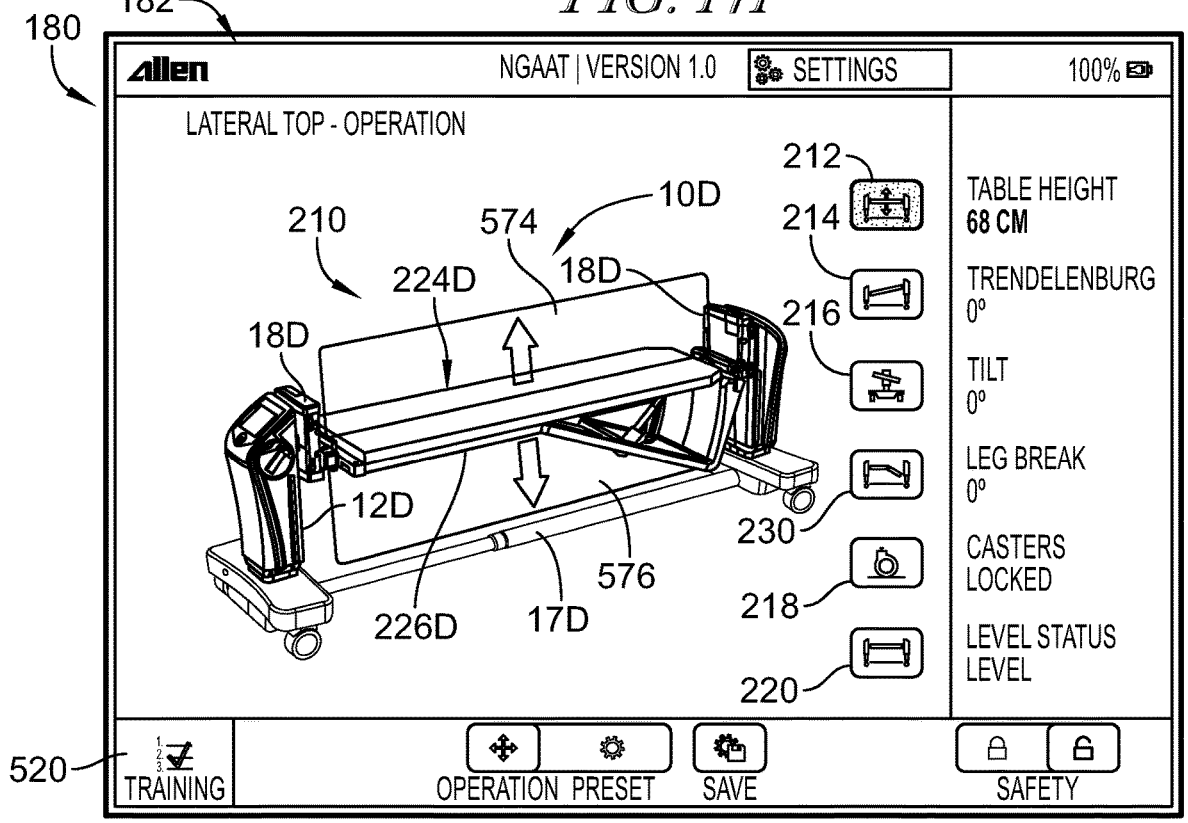

Referring to FIG. 142, the table height icon 212 has been selected by the user. The table height icon 212 selection is indicated by highlighting of the icon 212 (represented by fill of icon 212) and highlighting the tower bases 12D and support top 224D (represented by bolding). Notably, previously selected features are illustratively deselected (no longer bolded) and the associated adjustment buttons have been removed. Table height adjustment buttons 574, 576 are presented in front of the patient support 10D near the middle of the patient support 10D. The adjustment buttons 574, 576 are embodied as a selectable upward button 570 and a selectable downward button 572 arranged in a stacked configuration similar to the intended direction of movement of each respective button. The user can selectively engage (contact or near contact) the upward button 574 to adjust the height of the patient support 10 higher, including coordinated raising of each tower base 12, and can selectively engage the downward button 576 to adjust the height of the patient support 10 lower, including coordinated lowering of each tower base 12.

Adjustment of the patient support height using the adjustment buttons 574, 576 provides simplified adjustment of the height of both of the tower bases 12 simultaneously. The GUI 180 depicts the transitioning height of the support top 224D and presents the current table height information (right of icon 212) as the height adjustment is performed.

Figure 143:
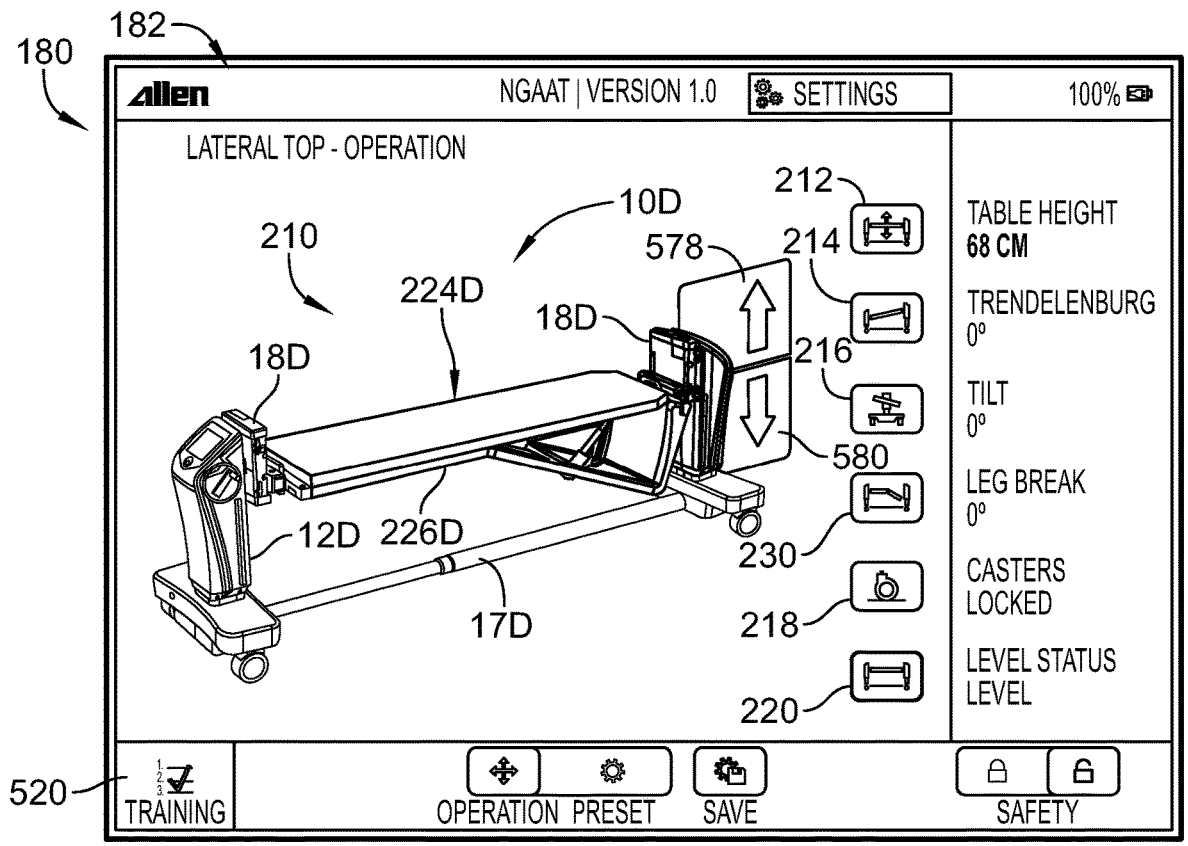

As shown in FIG. 143, an adjustment operation of the foot end tower base 12 is shown. Responsive to the user's selection of the foot end tower base 12D, the foot end tower base 12D and the lateral support top 224D are highlighted (represented as bolding), and height adjustment buttons 578, 580 are displayed near the foot end. Notably, previously selected features (e.g., head end tower base 12D) are illustratively deselected (no longer bolded) and the associated adjustment buttons have been removed. The adjustment buttons 578, 580 are embodied as a selectable upward button 578 and a selectable downward button 580 arranged in a stacked configuration similar to the intended direction of movement of each respective button. The user can selectively engage (contact or near contact) the upward button 578 to adjust the height of the foot end base tower 12 higher, including coordinated raising of each tower base 12, and can selectively engage the downward button 576 to adjust the height of the foot end base tower 12 lower, (independently from the height of the head end tower base 12). The GUI 180 depicts the transitioning height of the foot end tower base 12D as the height adjustment is performed.

Figure 144:
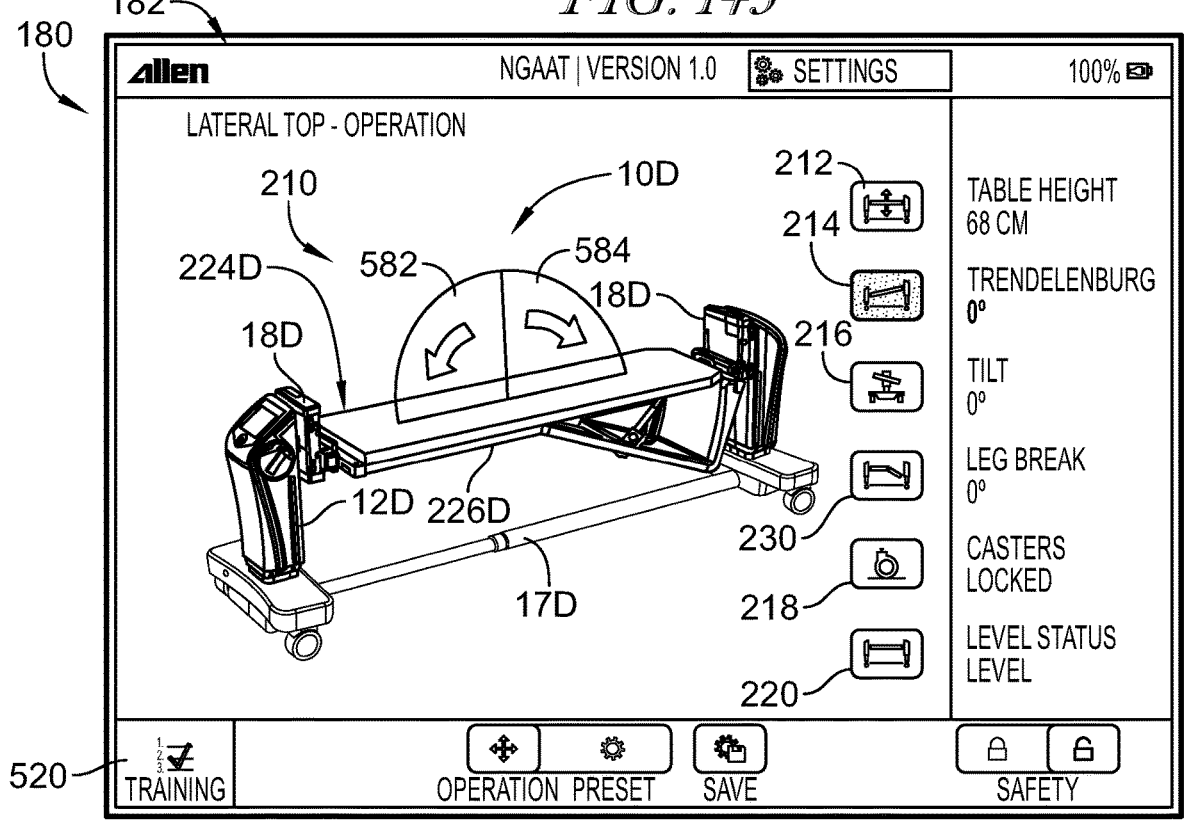
Figure 145:
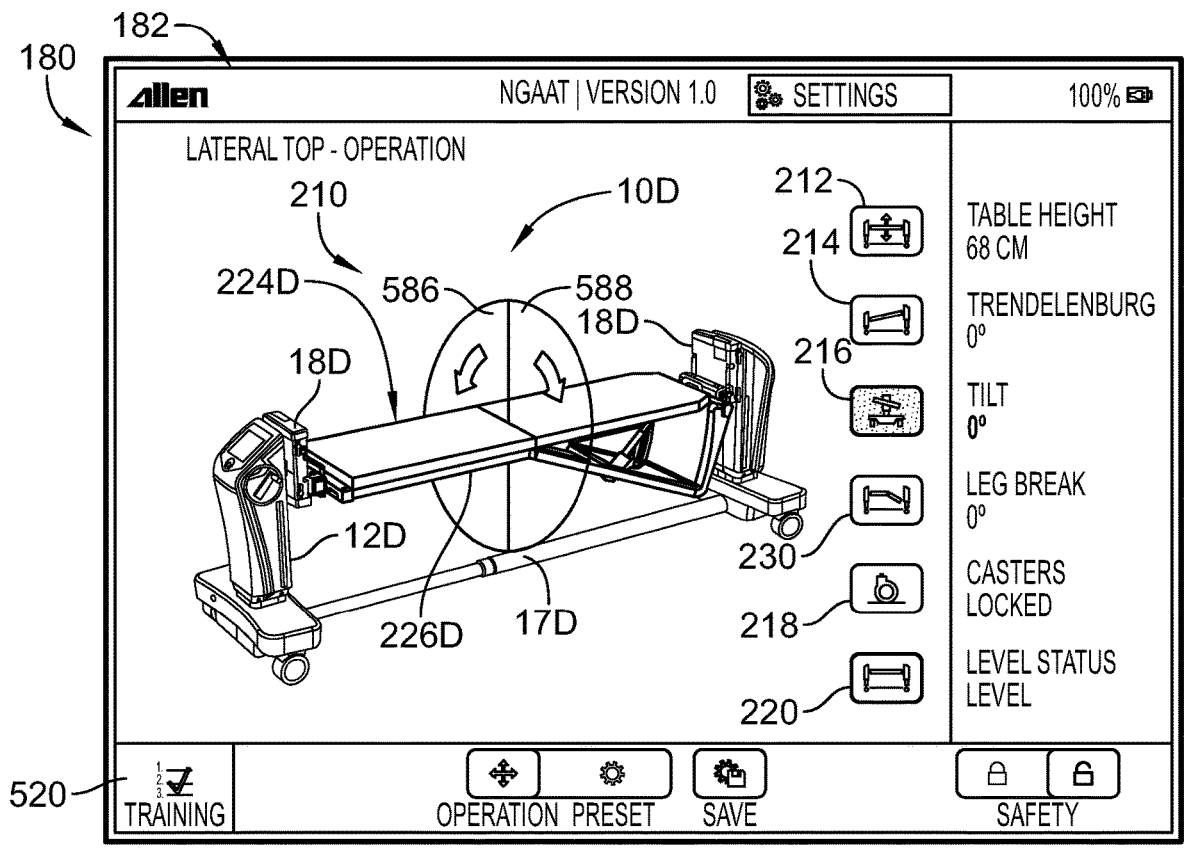

As shown in FIG. 144, the tilt icon 216 has been selected by the user by engagement with the icon 216. The selection is indicated by highlighting the icon 216 (represented by fill of icon 216) and highlighting the support top 224D (represented by bolding). Notably, previously selected features are illustratively deselected (no longer bolded) and the associated adjustment buttons have been removed. The tilt adjustment buttons 586, 588 are embodied as a selectable counterclockwise button 578 and a selectable clockwise button 580 each button having semi-circular shape to suggest the intended direction of movement for each respective button and arranged in a side-by-side configuration to form a circle. The user can selectively engage (contact or near contact) the counterclockwise button 586 to adjust the tilt position of the support top 14 towards the counterclockwise direction (relative to the perspective view in FIG. 145), including coordinated rotation of each connection assembly 18 via the connection rod 16, and can selectively engage the clockwise button 588 to adjust the tilt position of the support top 14 towards the counterclockwise direction (relative to the perspective view in FIG. 145), including coordinated rotation of each connection assembly 18 via the connection rod 16. The GUI 180 depicts the transitioning tilt angle of the support top 224 (as 224D) and presents the current tilt information (right of icon 216) as the tilt adjustment is performed.

Figure 146:
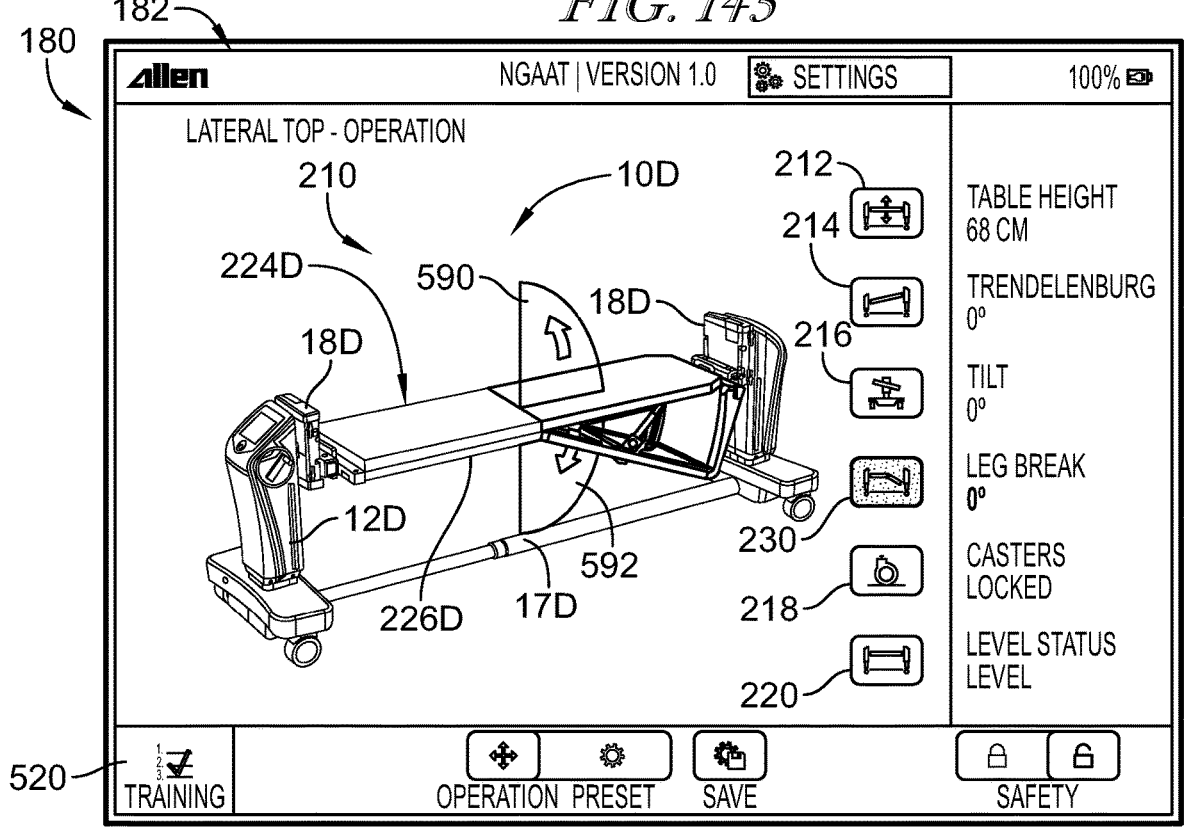

As shown in FIG. 146, the leg break icon 230 has been selected by the user to activate the leg break adjustment. The selection of the leg break icon 230 is indicated by highlighting the icon 230 (represented by fill of icon 230) and highlighting the leg portion of the support top 224D (represented by bolding). Leg break adjustment buttons 590, 592 are illustratively presented near the leg portion of the support top 224D each having quarter-circle shape. The quarter-circle shape of each buttons illustratively extends in a plane defined in the vertical dimension and the longitudinal dimension of the support top 224D, such that the quarter-circle shape is flat or without dimensional thickness can suggest the direction of movement achieved by the respective button. The leg break adjustment buttons 590, 592 are arranged respectively above and below the support top 224D and separated by the support top 224D to form a semi-circle corresponding to the available movement of the leg portion of the support top 224D under leg break adjustment (pivoting of the leg portion about the mid-section of the support top 224D corresponding with the patient's hip in the lateral position). The user can selectively engage (contact or nearly contact) the upward button 590 to adjust the angle of leg break of the support top 14 upward (counterclockwise relative to the perspective view in FIG. 146), and can selectively engage the downward button 592 to adjust the angle of leg break of the support top 14 downward (counterclockwise direction relative to the perspective view in FIG. 146). The GUI 180 depicts the transitioning leg break angle of the support top 224D and presents the current leg break angle information (right of icon 230) as the leg break adjustment is performed.

Current operating room tables, for example, the Allen Advance Table (AAT) available from Allen Medical Systems, Inc. of Batesville, Indiana—and many other two-column operating room tables indicated for complex spinal procedures— can allow the user to perform a 180 degree flip of the patient for procedures that require anterior and posterior incisions. The present disclosure includes devices, systems, and methods for performing a rotation flip of a patient's body. The present disclosure includes rotation flip of the patient while initially supported by a supine top (with the patient in the supine position) and a secondary prone top positioned above the patient. This prone top attached to the table and adjusted to secure or sandwich the patient in preparation for a rotation flip. A member of the clinical staff can release a Flip Rotation Axis (FRA) of the table by activing a rotation lever. Activating the lever can be achieved by a two-step process including depressing a trigger and rotating the lever. In some embodiments, a safety button must first be depressed before pulling the trigger. Upon release of the FRA, the clinical staff can manually roll the sandwiched patient 180 degrees along the longitudinal axis, thereby flipping the patient. A member of the clinical staff can lock the FRA by re-engaging the lever. After flip rotation, with the patient fully supported by the prone top, the supine top can be detached from the table.

As described above, releasing the FRA is necessary in order to flip the patient. Under unintentional or unknowing release the BRA, the patient could be subjected to a hazardous situation, potentially resulting in patient harm. For example, if a patient is on the table and supported only by a single top (i.e. they are not sandwiched between two tops) and the FRA is released, the patient could be dropped. Additionally, if the patient is transferred from a gurney or stretcher to the table and the FRA is released, the patient could also be dropped. Although certain risks can be reduced by providing notification to the user that the FRA is released, without active lockout of the BRA from being released (absent confirmation criteria), fall risks can persist. Affirmative safety lockout can avoid releasing the FRA when there is only one top secured with the table.

The present disclosure can include a functional behavior of the table. If a user attempts to activate the rotation lever to release the FRA without confirming the desire for release by at least one of additional input and confirmation signal, the BRA will not be permitted to release. For example, in some embodiments, release of the FRA requires depressing a safety trigger together with manual rotation of the rotation lever. In some embodiments, when a presence sensing system determines that there is only one patient support top connected with the connection bar of the table, the table will prevent the FRA from being released. The user will be notified that this release action is not allowed upon pressing the trigger and/or safety button (the first steps in the process of activating the lever).

The present disclosure includes devices, systems, and methods for top presence sensing wherein the table can include one or more sensors to detect the number of support tops attached with the connection bars, for example, whether one or two tops are attached to the table. The present disclosure includes devices, systems, and methods for Flip Rotation Axis (FRA) lockout wherein the table can include an actuator and lockout assembly that can selectively allow or prevent the activation of the lever that releases the FRA. The present disclosure includes devices, systems, and methods for Graphical User Interface (GUI) wherein the table can include display means for displaying an indication that the FRA cannot be released in the event that there is one top on the table and the user attempts release, (e.g., presses the trigger or the safety button (the first steps in activating the lever). The present disclosure includes devices, systems, and methods for system on a module (SoM) and device communication to control and direct the system behavior.

The present disclosure includes use of slider bars and slider to allow user activation of features, such as position adjustment. In some embodiments, the speed of adjustment may increase with additional dragging distance from the slider's initial (default) position such that partial dragging and holding of the slider adjusts the patient support at a first speed, and full dragging and holding of the slider at the maximum position from the initial position adjusts the patient support at another speed greater than the first. In some embodiments, no automatic trigger point may be provided such that the user must maintain the slider actuation for the extent of the actuation. In some embodiments, a single speed of operation may be provided and actuation may require dragging the slider to the maximum position away from the default position. In some embodiments, in predetermined or preset position adjustments, fully dragging the slider to the maximum position initiates an automatic positioning which proceeds to adjust the patient support to the predetermined or preset position even upon release of the slider to return to its initial position.

The patient supports of the present disclosure include devices, systems, and method for securing support tops with connection assemblies without the use of removable parts, such as pins, which can promote speed and ease of use in removable support tops for patient support.

The present disclosure includes devices, systems, and methods for user interface to operate the patient support. In some embodiments, activation of adjustment features, such as position adjustment of the patient support, may be initiated by selection of the desired section of the patient support for adjustment on a graphical depiction of a user interface. For example, adjustment of a head end tower base may be activated by user selection of the head end tower base on the depiction. The present disclosure includes graphical depictions of the patient support which conduct real time position tracking of the features of the patient support.

Although certain illustrative embodiments have been described in detail above, variations and modifications exist within the scope and spirit of this disclosure as described and as defined in the following claims.

We claim:

1. A patient support device comprising:
   at least one patient top for supporting a patient's body above the floor, the at least one patient top including at least one tube connector for receiving support connection,
   at least one end support for connection with the patient top to support the patient top for selective rotation about a rotation axis, and
   a connection assembly for selectively connecting the at least one patient support top with the at least one end support, the connection assembly including at least one docking receiver defining a tube slot for receiving the at least one tube connector, and a docking gate for selectively blocking against disconnection of the patient top with the at least one end support, the docking gate movable between an unlocked position clear from an entrance of the tube slot and a locked position extending across at least a portion of the entrance to block removal of the at least one tube connector, wherein the entrance opens outwardly from the rotation axis,
  wherein the docking gate includes at least one gate latch including a body and an arm extending from the body for selective interaction with the tube slot, the arm extending across the entrance in the locked position to block removal of the tube connector from the tube slot and clear from the entrance in the unlocked position, the connection assembly includes a lock pin moveable between a disengaged position permitting movement of the docking gate out from the locked position and an engaged position blocking the docking gate from movement out from the locked position, and the lock pin is concentrically mounted on an actuation rod that is translatable to achieve the engaged and disengaged positions of the lock pin.

2. The patient support device of claim 1, wherein the at least one docking receiver includes at least one end stop defining a receiver slot as at least a portion of the tube slot, the receiver slot having an opening facing radially outward relative to the rotation axis.

3. The patient support device of claim 2, wherein the at least one docking receiver is arranged as a bottom docking receiver and the receiver slot faces downward when the connection assembly is arranged in a level position.

4. The patient support device of claim 1, wherein in the engaged position the lock pin is inserted into a pin slot of the body.

5. The patient support device of claim 4, wherein, in the locked position of the docking gate, the pin slot is positioned in correspondence with the lock pin and the pin slot is out of correspondence with the lock pin in positions of the docking gate other than the locked position.

6. The patient support device of claim 4, wherein the body includes a wing extending from an interior surface of the pin slot preventing removal of the pin without unloading.

7. The patient support device of claim 1, wherein the actuation rod includes a second lock pin for engagement with a second gate latch of the docking gate.

8. The patient support device of claim 7, wherein each of the first and second lock pins are moveable between engaged and disengaged positions under the movement of the actuation rod.

9. The patient support device of claim 1, wherein the at least one docking receiver is mounted to a slide assembly for positioning the docking receiver relative to the end support.

10. The patient support device of claim 9, wherein the slide assembly includes a ratchet assembly for controlled positioning of the docking receiver.

11. The patient support device of claim 10, wherein the slide assembly includes a slide plate having the docking receiver mounted thereon, the slide plate translatably connected with a frame of the connection assembly, wherein the ratchet assembly includes a first portion mounted on the frame and a second portion mounted on the slide plate, the first and second portions arranged for selective engagement with each other to define the position of the slide plate relative to the frame.

12. The patient support device of claim 11, wherein the first portion of the ratchet assembly is one of a pawl and a ratchet track and the second portion of the ratchet assembly is the other of the pawl and the ratchet track.

13. The patient support device of claim 11, wherein the first portion is connected with a handle extending from the frame for engagement by a user's hand, the handle being operable between a latched position arranging the first portion in engagement with the second portion, and an unlatched position removing the first portion from engagement with the second portion.

14. The patient support device of claim 11, further comprising a position sensor arranged to determine a position of the slide plate relative to the frame.

15. The patient support device of claim 11, wherein the slide assembly includes another slide plate having another docking receiver to receive connection of another patient top.

16. The patient support device of claim 15, wherein the another slide plate is arranged opposite the slide plate for rotating a patient into another position.

17. The patient support device of claim 9, wherein the slide assembly includes a slide plate having the docking receiver mounted thereon, the slide plate translatably connected with a frame of the connection assembly, the slide assembly including a damper assembly coupled with the slide plate to dampen the movement of the slide plate relative to the frame.

18. The patient support device of claim 17, wherein the damper assembly includes a rack portion and a pinion portion engaged with each other to provide a dampening force by their interaction, one of the rack and pinion portions secured with the slide plate and the other of the rack and pinion portions secured with the frame.

19. The patient support device of claim 18, wherein the pinion portion is formed as a gear arranged to provide a dampening rotational force by translation of the slide plate.

20. The patient support device of claim 1, wherein the connection assembly includes a base frame, and the patient support device further comprises a lateral extension selectively connectible with the base frame to extend laterally from the frame and including a docking receiver mounted on the lateral extension.

21. The patient support device of claim 20, wherein the docking receiver mounted on the lateral extension is arranged orthogonal to the at least one docking receiver when the lateral extension is connected with the base frame.

22. A patient support device comprising:
  at least one patient top for supporting a patient's body above the floor, the at least one patient top including at least one tube connector for receiving support connection,
  at least one end support for connection with the patient top to support the patient top for selective rotation about a rotation axis, and
  a connection assembly for selectively connecting the at least one patient support top with the at least one end support, the connection assembly including at least one docking receiver defining a tube slot for receiving the at least one tube connector, and a docking gate for selectively blocking against disconnection of the patient top with the at least one end support, the docking gate movable between an unlocked position clear from an entrance of the tube slot and a locked position extending across at least a portion of the entrance to block removal of the at least one tube connector, wherein the entrance opens outwardly from the rotation axis,
  wherein the docking gate includes at least one gate latch including a body and an arm extending from the body for selective interaction with the tube slot, the arm extending across the entrance in the locked position to block removal of the tube connector from the tube slot and clear from the entrance in the unlocked position, the connection assembly includes a lock pin moveable between a disengaged position permitting movement of the docking gate out from the locked position and an engaged position blocking the docking gate from movement out from the locked position, wherein in the engaged position the lock pin is inserted into a pin slot of the body, and in the locked position of the docking gate, the pin slot is positioned in correspondence with the lock pin and the pin slot is out of correspondence with the lock pin in positions of the docking gate other than the locked position.

23. The patient support device of claim 22, wherein the at least one docking receiver includes at least one end stop defining a receiver slot as at least a portion of the tube slot, the receiver slot having an opening facing radially outward relative to the rotation axis.

24. The patient support device of claim 23, wherein the at least one docking receiver is arranged as a bottom docking receiver and the receiver slot faces downward when the connection assembly is arranged in a level position.

25. The patient support device of claim 22, wherein the body includes a wing extending from an interior surface of the pin slot preventing removal of the pin without unloading.

26. The patient support device of claim 22, wherein the at least one docking receiver is mounted to a slide assembly for positioning the docking receiver relative to the end support.

27. The patient support device of claim 26, wherein the slide assembly includes a ratchet assembly for controlled positioning of the docking receiver.

28. A patient support device comprising:
   at least one patient top for supporting a patient's body above the floor, the at least one patient top including at least one tube connector for receiving support connection,
   at least one end support for connection with the patient top to support the patient top for selective rotation about a rotation axis, and
   a connection assembly for selectively connecting the at least one patient support top with the at least one end support, the connection assembly including at least one docking receiver defining a tube slot for receiving the at least one tube connector, and a docking gate for selectively blocking against disconnection of the patient top with the at least one end support, the docking gate movable between an unlocked position clear from an entrance of the tube slot and a locked position extending across at least a portion of the entrance to block removal of the at least one tube connector, wherein the entrance opens outwardly from the rotation axis,
   wherein the docking gate includes at least one gate latch including a body and an arm extending from the body for selective interaction with the tube slot, the arm extending across the entrance in the locked position to block removal of the tube connector from the tube slot and clear from the entrance in the unlocked position, the connection assembly includes a lock pin moveable between a disengaged position permitting movement of the docking gate out from the locked position and an engaged position blocking the docking gate from movement out from the locked position, wherein in the engaged position the lock pin is inserted into a pin slot of the body, and the body includes a wing extending from an interior surface of the pin slot preventing removal of the pin without unloading.

29. The patient support device of claim 28, wherein the lock pin is coupled with an actuation rod which includes a second lock pin for engagement with a second gate latch of the docking gate.

30. The patient support device of claim 29, wherein each of the first and second lock pins are moveable between engaged and disengaged positions under the movement of the actuation rod.

* * * * *